United States Patent
Kondo et al.

[11] Patent Number: 6,051,288
[45] Date of Patent: *Apr. 18, 2000

[54] FLUORINE-SUBSTITUTED LIQUID-CRYSTAL COMPOUND, LIQUID-CRYSTAL COMPOSITION AND LIQUID-CRYSTAL DISPLAY DEVICE

[75] Inventors: Tomoyuki Kondo; Yasuhiro Haseba; Yasuyuki Koizumi; Kazutoshi Miyazawa; Norihisa Hachiya; Etsuo Nakagawa, all of Chiba, Japan

[73] Assignee: Chisso Corporation, Osaka, Japan

[*] Notice: This patent is subject to a terminal disclaimer.

[21] Appl. No.: 08/913,022

[22] PCT Filed: Apr. 12, 1996

[86] PCT No.: PCT/JP96/01010

§ 371 Date: Sep. 26, 1997

§ 102(e) Date: Sep. 26, 1997

[87] PCT Pub. No.: WO96/32365

PCT Pub. Date: Oct. 17, 1996

[30] Foreign Application Priority Data

Apr. 12, 1995 [JP] Japan .................................. 7-112551

[51] Int. Cl.$^7$ .......................... C09K 19/20; C09K 19/34; G02F 1/13; C07C 69/76; C07D 239/02

[52] U.S. Cl. .................. 428/1; 252/299.61; 252/299.63; 252/299.64; 252/299.65; 252/299.66; 252/299.67; 544/298; 544/335; 546/346; 549/374; 560/65; 560/83

[58] Field of Search .................. 252/299.01, 299.63, 252/299.64, 299.65, 299.66, 299.67; 560/65, 83; 544/298, 335; 546/346; 549/374; 570/127, 131; 428/1

[56] References Cited

U.S. PATENT DOCUMENTS

| | | | |
|---|---|---|---|
| 5,069,814 | 12/1991 | Suzuki et al. | 252/299.67 |
| 5,308,541 | 5/1994 | Hittich et al. | 252/299.63 |
| 5,733,477 | 3/1998 | Kondo et al. | 252/299.67 |
| 5,755,994 | 5/1998 | Kondo et al. | 252/299.61 |
| 5,820,784 | 10/1998 | Kondo et al. | 252/299.63 |

FOREIGN PATENT DOCUMENTS

| | | |
|---|---|---|
| 55-40660 | 3/1980 | Japan . |
| 4-300861 | 10/1992 | Japan . |
| 7-306417 | 11/1995 | Japan . |
| 2232156 | 12/1990 | United Kingdom . |
| WO89/02884 | 4/1989 | WIPO . |
| WO89/08102 | 9/1989 | WIPO . |
| WO90/01056 | 2/1990 | WIPO . |

OTHER PUBLICATIONS

Gray et al., "The Synthesis and Transition Temperatures of Some Fluoro–Substituted 4–Cyanophenyl and 4–Cyanobiphenyl-4'–yl 4–Pentyl– and 4–Butoxy–Benzoates", Mol. Cryst. Liq. Cryst. 1989, vol. 172, pp. 165–189.

*Primary Examiner*—Shean C. Wu
*Attorney, Agent, or Firm*—Wenderoth, Lind & Ponack, L.L.P.

[57] ABSTRACT

An object of the present invention is to provide a novel liquid crystalline compound having a large dielectric anisotropy, small change in threshold voltage depending on temperature, and an improved solubility to other liquid crystal materials at low temperatures, and expressed by the following general formula (1):

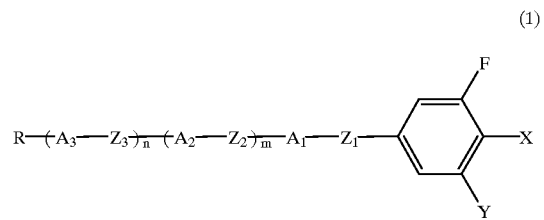

(1)

wherein R represents, for example, an alkyl group or alkoxy group having 1 to 10 carbon atoms, m and n are independently 0 or 1, $A_1$, $A_2$, and $A_3$ are independently, for example, trans-1,4-cyclohexylene group, 1,4-phenylene group one or more hydrogen atoms on the ring of which may be replaced by F, $Z_1$, $Z_2$, and $Z_3$ independently represent —COO—, —OCO—, —(CH$_2$)$_2$—, —CH$_2$O—, —OCH$_2$—, or a covalent bond provided that at least one of $Z_1$, $Z_2$, and $Z_3$ represents ester bond, —CH$_2$O—, or —OCH$_2$—, X represents, for example, CF$_3$, CF$_2$H, and Y represents H or F. Another object of the present invention is to provide a liquid crystal composition containing the liquid crystalline compound.

21 Claims, No Drawings

FLUORINE-SUBSTITUTED LIQUID-CRYSTAL COMPOUND, LIQUID-CRYSTAL COMPOSITION AND LIQUID-CRYSTAL DISPLAY DEVICE

This application is a 371 application of International Application No. PCT/JP96/01010 filed Apr. 12, 1996.

TECHNICAL FIELD

The present invention relates to a liquid crystalline compound and a liquid crystal composition. More specifically, the present invention relates to a novel fluorine substituted compound having 3-fluoro-4-substituted phenyl group or 3,5-difluoro-4-substituted phenyl group, a liquid crystal composition containing the fluorine substituted compound, and a liquid crystal display device comprising the liquid crystal composition.

BACKGROUND ART

Liquid crystal display devices comprising liquid crystalline compounds have widely been used for displays of watches, tabletop calculators, word processors, and others. These display devices employ the optical anisotropy and dielectric anisotropy of liquid crystalline compounds.

While liquid crystal phase includes a nematic liquid crystal phase, smectic liquid crystal phase, and cholesteric liquid crystal phase, display devices employing the nematic liquid crystal phase have most widely been used. As their display mode, dynamic scattering (DS) type, deformation of aligned phase (DAP) type, guest-host (GH) type, twisted nematic (TN) type, super twisted nematic (STN) type, and thin film transistor (TFT) type are known.

Whereas liquid crystalline compounds employed in these display modes must exhibit a liquid crystal phase at a wide temperature range having its center at room temperature, must be sufficiently stable under conditions in which the liquid crystalline compounds are used, and must have characteristics sufficient to drive the display devices, no compound which satisfies those requirements by its self has been found. Accordingly, it is an actual circumstance that several kinds to several tens kinds of liquid crystalline compounds are mixed, together with not-liquid crystalline compounds when necessary, to produce a liquid crystal composition provided with required characteristics. These liquid crystal compositions are required to be stable against moisture, light, heat, and air which usually exist under the conditions in which display devices are used, to be stable against electric field and electromagnetic radiation, and further to be chemically stable against the compounds to be mixed. The liquid crystal compositions are also required to have appropriate physical parameters such as the value of optical anisotropy ($\Delta n$) and dielectric anisotropy ($\Delta \epsilon$) depending on the display mode and the shape of display devices. Still further, it is important that each of the components in the liquid crystal compositions have good solubility to each other.

Especially, the demand for lowering threshold voltage still more which largely contributes to high speed response necessary for expanding the screen of liquid crystal display devices has been increased. For that purpose, liquid crystalline compounds having a large $\Delta \epsilon$ are necessary (E. Jakeman et al., Phys. Lett., 39A. 69 (1972)).

Also, liquid crystalline compounds having a small change of threshold voltage depending on temperature are considered to be necessary.

In order to achieve these purposes, the compounds expressed by formula (a), (b), or (c) are disclosed in Laid-open Japanese Patent Publication No. Sho 55-40660, Laid-open WO Japanese Patent Publication No. Hei 2-501311, or Laid-open WO Japanese Patent Publication No. Hei 3-500413. However, $\Delta \epsilon$ of these compounds is not yet sufficiently large and the change of their threshold voltage due to the change of temperature can not be said to be small.

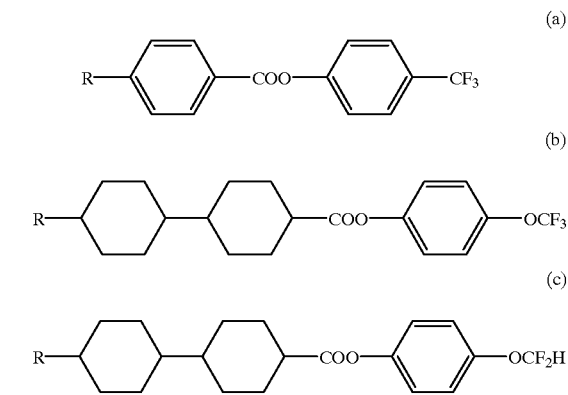

Further, the compounds expressed by formula (d) or (e) are known in public through Laid-open WO Japanese Patent Publication No. Hei 3-503637 or Laid-open Japanese Patent Publication No. Hei 4-279560. However, these compounds have problems that the temperature range of liquid crystal phase is narrow or the solubility to other liquid crystal materials at low temperatures is not sufficient whereas the compounds have a large $\Delta \epsilon$.

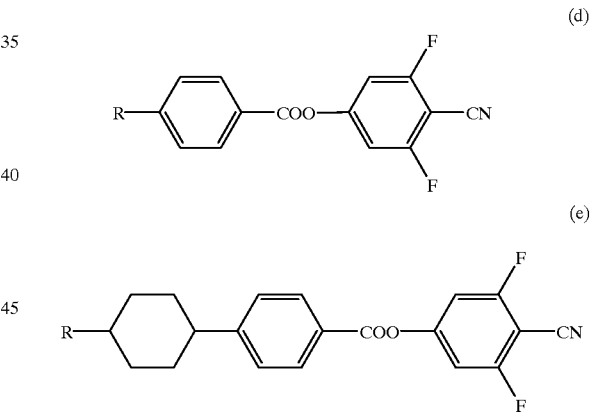

DISCLOSURE OF THE INVENTION

An object of the present invention is to solve the defects in the prior art mentioned above; particularly to provide a fluorine substituted compound which has a large $\Delta \epsilon$ and small change of threshold voltage depending on temperature, is excellent in stability, and is improved in solubility to other liquid crystal materials at low temperatures; to provide a liquid crystal composition containing the compound; and to provide a liquid crystal display device comprising the liquid crystal composition.

In order to achieve the objects mentioned above, the present invention is described as follows:

(1) A liquid crystalline compound expressed by general formula (1)

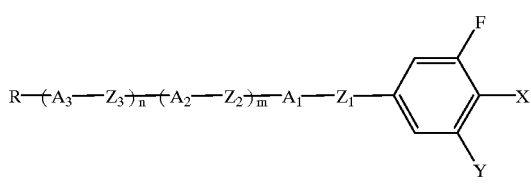

(1)

wherein R represents an alkyl group or alkoxy group having 1 to 10 carbon atoms, or an alkenyl group having 2 to 10 carbon atoms, any methylene group (—$CH_2$—) in the alkenyl group may be replaced by oxygen atom (—O—) provided that in no case two or more methylene groups are continually replaced by oxygen atom, m and n are independently 0 or 1, $A_1$, $A_2$, and $A_3$ are independently trans-1,4-cyclohexylene group, 1,4-phenylene group one or more hydrogen atoms on the ring of which may be replaced by F, pyrimidine-2,5-diyl group, pyridine-2,5-diyl group, or 1,3-dioxane-2,5-diyl group, $Z_1$, $Z_2$, and $Z_3$ independently represent —COO—, —OCO—, —$(CH_2)_2$—, —$CH_2O$—, —$OCH_2$—, or a covalent bond is provided that at least one of $Z_1$, $Z_2$, and $Z_3$ represents ester bond, —$CH_2O$—, or —$OCH_2$—; X represents $CF_3$, $CF_2H$, $CFH_2$, $OCF_3$, $OCF_2H$, or CN, and Y represents H or F, provided that when X is CN, n is 0, $A_2$ is trans-1,4-cyclohexylene group, $A_1$ is 1,4-phenylene group one or more hydrogen atoms on the ring of which may be replaced by F, $Z_2$ represents —$(CH_2)_2$— or a covalent bond, $Z_1$ is ester bond, and Y represent F.

(2) The liquid crystalline compound recited in (1) above wherein m and n are 0.

(3) The liquid crystalline compound recited in (1) above wherein m is 1, and n is 0.

(4) The liquid crystalline compound recited in (1) wherein both m and n are 1.

(5) The liquid crystalline compound recited in (2) above wherein $A_1$ is 1,4-phenylene group one or more hydrogen atoms on the ring of which may be replaced by F.

(6) The liquid crystalline compound recited in (2) above wherein $A_1$ is trans-1,4-cyclohexylene group.

(7) The liquid crystalline compound recited in (3) above wherein $A_2$ is trans-1,4-cyclohexylene group.

(8) The liquid crystalline compound recited in (4) above wherein both $A_2$ and $A_3$ are trans-1,4-cyclohexylene group, and $Z_3$ is a covalent bond.

(9) The liquid crystalline compound recited in (7) above wherein $A_1$ is 1,4-phenylene group one or more hydrogen atoms on the ring of which may be replaced by F, and $Z_2$ is a covalent bond.

(10) The liquid crystalline compound recited in (7) above wherein $A_1$ is trans-1,4-cyclohexylene group, and $Z_2$ is a covalent bond.

(11) The liquid crystalline compound recited in (7) above wherein $A_1$ is 1,4-phenylene group one or more hydrogen atoms on the ring of which may be replaced by F, $Z_1$ is ester bond, $Z_2$ is —$(CH_2)_2$— or a covalent bond, X is CN, and Y is F.

(12) The liquid crystalline compound recited in (8) above wherein $A_1$ is 1,4-phenylene group one or more hydrogen atoms on the ring of which may be replaced by F, and $Z_2$ is a covalent bond.

(13) The liquid crystalline compound recited in (8) above wherein $A_1$ is trans-1,4-cyclohexylene group or 1,4-phenylene group one or more hydrogen atoms on the ring of which may be replaced by F, and $Z_1$ is a covalent bond.

(14) A liquid crystal composition containing at least one liquid crystalline compound recited in any one of (1) to (13) above.

(15) A liquid crystal composition containing, as a first component, at least one liquid crystalline compound recited in any one of (1) to (13) above, and containing, as a second component, at least one compound selected from the group consisting of the compounds expressed by any one of general formulas (2), (3), and (4)

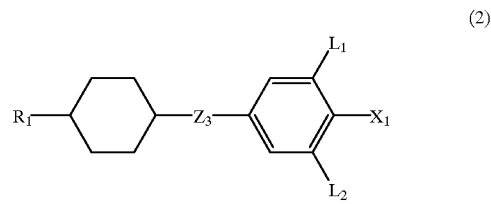

(2)

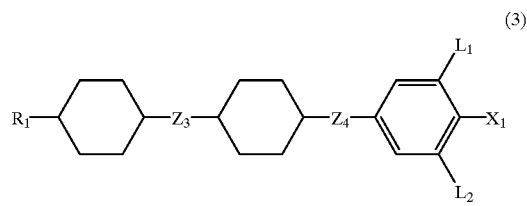

(3)

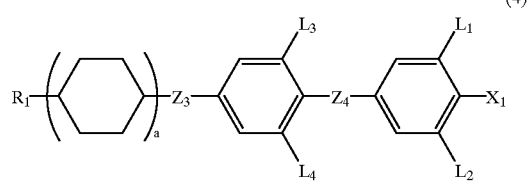

(4)

wherein $R_1$ represents an alkyl group having 1 to 10 carbon atoms, $X_1$ represents F, Cl, $OCF_3$, $OCF_2H$, $CF_3$, $CF_2H$, or $CFH_2$, $L_1$, $L_2$, $L_3$, and $L_4$ independently represent H or F, $Z_4$ and $Z_5$ independently represent —$(CH_2)_2$—, —CH=CH—, or a covalent bond, and a is 1 or 2.

(16) A liquid crystal composition containing, as a first component, at least one liquid crystalline compound recited in any one of (1) to (13) above, and containing, as a second component, at least one compound selected from the group consisting of the compounds expressed by any one of general formulas (5), (6), (7), (8), and (9)

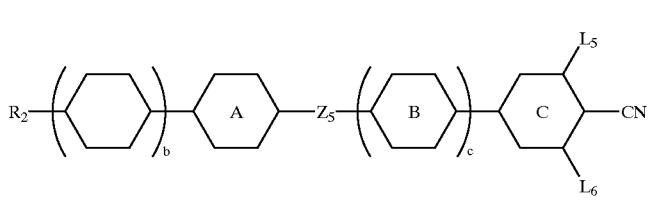

(5)

wherein $R_2$ represents F, an alkyl group having 1 to 10 carbon atoms or an alkenyl group having 2 to 10 carbon atoms, any methylene group (—$CH_2$—) in the alkyl group or alkenyl group may be replaced by oxygen atom (—O—) provided that in no case two or more methylene groups are continually replaced by oxygen atom, ring A represents trans-1,4-cyclohexylene group, 1,4-phenylene group, or 1,3-dioxane-2,5-diyl group, ring B represents trans-1,4-cyclohexylene group, 1,4-phenylene group, or pyrimidine-2,5-diyl group, ring C represents trans-1,4-cyclohexylene group, or 1,4-phenylene group, $Z_6$ represents —$(CH_2)_2$—, —COO—, or a covalent bond, $L_5$ and $L_6$ independently represent H or F, and b and c are independently 0 or 1,

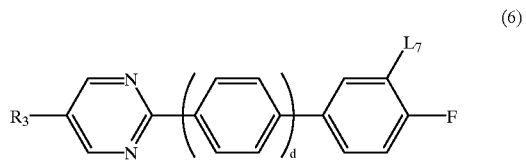

(6)

wherein $R_3$ represents an alkyl group having 1 to 10 carbon atoms, $L_7$ represents H or F, and d is 0 or 1,

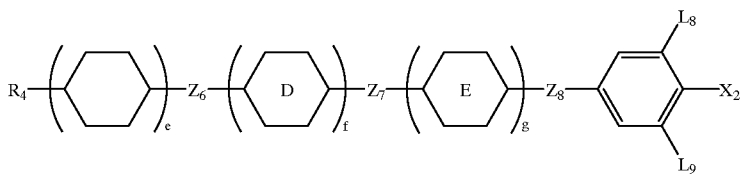

(7)

wherein $R_4$ represents an alkyl group having 1 to 10 carbon atoms, rings D and E independently represent trans-1,4-cyclohexylene group or 1,4-phenylene group, $Z_7$ and $Z_8$ independently represent —COO— or a covalent bond, $Z_9$ represents —COO— or —C≡C—, $L_8$ and $L_9$ independently represent H or F, $X_2$ represents F, $OCF_3$, $OCF_2H$, $CF_3$, $CF_2H$, or $CFH_2$ provided that when $X_2$ represents $OCF_3$, $OCF_2H$, $CF_3$, $CF_2H$, or $CFH_2$, both $L_8$ and $L_9$ represent H; and e, f, and g are independently 0 or 1,

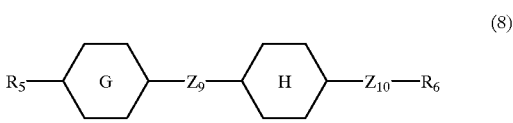

(8)

wherein $R_5$ and $R_6$ independently represent an alkyl group having 1 to 10 carbon atoms or an alkenyl group having 2 to 10 carbon atoms, in either case any methylene group (—$CH_2$—) in the alkyl group or alkylene group may be replaced by oxygen atom (—O—) provided that in no case two or more methylene groups are continually replaced by oxygen atom, ring G represents trans-1,4-cyclohexylene group, 1,4-phenylene group, or pyrimidine-2,5-diyl group, ring H represents trans-1,4-cyclohexylene group or 1,4-phenylene group, $Z_{10}$ represents —C≡C—, —COO—, —$(CH_2)_2$—, —CH=CH—C≡C—, or a covalent bond, and $Z_{11}$ represents —COO— or a covalent bond,

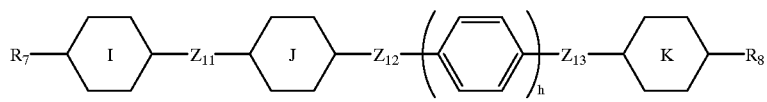

(9)

wherein $R_7$ and $R_8$ independently represent an alkyl group having 1 to 10 carbon atoms or an alkenyl group having 2 to 10 carbon atoms, in either case any methylene group (—$CH_2$—) in the alkyl group or alkylene group may be replaced by oxygen atom (—O—) provided that in no case two or more methylene groups are continually replaced by oxygen atom, ring 1 represents trans-1,4-cyclohexylene group, 1,4-phenylene group, or pyrimidine-2,5-diyl group, ring J represents trans-1,4-cyclohexylene group, 1,4-phenylene group one or more hydrogen atom on the ring of which may be replaced by F, or pyrimidine-2,5-diyl group, ring K represents trans-1,4-cyclohexylene group or 1,4-phenylene group, $Z_{12}$ and $Z_{14}$ independently represent —COO—, —(CH$_2$)$_2$—, or a covalent bond, $Z_{13}$ represents —CH=CH—, —C≡C—, —COO—, or a covalent bond, and h is 0 or 1.

(17) A liquid crystal composition containing, as a first component, at least one liquid crystalline compound recited in any one of (1) to (13) above, containing, as a part of a second component, at least one liquid crystalline compound selected from the group consisting of the compounds expressed by any one of general formulas (2), (3), and (4) recited in aspect (15) above, and containing, as the other part of the second component, at least one liquid crystalline compound selected from the group consisting of the compounds expressed by any one of general formulas (5), (6), (7), (8), and (9) recited in aspect (16) above.

(18) A liquid crystal display device comprising a liquid crystal composition recited in any one of (14) to (17) above.

Liquid crystalline compounds of the present invention expressed by general formula (1) have a large Δε and small change of threshold voltage depending on temperature. These liquid crystalline compounds are physically and chemically stable to a sufficient extent under the conditions in which display devices are ordinarily used, and excellent in solubility at low temperatures. Further, they can be derived into compounds of desired physical parameters by suitably selecting the 6-membered ring, substituent and/or bonding group from the group of the elements which form the molecule. Accordingly, when the compound of the present invention was used as a component of liquid crystal compositions, novel liquid crystal compositions having preferable characteristics can be provided.

BEST MODE FOR CARRYING OUT THE INVENTION

Compounds of the present invention expressed by general formula (1) are classified as follows:

In the following, Q represents the group shown just below.

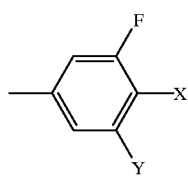

Cyc represents trans-1,4-cyclohexylene group, Phe does 1,4-phenylene group, Pyr does pyrimidine-2,5-diyl group, Pyd does pyridine-2,5-diyl group, and Dio represents 1,3-dioxane-2,5-diyl group; one or more hydrogen atoms in the Phe may be replaced by F; $A_1$, $A_2$, and $A_3$ are selected from the group consisting of Cyc, Phe, Pyr, Pyd, and Dio, and preferably two or more Pyr, Pyd, or Dio are not contained in one molecule.

Compounds having 2 six-membered rings:

| | |
|---|---|
| R-A$_1$-COO-Q | (1a) |
| R-A$_1$-OCO-Q | (1b) |
| R-A$_1$-CH$_2$O-Q | (1c) |
| R-A$_1$-OCH$_2$-Q | (1d) |

Compounds having 3 six-membered rings:

| | |
|---|---|
| R-A$_1$-A$_2$-COO-Q | (1e) |
| R-A$_1$-COO-A$_2$-Q | (1f) |
| R-A$_1$-A$_2$-OCO-Q | (1g) |
| R-A$_1$-OCO-A$_2$-Q | (1h) |
| R-A$_1$-(CH$_2$)$_2$-A$_2$-COO-Q | (1i) |
| R-A$_1$-COO-A$_2$-COO-Q | (1j) |
| R-A$_1$-A$_2$-CH$_2$O-Q | (1k) |
| R-A$_1$-CH$_2$O-A$_2$-Q | (1l) |
| R-A$_1$-A$_2$-OCH$_2$-Q | (1m) |
| R-A$_1$-OCH$_2$-A$_2$-Q | (1n) |
| R-A$_1$-(CH$_2$)$_2$-A$_2$-CH$_2$O-Q | (1o) |
| R-A$_1$-(CH$_2$)$_2$-A$_2$-OCH$_2$-Q | (1p) |

Compounds having 4 six-membered rings:

| | |
|---|---|
| R-A$_1$-COO-A$_2$-A$_3$-Q | (1q) |
| R-A$_1$-A$_2$-COO-A$_3$-Q | (1r) |
| R-A$_1$-A$_2$-A$_3$-COO-Q | (1s) |
| R-A$_1$-COO-A$_2$-COO-A$_3$-Q | (1t) |
| R-A$_1$-(CH$_2$)$_2$-A$_2$-COO-A$_3$-Q | (1u) |
| R-A$_1$-A$_2$-(CH$_2$)$_2$-A$_3$-COO-Q | (1v) |
| R-A$_1$-CH$_2$O-A$_2$-A$_3$-Q | (1w) |
| R-A$_1$-A$_2$-CH$_2$O-A$_3$-Q | (1x) |
| R-A$_1$-A$_2$-A$_3$-CH$_2$O-Q | (1y) |
| R-A$_1$-A$_2$-OCH$_2$-A$_3$-Q | (1z) |

Compounds expressed by formula (1a) are developed further to the compounds expressed by one of the following formulas (1aa) to (1ae):

| | |
|---|---|
| R-Cyc-COO-Q | (1aa) |
| R-Phe-COO-Q | (1ab) |
| R-Phr-COO-Q | (1ac) |
| R-Pyd-COO-Q | (1ad) |
| R-Dio-COO-Q | (1ae) |

Among these compounds, particularly the compounds expressed by formula (1aa) or (1ab) are preferable.

Compounds expressed by formula (1b) are developed further to the compounds expressed by one of the following formulas (1ba) to (1be):

| | |
|---|---|
| R-Cyc-OCO-Q | (1ba) |
| R-Phe-OCO-Q | (1bb) |
| R-Pyr-OCO-Q | (1bc) |
| R-Pyd-OCO-Q | (ibd) |
| R-Dio-OCO-Q | (1be) |

Among these compounds, particularly the compounds expressed by formula (1ba) or (1bb) are preferable.

Compounds expressed by formula (1c) are developed further to the compounds expressed by one of the following formulas (1ca) to (1ce):

| | |
|---|---|
| R-Cyc-CH$_2$O-Q | (1ca) |
| R-Phe-CH$_2$O-Q | (1cb) |
| R-Pyr-CH$_2$O-Q | (1cc) |
| R-Pyd-CH$_2$O-Q | (1cd) |
| R-Dio-CH$_2$O-Q | (1ce) |

Among these compounds, particularly the compounds expressed by formula (1ca), (1cb), or (1ce) are preferable.

Compounds expressed by formula (1d) are developed further to the compounds expressed by one of the following formulas (1da) to (1de):

| | |
|---|---|
| R-Cyc-OCH$_2$-Q | (1da) |
| R-Phe-OCH$_2$-Q | (1db) |
| R-Pyr-OCH$_2$-Q | (1dc) |
| R-Pyd-OCH$_2$-Q | (1dd) |
| R-Dio-OCH$_2$-Q | (1de) |

Among these compounds, particularly the compounds expressed by formula (1da) or (1db) are preferable.

Compounds expressed by formula (1e) are developed further to the compounds expressed by any one of the following formulas (1ea) to (1ej):

| | |
|---|---|
| R-Cyc-Cyc-COO-Q | (1ea) |
| R-Cyc-Phe-COO-Q | (1eb) |
| R-Phe-Cyc-COO-Q | (1ec) |
| R-Phe-Phe-COO-Q | (1ed) |
| R-Pyr-Phe-COO-Q | (1ee) |
| R-Pyr-Cyc-COO-Q | (1ef) |
| R-Pyd-Phe-COO-Q | (1eg) |
| R-Pyd-Cyc-COO-Q | (1eh) |
| R-Dio-Phe-COO-Q | (1ei) |
| R-Dio-Cyc-COO-Q | (1ej) |

Among these compounds, particularly the compounds expressed by one of the formulas (1ea) to (1ee), or formula (1ej) are preferable.

Compounds expressed by formula (1f) are developed further to the compounds expressed by one of the following formulas (1fa) to (1fn):

| | |
|---|---|
| R-Cyc-COO-Cyc-Q | (1fa) |
| R-Cyc-COO-Phe-Q | (1fb) |
| R-Cyc-COO-Pyr-Q | (1fc) |
| R-Cyc-COO-Pyd-Q | (1fd) |
| R-Phe-COO-Cyc-Q | (1fe) |
| R-Phe-COO-Phe-Q | (1ff) |
| R-Phe-COO-Pyr-Q | (1fg) |
| R-Phe-COO-Pyd-Q | (1fh) |
| R-Pyr-COO-Phe-Q | (1fi) |
| R-Pyr-COO-Cyc-Q | (1fj) |
| R-Pyd-COO-Phe-Q | (1fk) |
| R-Pyd-COO-Cyc-Q | (1fl) |
| R-Dio-COO-Phe-Q | (1fm) |
| R-Dio-COO-Cyc-Q | (1fn) |

Among these compounds, particularly the compounds expressed by formula (1fa), (1fb), (1fe), or (1ff) are preferable.

Compounds expressed by formula (1g) are developed further to the compounds expressed by one of the following formulas (1ga) to (1gj):

| | |
|---|---|
| R-Cyc-Cyc-OCO-Q | (1ga) |
| R-Cyc-Phe-OCO-Q | (1gb) |
| R-Phe-Cyc-OCO-Q | (1gc) |
| R-Phe-Phe-OCO-Q | (1gd) |
| R-Pyr-Phe-OCO-Q | (1ge) |
| R-Pyr-Cyc-OCO-Q | (1gf) |
| R-Pyd-Phe-OCO-Q | (1gg) |
| R-Pyd-Cyc-OCO-Q | (1gh) |
| R-Dio-Phe-OCO-Q | (1gi) |
| R-Dio-Cyc-OCO-Q | (1gj) |

Among these compounds, particularly the compounds expressed by one of formulas (1ga) to (1ge), or (1gi) are preferable.

Compounds expressed by formula (1h) are developed further to the compounds expressed by one of the following formulas (1ha) to (1hn):

| | |
|---|---|
| R-Cyc-OCO-Cyc-Q | (1ha) |
| R-Cyc-OCO-Phe-Q | (1hb) |
| R-Cyc-OCO-Pyr-Q | (1hc) |
| R-Cyc-OCO-Pyd-Q | (1hd) |
| R-Phe-OCO-Cyc-Q | (1he) |
| R-Phe-OCO-Phe-Q | (1hf) |
| R-Phe-CO-Pyr-Q | (1hg) |
| R-Phe-OCO-Pyd-Q | (1hh) |
| R-Pye-OCO-Phe-Q | (1hi) |
| R-Pyr-OCO-Cyc-Q | (1hj) |
| R-Pyd-OCO-Phe-Q | (1hk) |
| R-Pyd-OCO-Cyc-Q | (1hl) |
| R-Dio-OCO-Phe-Q | (1hm) |
| R-Dio-OCO-Cyc-Q | (1hn) |

Among these compounds, particularly the compounds expressed by formula (1ha), (1hb), (1he), or (1hf) are preferable.

Compounds expressed by formula (1i) are developed further to the compounds expressed by one of the following formulas (1ia) to (1ik):

| | |
|---|---|
| R-Cyc-(CH$_2$)$_2$-Cyc-COO-Q | (1ia) |
| R-Cyc-(CH$_2$)$_2$-Phe-COO-Q | (1ib) |
| R-Phe-(CH$_2$)$_2$-Cyc-COO-Q | (1ic) |
| R-Phe-(CH$_2$)$_2$-Phe-COO-Q | (1id) |
| R-Phe-(CH$_2$)$_2$-Pyr-COO-Q | (1ie) |
| R-Pyr-(CH$_2$)$_2$-Phe-COO-Q | (1if) |
| R-Pyr-(CH$_2$)$_2$-Cyc-COO-Q | (1ig) |
| R-Pyd-(CH$_2$)$_2$-Phe-COO-Q | (1ih) |
| R-Pyd-(CH$_2$)$_2$-Cyc-COO-Q | (1ii) |
| R-Dio-(CH$_2$)$_2$-Phe-COO-Q | (1ij) |
| R-Dio-(CH$_2$)$_2$-Cyc-COO-Q | (1ik) |

Among these compounds, particularly the compounds expressed by one of formulas (1ia) to (1id) are preferable.

Compounds expressed by formula (1j) are developed further to the compounds expressed by any one of the following formulas (1ja) to (1jk):

| | |
|---|---|
| R-Cyc-COO-Cyc-COO-Q | (1ja) |
| R-Cyc-COO-Phe-COO-Q | (1jb) |
| R-Phe-COO-Cyc-COO-Q | (1jc) |
| R-Phe-COO-Phe-COO-Q | (1jd) |
| R-Phe-COO-Pyr-COO-Q | (1je) |
| R-Pyr-COO-Phe-COO-Q | (1jf) |
| R-Pyr-COO-Cyc-COO-Q | (1jg) |
| R-Pyd-COO-Phe-COO-Q | (1jh) |
| R-Pyd-COO-Cyc-COO-Q | (1ji) |
| R-Dio-COO-Phe-COO-Q | (1jj) |
| R-Dio-COO-Cyc-COO-Q | (1jk) |

Among these compounds, particularly the compounds expressed by one of formulas (1ja) to (1jd) are preferable.

Compounds expressed by formula (1k) are developed further to the compounds expressed by ne of the following formulas (1ka) to (1kj):

| | |
|---|---|
| R-Cyc-Cyc-CH$_2$O-Q | (1ka) |
| R-Cyc-Phe-CH$_2$O-Q | (1kb) |
| R-Phe-Cyc-CH$_2$O-Q | (1kc) |
| R-Phe-Phe-CH$_2$O-Q | (1kd) |
| R-Pyr-Phe-CH$_2$O-Q | (1ke) |
| R$_9$-Pyr-Cyc-CH$_2$O-Q | (1kf) |
| R$_9$-Pyd-Phe-CH$_2$O-Q | (1kg) |
| R$_9$-Pyd-Cyc-CH$_2$O-Q | (1kh) |
| R$_9$-Dio-Phe-CH$_2$O-Q | (1ki) |
| R$_9$-Dio-Cyc-CH$_2$O-Q | (1kj) |

Among these compounds, particularly the compounds expressed by one of formulas (1ka) to (1ke), or formula (1ki) are preferable.

Compounds expressed by formula (1l) are developed further to the compounds expressed by any one of the following formulas (1la) to (1ln):

| | |
|---|---|
| R$_9$-Cyc-CH$_2$O-Cyc-Q | (1la) |
| R$_9$-Cyc-CH$_2$O-Phe-Q | (1lb) |
| R$_9$-Cyc-CH$_2$O-Pyr-Q | (1lc) |
| R$_9$-Cyc-CH$_2$O-Pyd-Q | (1ld) |
| R$_9$-Phe-CH$_2$O-Cyc-Q | (1le) |
| R$_9$-Phe-CH$_2$O-Phe-Q | (1lf) |
| R$_9$-Phe-CH$_2$O-Pyr-Q | (1lg) |
| R$_9$-Phe-CH$_2$O-Pyd-Q | (1lh) |
| R$_9$-Pyr-CH$_2$O-Phe-Q | (1li) |
| R$_9$-Pyr-CH$_2$O-Cyc-Q | (1lj) |
| R$_9$-Pyd-CH$_2$O-Phe-Q | (1lk) |
| R$_9$-Pyd-CH$_2$O-Cyc-Q | (1ll) |
| R$_9$-Dio-CH$_2$O-Phe-Q | (1lm) |
| R$_9$-Dio-CH$_2$O-Cyc-Q | (1ln) |

Among these compounds, particularly the compounds expressed by formula (1la), (1lb), (1le), or (1lf) are referable.

Compounds expressed by formula (1m) are developed further to the compounds expressed by any one of the following formulas (1ma) to (1mj):

| | |
|---|---|
| R$_9$-Cyc-Cyc-OCH$_2$-Q | (1ma) |
| R$_9$-Cyc-Phe-OCH$_2$-Q | (1mb) |
| R$_9$-Phe-Cyc-OCH$_2$-Q | (1mc) |
| R$_9$-Phe-Phe-OCH$_2$-Q | (1md) |
| R$_9$-Pyr-Phe-OCH$_2$-Q | (1me) |
| R$_9$-Pyr-Cyc-OCH$_2$-Q | (1mf) |
| R$_9$-Pyd-Phe-OCH$_2$-Q | (1mg) |
| R$_9$-Pyd-Cyc-OCH$_2$-Q | (1mh) |
| R$_9$-Dio-Phe-OCH$_2$-Q | (1mi) |
| R$_9$-Dio-Cyc-OCH$_2$-Q | (1mj) |

Among these compounds, particularly the compounds expressed by any one of formulas (1ma) to (1me), or (1mi) are preferable.

Compounds expressed by formula (1n) are developed further to the compounds expressed by any one of the following formulas (1na) to (1nn):

| | |
|---|---|
| R$_9$-Cyc-OCH$_2$-Cyc-Q | (1na) |
| R$_9$-Cyc-OCH$_2$-Phe-Q | (1nb) |
| R$_9$-Cyc-OCH$_2$-Pyr-Q | (1nc) |
| R$_9$-Cyc-OCH$_2$-Pyd-Q | (1nd) |
| R$_9$-Phe-OCH$_2$-Cyc-Q | (1ne) |
| R$_9$-Phe-OCH$_2$-Phe-Q | (1nf) |

-continued

| | |
|---|---|
| R$_9$-Phe-OCH$_2$-Pyr-Q | (1ng) |
| R$_9$-Phe-OCH$_2$-Pyd-Q | (1nh) |
| R$_9$-Pyr-OCH$_2$-Phe-Q | (1ni) |
| R$_9$-Pyr-OCH$_2$-Cyc-Q | (1nj) |
| R$_9$-Pyd-OCH$_2$-Phe-Q | (1nk) |
| R$_9$-Pyd-OCH$_2$-Cyc-Q | (1nl) |
| R$_9$-Dio-OCH$_2$-Phe-Q | (1nm) |
| R$_9$-Dio-OCH$_2$-Cyc-Q | (1nn) |

Among these compounds, particularly the compounds expressed by formula (1na), (1nb), (1ne), or (1nf) are preferable.

Compounds expressed by formula (1o) are developed further to the compounds expressed by any one of the following formulas (1oa) to (1ok):

| | |
|---|---|
| R$_9$-Cyc-(CH$_2$)$_2$-Cyc-CH$_2$O-Q | (1oa) |
| R$_9$-Cyc-(CH$_2$)$_2$-Phe-CH$_2$O-Q | (1ob) |
| R$_9$-Phe-(CH$_2$)$_2$-Cyc-CH$_2$O-Q | (1oc) |
| R$_9$-Phe-(CH$_2$)$_2$-Phe-CH$_2$O-Q | (1od) |
| R$_9$-Phe-(CH$_2$)$_2$-Pyr-CH$_2$O-Q | (1oe) |
| R$_9$-Pyr-(CH$_2$)$_2$-Phe-CH$_2$O-Q | (1of) |
| R$_9$-Pyr-(CH$_2$)$_2$-Cyc-CH$_2$O-Q | (1og) |
| R$_9$-Pyd-(CH$_2$)$_2$-Phe-CH$_2$O-Q | (1oh) |
| R$_9$-Pyd-(CH$_2$)$_2$-Cyc-CH$_2$O-Q | (1oi) |
| R$_9$-Dio-(CH$_2$)$_2$-Phe-CH$_2$O-Q | (1oj) |
| R$_9$-Dio-(CH$_2$)$_2$-Cyc-CH$_2$O-Q | (1ok) |

Among these compounds, the compounds expressed by any one of formulas (1oa) to (1od) are preferable.

Compounds expressed by formula (1p) are developed further to the compounds expressed by any one of the following formulas (1pa) to (1pk):

| | |
|---|---|
| R$_9$-Cyc-(CH$_2$)$_2$-Cyc-OCH$_2$-Q | (1pa) |
| R$_9$-Cyc-(CH$_2$)$_2$-Phe-OCH$_2$-Q | (1pb) |
| R$_9$-Phe-(CH$_2$)$_2$-Cyc-OCH$_2$-Q | (1pc) |
| R$_9$-Phe-(CH$_2$)$_2$-Phe-OCH$_2$-Q | (1pd) |
| R$_9$-Phe-(CH$_2$)$_2$-Pyr-OCH$_2$-Q | (1pe) |
| R$_9$-Pyr-(CH$_2$)$_2$-Phe-OCH$_2$-Q | (1pf) |
| R$_9$-Pyr-(CH$_2$)$_2$-Cyc-OCH$_2$-Q | (1pg) |
| R$_9$-Pyd-(CH$_2$)$_2$-Phe-OCH$_2$-Q | (1ph) |
| R$_9$-Pyd-(CH$_2$)$_2$-Cyc-OCH$_2$-Q | (1pi) |
| R$_9$-Dio-(CH$_2$)$_2$-Phe-OCH$_2$-Q | (1pj) |
| R$_9$-Dio-(CH$_2$)$_2$-Cyc-OCH$_2$-Q | (1pk) |

Among these compounds, particularly the compounds expressed by any one of formulas (1pa) to (1pd) are preferable.

Compounds expressed by formula (1q) are developed further to the compounds expressed by one of the following formulas (1qa) to (1qh):

| | |
|---|---|
| R$_9$-Cyc-COO-Cyc-Cyc-Q | (1qa) |
| R$_9$-Cyc-COO-Cyc-Phe-Q | (1qb) |
| R$_9$-Cyc-COO-Phe-Phe-Q | (1qc) |
| R$_9$-Cyc-COO-Phe-Cyc-Q | (1qd) |
| R$_9$-Phe-COO-Cyc-Cyc-Q | (1qe) |
| R$_9$-Phe-COO-Cyc-Phe-Q | (1qf) |
| R$_9$-Phe-COO-Phe-Cyc-Q | (1qg) |
| R$_9$-Phe-COO-Phe-Phe-Q | (1qh) |

Among these compounds, particularly the compounds expressed by formula (1qb), (1qc), (1qf), or (1qh) are preferable.

Compounds expressed by formula (1r) are developed further to the compounds expressed by one of the following formulas (1ra) to (1rh):

| | |
|---|---|
| R$_9$-Cyc-Cyc-COO-Cyc-Q | (1ra) |
| R$_9$-Cyc-Cyc-COO-Phe-Q | (1rb) |
| R$_9$-Cyc-Phe-COO-Cyc-Q | (1rc) |
| R$_9$-Cyc-Phe-COO-Phe-Q | (1rd) |
| R$_9$-Phe-Cyc-COO-Cyc-Q | (1re) |
| R$_9$-Phe-Cyc-COO-Phe-Q | (1rf) |
| R$_9$-Phe-Phe-COO-Cyc-Q | (1rg) |
| R$_9$-Phe-Phe-COO-Phe-Q | (1rh) |

Among these compounds, particularly the compounds expressed by formula (1rb), (1rc), or (1rd) are preferable.

Compounds expressed by formula (1s) are developed further to the compounds expressed by one of the following formulas (1sa) to (1sh):

| | |
|---|---|
| R$_9$-Cyc-Cyc-Cyc-COO-Q | (1sa) |
| R$_9$-Cyc-Cyc-Phe-COO-Q | (1sb) |
| R$_9$-Cyc-Phe-Phe-COO-Q | (1sc) |
| R$_9$-Cyc-Phe-Cyc-COO-Q | (1sd) |
| R$_9$-Phe-Cyc-Cyc-COO-Q | (1se) |
| R$_9$-Phe-Phe-Cyc-COO-Q | (1sf) |
| R$_9$-Phe-Cyc-Phe-COO-Q | (1sg) |
| R$_9$-Phe-Phe-Phe-COO-Q | (1sh) |

Among these compounds, particularly the compounds expressed by formula (1sa) or (1sb) are preferable.

Compounds expressed by formula (1x) are developed further to the compounds expressed by one of the following formulas (1xa) to (1xh):

| | |
|---|---|
| R$_9$-Cyc-Cyc-CH$_2$O-Cyc-Q | (1xa) |
| R$_9$-Cyc-Cyc-CH$_2$O-Phe-Q | (1xb) |
| R$_9$-Cyc-Phe-CH$_2$O-Cyc-Q | (1xc) |
| R$_9$-Cyc-Phe-CH$_2$O-Phe-Q | (1xd) |
| R$_9$-Phe-Cyc-CH$_2$O-Cyc-Q | (1xe) |
| R$_9$-Phe-Cyc-CH$_2$O-Phe-Q | (1xf) |
| R$_9$-Phe-Phe-CH$_2$O-Cyc-Q | (1xg) |
| R$_9$-Phe-Phe-CH$_2$O-Phe-Q | (1xh) |

Among these compounds, particularly the compounds expressed by formula (1xb), (1xc), or (1xd) are preferable.

Compounds expressed by formula (1z) are developed further to the compounds expressed by one of the following formulas (1za) to (1zh):

| | |
|---|---|
| R$_9$-Cyc-Cyc-OCH$_2$-Cyc-Q | (1za) |
| R$_9$-Cyc-Cyc-OCH$_2$-Phe-Q | (1zb) |
| R$_9$-Cyc-Phe-OCH$_2$-Cyc-Q | (1zc) |
| R$_9$-Cyc-Phe-OCH$_2$-Phe-Q | (1zd) |
| R$_9$-Phe-Cyc-OCH$_2$-Cyc-Q | (1ze) |
| R$_9$-Phe-Cyc-OCH$_2$-Phe-Q | (1zf) |
| R$_9$-Phe-Phe-OCH$_2$-Cyc-Q | (1zg) |
| R$_9$-Phe-Phe-OCH$_2$-Phe-Q | (1zh) |

Among these compounds, particularly the compounds expressed by formula (1zb), (1zc), or (1zd) are preferable.

In all of the compounds mentioned above, R$_9$ represents an alkyl group or alkoxy group having 1 to 10 carbon atoms or an alkenyl group having 2 to 10 carbon atoms (any methylene group (—CH$_2$—) in the alkenyl group may be replaced by oxygen atom (—O—) provided that in no case two or more methylene groups are continually replaced by oxygen atom). Among them, most preferable groups are methyl, ethyl, propyl, butyl, pentyl, hexyl, heptyl, decyl, methoxy, ethoxy, propoxy, butoxy, pentyloxy, hexyloxy, heptyloxy, nonyloxy, ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 3-hexenyl, 5-hexenyl, 1-heptenyl, 3-heptenyl, 5-heptenyl, 6-heptenyl, 2-propenyloxy, 3-butenyloxy, 3-methoxypropenyl, 2-propenyloxymethy 1, and 6-methoxy-3-hexenyl group.

As mentioned above, the compounds expressed by one of the following formulas can be considered to be particularly preferable examples:

(1aa), (1ab), (1ba), (1bb), (1ca), (1cb), (1ce), (1da), (1db), (1ea) to (1ee), (1ej), (1fa), (1fb), (1fe), (1ff), (1ga) to (1ge), (1gi), (1ha), (1hb), (1he), (1hf), (1ia) to (1id), (1ja) to (1jd), (1ka) to (1ke), (1ki), (1la), (1lb), (1le), (1lf), (1ma) to (1me), (1mi), (1na), (1nb), (1ne), (1nf), (1oa) to (1od), (1pa) to (1pd), (1qb), (1qc), (1qf), (1qh), (1rb) to (1rd), (1sa), (1sb), (1xb), (1xc), (1za), (1zb), and (1zd).

Among them, the compounds expressed by one of the following formulas (1-1) to (1-43) can be mentioned as more desirable ones:

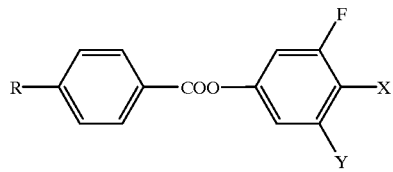
(1-1)

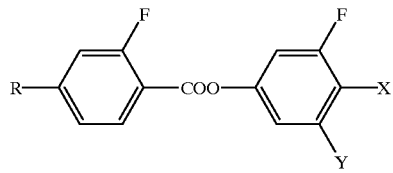
(1-2)

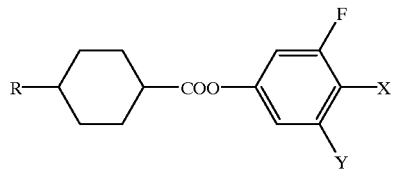
(1-3)

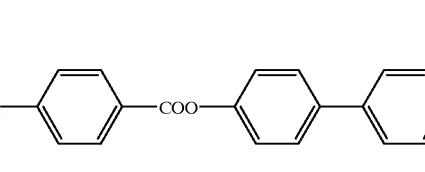
(1-4)

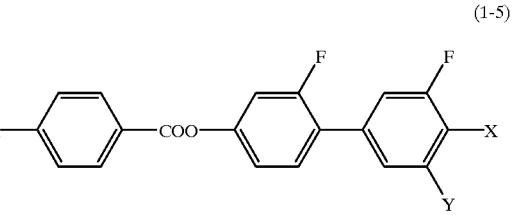
(1-5)

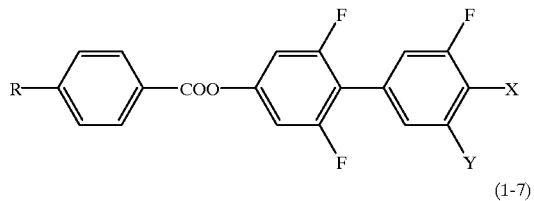
(1-6)
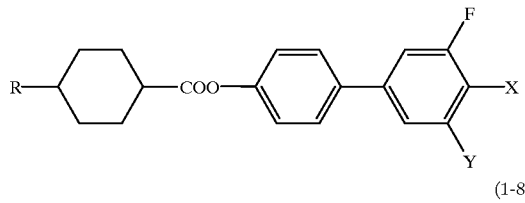
(1-7)
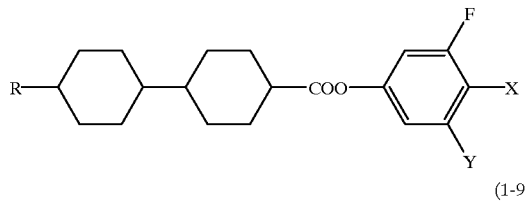
(1-8)
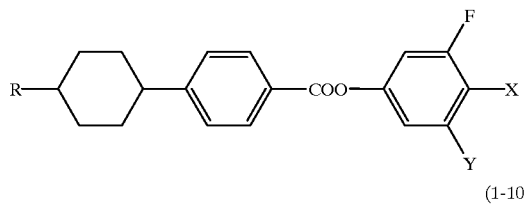
(1-9)
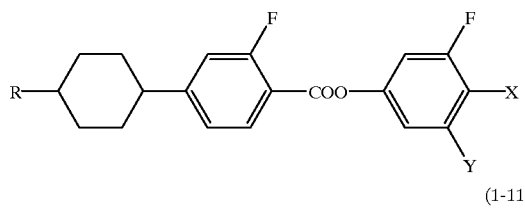
(1-10)
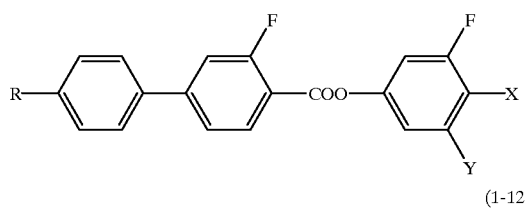
(1-11)
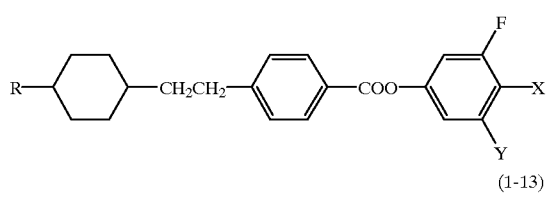
(1-12)
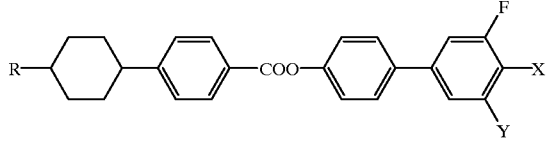
(1-13)
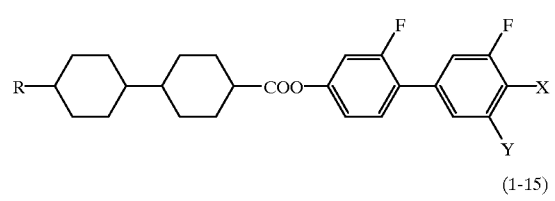
(1-14)
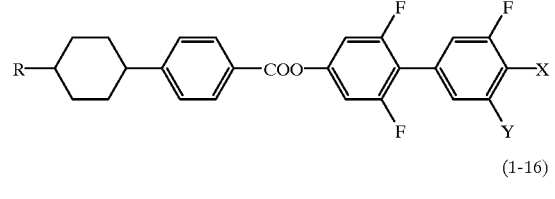
(1-15)
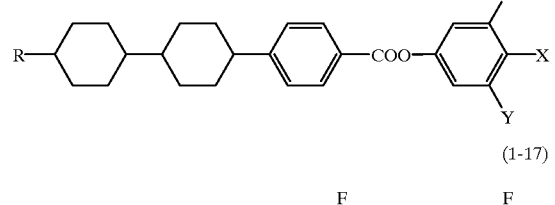
(1-16)
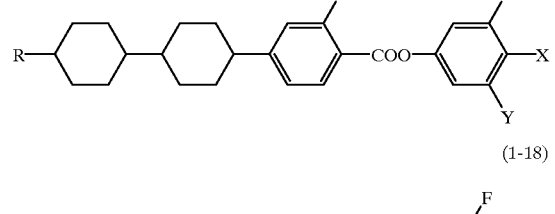
(1-17)
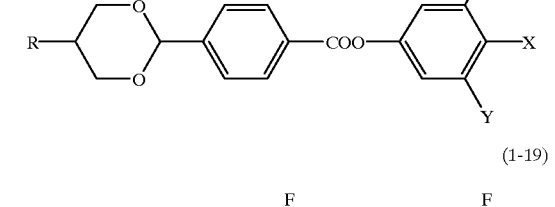
(1-18)
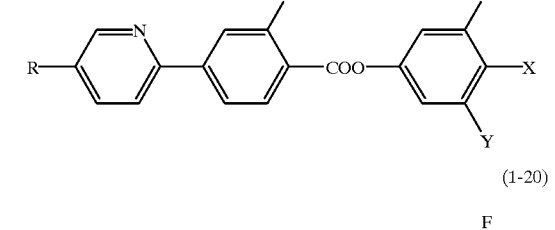
(1-19)
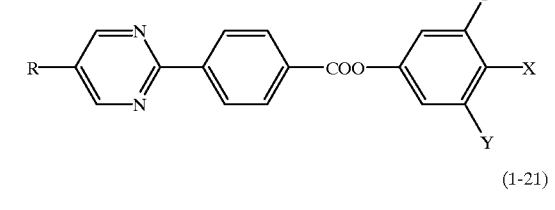
(1-20)
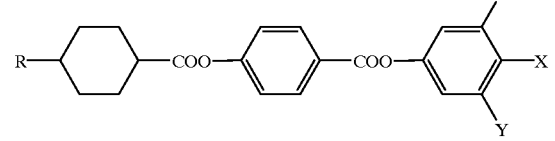
(1-21)

(1-22)
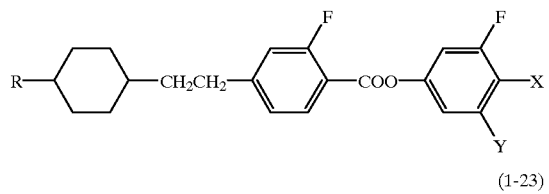
(1-23)
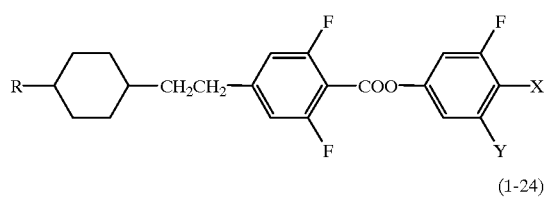
(1-24)
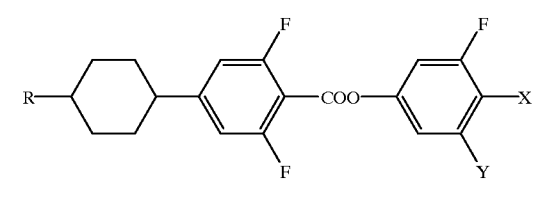
(1-25)
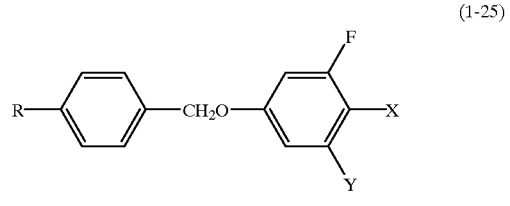
(1-26)
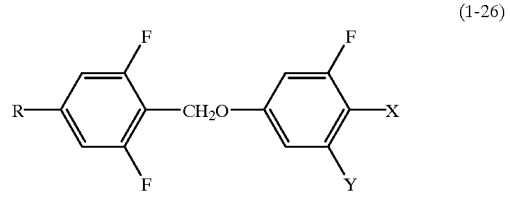
(1-27)
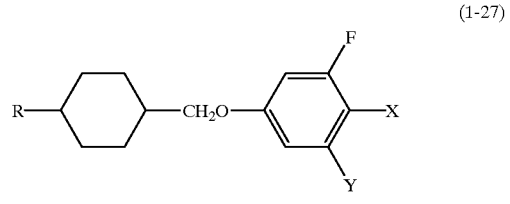
(1-28)
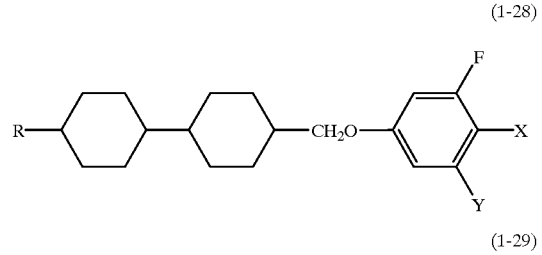
(1-29)
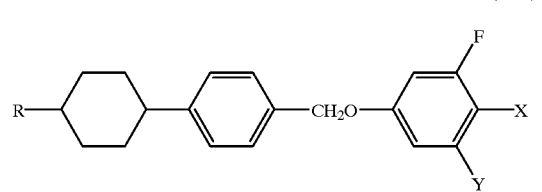
(1-30)
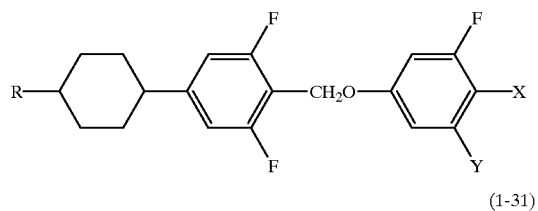
(1-31)
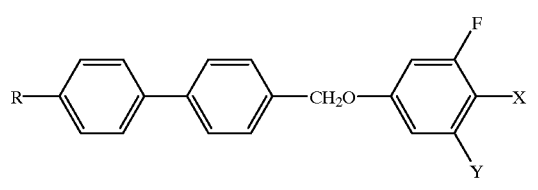
(1-32)
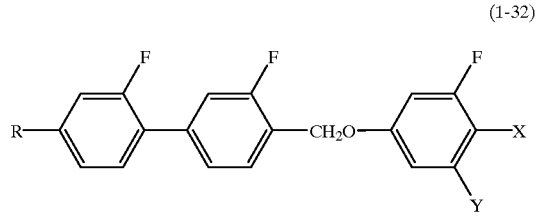
(1-33)
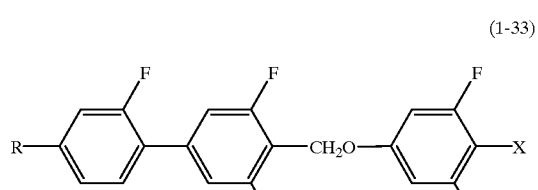
(1-34)
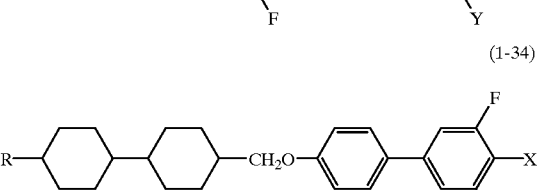
(1-35)
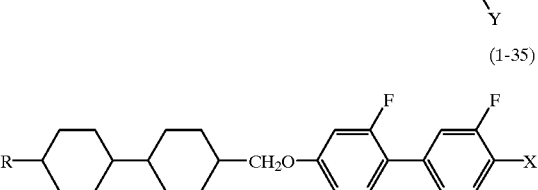
(1-36)
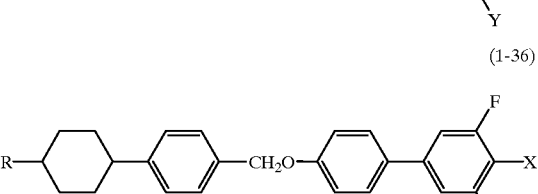
(1-37)
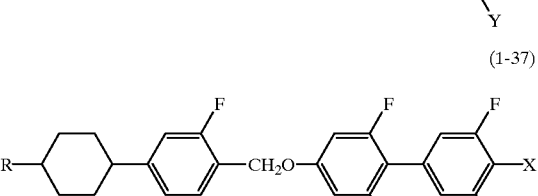

(1-38)
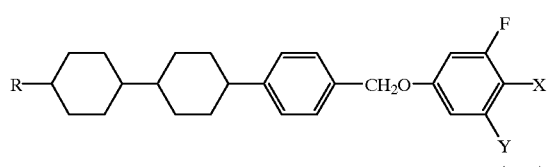
(1-39)
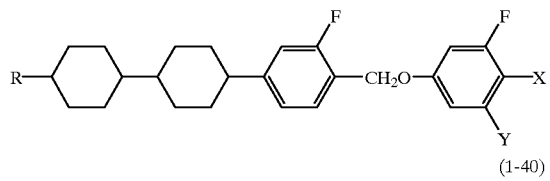
(1-40)
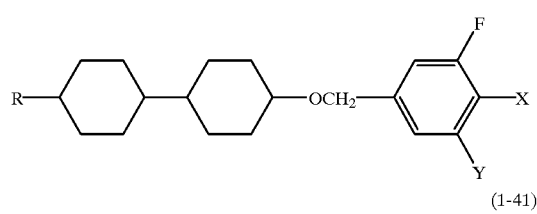
(1-41)
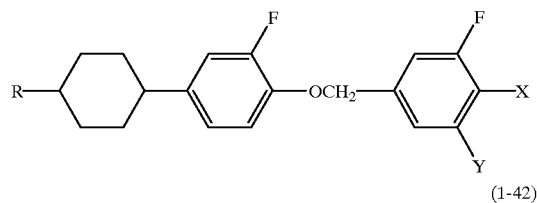
(1-42)
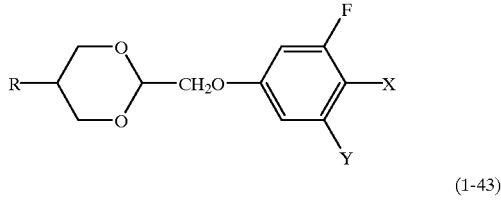
(1-43)
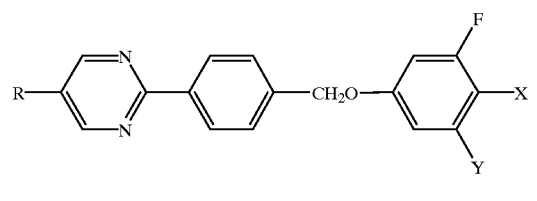
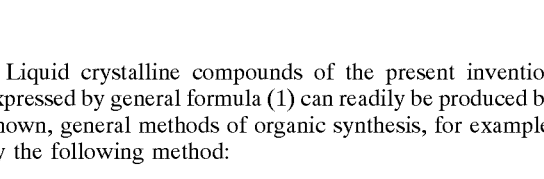
Liquid crystalline compounds of the present invention expressed by general formula (1) can readily be produced by known, general methods of organic synthesis, for example, by the following method:
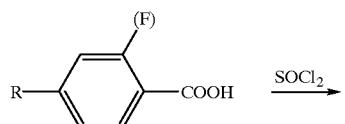
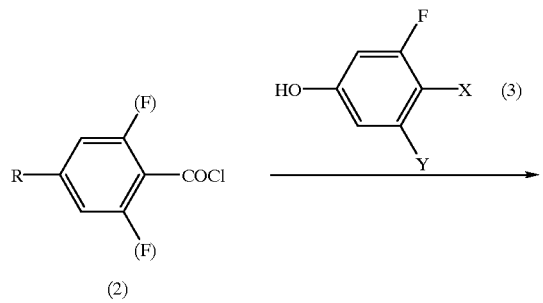
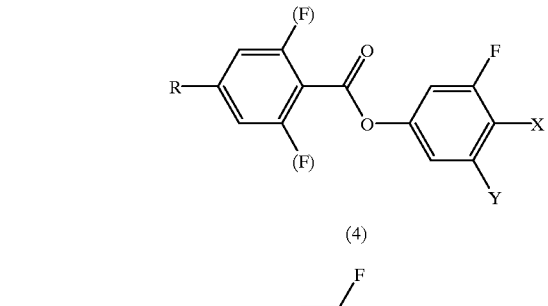
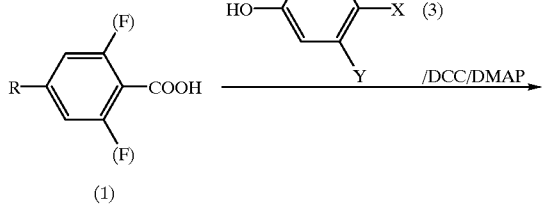
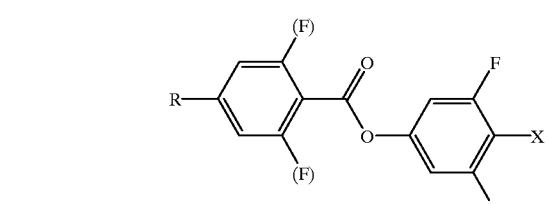
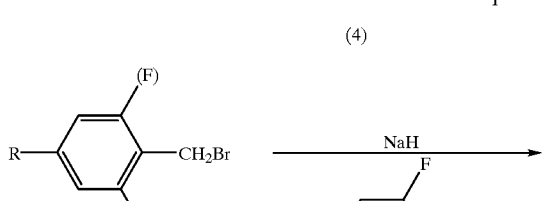
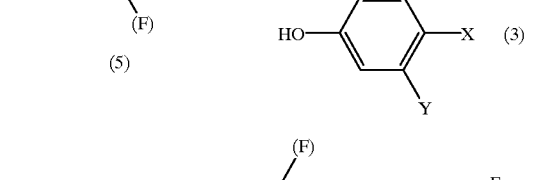
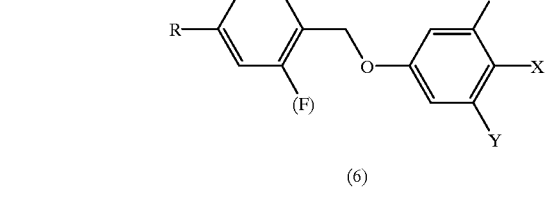

-continued

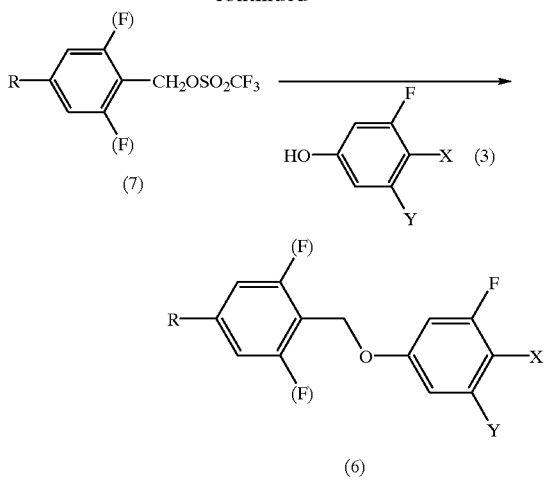

First, in the case of a compound having an ester bond, a carboxylic acid derivative (1) is converted into an acid halide (2) with a halogenating reagent such as thionyl chloride in a solvent such as toluene and benzene, or in the absence of a solvent. The objective compound (4) can be obtained by reacting the acid halide with a phenol derivative (3) in a solvent such as toluene and benzene. A series of the reactions are preferably conducted at a temperature between room temperature and the boiling point of the solvent and further in the presence of a base such as pyridine (E. J. Corey et al., The Journal of Organic Chemistry, 38, 3223 (1973)), triethylamine (B. Iselin et al., Helvetica Chimica Acta, 40, 373 (1957)), dimethyl aniline (C. Raha, Organic Synthesis, IV, 263 (1963)), or tetramethyl urea (M. S. Newman et al., Tetrahedron Letters, 3267 (1967)).

Alternatively, the objective compound (4) can also be obtained by reacting a carboxylic acid derivative (1) with a phenol derivative (3) in a solvent such as dichloromethane and chloroform in the presence of dicyclohexylcarbodiimide (DCC) or 4-dimethylaminopyridine (DMAP) (B. Neises et al., Organic Synthesis, 63, 183 (1985)).

In the case of the compounds having —CH$_2$O— or —OCH$_2$— bond, the objective compound (6) can be produced by reacting an α-halogenomethyl compound (5) with a corresponding alcohol derivative, phenol derivative (3), or cyclohexanol derivative in a solvent such as dimethyl sulfoxide, dimethyl formamide (DMF), 1,2-dimethoxyethane, tetrahydrofuran, hexamethylphosphoric triamide, and toluene in the presence of a base, for example, sodium amide (J. B. Wright et al., Journal of the American Chemical Society, 70, 3098 (1948)), potassium carbonate (W. T. Olson et al., Journal of the American Chemical Society, 69, 2451 (1947)), triethylamine (R. L. Merker et al., The Journal of Organic Chemistry, 26, 5180 (1961)), sodium hydroxide (C. Wilkins, Synthesis, 156 (1973), potassium hydroxide (J. Rebek et al., The Journal of Organic Chemistry, 44, 1485 (1979)), barium oxide (N. Kawabe et al., The Journal of Organic Chemistry, 37, 4210 (1972)), or sodium hydride (C. J. Stark, Tetrahedron Letters, 22, 2089 (1981), and K. Takai et al., Tetrahedron Letters, 21, 1657 (1980)).

Alternatively, the objective compound (6) can be produced from the reaction of an ester derivative (7) such as a sulfonic acid ester (T. Gramstad et al., Journal of the Chemical Society, 4069 (1957), and P. M. Dewick, Synthetic Communications, 11, 853 (1981)), carbonic acid ester (D. Grobelny et al, Tetrahedron Letters, 2639 (1979), M. Lissel et al., Synthesis, 382 (1986), and R. Lakhmiri et al., Tetrahedron Letters, 30, 4669 (1989)), and phosphorous acid ester (Y. Kashman, The Journal of Organic Chemistry, 37, 912 (1972)) with a corresponding alcohol derivative, phenol derivative (3), or cyclohexanol derivative.

Carboxylic acid derivative as a raw material can be produced by known, general procedures of organic synthesis or their combination. For instance, the derivatives can readily be produced by methods, such as hydrolysis of a nitrile derivative (R. C. Fuson et al., Organic Synthesis, III, 557 (1955), and P. G. Baraldi et al., The Journal of Organic Chemistry, 50, 23 (1985)), reaction of Grignard reagent or a lithium compound with carbon dioxide (H. Gilman et al., Organic Synthesis, I, 361 (1941), and Y. Fukuyama et al., Synthesis, 443 (1974)), hydrolysis of a halide (N. O.V. Sonntag, Chemical Review, 52, 237 (1953)), and oxidation of an alkyl, alcohol, or aldehyde derivative (L. Friedman, Organic Synthesis, V, 810 (1973), E. Turos et al., Journal of the American Chemical Society, 111, 8231 (1989), R. L. Shriner et al., Organic Synthesis II, 538 (1943), D. Vakentine., Jr. et al., The Journal of Organic Chemistry, 45, 3698 (1980), E. Dalcanale et al., The Journal of Organic Chemistry, 51, 567 (1986), and E. J. Corey et al., Tetrahedron Letters, 399 (1979)). In more specific explanation with reference to an example, carboxylic acid derivative (8) can be obtained by preparing Grignard reagent of 4-alkylhalogenobenzene and then reacting it with carbon dioxide.

Fluorine substituted compound (9) is converted into a compound protected with, for example, 1,3-dioxolane or 1,3-dioxane, and then alkylated by the method of L. Friedman et al. (Journal of the American Chemical Society, 96, 7101 (1974)) or M. Tiecco et al. (Tetrahedron Letters, 23, 4629 (1982)). Subsequently, it is deprotected, and the aldehyde (10) thus obtained is oxidized with an oxidizing agent such as chrome oxide, dichromic acid, active manganese dioxide, silver oxide, and sodium chlorite to obtain carboxylic acid derivative (11).

Further, another fluorine substituted compound (12) is alkylated by the method mentioned above, and then reacted with an organic lithium reagent such as n-butyl lithium, and carbon dioxide to obtain carboxylic acid derivative (13).

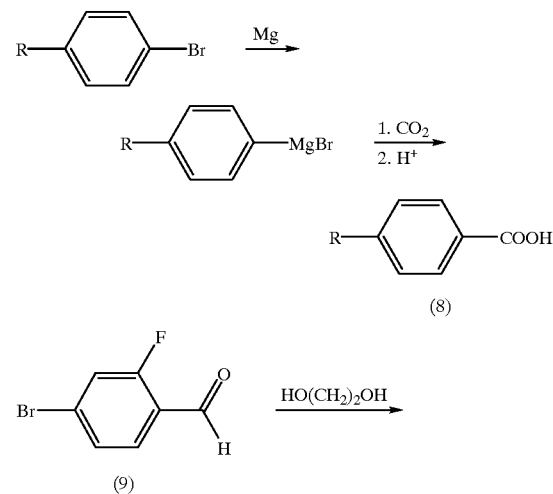

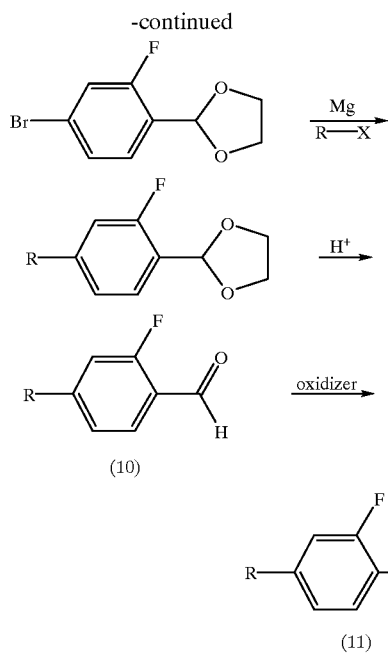
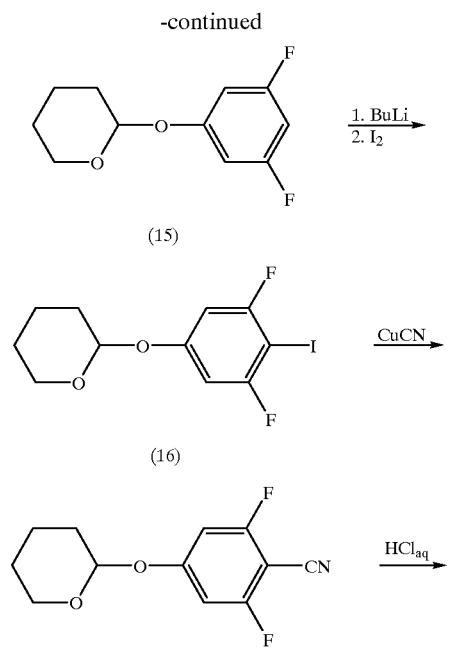
X = halogen atom
X = halogen atom
Phenol derivative can be produced, for instance, by the following method:
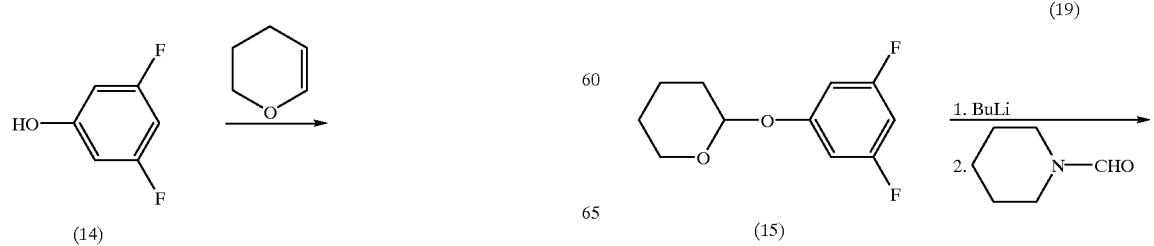
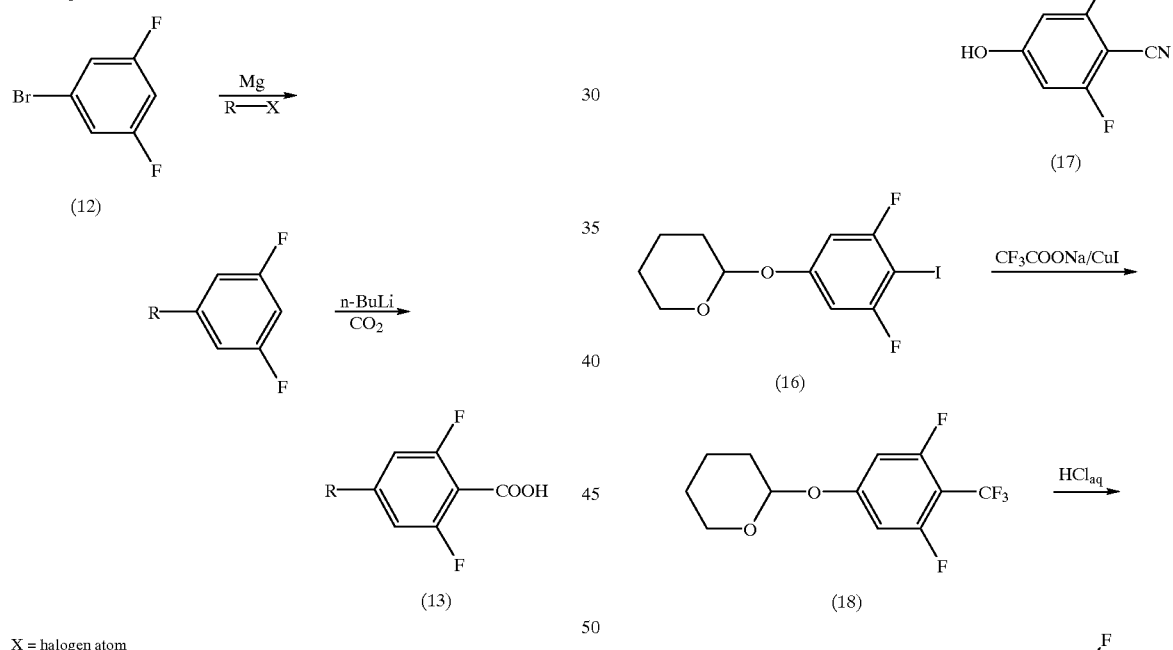

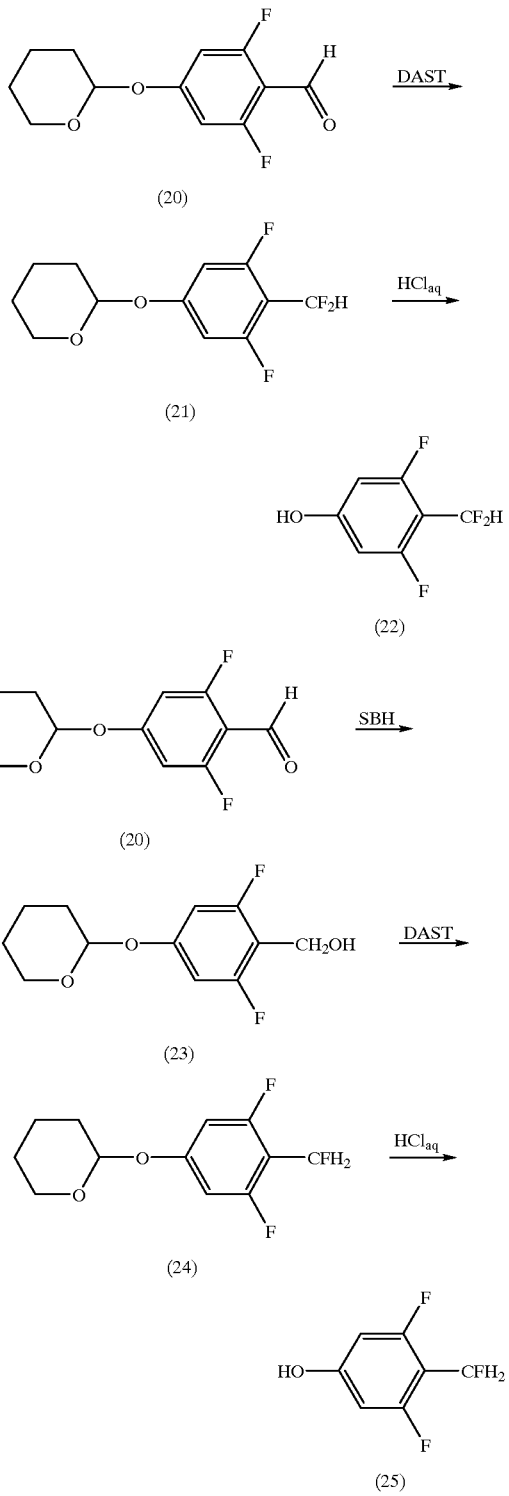

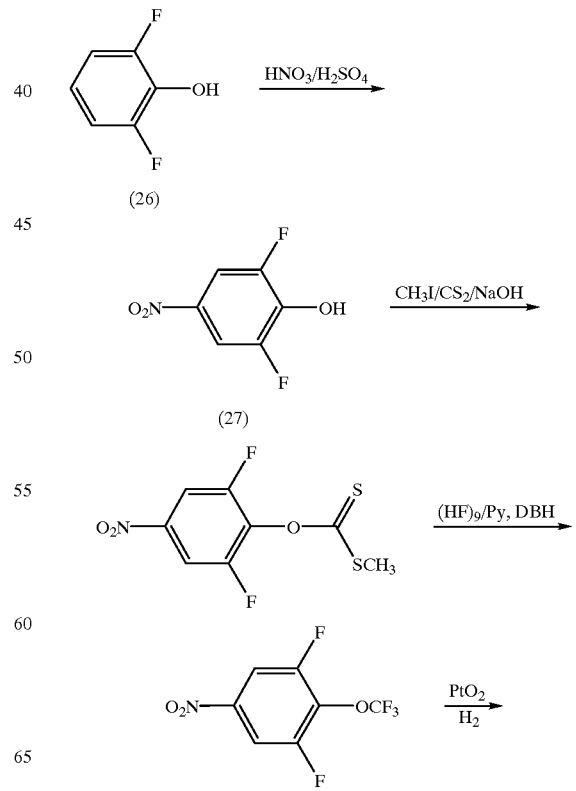

Society, Perkin Trans Reactions I, 921, (1988) or methyl fluorosulfonyl-difluoroacetate/copper iodide (I) (Q. Y. Chen et al., Journal of the Chemical Society, Chemical Communications, 705 (1989) to form methyl trifluoride (18) and then deprotecting the fluoride.

The ether (15) mentioned above is reacted with an organic lithium reagent such as n-butyl lithium or phenyl lithium, and a formylating agent such as N-formylpiperidine (G. A. Olah et al., Angewandte Chemie, International Edition in English, 20, 878 (1981), N-formylmorpholine (G. A. Olah et al., The Journal of Organic Chemistry, 49, 385 (1984)), and DMF (G. Boss et al., Chemische Berichte, 1199 (1989) to form an aldehyde (20), and then reacting the aldehyde with a fluorinating agent such as diethylamino-sulfur trifluoride (DAST) (W. J. Middleton et al., The Journal of Organic Chemistry 40, 574 (1975), S. Rozen et al., Tetrahedron Letters, 41, 111 (1985), M. Hudlicky, Organic Reactions, 35, 513 (1988), and P. A. Messina et al., Journal of Fluorine Chemistry, 42, 137 (1989)) to form a difluoromethyl compound (21). Phenol derivative (22) can be obtained by deprotecting the compound (21).

Aldehyde (20) is reduced by a reducing agent such as sodium boron hydride (SBH), lithium aluminum hydride (LAH), diisobutyl aluminum hydride (DIBAL), and sodium bis(2-methoxyethoxy) aluminum hydride (SBMEA) to form an alcohol (23), and the alcohol is reacted with a fluorinating agent such as DAST to form a monofluoromethyl compound (24). Phenol derivative (25) can be obtained by deprotecting the compound (24).

That is, a substituted phenol (14) is converted into an ether (15) with a protecting group such as tetrahydropyranyl group and then reacted with an organic lithium reagent such as n-butyl lithium, and iodine to form an iodide (16). Phenol derivative (17) can be obtained by cyanogenating the iodide and then deprotecting the cyanide.

Phenol derivative (19) can be obtained by reacting the iodide (16) mentioned above with sodium trifluoroacetate/copper iodide (I) (G. E. Carr et al., Journal of the Chemical

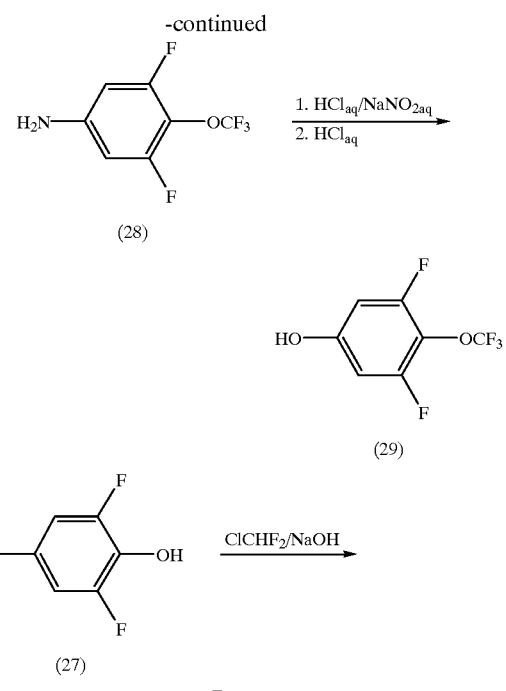

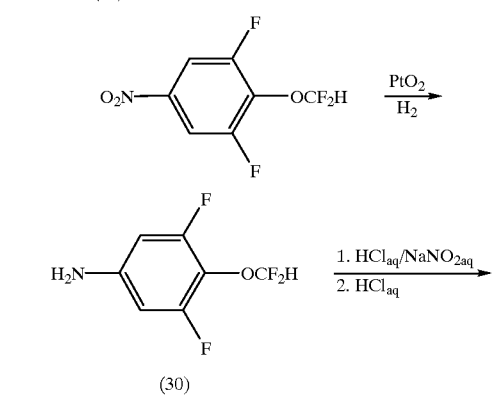

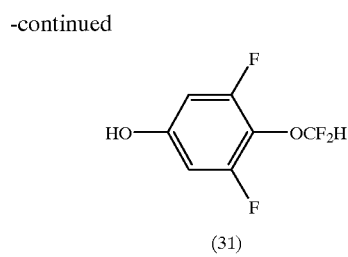

Another substituted phenol (26) is treated in the presence of nitric acid and sulfuric acid to form a nitro compound (27) and then converted into a xanthate by the method of Albert et al., (Synthetic Communications, 19, 547 (1989). This xanthate is fluorinated by the method of Kurohoshi et al., (Tetrahedron Letters, 33, 29, 4173 (1992) and then catalytically reduced in the presence of platinum catalyst to convert it into compound (28). Phenol derivative (2) can be obtained by subsequently reacting the compound (28) with hydrochloric acid and sodium nitrite, and then hydrolyzing the diazonium salt thus obtained.

Nitro compound (27) is reacted in the system of chlorodifluoromethane/sodium hydroxide (Laid-open WO Japanese Patent Publication No. Hei 3-500413) to fluorinate, and catalytically reduced with hydrogen in the presence of a platinum catalyst to convert it into compound (30). Phenol derivative (31) can be obtained by subsequently reacting the compound (30) with hydrochloric acid and sodium nitrite, and then hydrolyzing the diazonium salt thus obtained.

Also, α-halogenomethyl compound can readily be produced by general procedures of organic synthesis known in the art.

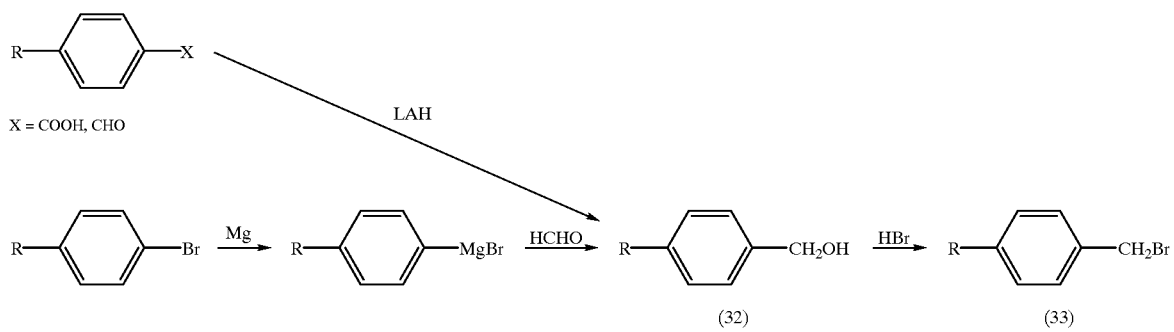

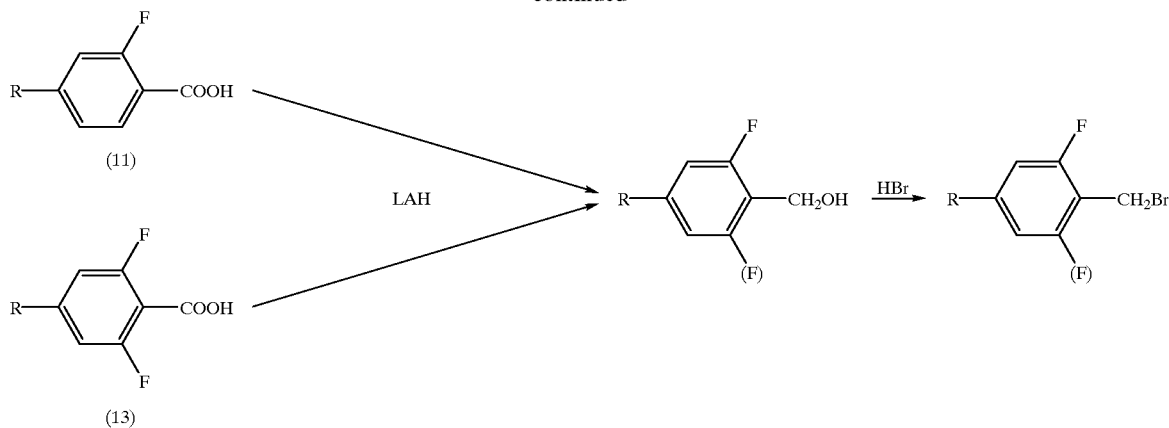

For instance, an alcohol (32) is obtained by the reduction of 4-alkylbenzoic acid or 4-alkylbenzaldehyde with a reducing agent such as SBH, LAH, DIBAL, SBMEA, or borane, or by the reaction of Grignard reagent of 4-alkylbenzhalide with formaldehyde (H. Gilman et al., Organic Synthesis, I, 188 (1941)). α-halogenomethyl compound (33) can be obtained by halogenating the alcohol (32) with a halogenating agent such as thionyl chloride, hydrobromic acid, hydroiodic acid, or potassium iodide.

Similarly, as to corresponding fluorine substituted compounds, fluorine substituted a-halogenomethyl compounds can be obtained through a reducing reaction and halogenating reaction of the carboxylic acid derivative (11) and (13) mentioned above.

Any of liquid crystalline compounds of the present invention obtained by such methods as mentioned above exhibits a large Δε, has a small change of threshold voltage depending on temperature, is excellent in stability, is readily mixed with various liquid crystal materials, and is good in solubility even at low temperatures. Thus, the compound is remarkably excellent as component for nematic liquid crystal compositions.

While the compounds of the present invention can be used as component even in any of the liquid crystal compositions of TFT mode, TN mode, and STN mode which have become current main streams, the compounds expressed by general formula (1) wherein X is CN are particularly preferable as ones for TN and STN, and the compounds expressed by general formula (1) wherein X is a group substituted with fluorine are particularly preferable as ones for TN and TFT since their stability is remarkably excellent.

When the compounds are used as component for nematic liquid crystal compositions, it is sufficient to use the compounds having 2 or 3 rings for producing liquid crystal compositions of a low viscosity, and it is sufficient to use the compounds having 3 or 4 rings for producing liquid crystal compositions exhibiting a wide temperature range of liquid crystal phase.

With respect to Δn, when the compounds having an aromatic ring were used, liquid crystal compositions exhibiting a large Δn can be produced, and when the compounds having a cyclohexane ring were used, liquid crystal compositions exhibiting a small Δn can be produced.

While the compounds of the present invention having 3-fluoro-4-substituted phenyl group or 3,5-difluoro-4-substituted phenyl group exhibit a large Δε, it is possible to impart a larger Δε by replacing the hydrogen atom in other ring structure by fluorine atom.

Based on these facts, liquid crystal compositions having desired physical characteristics can be obtained by properly selecting the compounds.

While the liquid crystal compositions provided according to the present invention may be composed only of the first component containing at least one liquid crystalline compound expressed by general formula (1), it is preferable that at least one compound selected from the group consisting of the compounds expressed by any one of general formulas (2), (3), and (4) (hereinafter referred to as second A component) and/or at least one compound selected from the group consisting of the compounds expressed by any one general formulas (5), (6), (7), (8), and (9) (hereinafter referred to as second B component) is mixed therein. Further, a known compound can be mixed as a third component for the purpose of adjusting threshold voltage, temperature range of liquid crystal phase, optical anisotropy, dielectric anisotropy, and viscosity of liquid crystal compositions.

Among the second A component mentioned above, the following (2-1) to (2-15) can be mentioned as examples of preferable compounds included in general formula (2); (3-1) to (3-48) can be mentioned as examples of preferable compounds included in general formula (3); and (4-1) to (4-55) can be mentioned as examples of preferable compounds included in general formula (4), respectively:

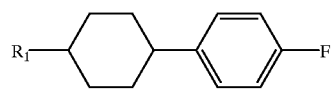

(2-1)

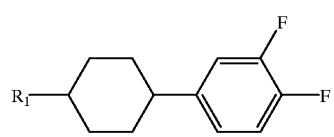

(2-2)

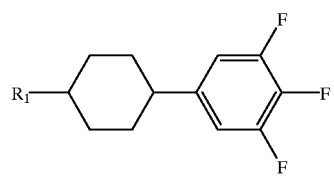

(2-3)

-continued
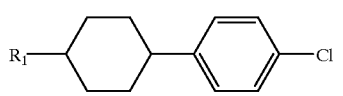 (2-4)
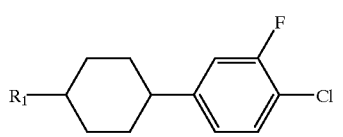 (2-5)
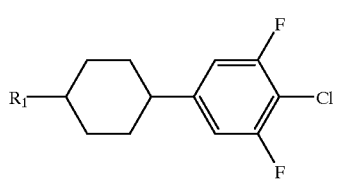 (2-6)
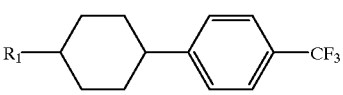 (2-7)
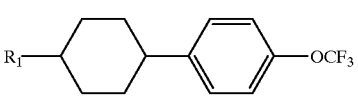 (2-8)
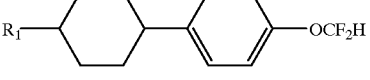 (2-9)
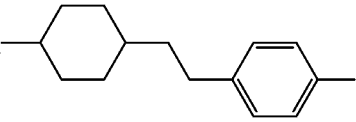 (2-10)
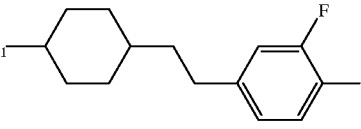 (2-11)
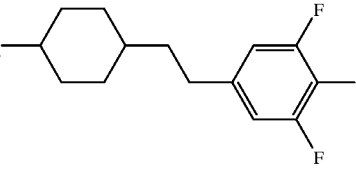 (2-12)
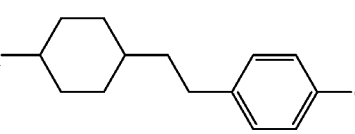 (2-13)
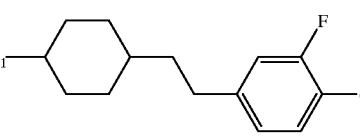 (2-14)
-continued
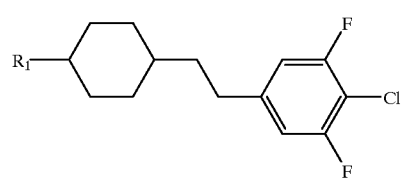 (2-15)
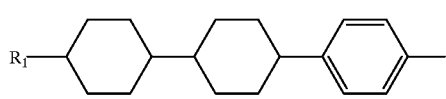 (3-1)
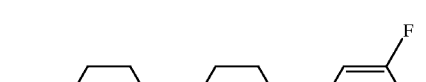 (3-2)
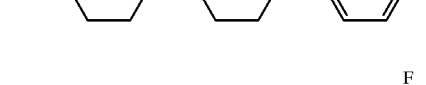 (3-3)
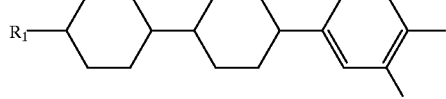 (3-4)
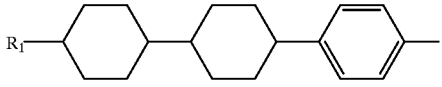 (3-5)
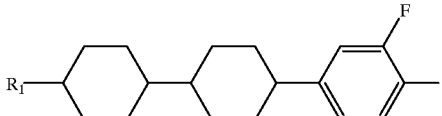 (3-6)
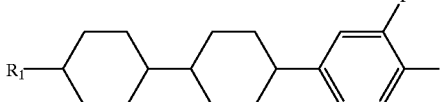 (3-7)
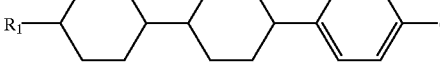 (3-7)
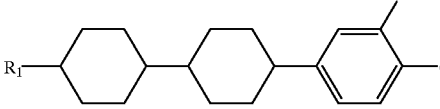 (3-8)
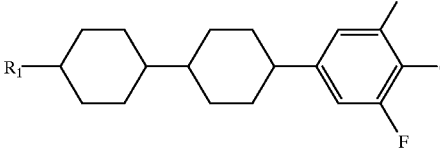 (3-9)

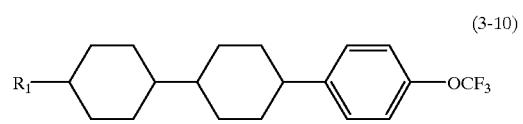
(3-10)
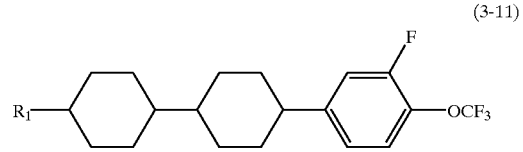
(3-11)
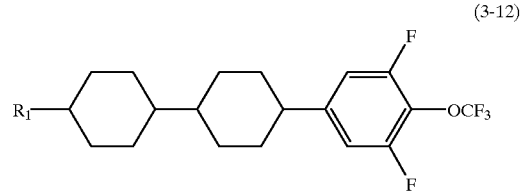
(3-12)
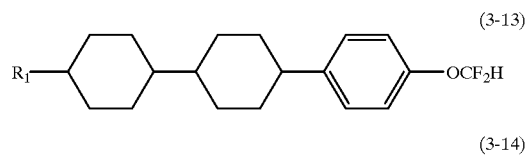
(3-13)
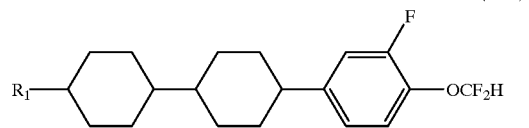
(3-14)
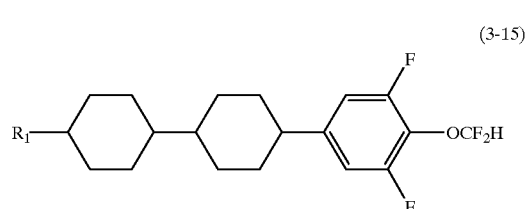
(3-15)
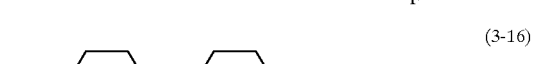
(3-16)
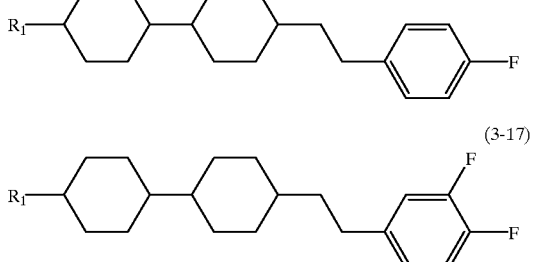
(3-17)
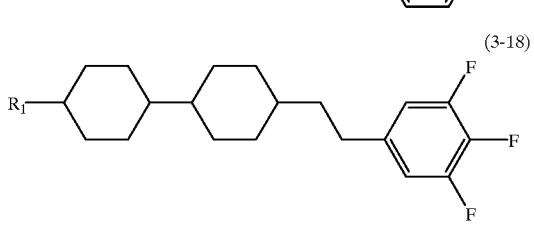
(3-18)
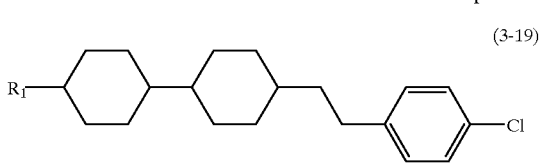
(3-19)
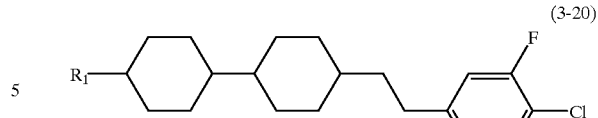
(3-20)
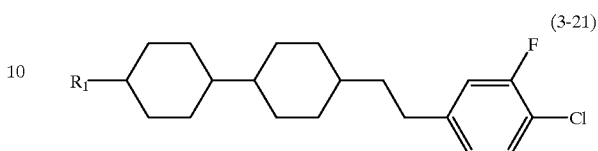
(3-21)
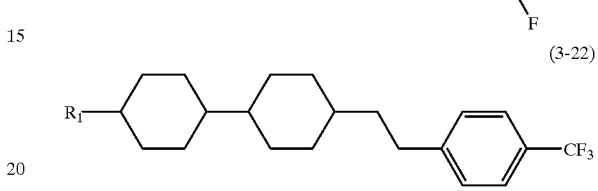
(3-22)
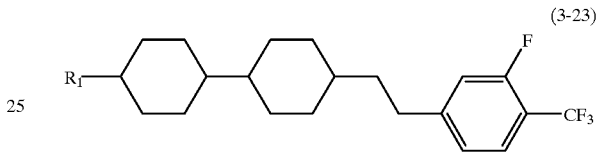
(3-23)
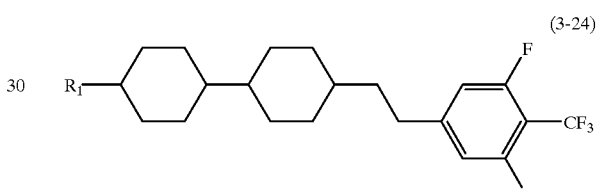
(3-24)
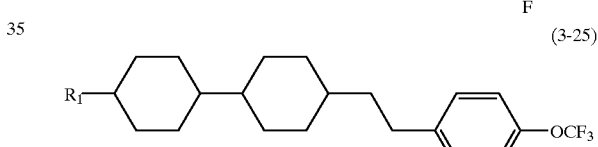
(3-25)
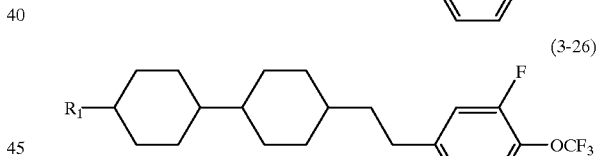
(3-26)
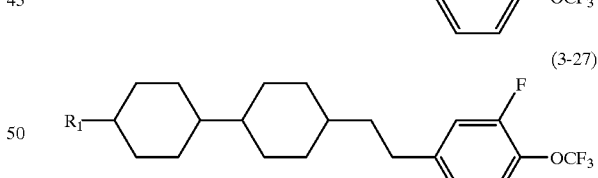
(3-27)
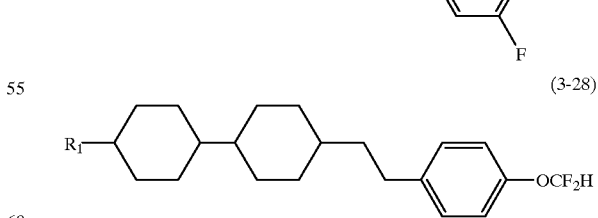
(3-28)
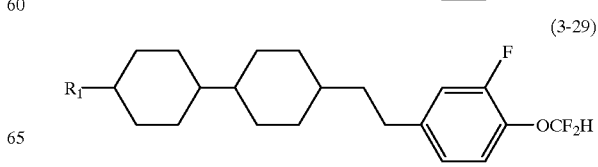
(3-29)

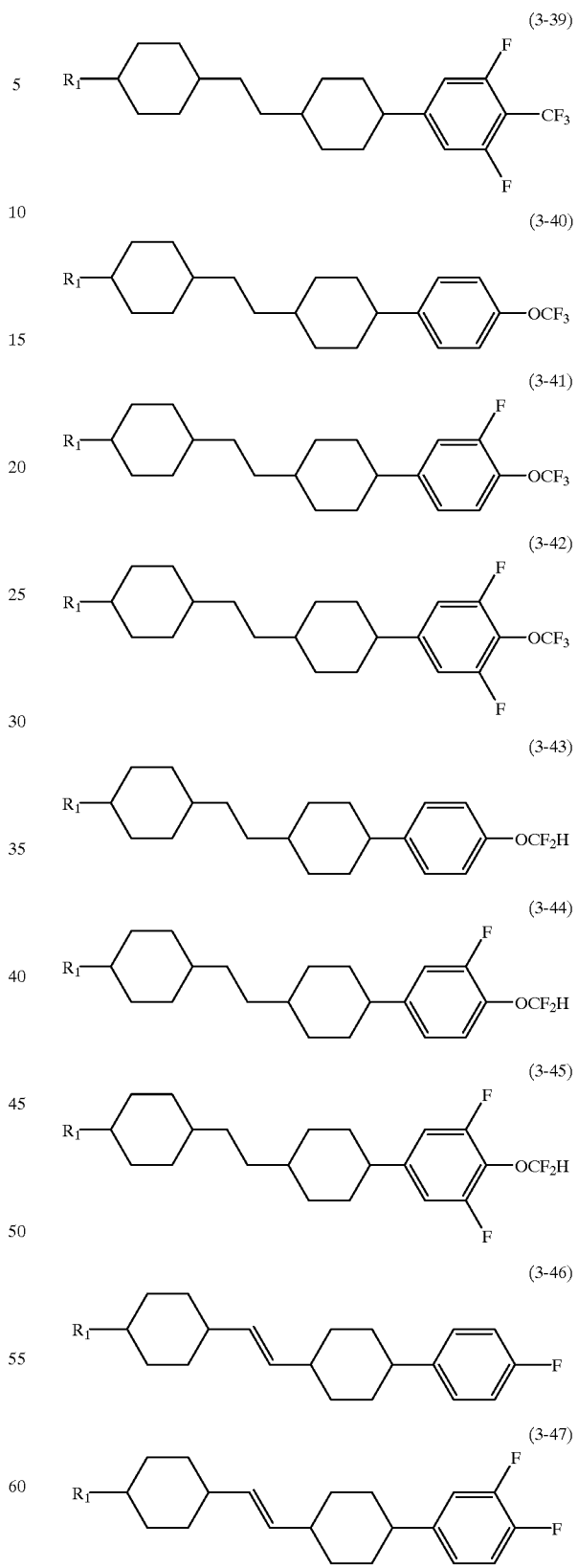

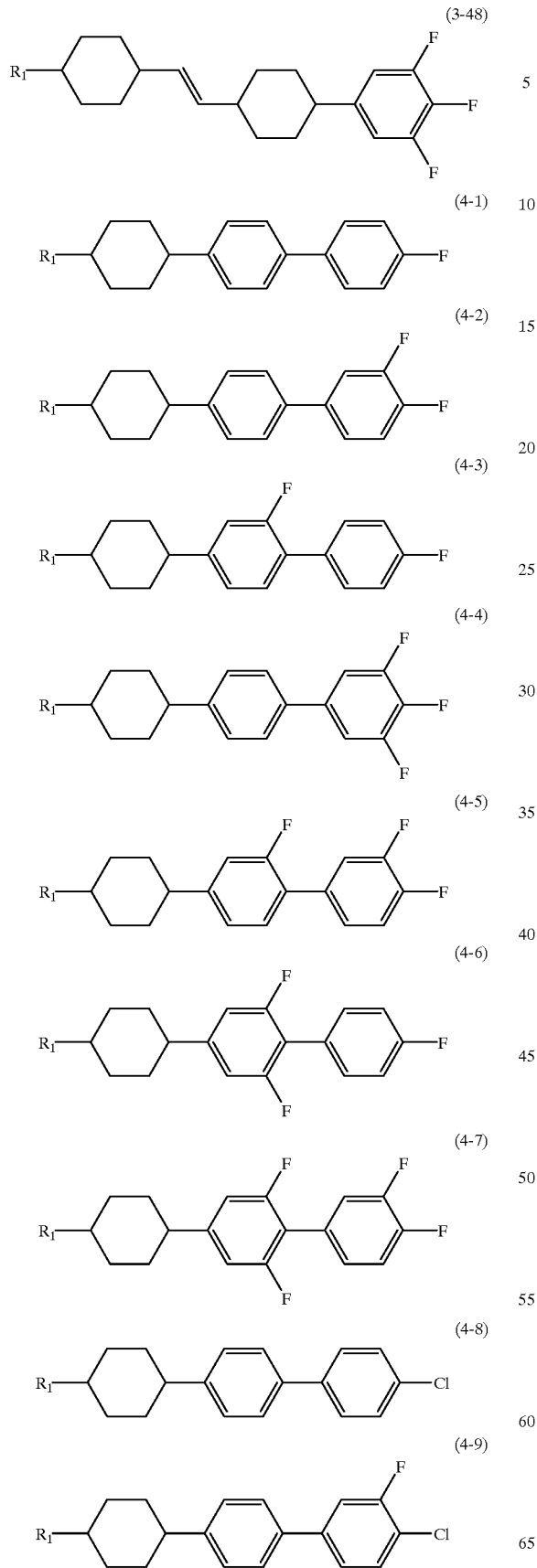
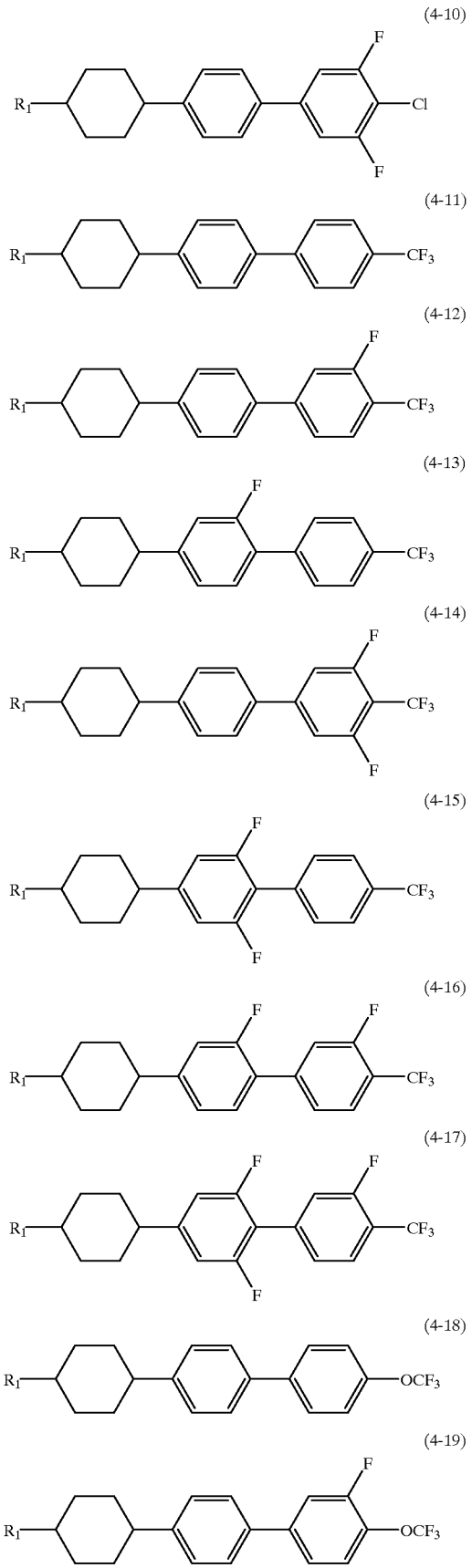

(4-20) 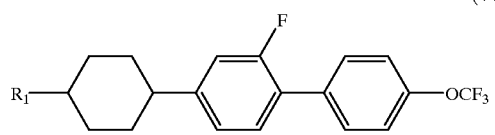
(4-21) 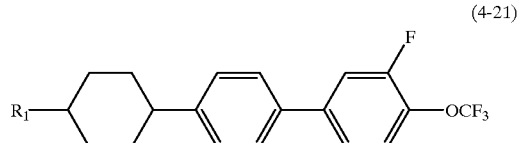
(4-22) 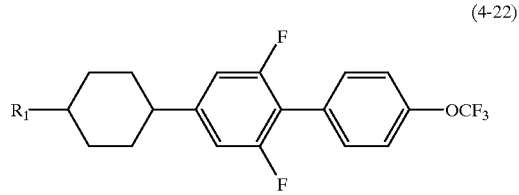
(4-23) 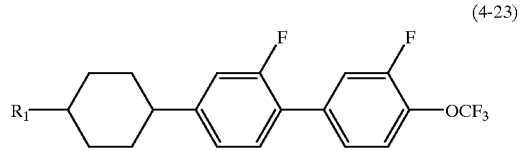
(4-24) 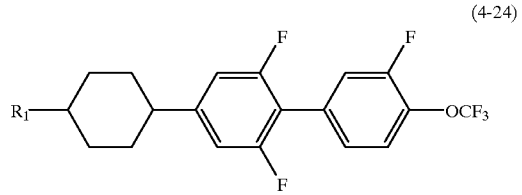
(4-25) 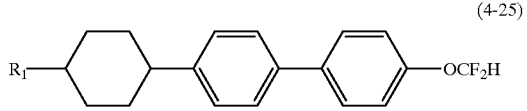
(4-26) 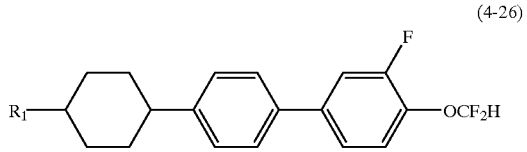
(4-27) 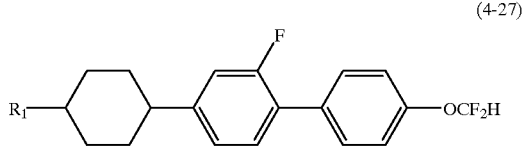
(4-28) 
(4-29) 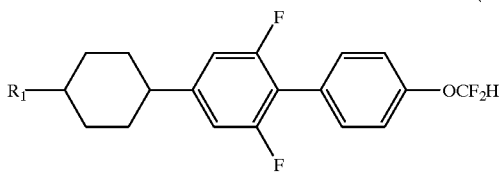
(4-30) 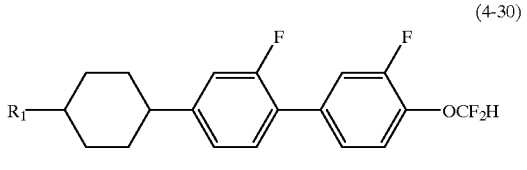
(4-31) 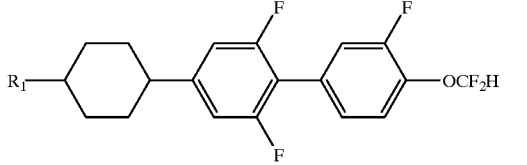
(4-32) 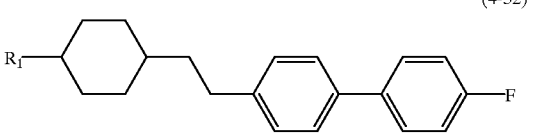
(4-33) 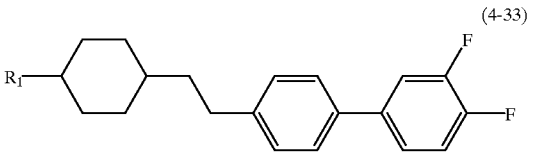
(4-34) 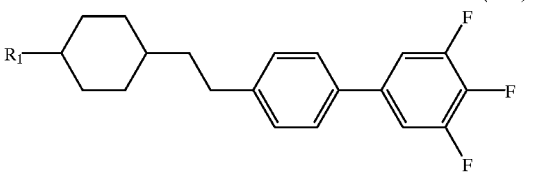
(4-35) 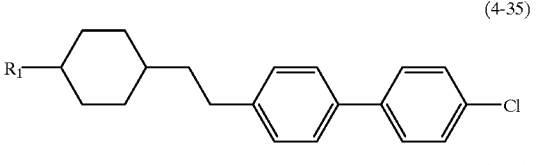
(4-36) 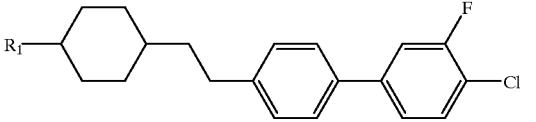
(4-37) 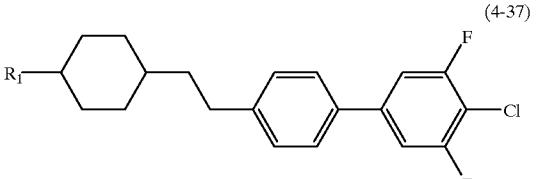

-continued (4-38) 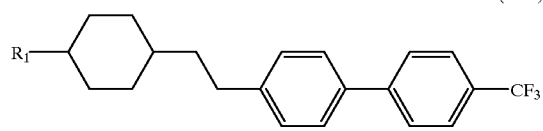

(4-39) 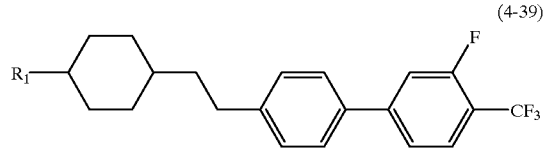

(4-40) 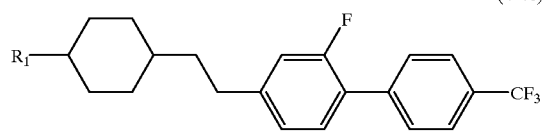

(4-41) 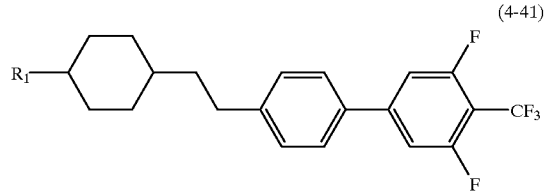

(4-42) 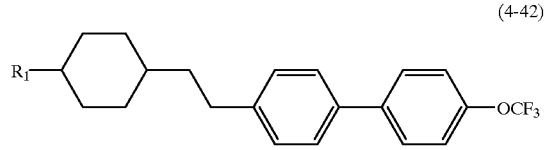

(4-43) 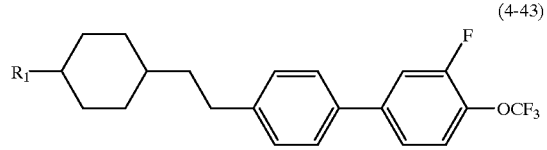

(4-44) 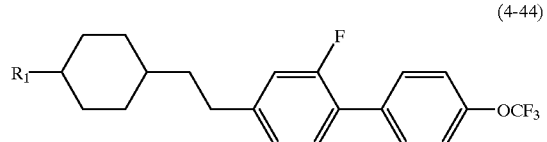

(4-45) 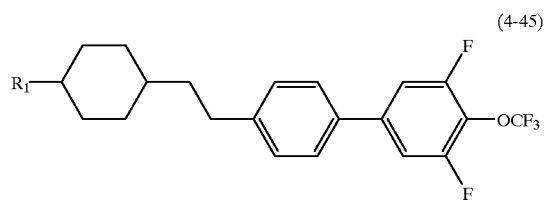

(4-46) 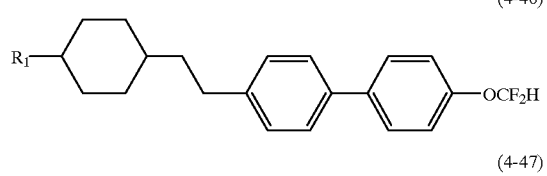

(4-47) 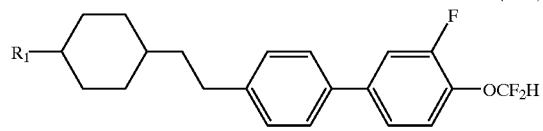

-continued (4-48) 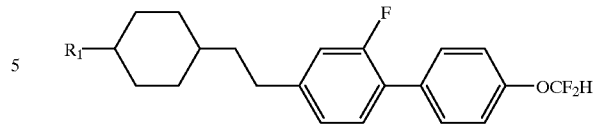

(4-49) 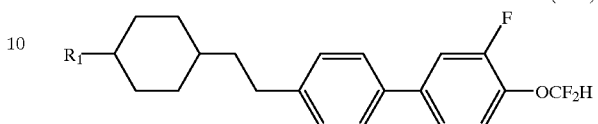

(4-50) 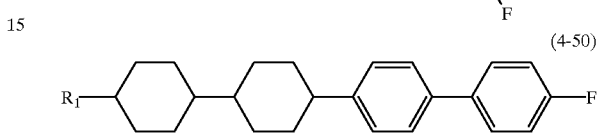

(4-51) 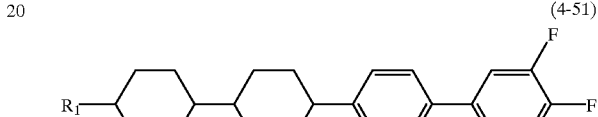

(4-52) 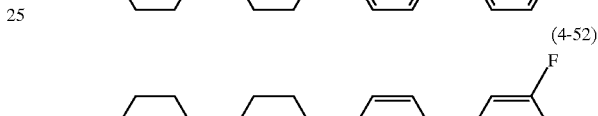

(4-53) 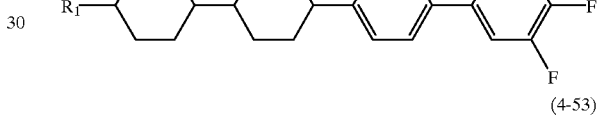

(4-54) 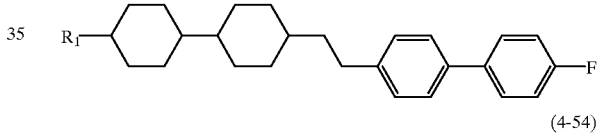

(4-55) 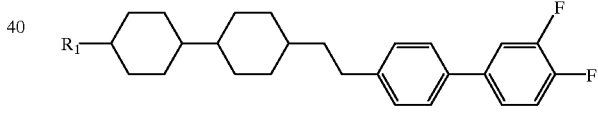

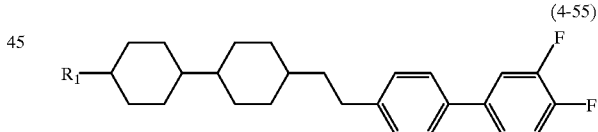

Compounds expressed by the general formulas (2) to (4) exhibit a positive value of dielectric anisotropy and are remarkably excellent in heat stability and chemical stability.

Amount of the compounds to be used is suitably in the range of 1 to 99% by weight, preferably 10 to 97% by weight, and more desirably 40 to 95% by weight based on the total amount of liquid crystal composition.

Next, among the second B component mentioned above, the following (5-1) to (5-24), (6-1) to (6-3), and (7-1) to (7-17) can be mentioned as examples of preferable compounds included in general formula (5), (6), or (7):

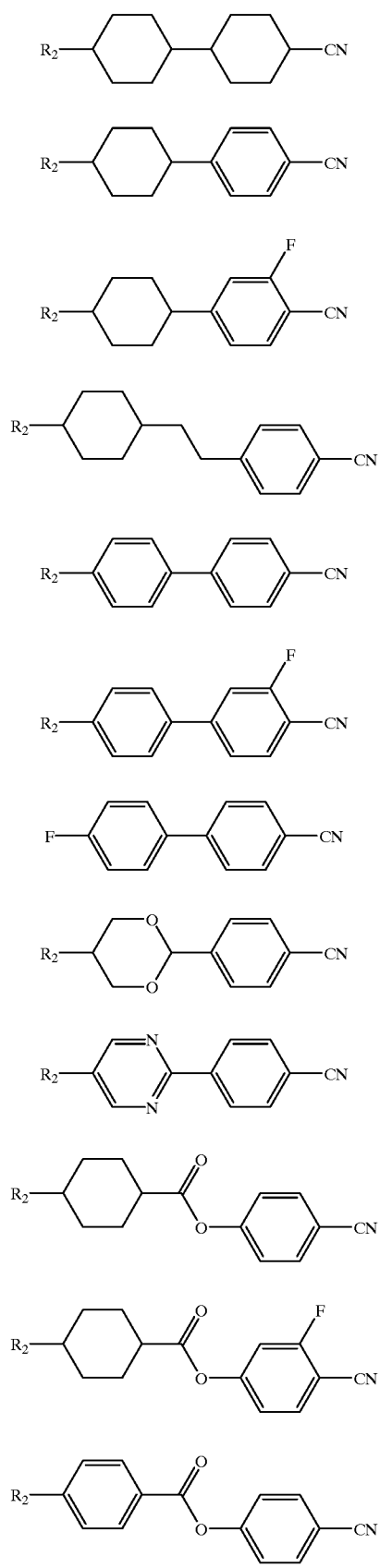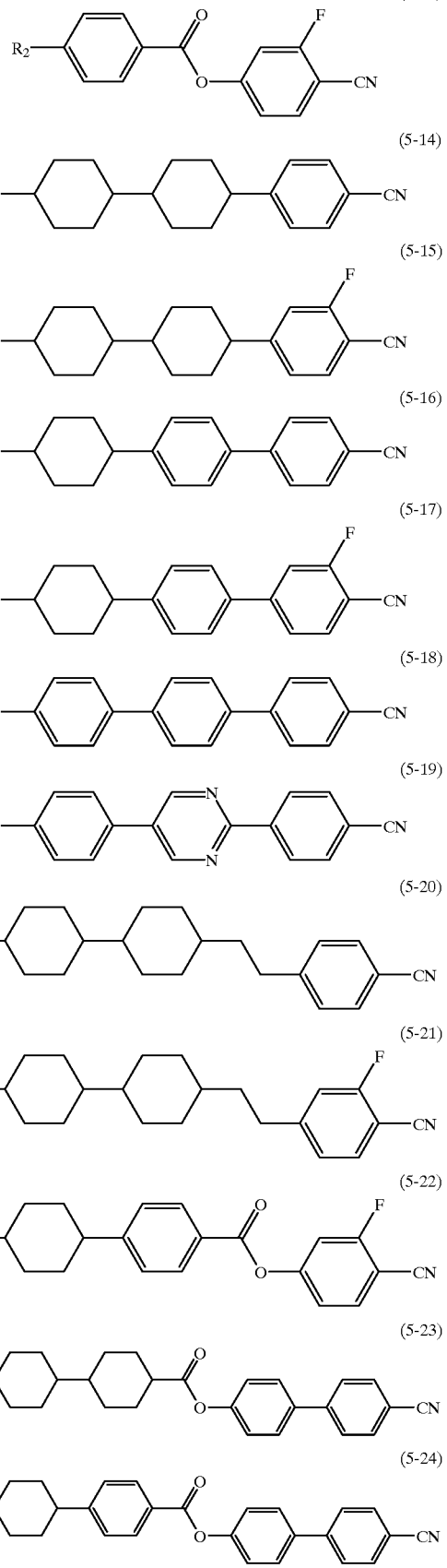

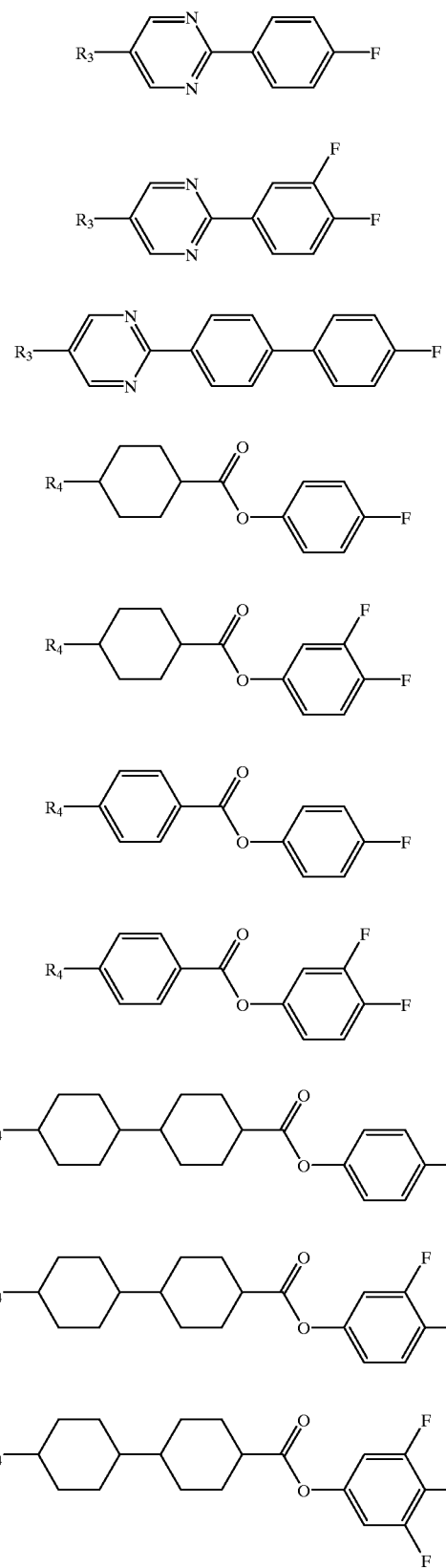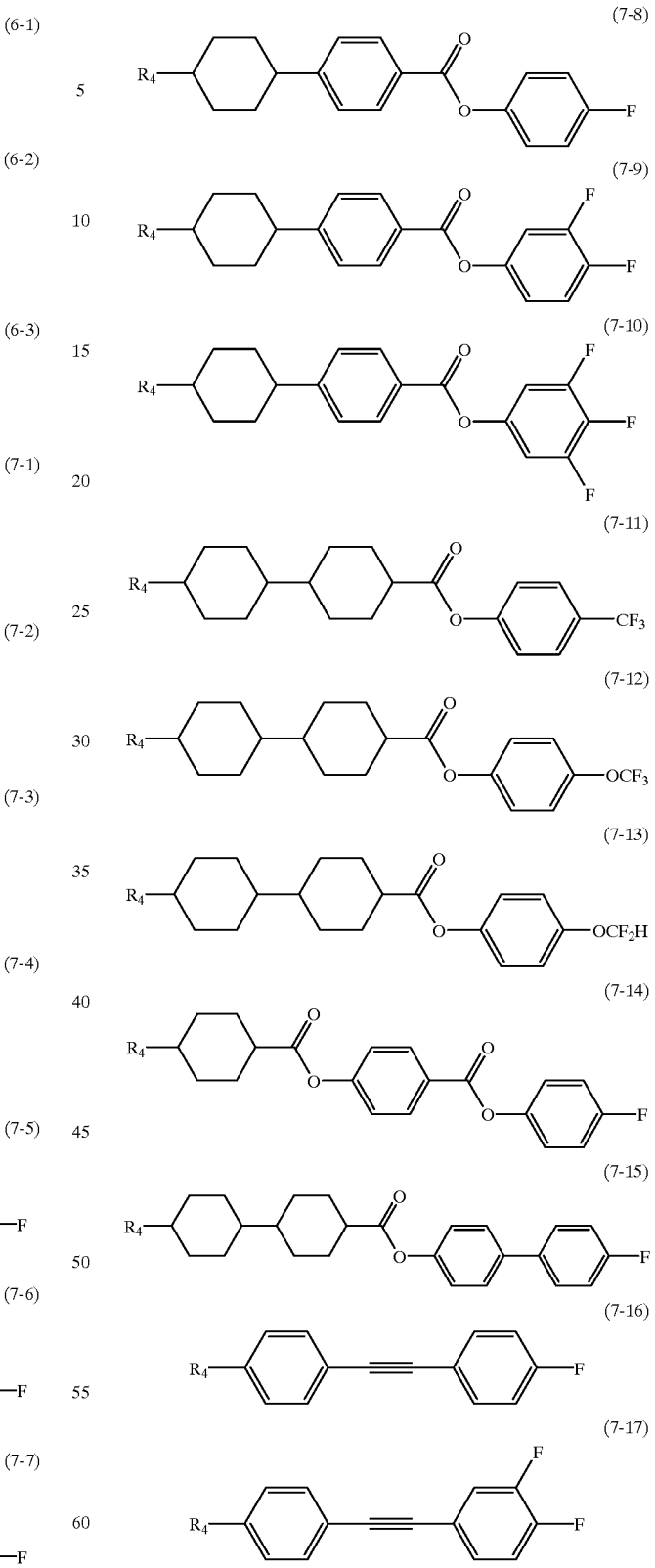
Compounds expressed by the general formulas (5) to (7) have a large positive value of dielectric anisotropy and are used as component of liquid crystal compositions particularly for the purpose of lowering threshold voltage. Also, they are used even for the purpose of adjusting viscosity, adjusting optical anisotropy, widening the temperature range of liquid crystal phase, and further for the purpose of improving steepness.

Among the second B component, the following (8-1) to (8-8) and (9-1) to (9-12) can be mentioned as examples of preferable compounds included in general formula (8) or (9):

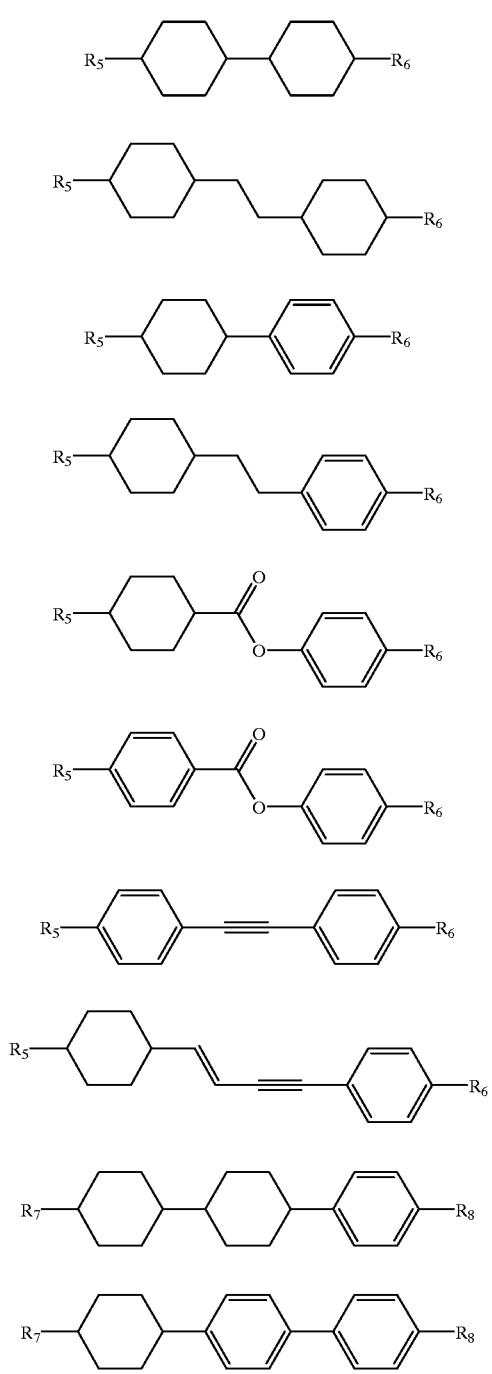

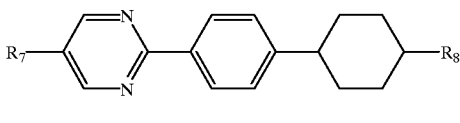

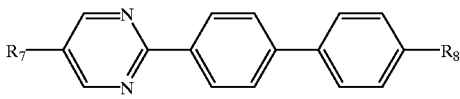

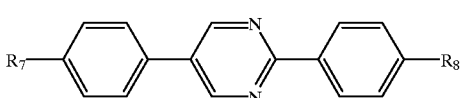

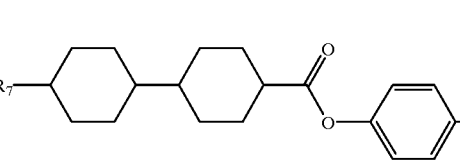

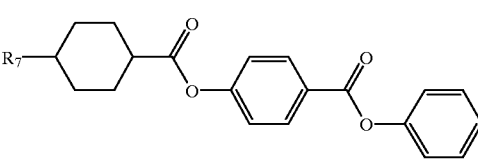

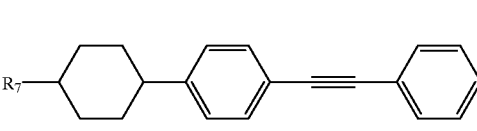

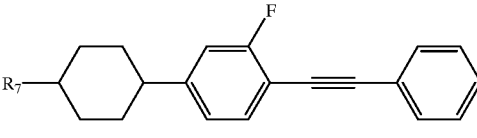

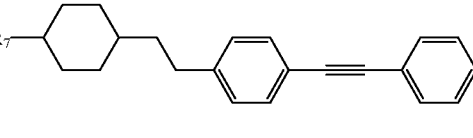

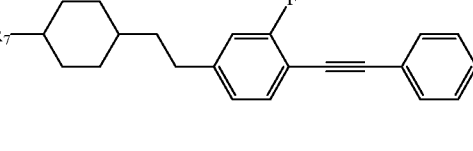

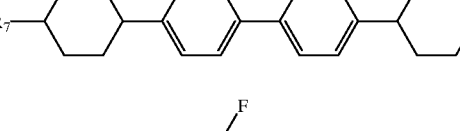

Compounds expressed by the general formulas (8) or (9) have a negative or small positive value of dielectric anisotropy. Among which, the compounds expressed by general formula (8) are used, as component of liquid crystal composition, for the purpose of reducing viscosity and adjusting optical anisotropy while the compounds expressed by general formula (9) are used for the purpose of widening the temperature range of liquid crystal phase and/or adjusting optical anisotropy.

Compounds expressed by the general formulas (5) to (9) are indispensable particularly when the liquid crystal compositions for STN display mode or ordinary TN display mode are produced. Amount of the compounds to be used is suitably 1 to 99% by weight, preferably 10 to 97% by weight, and more desirably 40 to 95% by weight based on the total amount of liquid crystal composition when liquid crystal compositions for STN display mode or ordinary TN display mode are produced.

Liquid crystal compositions provided according to the present invention preferably contain at least one liquid crystalline compound expressed by general formula (1) in an amount of 0.1 to 99% by weight to develop excellent characteristics.

The liquid crystal compositions are generally produced by the methods which are already known in the art, for instance, by the method in which various components are dissolved with each other at a high temperature. Also, they are improved, depending on the intended uses, by adding a suitable additive to optimize. Such additives are well known in the art and described in literatures in detail. Usually, a chiral dopant or likes are added which has an effect of causing a helical structure of liquid crystal to adjust a required twisting angle, and avoiding reverse-twist.

Further, the liquid crystal compositions can be used as liquid crystal compositions for guest-host (GH) mode by adding a dichroic dye such as merocyanine type, styryl type, azo type, azomethine type, azoxy type, quinophthalone type, anthraquinone type, and tetrazine type dye. Alternatively, the liquid crystal compositions of the present invention can also be used in the form of a NCAP which is prepared by forming a nematic liquid crystal into a microcapsule, or used as for polymer dispersion type liquid crystal display devices (PDLCD) which are produced by forming a polymer in the form of a three dimensional net work structure in a liquid crystal display, for example, for a polymer net work liquid crystal display device (PNLCD), as well as for electrically controlled birefringence (ECB) mode or dynamic scattering (DS) mode.

As the examples of the liquid crystal compositions containing the compounds of the present invention, the followings can be mentioned in which the number of compounds is the same as that shown in Examples below:

Composition Example 1

$C_2H_5$—⟨phenyl⟩—COO—⟨2,6-difluoro-4-CF$_3$-phenyl⟩ (No. 3) 7 wt. %

$C_5H_{11}$—⟨phenyl⟩—COO—⟨2,6-difluoro-4-CF$_3$-phenyl⟩ (No. 1) 7 wt. %

$C_2H_5$—⟨cyclohexyl⟩—⟨cyclohexyl⟩—COO—⟨3-fluoro-4-OCF$_3$-phenyl⟩ (No. 235) 13 wt. %

$C_3H_7$—⟨cyclohexyl⟩—⟨cyclohexyl⟩—COO—⟨3-fluoro-4-OCF$_3$-phenyl⟩ (No. 236) 13 wt. %

$C_5H_{11}$—⟨cyclohexyl⟩—⟨cyclohexyl⟩—COO—⟨3-fluoro-4-OCF$_3$-phenyl⟩ (No. 237) 13 wt. %

-continued
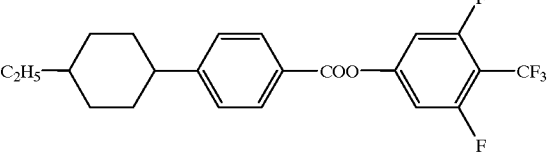
(No. 174) 7 wt. %
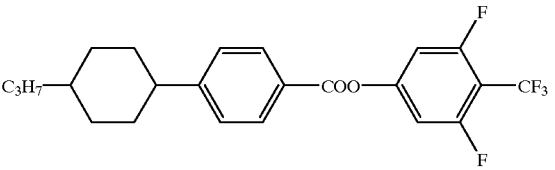
(No. 175) 8 wt. %
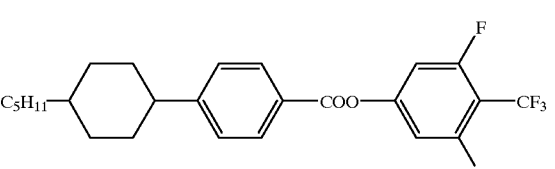
(No. 176) 8 wt. %
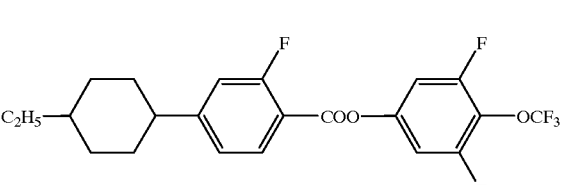
(No. 194) 10 wt. %
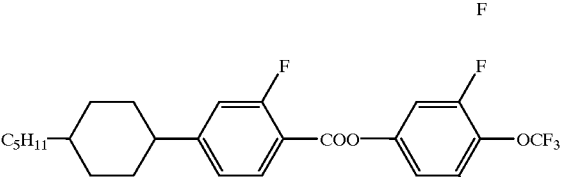
(No. 197) 10 wt. %
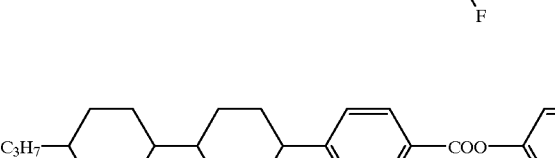
(No. 366) 2 wt. %
(No. 350) 2 wt. %
Composition Example 2
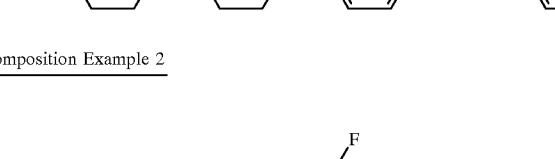
(No. 113) 5 wt. %

-continued
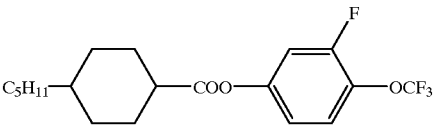 (No. 150) 5 wt. %
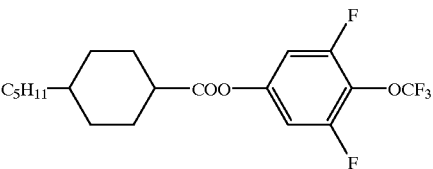 (No. 152) 5 wt. %
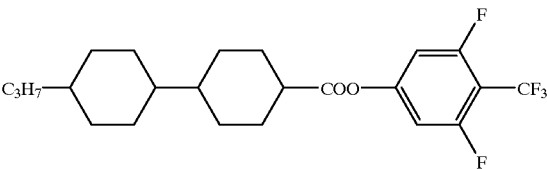 (No. 219) 10 wt. %
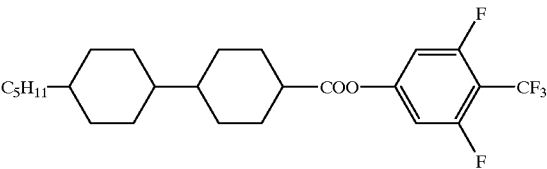 (No. 220) 10 wt. %
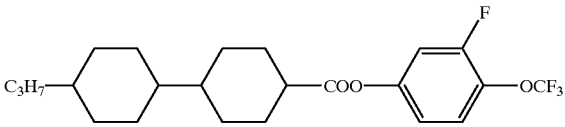 (No. 236) 10 wt. %
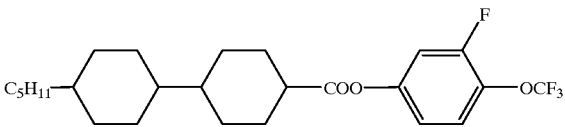 (No. 237) 10 wt. %
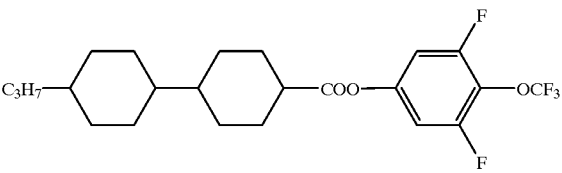 (No. 213) 10 wt. %
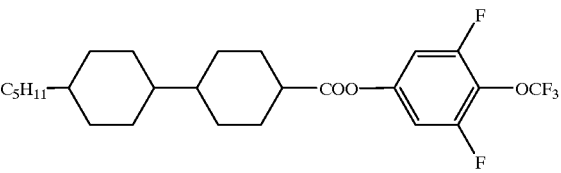 (No. 239) 10 wt. %
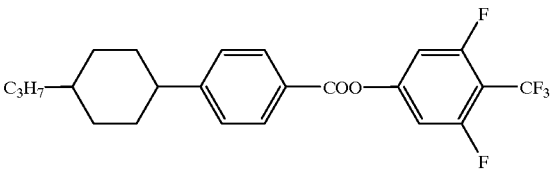 (No. 175) 5 wt. %

-continued
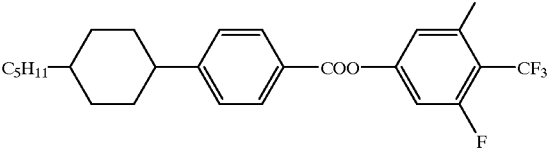 (No. 176) 4 wt. %
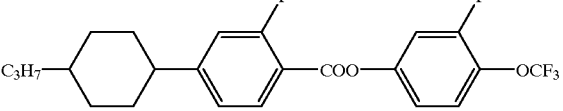 (No. 195) 4 wt. %
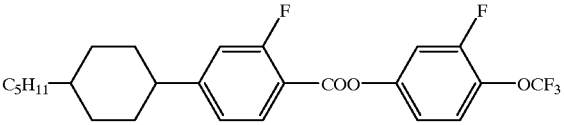 (No. 196) 4 wt. %
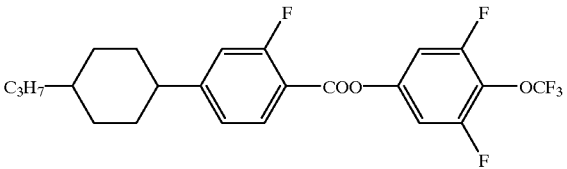 (No. 191) 4 wt. %
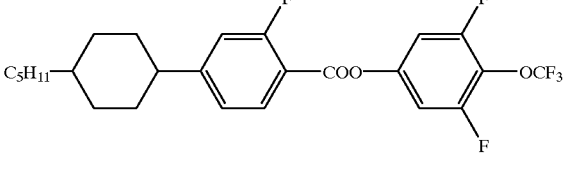 (No. 192) 4 wt. %
Composition Example 3
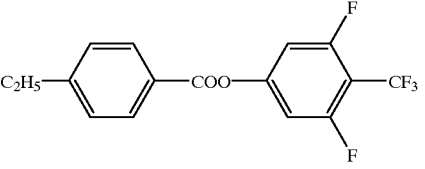 (No. 3) 4 wt. %
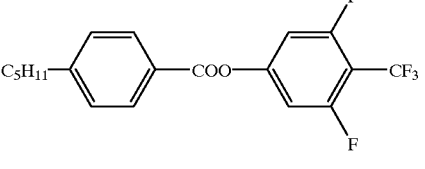 (No. 1) 4 wt. %
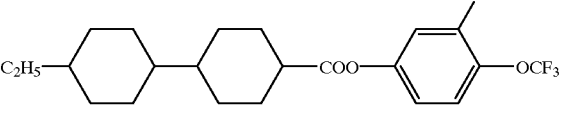 (No. 235) 8 wt. %
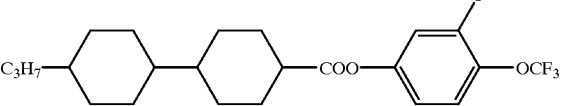 (No. 236) 8 wt. %

-continued

| Structure | No. | wt. % |
|---|---|---|
| C₅H₁₁–Cy–Cy–COO–Ph(3-F, 4-OCF₃) | (No. 237) | 8 wt. % |
| C₂H₅–Cy–Ph–COO–Ph(3,5-F, 4-CF₃) | (No. 174) | 4 wt. % |
| C₃H₇–Cy–Ph–COO–Ph(3,5-F, 4-CF₃) | (No. 175) | 4 wt. % |
| C₅H₁₁–Cy–Ph–COO–Ph(3,5-F, 4-CF₃) | (No. 176) | 4 wt. % |
| C₂H₅–Cy–Ph(2-F)–COO–Ph(3,5-F, 4-OCF₃) | (No. 194) | 6 wt. % |
| C₅H₁₁–Cy–Ph(2-F)–COO–Ph(3,5-F, 4-OCF₃) | (No. 197) | 6 wt. % |
| C₃H₇–Cy–Cy–Ph–COO–Ph(3,5-F, 4-OCF₃) | (No. 366) | 2 wt. % |
| C₃H₇–Cy–Cy–Ph–COO–Ph(3-F, 4-CF₃) | (No. 350) | 2 wt. % |
| C₇H₁₅–Cy–Ph(3,4,5-F) | | 6 wt. % |

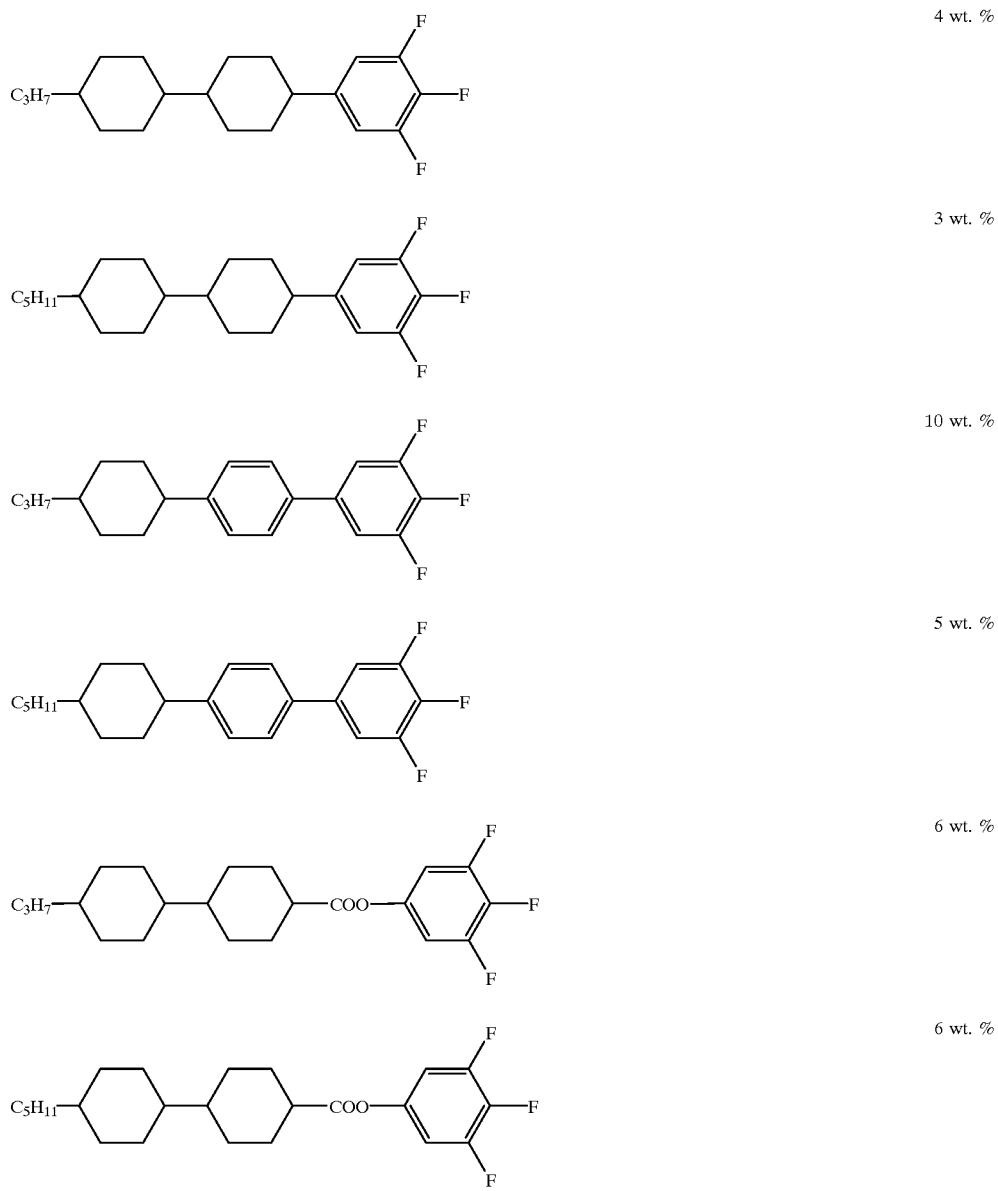
| | |
|---|---|
| | 4 wt. % |
| | 3 wt. % |
| | 10 wt. % |
| | 5 wt. % |
| | 6 wt. % |
| | 6 wt. % |
Composition Example 4
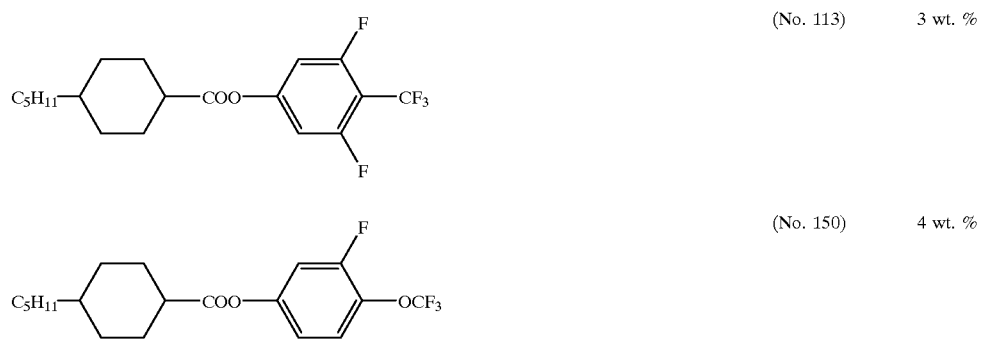
| | | |
|---|---|---|
| | (No. 113) | 3 wt. % |
| | (No. 150) | 4 wt. % |

-continued

| | | |
|---|---|---|
| C5H11-⬡-COO-⌬(F,F)-OCF3 | (No. 152) | 3 wt. % |
| C3H7-⬡-⬡-COO-⌬(F,F)-CF3 | (No. 219) | 7 wt. % |
| C5H11-⬡-⬡-COO-⌬(F,F)-CF3 | (No. 220) | 7 wt. % |
| C3H7-⬡-⬡-COO-⌬(F)-OCF3 | (No. 236) | 7 wt. % |
| C5H11-⬡-⬡-COO-⌬(F)-OCF3 | (No. 237) | 7 wt. % |
| C3H7-⬡-⬡-COO-⌬(F,F)-OCF3 | (No. 213) | 7 wt. % |
| C5H11-⬡-⬡-COO-⌬(F,F)-OCF3 | (No. 239) | 7 wt. % |
| C3H7-⬡-⌬-COO-⌬(F,F)-CF3 | (No. 175) | 4 wt. % |
| C5H11-⬡-⌬-COO-⌬(F,F)-CF3 | (No. 176) | 3 wt. % |

-continued

| Structure | No. | wt % |
|---|---|---|
| C₃H₇–[Cy]–[Ph(2-F)]–COO–[Ph(3-F,4-OCF₃)] | (No. 195) | 3 wt. % |
| C₅H₁₁–[Cy]–[Ph(2-F)]–COO–[Ph(3-F,4-OCF₃)] | (No. 196) | 3 wt. % |
| C₃H₇–[Cy]–[Ph]–COO–[Ph(3,5-F,4-OCF₃)] | (No. 191) | 3 wt. % |
| C₅H₁₁–[Cy]–[Ph]–COO–[Ph(3,5-F,4-OCF₃)] | (No. 192) | 2 wt. % |
| C₅H₁₁–[Cy]–CH₂CH₂–[Ph(3,4-F)] | | 6 wt. % |
| C₂H₅–[Cy]–[Cy]–[Ph(3,4-F)] | | 8 wt. % |
| C₃H₇–[Cy]–[Cy]–[Ph(3,4-F)] | | 8 wt. % |
| C₅H₁₁–[Cy]–[Cy]–[Ph(3,4-F)] | | 8 wt. % |

Composition Example 5

| Structure | No. | wt % |
|---|---|---|
| C₃H₇–[Ph]–COO–[Ph(3-F,4-OCF₃)] | (No. 42) | 3 wt. % |

-continued

| Structure | No. | wt. % |
|---|---|---|
| C₂H₅-Cy-Cy-COO-Ph(F)-OCF₃ | (no. 235) | 4 wt. % |
| C₃H₇-Cy-Cy-COO-Ph(F)-OCF₃ | (No. 236) | 4 wt. % |
| C₂H₅-Cy-Ph-COO-Ph(F)-OCF₃ | (No. 189) | 4 wt. % |
| C₅H₁₁-Cy-Ph-COO-Ph(F)-OCF₃ | (No. 190) | 3 wt. % |
| C₂H₅-Ph-Ph-COO-Ph(F)-OCF₃ | (No. 343) | 2 wt. % |
| C₇H₁₅-Cy-Ph(F,F) | | 10 wt. % |
| C₂H₅-Cy-Cy-Ph(F,F) | | 12 wt. % |
| C₃H₇-Cy-Cy-Ph(F,F) | | 12 wt. % |
| C₅H₁₁-Cy-Cy-Ph(F,F) | | 12 wt. % |
| C₂H₅-Cy-CH₂CH₂-Cy-Ph(F,F) | | 4 wt. % |

-continued
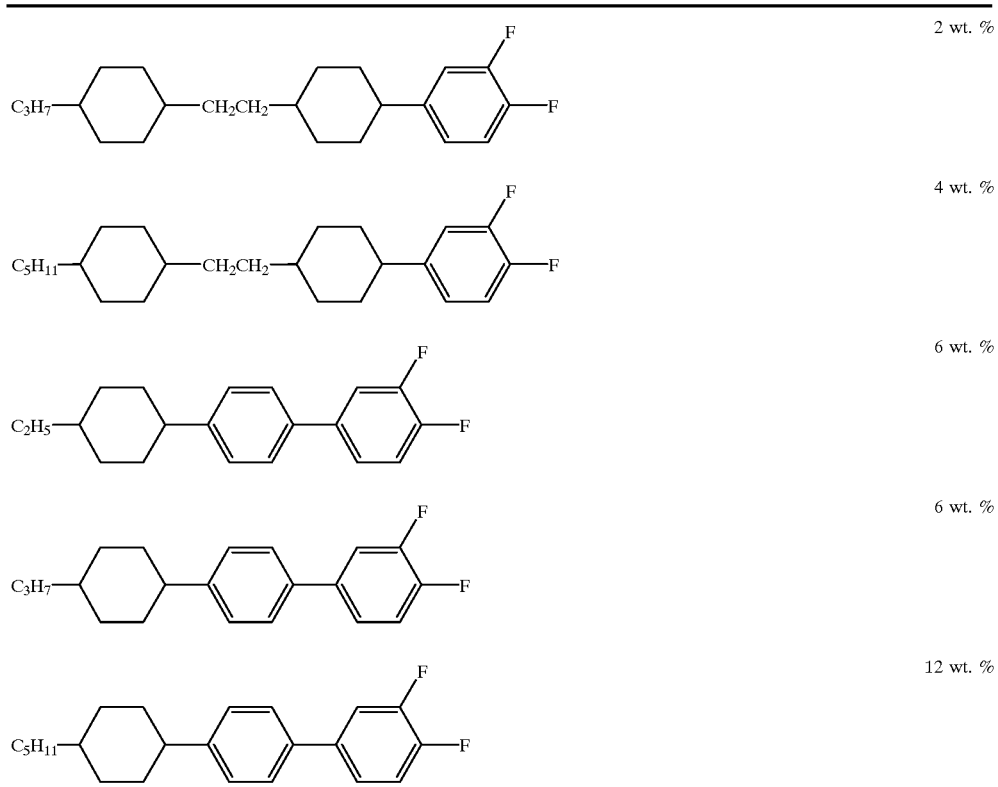
| | |
|---|---|
| | 2 wt. % |
| | 4 wt. % |
| | 6 wt. % |
| | 6 wt. % |
| | 12 wt. % |
Composition Example 6
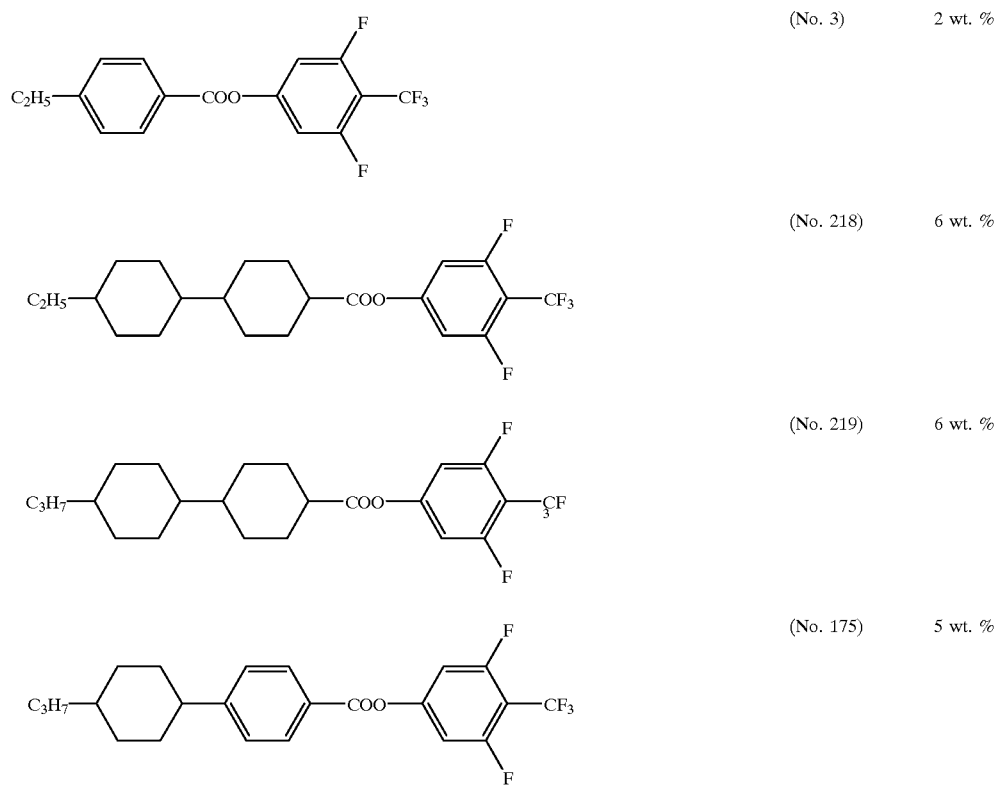
| | | |
|---|---|---|
| (No. 3) | 2 wt. % |
| (No. 218) | 6 wt. % |
| (No. 219) | 6 wt. % |
| (No. 175) | 5 wt. % |

-continued

| | | |
|---|---|---|
| C₃H₇-(Cy)-(Ph: 2-F, COO-Ph: 3,5-F, 4-CF₃) | (No. 177) | 5 wt. % |
| C₅H₁₁-(Cy)-(Ph: 2-F, COO-Ph: 3,5-F, 4-CF₃) | (No. 178) | 4 wt. % |
| C₇H₁₅-(Cy)-(Ph: 3,4,5-F) | | 3 wt. % |
| C₃H₇-(Cy)-(Cy)-(Ph: 3,4,5-F) | | 5 wt. % |
| C₃H₇-(Cy)-CH₂CH₂-(Cy)-(Ph: 3,4,5-F) | | 5 wt. % |
| C₃H₇-(Cy)-(Ph)-(Ph: 3,4,5-F) | | 10 wt. % |
| C₅H₁₁-(Cy)-(Ph)-(Ph: 3,4,5-F) | | 10 wt. % |
| C₃H₇-(Cy)-CH₂CH₂-(Ph)-(Ph: 3,4,5-F) | | 5 wt. % |

-continued
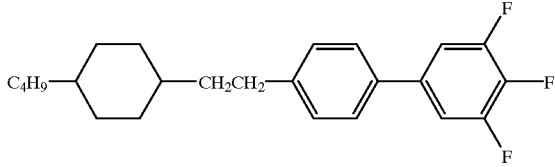
5 wt. %
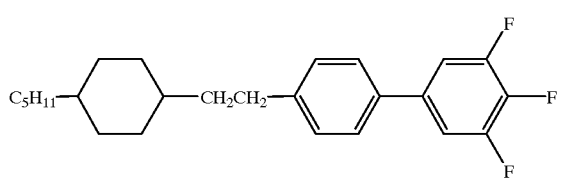
5 wt. %
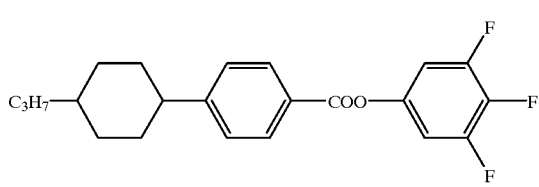
3 wt. %
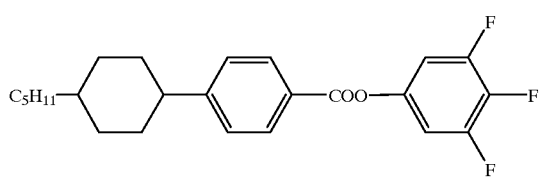
5 wt. %
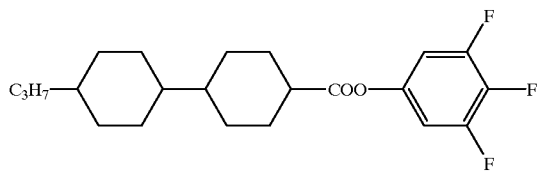
10 wt. %
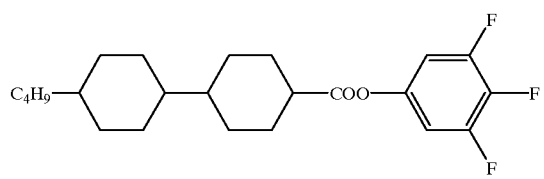
3 wt. %
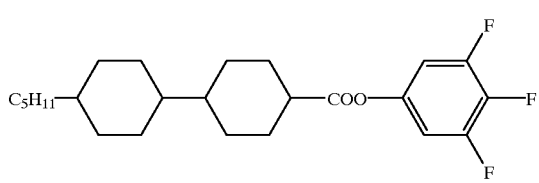
3 wt. %
Composition Example 7
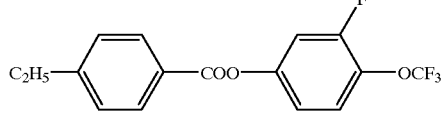
(No. 40)  5 wt. %

-continued

| Structure | No. | wt. % |
|---|---|---|
| C₃H₇–⌬–COO–⌬(F)(OCF₃) | (No. 42) | 5 wt. % |
| C₅H₁₁–⌬–COO–⌬(F)(OCF₃) | (No. 45) | 2 wt. % |
| C₃H₇–⌬–⌬–COO–⌬(F)(OCF₃) | (No. 236) | 3 wt. % |
| C₃H₇–⌬–⌬(F)–COO–⌬(F)(OCF₃) | (No. 195) | 3 wt. % |
| C₇H₁₅–⌬–⌬(F,F) | | 10 wt. % |
| C₅H₁₁–⌬–⌬–COO–⌬(F,F,CF₃) | | 8 wt. % |
| C₂H₅–⌬–⌬–⌬(F,F) | | 8 wt. % |
| C₃H₇–⌬–⌬–⌬(F,F) | | 8 wt. % |
| C₅H₁₁–⌬–⌬–⌬(F,F) | | 8 wt. % |
| C₂H₅–⌬–⌬–⌬(F,F) | | 10 wt. % |

-continued
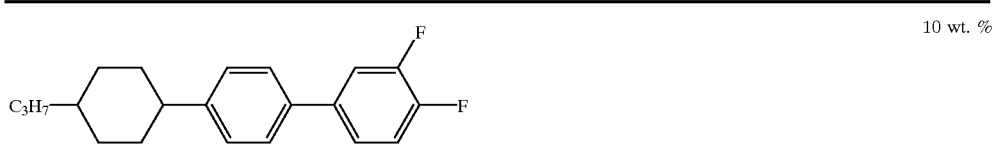  10 wt. %
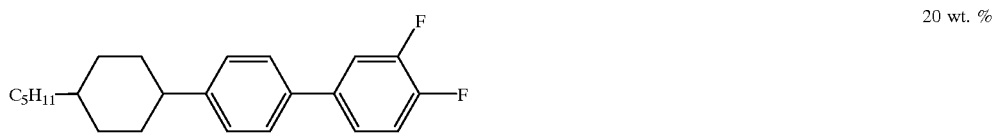  20 wt. %
Composition Example 8
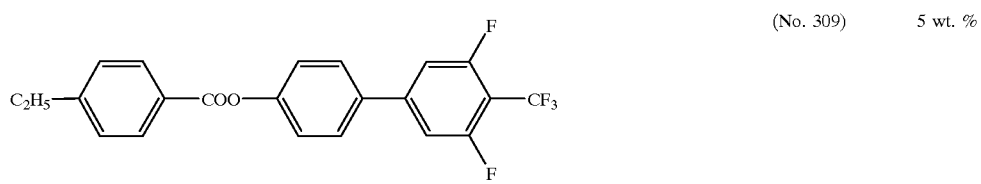  (No. 309)  5 wt. %
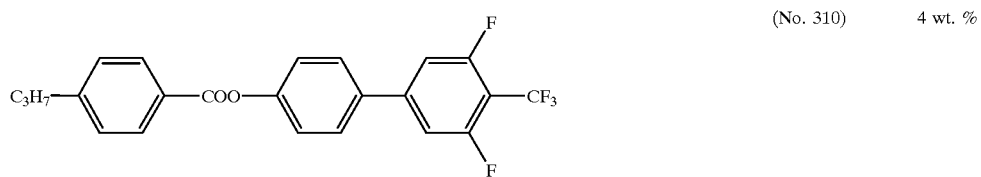  (No. 310)  4 wt. %
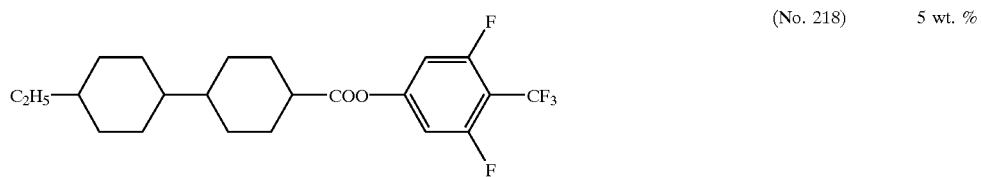  (No. 218)  5 wt. %
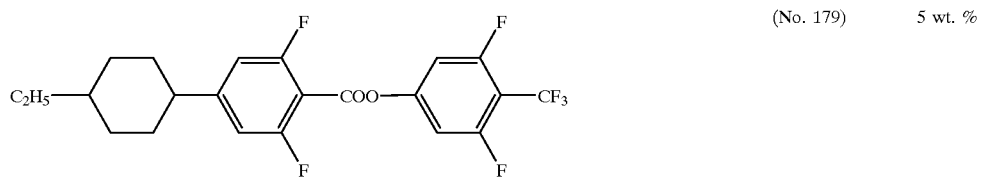  (No. 179)  5 wt. %
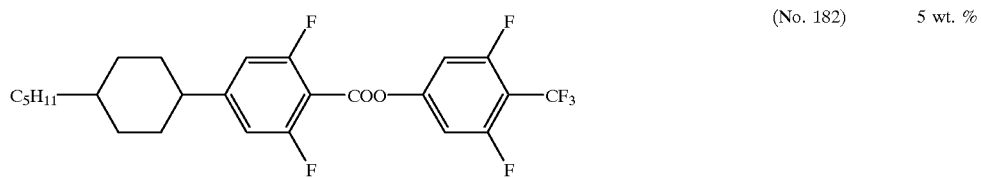  (No. 182)  5 wt. %
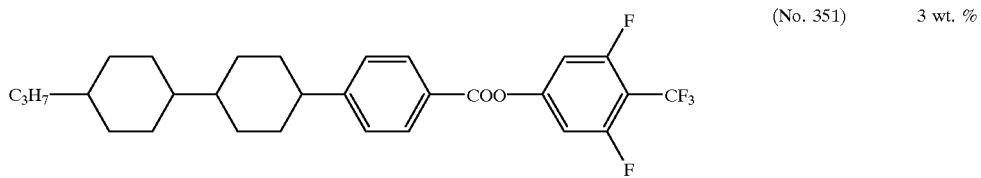  (No. 351)  3 wt. %

-continued
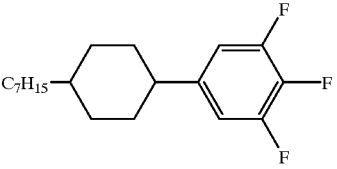 2 wt. %
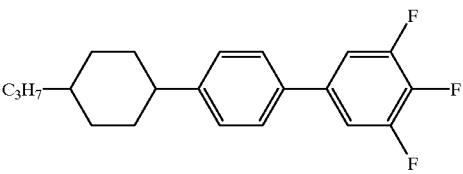 5 wt. %
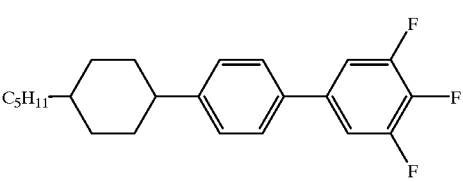 5 wt. %
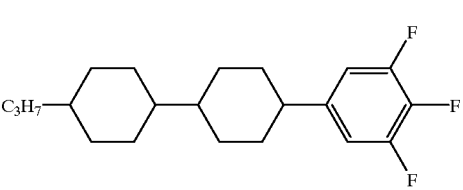 3 wt. %
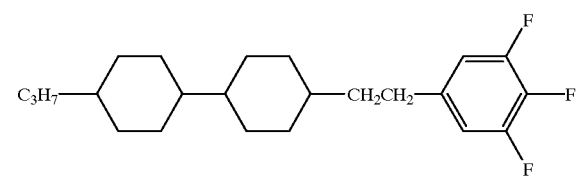 8 wt. %
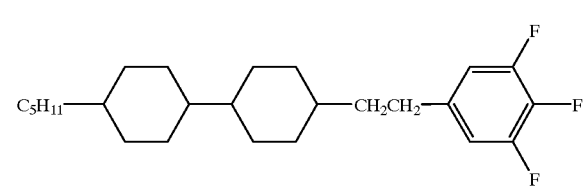 5 wt. %
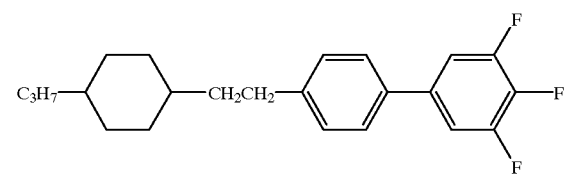 8 wt. %
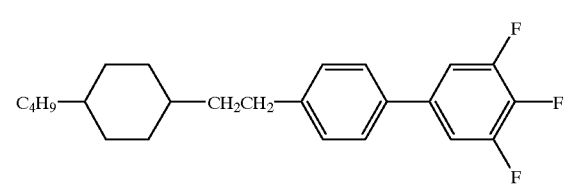 8 wt. %

-continued
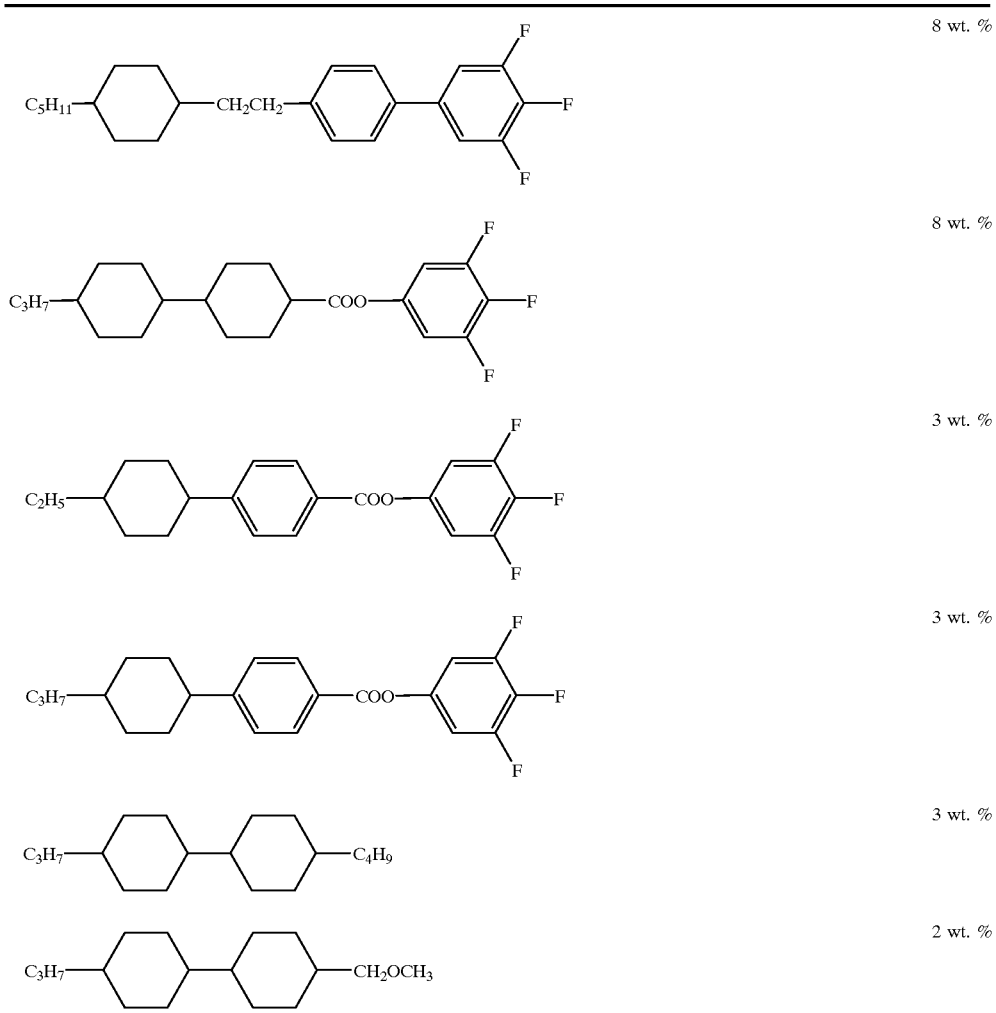
| | |
|---|---|
| | 8 wt. % |
| | 8 wt. % |
| | 3 wt. % |
| | 3 wt. % |
| | 3 wt. % |
| | 2 wt. % |
Composition Example 9
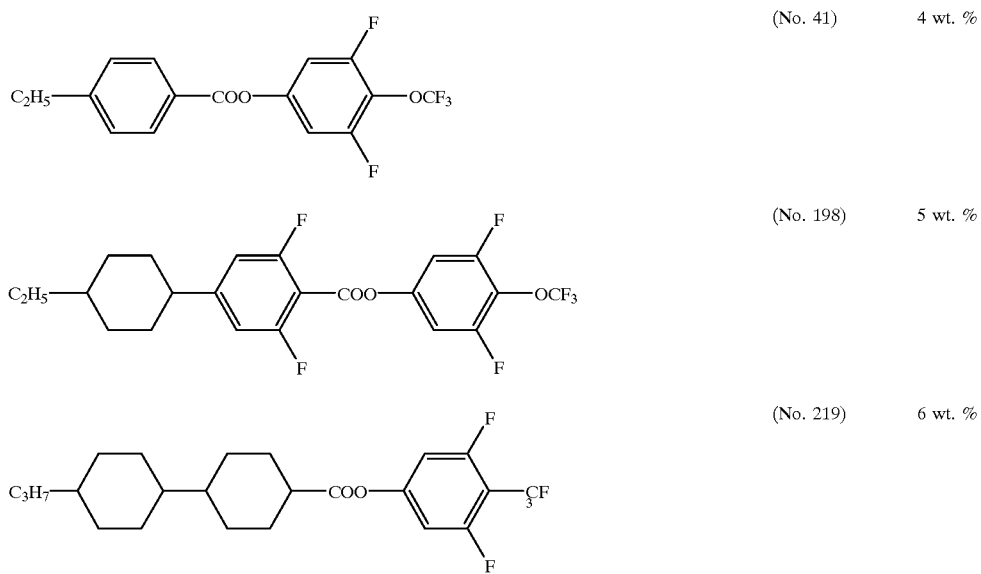
| | | |
|---|---|---|
| (No. 41) | 4 wt. % |
| (No. 198) | 5 wt. % |
| (No. 219) | 6 wt. % |

-continued
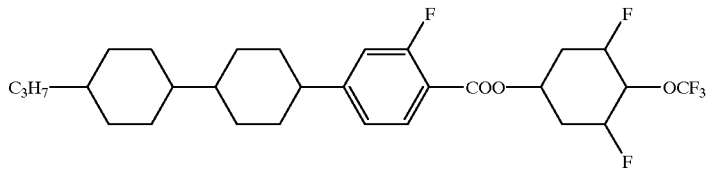 (No. 368) 2 wt. %
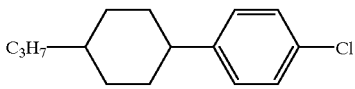 5 wt. %
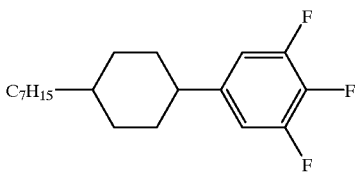 8 wt. %
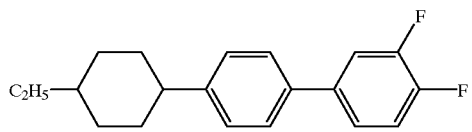 7 wt. %
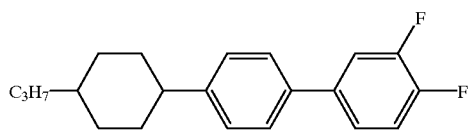 7 wt. %
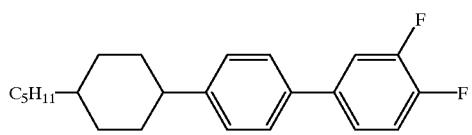 14 wt. %
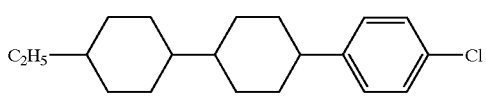 3 wt. %
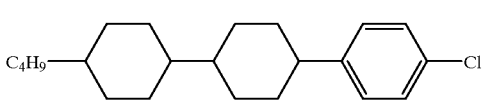 8 wt. %
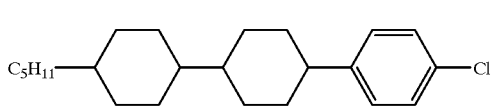 3 wt. %
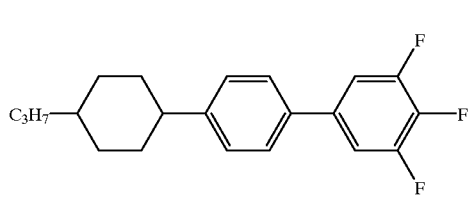 10 wt. %

-continued
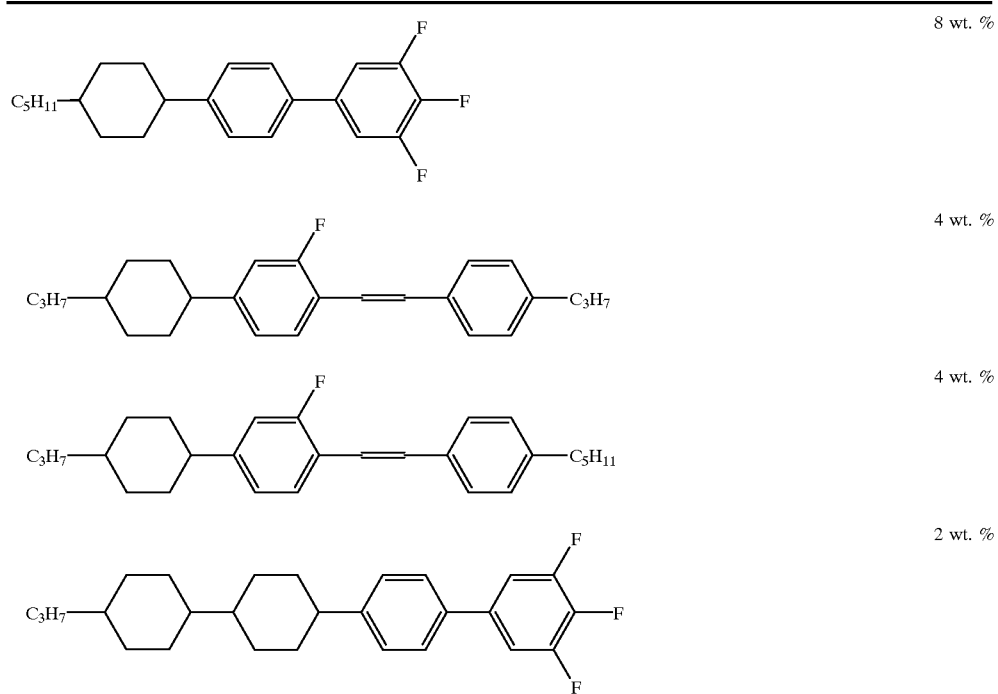
8 wt. %
4 wt. %
4 wt. %
2 wt. %
Composition Example 10
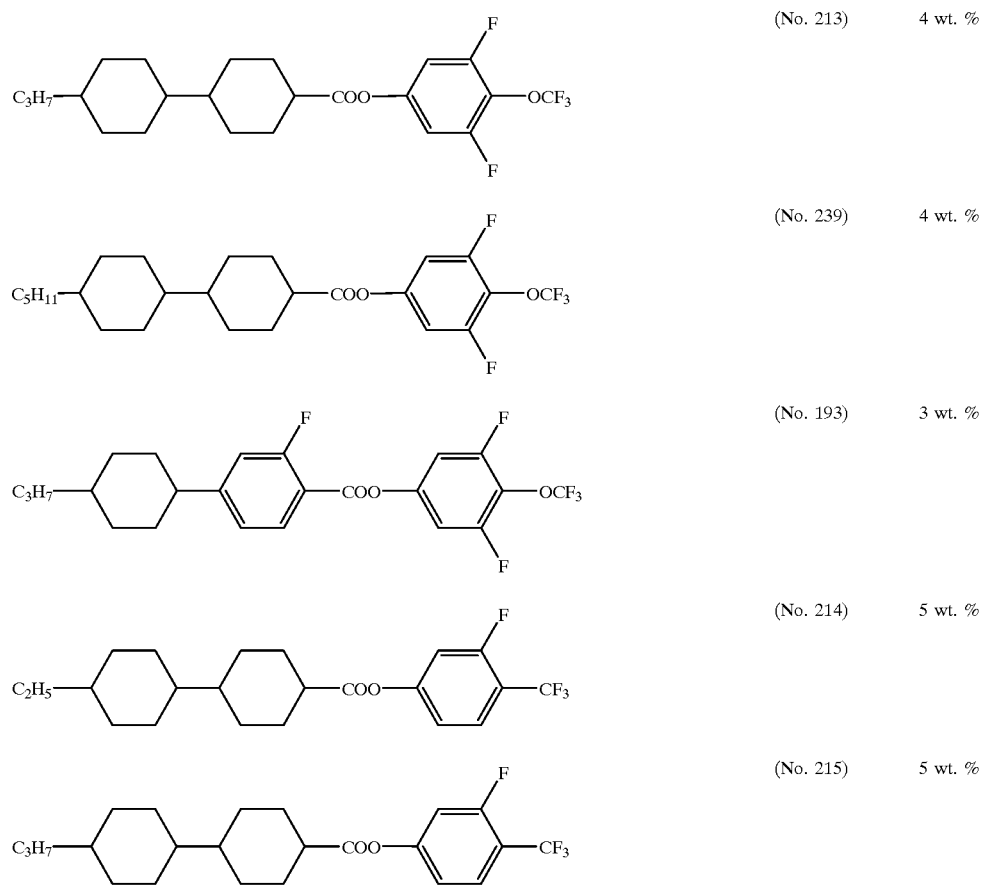
(No. 213) 4 wt. %
(No. 239) 4 wt. %
(No. 193) 3 wt. %
(No. 214) 5 wt. %
(No. 215) 5 wt. %

-continued
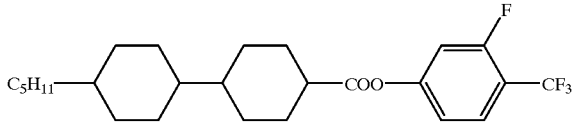 (No. 216) 4 wt. %
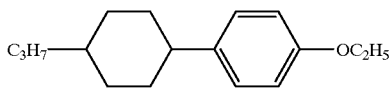 5 wt. %
 2 wt. %
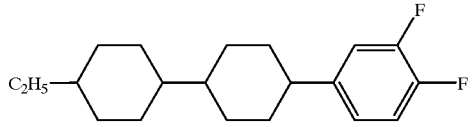 8 wt. %
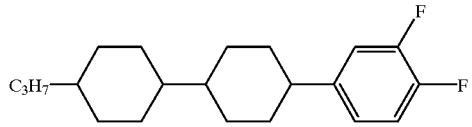 8 wt. %
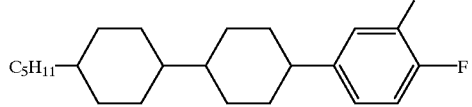 8 wt. %
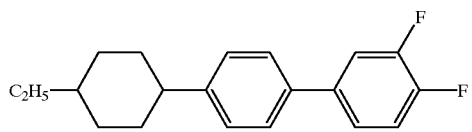 5 wt. %
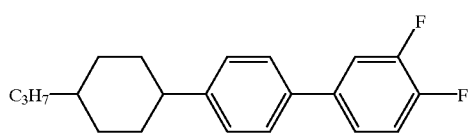 5 wt. %
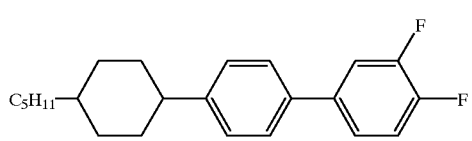 10 wt. %
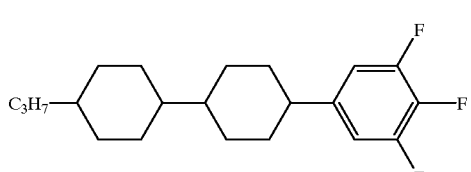 5 wt. %

-continued
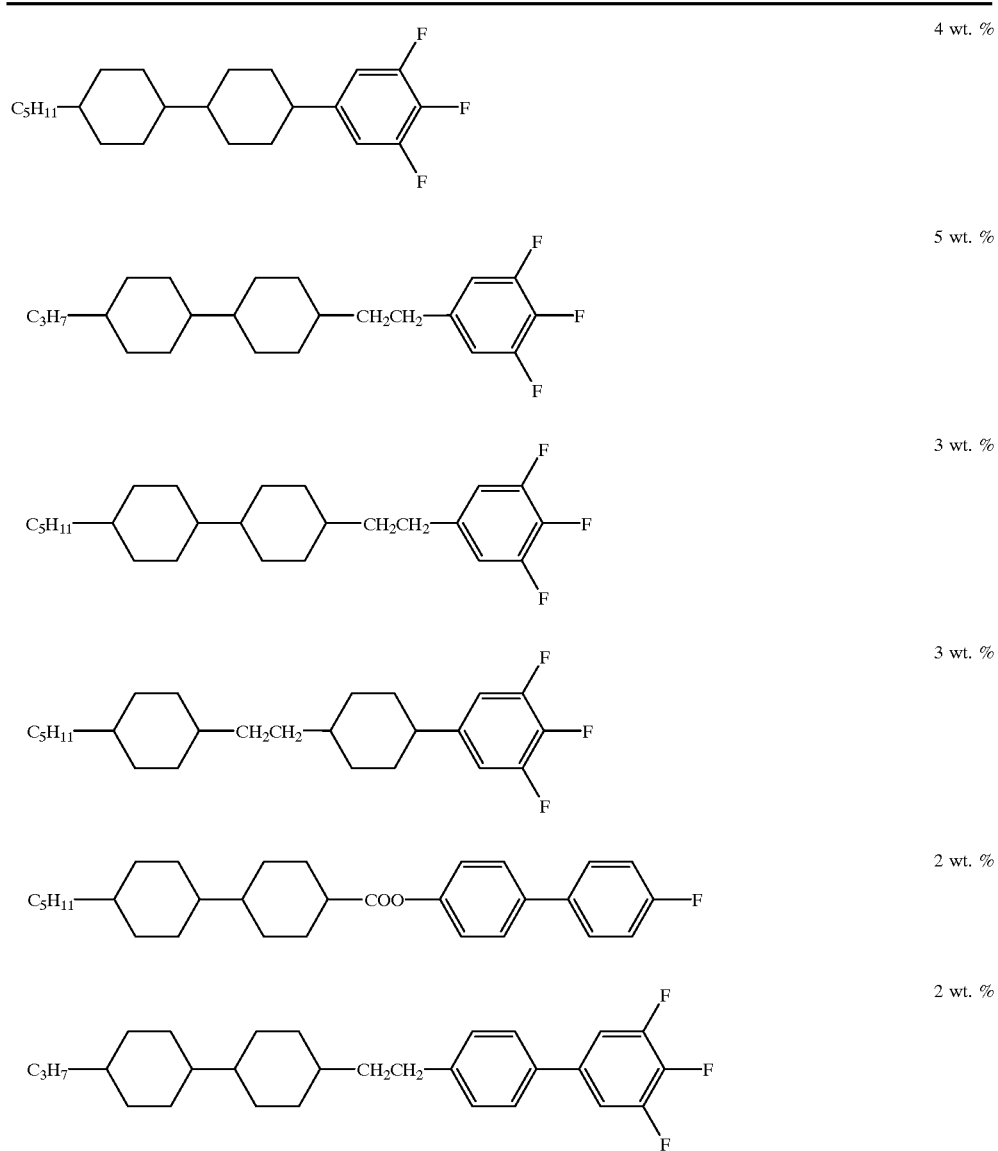
4 wt. %
5 wt. %
3 wt. %
3 wt. %
2 wt. %
2 wt. %
Composition Example 11
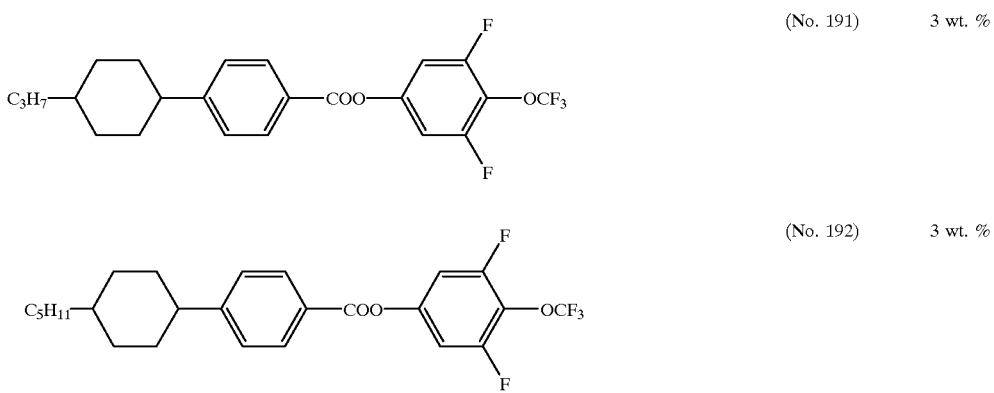
(No. 191)  3 wt. %
(No. 192)  3 wt. %

-continued

| Structure | No. | wt. % |
|---|---|---|
| C₂H₅–C₆H₄–C₆H₄–COO–C₆H₂(F)(CF₃)(F) | (No. 334) | 2 wt. % |
| C₃H₇–Cy–C₆H₄–COO–C₆H₂(F)(CF₃)(F) | (No. 175) | 6 wt. % |
| C₅H₁₁–Cy–C₆H₄–COO–C₆H₂(F)(CF₃)(F) | (No. 176) | 6 wt. % |
| C₃H₇–Cy–C₆H₃(F)–COO–C₆H₂(F)(CF₃)(F) | (No. 177) | 2 wt. % |
| C₅H₁₁–Cy–C₆H₃(F)–COO–C₆H₂(F)(CF₃)(F) | (No. 178) | 2 wt. % |
| C₇H₁₅–Cy–C₆H₃(F)(F) | | 3 wt. % |
| C₃H₇–Cy–C₆H₄–OC₂H₅ | | 5 wt. % |
| C₂H₅–Cy–Cy–C₆H₃(F)(F) | | 7 wt. % |
| C₃H₇–Cy–Cy–C₆H₃(F)(F) | | 7 wt. % |

-continued
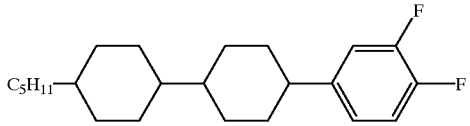 7 wt. %
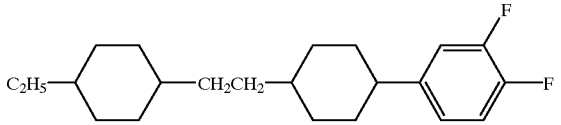 6 wt. %
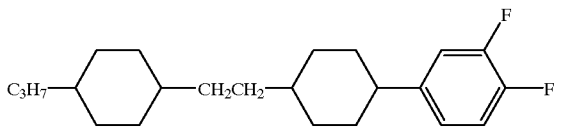 3 wt. %
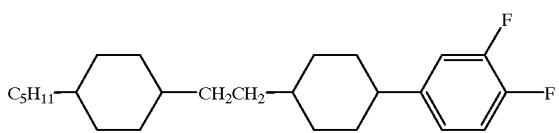 6 wt. %
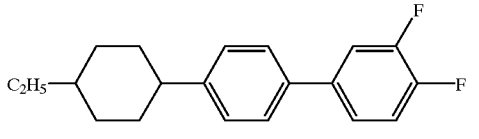 3 wt. %
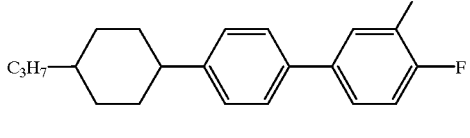 3 wt. %
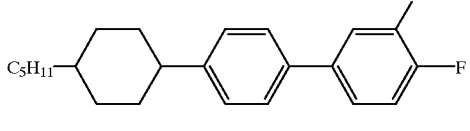 6 wt. %
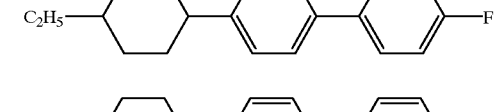 4 wt. %
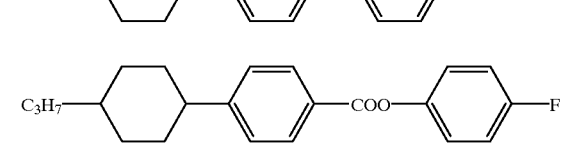 3 wt. %
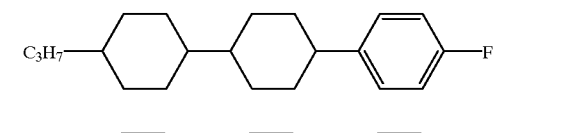 3 wt. %
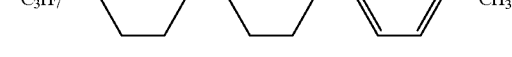 3 wt. %
5 wt. %

-continued
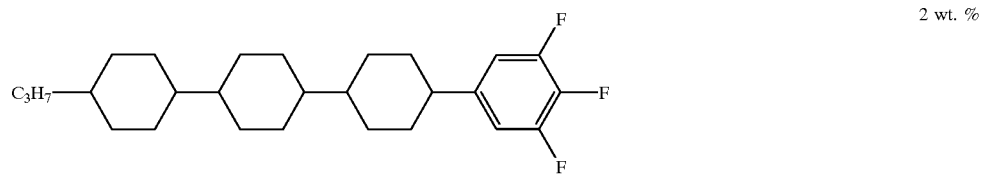 2 wt. %
Composition Example 12
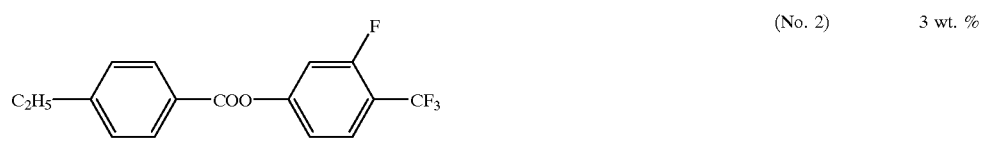 (No. 2) 3 wt. %
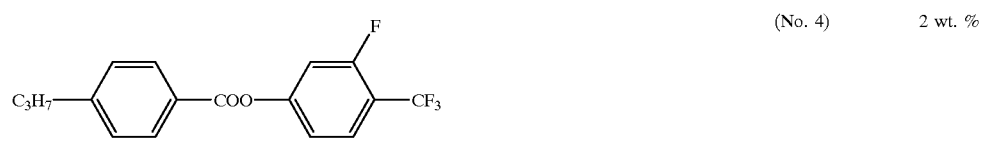 (No. 4) 2 wt. %
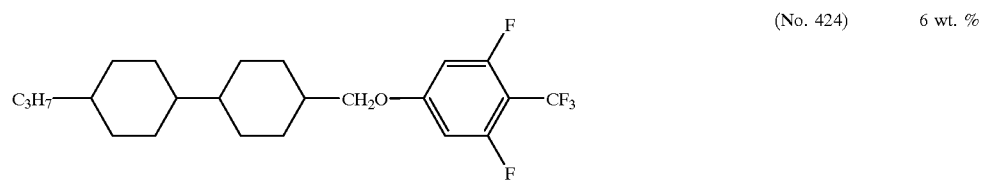 (No. 424) 6 wt. %
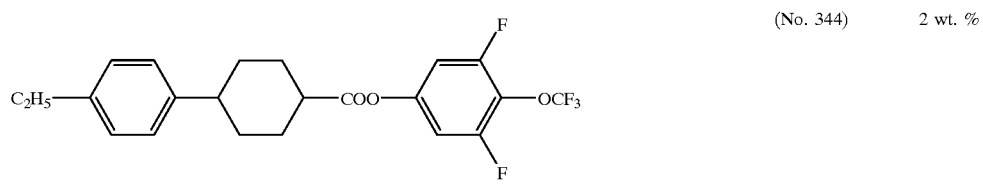 (No. 344) 2 wt. %
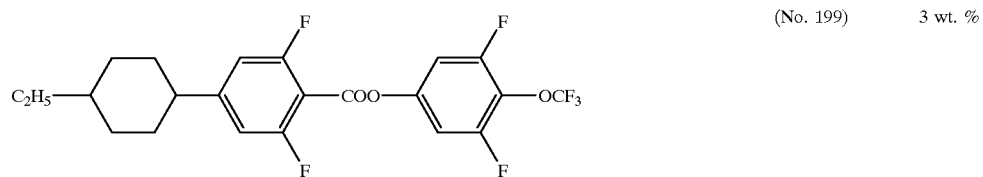 (No. 199) 3 wt. %
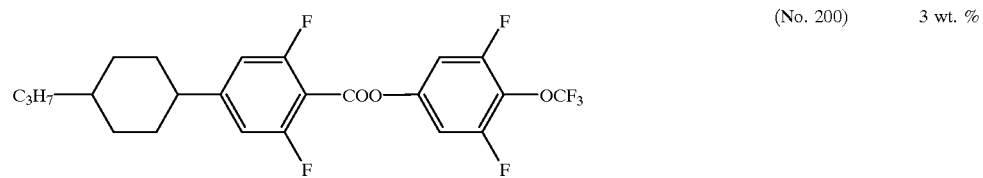 (No. 200) 3 wt. %
 5 wt. %

-continued
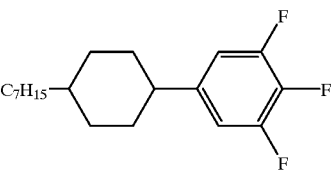 6 wt. %
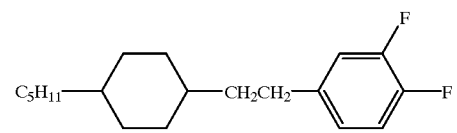 5 wt. %
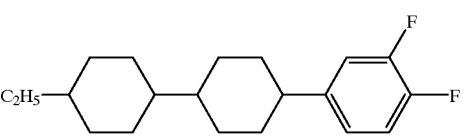 4 wt. %
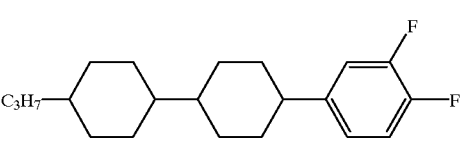 4 wt. %
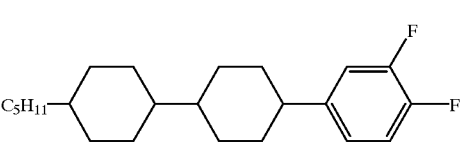 4 wt. %
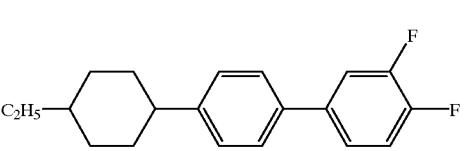 7 wt. %
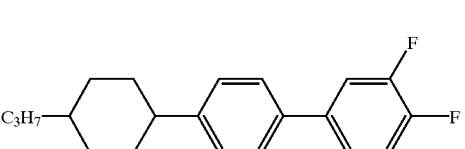 7 wt. %
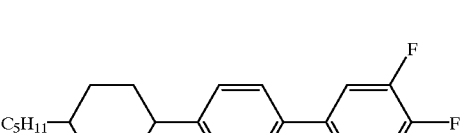 14 wt. %
 2 wt. %
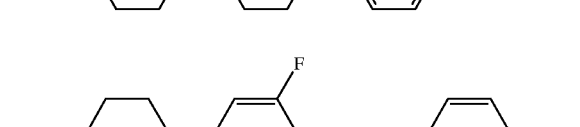 5 wt. %

-continued
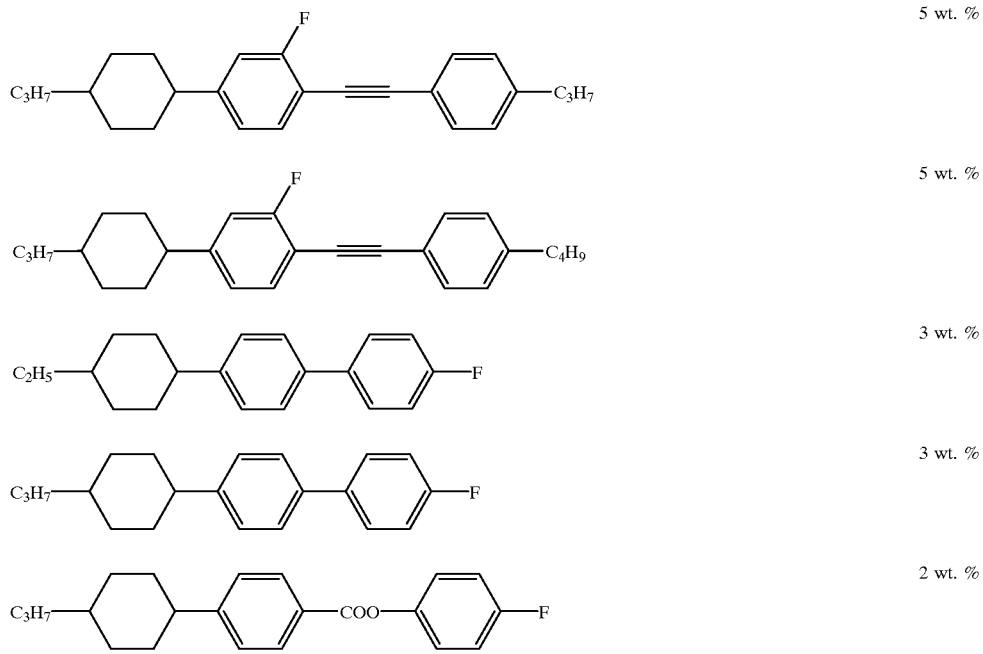
5 wt. %
5 wt. %
3 wt. %
3 wt. %
2 wt. %
Composition Example 13
(No. 355)   2 wt. %
(No. 365)   2 wt. %
(No. 214)   3 wt. %
(No. 216)   2 wt. %
5 wt. %

-continued
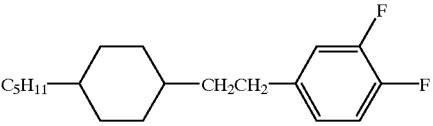 6 wt. %
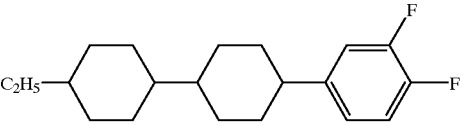 12 wt. %
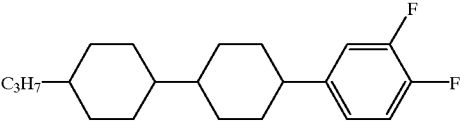 12 wt. %
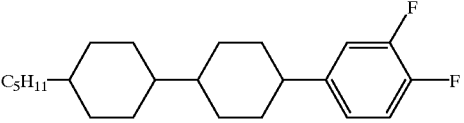 12 wt. %
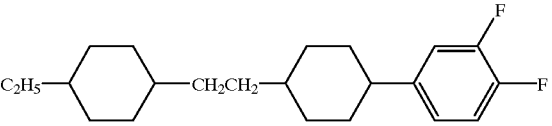 4 wt. %
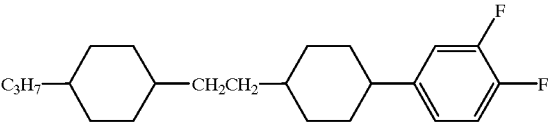 2 wt. %
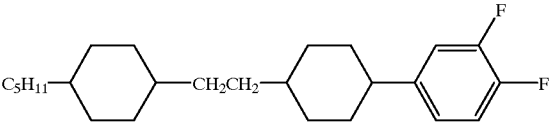 4 wt. %
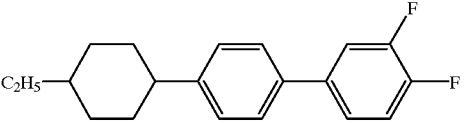 5 wt. %
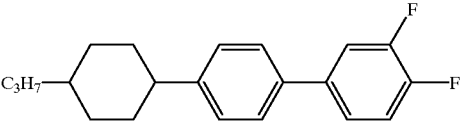 5 wt. %
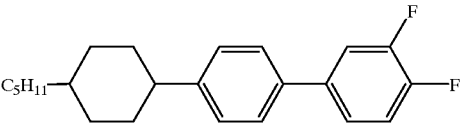 10 wt. %
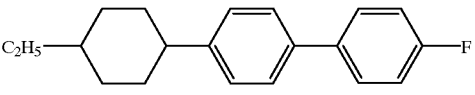 3 wt. %

-continued
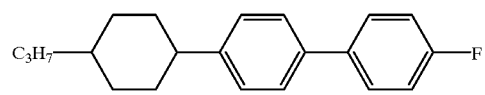 3 wt. %
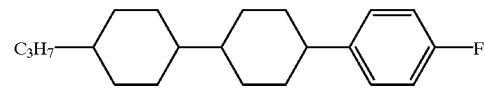 3 wt. %
 5 wt. %
Composition Example 14
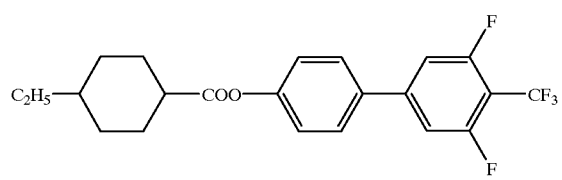 (No. 309) 6 wt. %
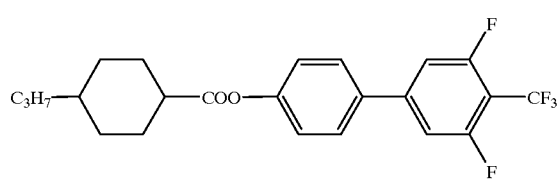 (No. 310) 4 wt. %
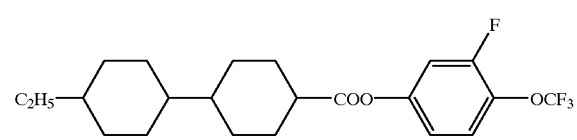 (No. 235) 6 wt. %
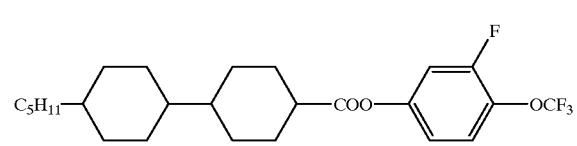 (No. 237) 6 wt. %
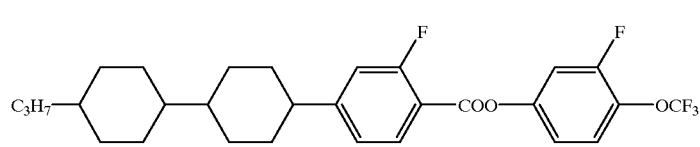 (No. 367) 2 wt. %
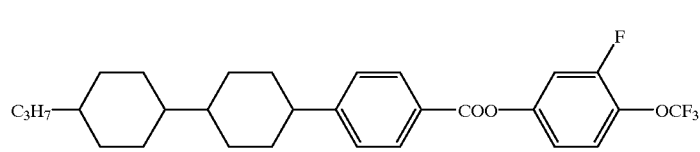 (No. 365) 2 wt. %
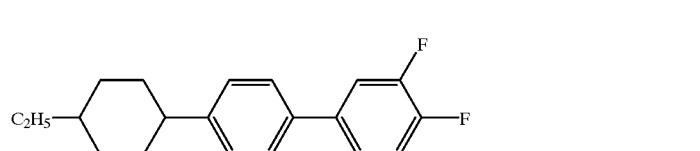 3 wt. %

-continued
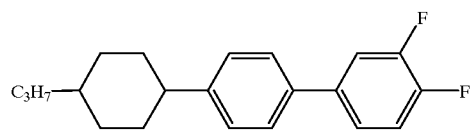 3 wt. %
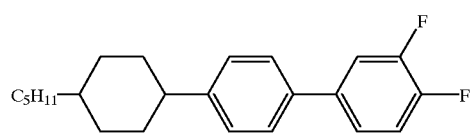 6 wt. %
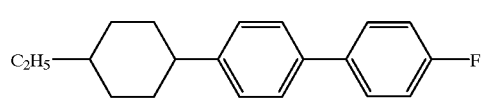 2 wt. %
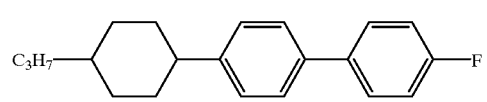 2 wt. %
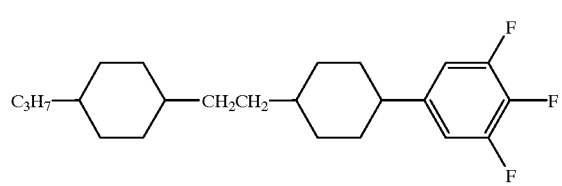 6 wt. %
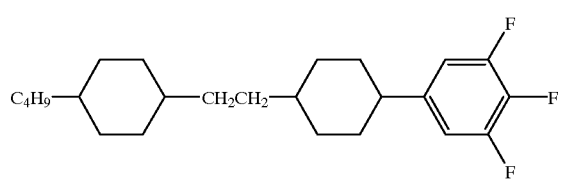 6 wt. %
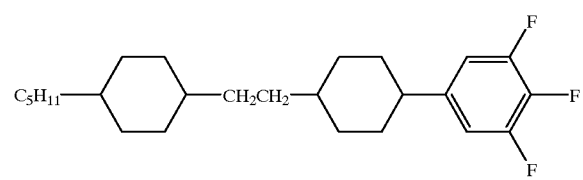 6 wt. %
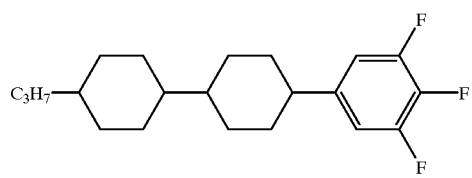 3 wt. %
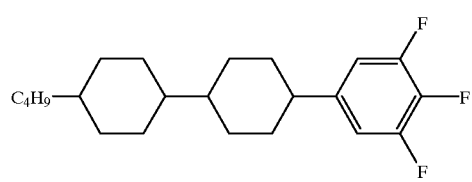 3 wt. %

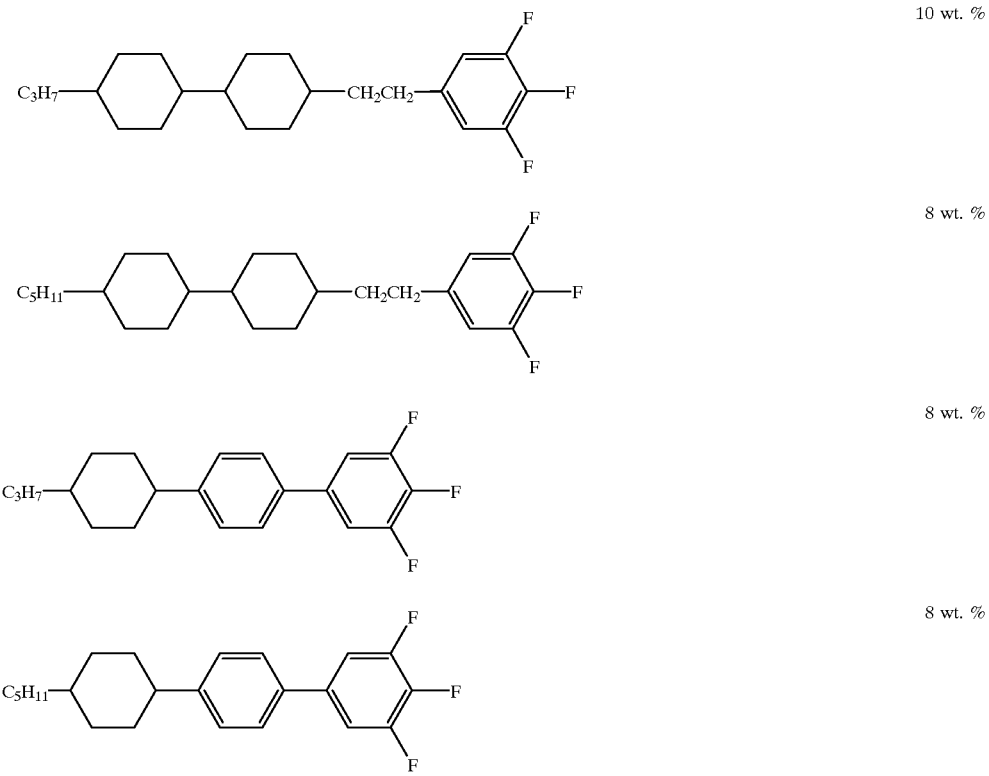
| | |
|---|---|
| | 10 wt. % |
| | 8 wt. % |
| | 8 wt. % |
| | 8 wt. % |
Composition Example 15
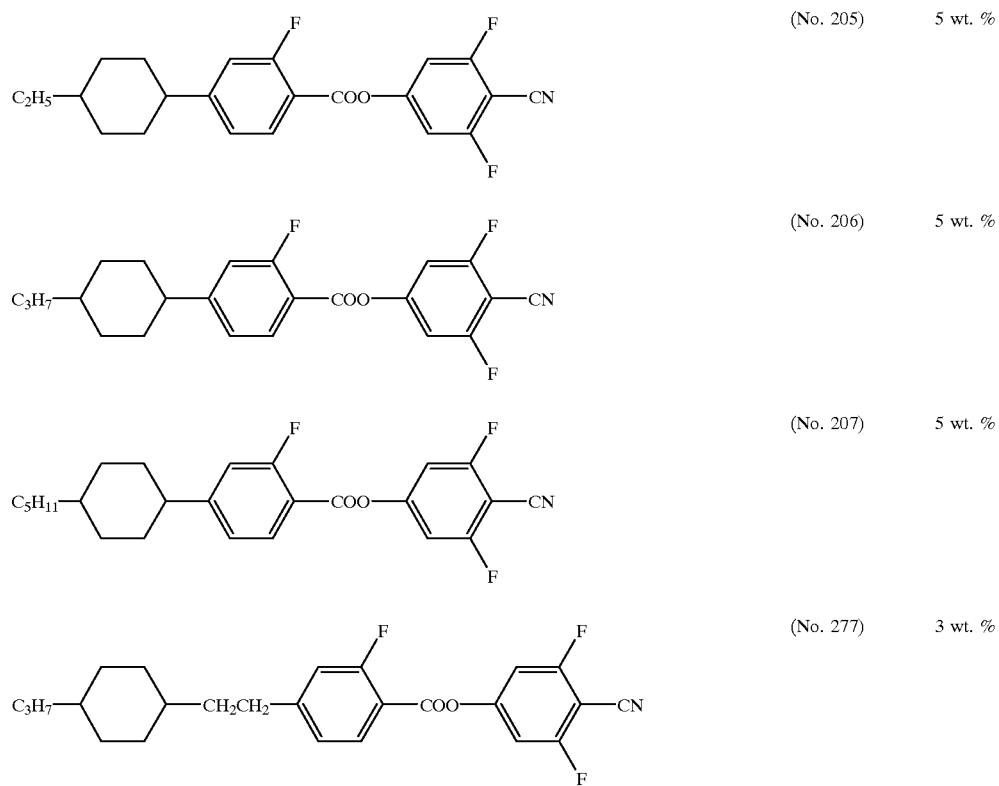
| | | |
|---|---|---|
| | (No. 205) | 5 wt. % |
| | (No. 206) | 5 wt. % |
| | (No. 207) | 5 wt. % |
| | (No. 277) | 3 wt. % |

-continued

| Structure | | |
|---|---|---|
| C₅H₁₁—⟨CH⟩—CH₂CH₂—⟨Ph(2-F)⟩—COO—⟨Ph(3,5-F₂)⟩—CN | (No. 249) | 3 wt. % |
| C₃H₇OCH₂—⟨Ph⟩—COO—⟨Ph(3-F)⟩—CN | | 7 wt. % |
| C₂H₄=C₃H₅—⟨CH⟩—⟨Ph⟩—CN | | 7 wt. % |
| C₃H₇—⟨CH⟩—⟨Ph⟩—OC₂H₅ | | 3 wt. % |
| C₂H₅—⟨Ph⟩—C≡C—⟨Ph⟩—OCH₃ | | 6 wt. % |
| C₃H₇—⟨Ph⟩—C≡C—⟨Ph⟩—OCH₃ | | 6 wt. % |
| C₄H₉—⟨Ph⟩—C≡C—⟨Ph⟩—OCH₃ | | 6 wt. % |
| C₄H₉—⟨Ph⟩—C≡C—⟨Ph⟩—OC₂H₅ | | 6 wt. % |
| C₅H₁₁—⟨Ph⟩—C≡C—⟨Ph⟩—OCH₃ | | 6 wt. % |
| C₃H₇—⟨CH⟩—⟨CH⟩—⟨Ph⟩—OCH₃ | | 2 wt. % |
| C₃H₇—⟨CH⟩—CH₂CH₂—⟨Ph⟩—C≡C—⟨Ph⟩—C₂H₅ | | 2 wt. % |
| C₃H₇—⟨CH⟩—CH₂CH₂—⟨Ph⟩—C≡C—⟨Ph⟩—C₃H₇ | | 3 wt. % |
| C₃H₇—⟨CH⟩—⟨Ph(3-F)⟩—C≡C—⟨Ph⟩—C₂H₅ | | 5 wt. % |

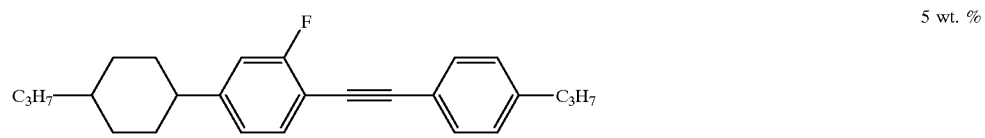
5 wt. %
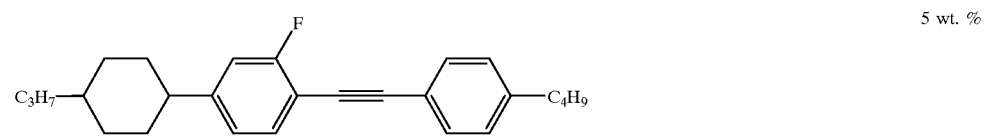
5 wt. %
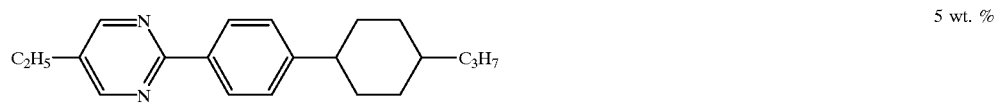
5 wt. %
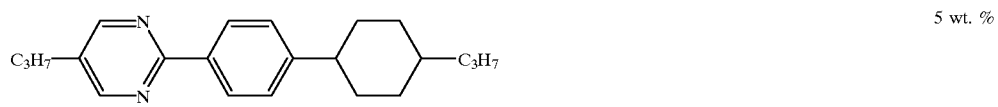
5 wt. %
Composition Example 16
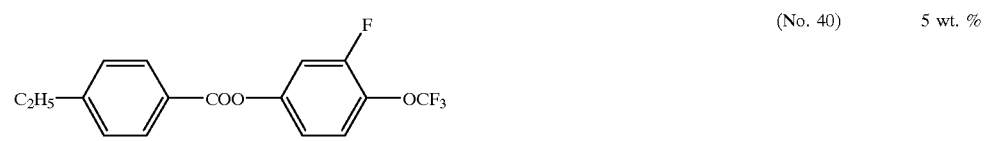
(No. 40)   5 wt. %
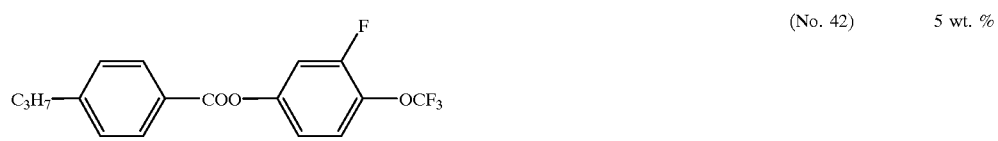
(No. 42)   5 wt. %
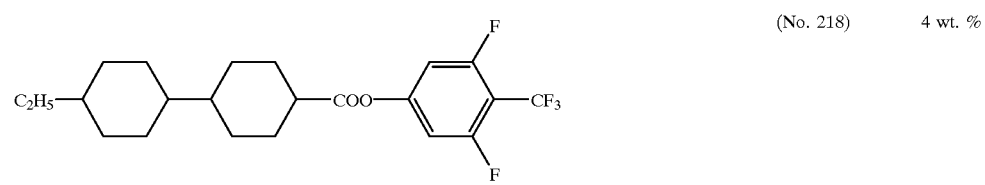
(No. 218)  4 wt. %
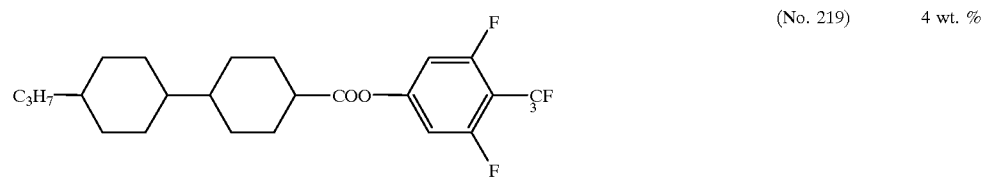
(No. 219)  4 wt. %
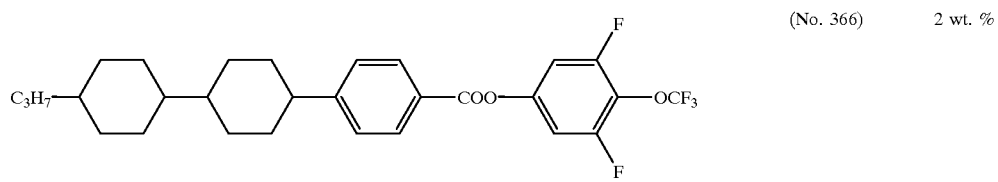
(No. 366)  2 wt. %
5 wt. %

-continued

| | |
|---|---|
| C₂H₄=C₃H₅—⟨cyclohexyl⟩—⟨phenyl⟩—CN | 5 wt. % |
| C₃H₇—⟨cyclohexyl⟩—⟨phenyl⟩—CN | 10 wt. % |
| CH₃OCH₂—⟨cyclohexyl⟩—⟨phenyl⟩—CN | 7 wt. % |
| C₂H₅OCH₂—⟨cyclohexyl⟩—⟨phenyl⟩—CN | 4 wt. % |
| C₃H₇—⟨cyclohexyl⟩—⟨cyclohexyl⟩—C₄H₉ | 10 wt. % |
| CH₃OCH₂—⟨cyclohexyl⟩—⟨cyclohexyl⟩—C₅H₁₁ | 8 wt. % |
| C₂H₅—⟨phenyl⟩—C≡C—⟨phenyl⟩—OCH₃ | 10 wt. % |
| C₂H₅—⟨cyclohexyl⟩—⟨cyclohexyl⟩—⟨phenyl⟩—CN | 3 wt. % |
| C₃H₇—⟨cyclohexyl⟩—⟨cyclohexyl⟩—⟨phenyl⟩—CN | 3 wt. % |
| C₃H₇—⟨cyclohexyl⟩—⟨cyclohexyl⟩—⟨phenyl⟩—CH₃ | 8 wt. % |
| C₃H₇—⟨cyclohexyl⟩—⟨cyclohexyl⟩—⟨phenyl⟩—C₃H₇ | 7 wt. % |

Composition Example 17

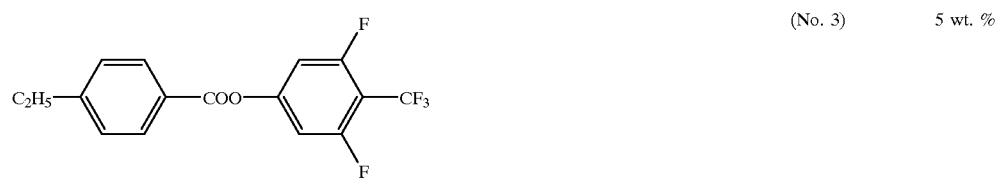

(No. 3)  5 wt. %

-continued
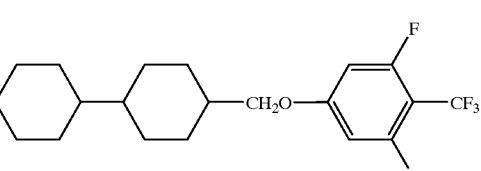 (No. 5) 5 wt. %
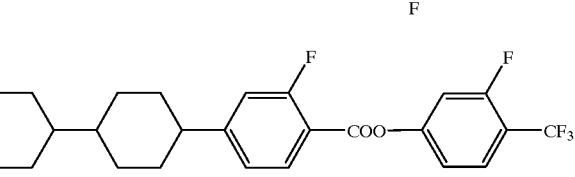 (No. 424) 6 wt. %
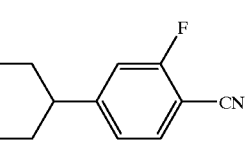 (No. 354) 2 wt. %
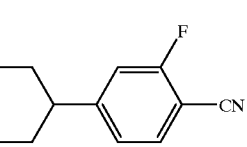 10 wt. %
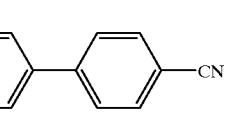 10 wt. %
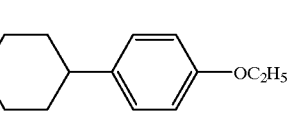 2 wt. %
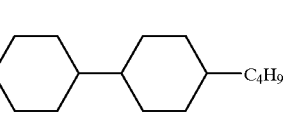 8 wt. %
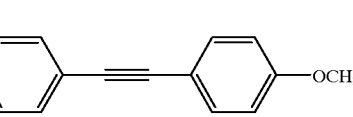 10 wt. %
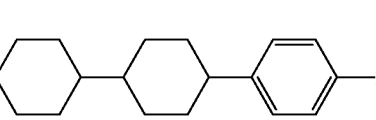 10 wt. %
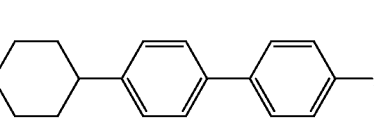 2 wt. %
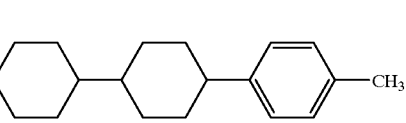 2 wt. %
 14 wt. %

-continued

C₃H₇—⌬—⌬—⌬—C₃H₇  4 wt. %

C₃H₇—⌬—⌬—⌬—OCH₃  4 wt. %

C₃H₇—⌬—CH₂CH₂—⌬—C≡C—⌬—C₂H₅  3 wt. %

C₃H₇—⌬—CH₂CH₂—⌬—C≡C—⌬—C₄H₉  3 wt. %

Composition Example 18

C₅H₁₁—⌬—COO—⌬(F,F)—OCF₃  (No. 46)  5 wt. %

C₂H₅—⌬—⌬—COO—⌬(F,F)—OCF₃  (No. 238)  5 wt. %

C₃H₇—⌬—⌬—COO—⌬(F,F)—OCF₃  (No. 213)  4 wt. %

C₂H₅—⌬—⌬—COO—⌬(F)—CF₃  (No. 335)  3 wt. %

C₂H₄=C₃H₅—⌬—COO—⌬(F,F)—CN  10 wt. %

C₃H₇OCH₂—⌬—COO—⌬(F,F)—CN  10 wt. %

-continued

| Structure | Amount |
|---|---|
| C₂H₅–(Cy)–(Ph)–CN | 10 wt. % |
| C₃H₇–(Cy)–(Ph)–CN | 15 wt. % |
| C₂H₅–(Pyrimidine)–(Ph)–F | 2 wt. % |
| C₃H₇–(Cy)–(Ph)–OC₂H₅ | 7 wt. % |
| C₃H₇–(Cy)–(Cy)–(Ph)–CH₃ | 5 wt. % |
| C₃H₇–(Cy)–(Cy)–(Cy)–OCH₃ | 4 wt. % |
| C₃H₇–(Cy)–CH₂CH₂–(Ph)–C≡C–(Ph)–C₂H₅ | 3 wt. % |
| C₃H₇–(Cy)–CH₂CH₂–(Ph)–C≡C–(Ph)–C₃H₇ | 2 wt. % |
| C₃H₇–(Cy)–COO–(Ph)–COO–(Ph)–F | 3 wt. % |
| C₂H₅–(Cy)–(Cy)–(Ph)–CN | 3 wt. % |
| C₃H₇–(Cy)–(Cy)–(Ph)–CN | 3 wt. % |
| C₄H₉–(Cy)–(Cy)–(Ph)–CN | 4 wt. % |
| C₃H₇–(Cy)–COO–(Ph)–COO–(Ph)–C₂H₅ | 2 wt. % |

-continued

Composition Example 19

C₂H₅—⟨C₆H₄⟩—COO—⟨C₆H₃(F)⟩—CF₃ (No. 2) 5 wt. %

C₃H₇—⟨Cy⟩—⟨C₆H₃(F)⟩—COO—⟨C₆H₂(F)(F)⟩—CN (No. 206) 5 wt. %

C₃H₇—⟨Cy⟩—⟨C₆H₂(F)(F)⟩—COO—⟨C₆H₃(F)⟩—CF₃ (No. 180) 3 wt. %

C₂H₅—⟨Cy⟩—COO—⟨C₆H₄⟩—⟨C₆H₂(F)(F)⟩—CF₃ (No. 309) 5 wt. %

C₂H₅—⟨Cy⟩—⟨Cy⟩—⟨C₆H₄⟩—CN (No. 367) 3 wt. %

C₅H₁₁—⟨C₆H₄⟩—⟨C₆H₄⟩—CN  4 wt. %

CH₃O—⟨C₆H₄⟩—COO—⟨C₆H₄⟩—C₂H₅  2 wt. %

C₃H₇—⟨Cy⟩—⟨C₆H₄⟩—OC₂H₅  10 wt. %

C₃H₇—⟨Cy⟩—⟨C₆H₄⟩—OC₄H₉  10 wt. %

C₂H₅—⟨Pyrimidine⟩—⟨C₆H₄⟩—C₂H₅  5 wt. %

C₃H₇—⟨Pyrimidine⟩—⟨C₆H₄⟩—C₂H₅  5 wt. %

-continued
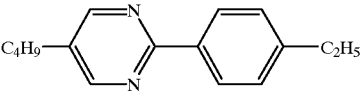 5 wt. %
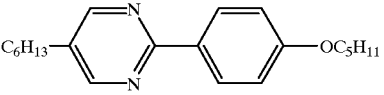 3 wt. %
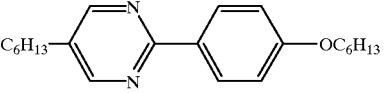 3 wt. %
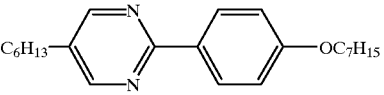 3 wt. %
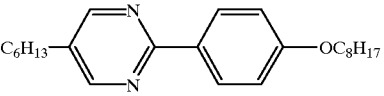 3 wt. %
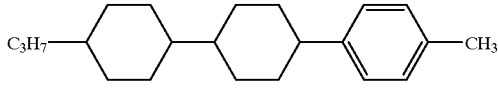 7 wt. %
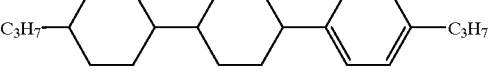 9 wt. %
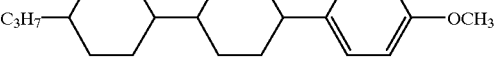 4 wt. %
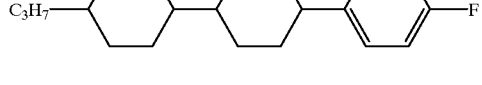 2 wt. %
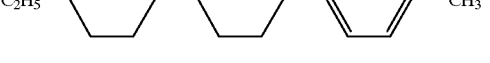 2 wt. %
Composition Example 20
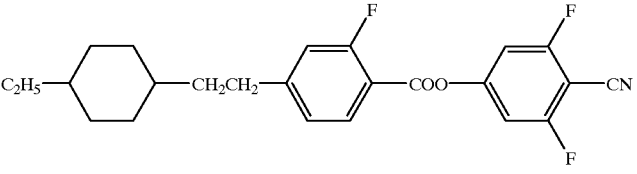 (No. 276) 5 wt. %
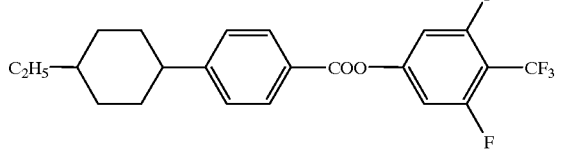 (No. 174) 5 wt. %

-continued

| Structure | | |
|---|---|---|
| C₃H₇–(cyclohexyl)–(phenyl)–COO–(3,5-difluoro-4-CF₃-phenyl) | (No. 175) | 5 wt. % |
| C₂H₅–(phenyl)–(phenyl)–COO–(3-fluoro-4-OCF₃-phenyl) | (No. 343) | 2 wt. % |
| C₅H₁₁–(pyrimidine)–(3,4-difluorophenyl) | | 8 wt. % |
| C₃H₇–(dioxane)–(phenyl)–CN | | 8 wt. % |
| C₄H₉–(dioxane)–(phenyl)–CN | | 8 wt. % |
| C₅H₁₁–(dioxane)–(phenyl)–CN | | 6 wt. % |
| C₂H₅–(phenyl)–COO–(phenyl)–CN | | 8 wt. % |
| C₂H₅–(pyrimidine)–(phenyl)–C₂H₅ | | 1 wt. % |
| C₃H₇–(pyrimidine)–(phenyl)–C₂H₅ | | 1 wt. % |
| C₄H₉–(pyrimidine)–(phenyl)–C₂H₅ | | 1 wt. % |
| C₃H₇–(cyclohexyl)–COO–(phenyl)–OC₄H₉ | | 5 wt. % |
| C₄H₉–(cyclohexyl)–COO–(phenyl)–OC₂H₅ | | 5 wt. % |

-continued

| | |
|---|---|
| C₄H₉—⬡—COO—◯—C₃H₇ | 5 wt. % |
| C₄H₉—⬡—COO—◯—C₄H₉ | 5 wt. % |
| C₃H₇—[pyrimidine]—◯—◯—F | 2 wt. % |
| C₃H₇—⬡—⬡—◯—C₃H₇ | 10 wt. % |
| C₃H₇—⬡—⬡—◯—OCH₃ | 4 wt. % |
| C₂H₅—[pyrimidine]—◯—⬡—C₃H₇ | 3 wt. % |
| C₂H₅—[pyrimidine]—◯—◯—C₃H₇ | 3 wt. % |

Composition Example 21

| | | |
|---|---|---|
| C₂H₅—⬡—◯—COO—◯(F)—OCF₃ | (No. 189) | 6 wt. % |
| C₃H₇—⬡—◯—COO—◯(F)—OCF₃ | (No. 173) | 6 wt. % |
| C₃H₇—⬡—◯(F)—COO—◯(F,F)—CF₃ | (No. 177) | 4 wt. % |
| C₅H₁₁—⬡—◯(F)—COO—◯(F,F)—CF₃ | (No. 178) | 4 wt. % |

-continued
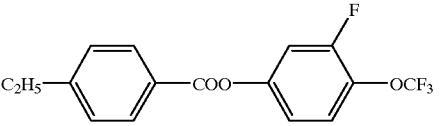 (No. 40) 5 wt. %
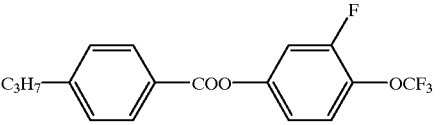 (No. 42) 4 wt. %
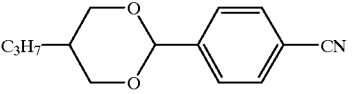 6 wt. %
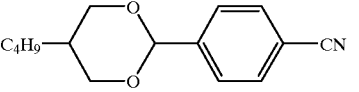 6 wt. %
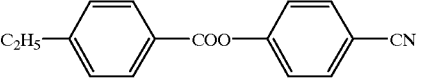 10 wt. %
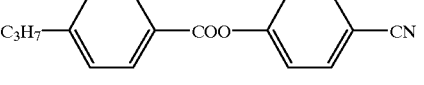 4 wt. %
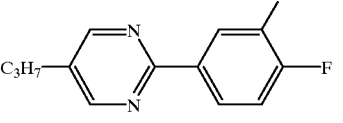 5 wt. %
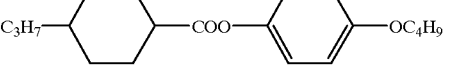 8 wt. %
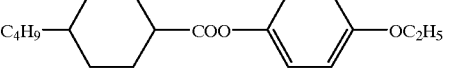 6 wt. %
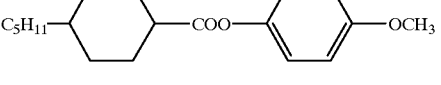 6 wt. %
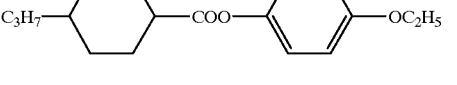 5 wt. %
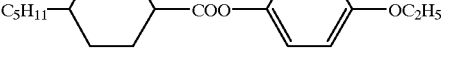 4 wt. %
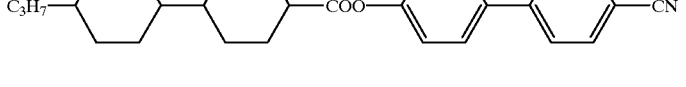 2 wt. %

-continued
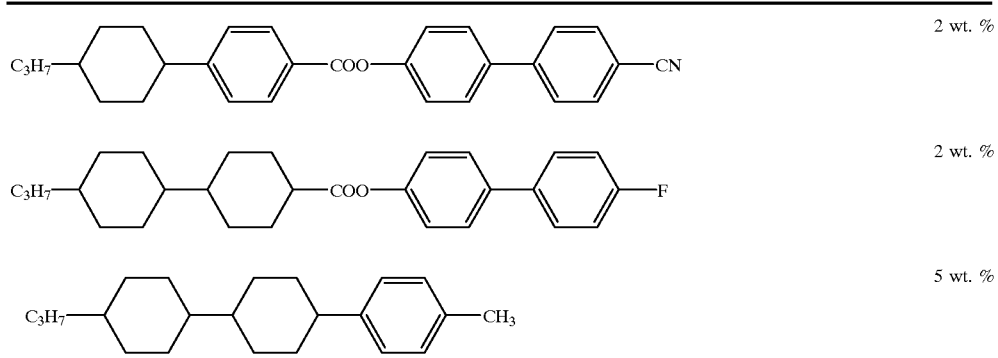
| | |
|---|---|
| | 2 wt. % |
| | 2 wt. % |
| | 5 wt. % |
Composition Example 22
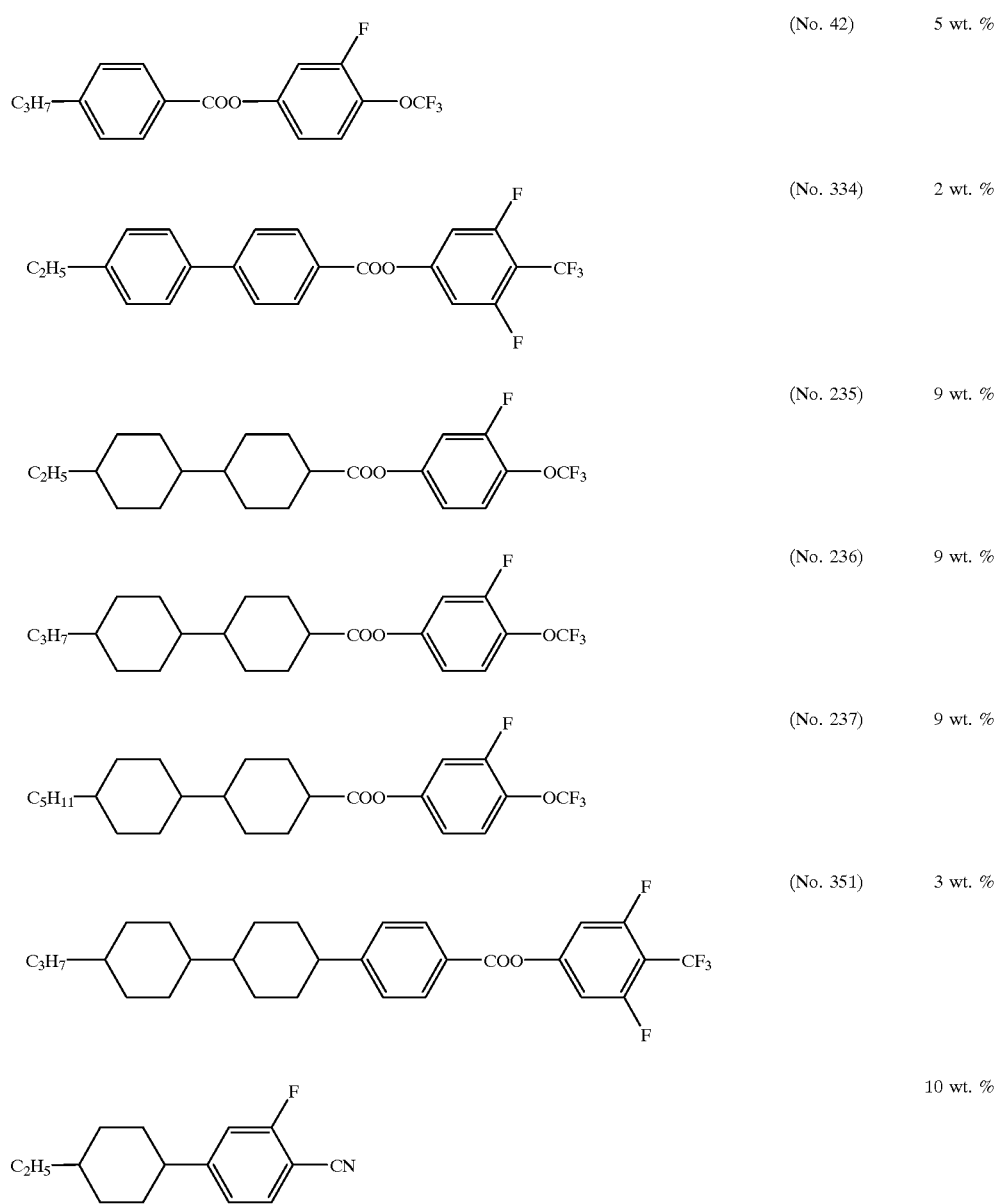
| | | |
|---|---|---|
| (No. 42) | 5 wt. % |
| (No. 334) | 2 wt. % |
| (No. 235) | 9 wt. % |
| (No. 236) | 9 wt. % |
| (No. 237) | 9 wt. % |
| (No. 351) | 3 wt. % |
| | 10 wt. % |

-continued
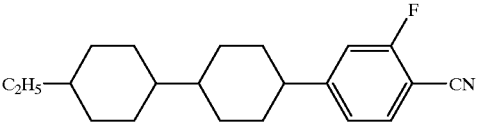 10 wt. %
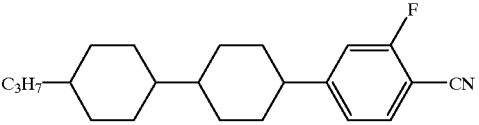 10 wt. %
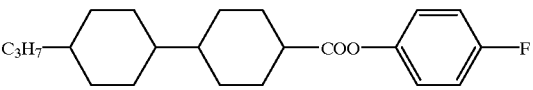 3 wt. %
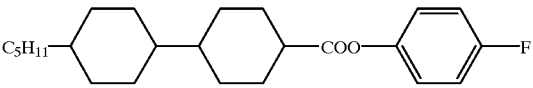 3 wt. %
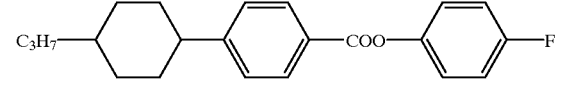 3 wt. %
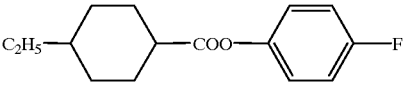 2 wt. %
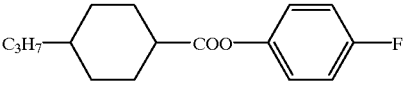 2 wt. %
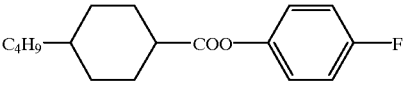 2 wt. %
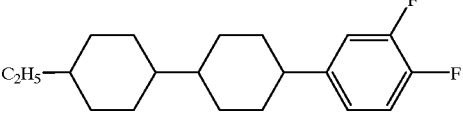 6 wt. %
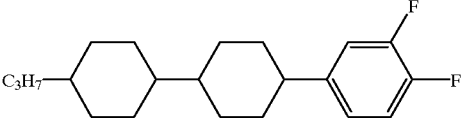 6 wt. %
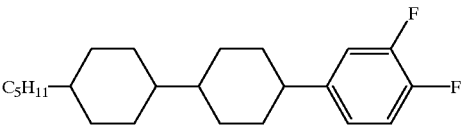 6 wt. %

-continued
Composition Example 23
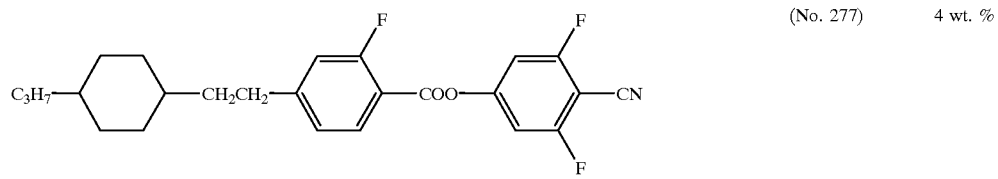 (No. 277) 4 wt. %
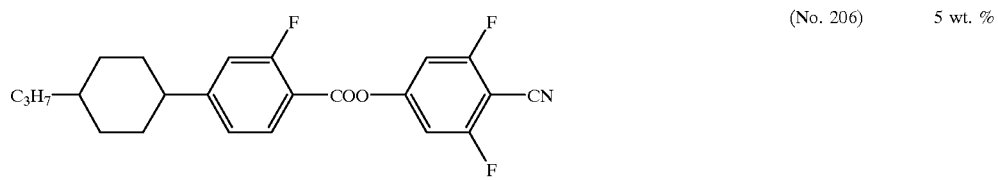 (No. 206) 5 wt. %
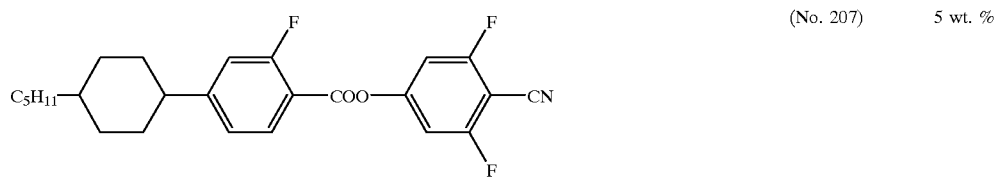 (No. 207) 5 wt. %
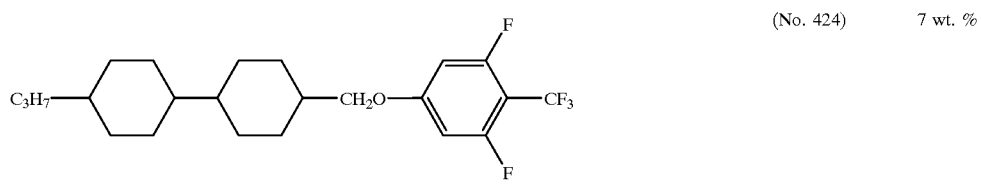 (No. 424) 7 wt. %
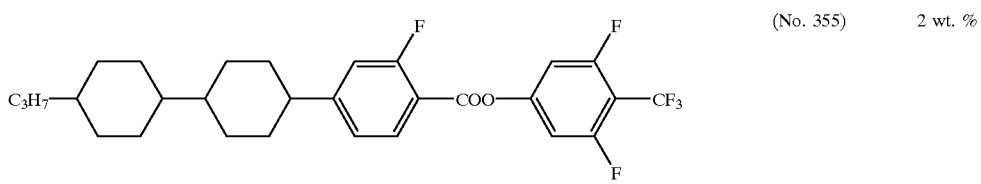 (No. 355) 2 wt. %
 8 wt. %
 7 wt. %
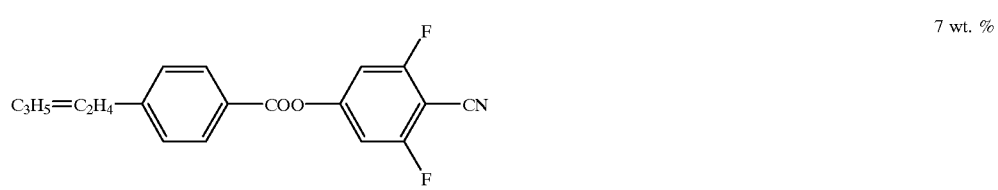 7 wt. %
 6 wt. %

-continued

| | |
|---|---|
| C₄H₉—⟨Cy⟩—C≡C—⟨Ph⟩—OC₂H₅ | 6 wt. % |
| C₅H₁₁—⟨Ph⟩—C≡C—⟨Ph⟩—OCH₃ | 6 wt. % |
| C₃H₇—⟨Cy⟩—⟨Cy⟩—C₄H₉ | 6 wt. % |
| C₃H₇—⟨Cy⟩—CH₂CH₂—⟨Ph⟩—C≡C—⟨Ph⟩—C₂H₅ | 4 wt. % |
| C₃H₇—⟨Cy⟩—CH₂CH₂—⟨Ph⟩—C≡C—⟨Ph⟩—C₃H₇ | 4 wt. % |
| C₃H₇—⟨Cy⟩—CH₂CH₂—⟨Ph⟩—C≡C—⟨Ph⟩—C₄H₉ | 4 wt. % |
| C₂H₅—⟨Cy⟩—CH₂CH₂—⟨Ph⟩—C≡C—⟨Ph⟩—C₂H₅ | 4 wt. % |
| C₃H₇—⟨Cy⟩—⟨Ph(3-F)⟩—C≡C—⟨Ph⟩—C₂H₅ | 5 wt. % |
| C₃H₇—⟨Cy⟩—⟨Ph(3-F)⟩—C≡C—⟨Ph⟩—C₃H₇ | 5 wt. % |
| C₃H₇—⟨Cy⟩—⟨Ph(3-F)⟩—C≡C—⟨Ph⟩—C₄H₉ | 5 wt. % |

Composition Example 24

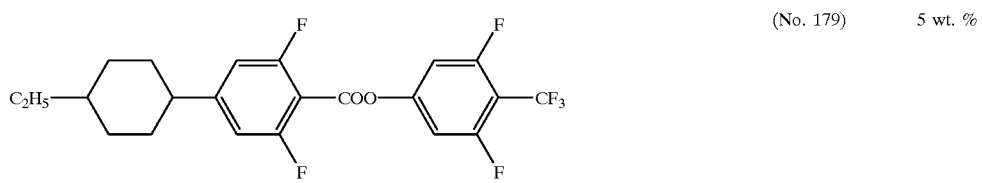

(No. 179)  5 wt. %

-continued
| Structure | No. | wt% |
|---|---|---|
| 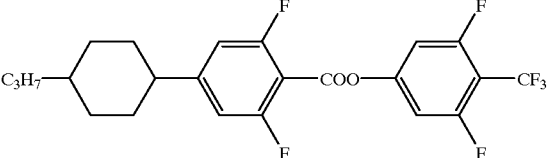 | (No. 181) | 5 wt. % |
| 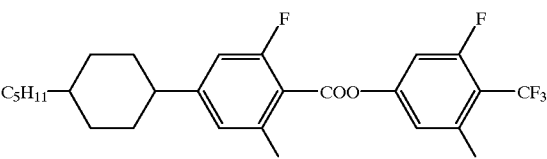 | (No. 182) | 5 wt. % |
| 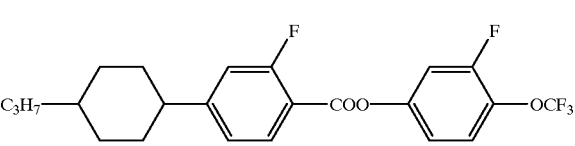 | (no. 195) | 5 wt. % |
| 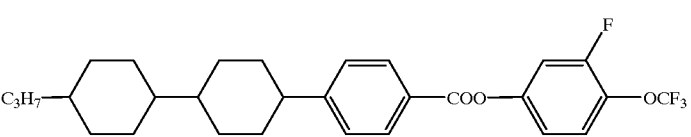 | (No. 365) | 2 wt. % |
|  | | 4 wt. % |
| 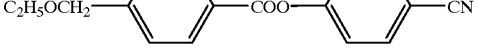 | | 5 wt. % |
|  | | 4 wt. % |
| 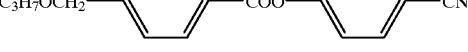 | | 10 wt. % |
|  | | 10 wt. % |
| 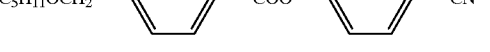 | | 5 wt. % |

-continued

| Structure | Amount |
|---|---|
| C₃H₇–(Cy)–(Cy)–COO–(Ph)–F | 3 wt. % |
| C₅H₁₁–(Cy)–(Cy)–COO–(Ph)–F | 3 wt. % |
| C₃H₇–(Cy)–(Ph)–COO–(Ph)–F | 3 wt. % |
| C₃H₇–(Cy)–(Cy)–(Ph)–F | 5 wt. % |
| C₃H₇–(Cy)–(Cy)–(Ph)–CH₃ | 6 wt. % |
| C₃H₇–(Cy)–(Cy)–(Ph)–C₃H₇ | 5 wt. % |
| C₃H₇–(Cy)–(Cy)–(Ph)–OCH₃ | 4 wt. % |
| C₃H₇–(Cy)–CH₂CH₂–(Ph)–C≡C–(Ph)–C₂H₅ | 4 wt. % |
| C₃H₇–(Cy)–CH₂CH₂–(Ph)–C≡C–(Ph)–C₃H₇ | 3 wt. % |
| C₃H₇–(Cy)–(Ph-3-F)–C≡C–(Ph)–C₂H₅ | 4 wt. % |

Composition Example 25

| Structure | No. | Amount |
|---|---|---|
| C₃H₇–(Ph)–COO–(Ph-3-F)–OCF₃ | (No. 42) | 5 wt. % |
| C₂H₅–(Cy)–(Cy)–COO–(Ph-3,5-F₂)–OCF₃ | (No. 235) | 8 wt. % |

-continued
| Structure | No. | wt% |
|---|---|---|
| 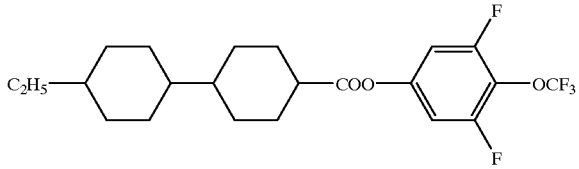 | (No. 236) | 8 wt. % |
| 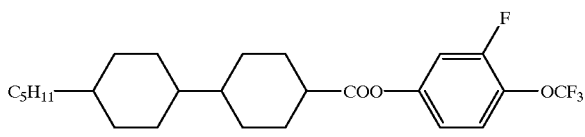 | (No. 237) | 7 wt. % |
| 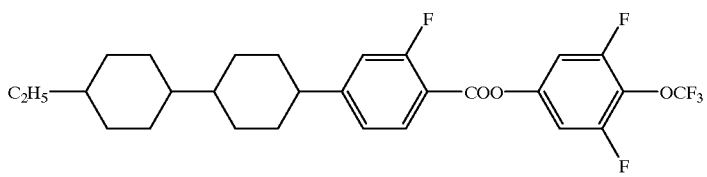 | (No. 355) | 5 wt. % |
| 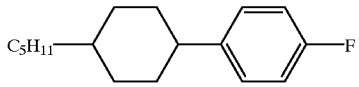 | | 10 wt. % |
| 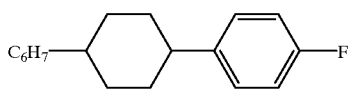 | | 10 wt. % |
|  | | 10 wt. % |
|  | | 7 wt. % |
| 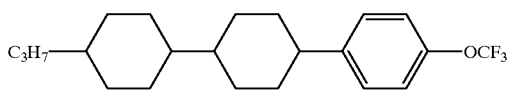 | | 7 wt. % |
| 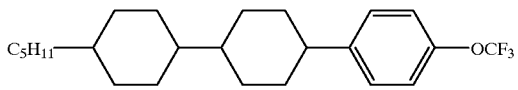 | | 7 wt. % |
| 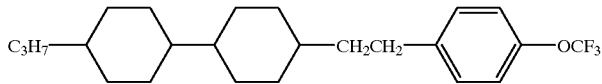 | | 6 wt. % |
| 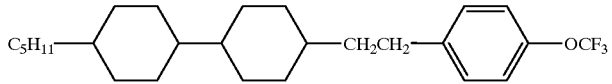 | | 5 wt. % |
| 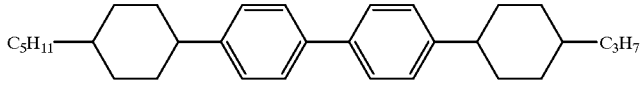 | | 5 wt. % |

-continued
Composition Example 26
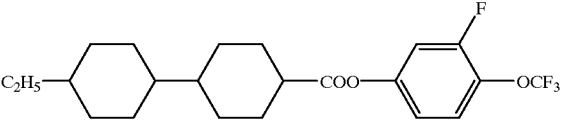 (No. 235) 5 wt. %
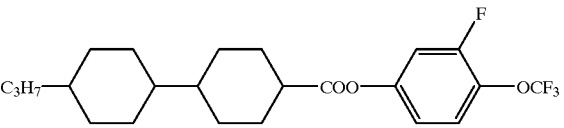 (No. 236) 5 wt. %
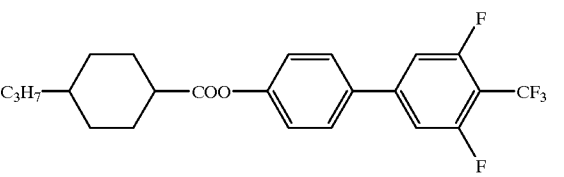 (No. 310) 5 wt. %
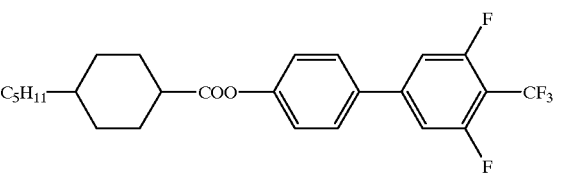 (no. 311) 5 wt. %
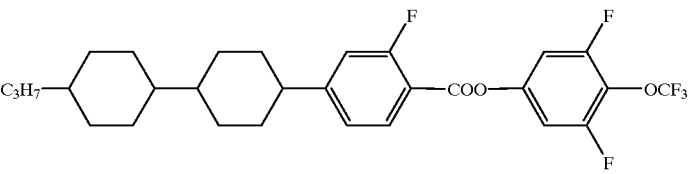 (No. 368) 2 wt. %
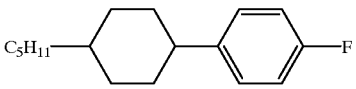 7 wt. %
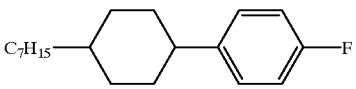 6 wt. %
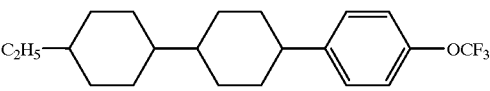 10 wt. %
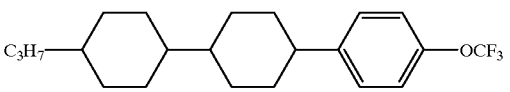 10 wt. %
 5 wt. %

-continued
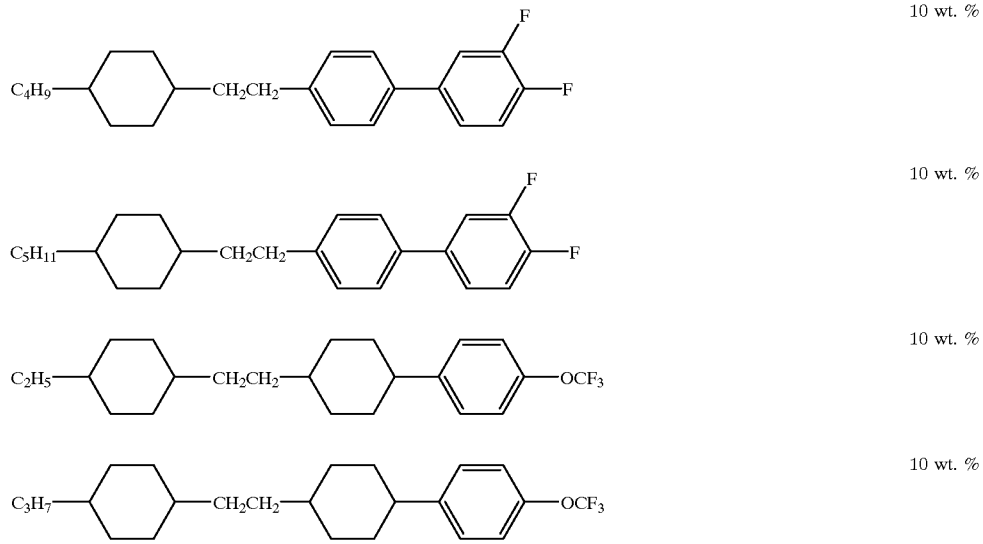
10 wt. %
10 wt. %
10 wt. %
10 wt. %
Composition Example 27
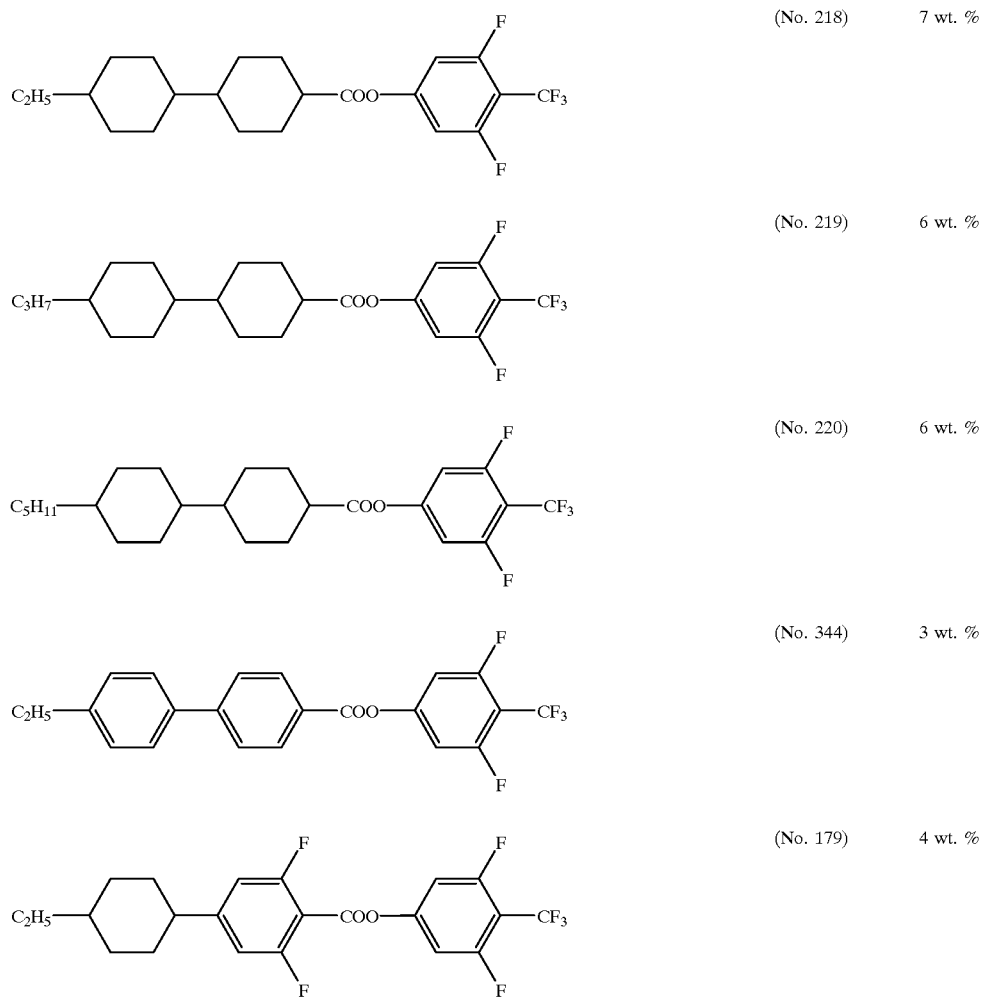
(No. 218)  7 wt. %
(No. 219)  6 wt. %
(No. 220)  6 wt. %
(No. 344)  3 wt. %
(No. 179)  4 wt. %

-continued
| | | |
|---|---|---|
| 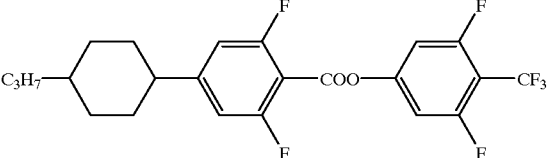 | (No. 181) | 4 wt. % |
| 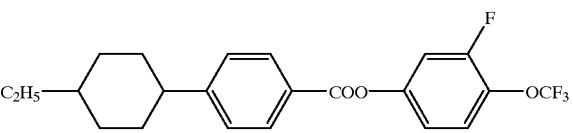 | (No. 189) | 3 wt. % |
| 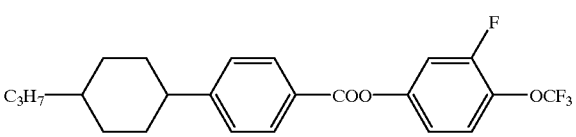 | (No. 173) | 3 wt. % |
| 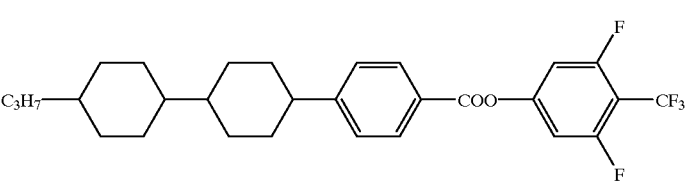 | (No. 351) | 3 wt. % |
| 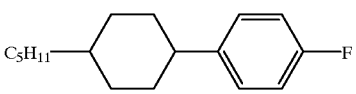 | | 10 wt. % |
| 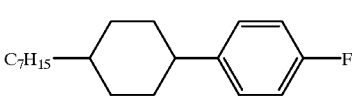 | | 7 wt. % |
| 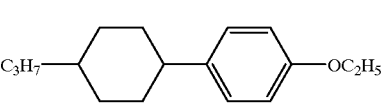 | | 4 wt. % |
| 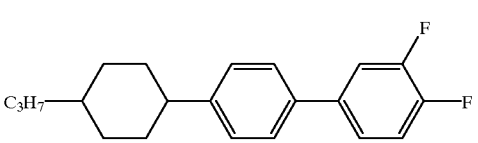 | | 13 wt. % |
| 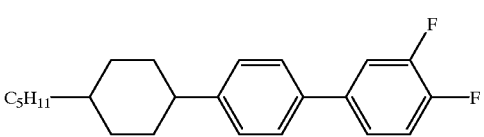 | | 13 wt. % |
| 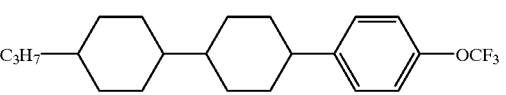 | | 7 wt. % |
| 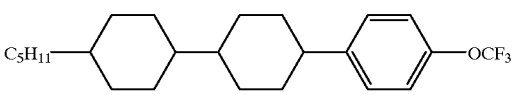 | | 7 wt. % |

Composition Example 28
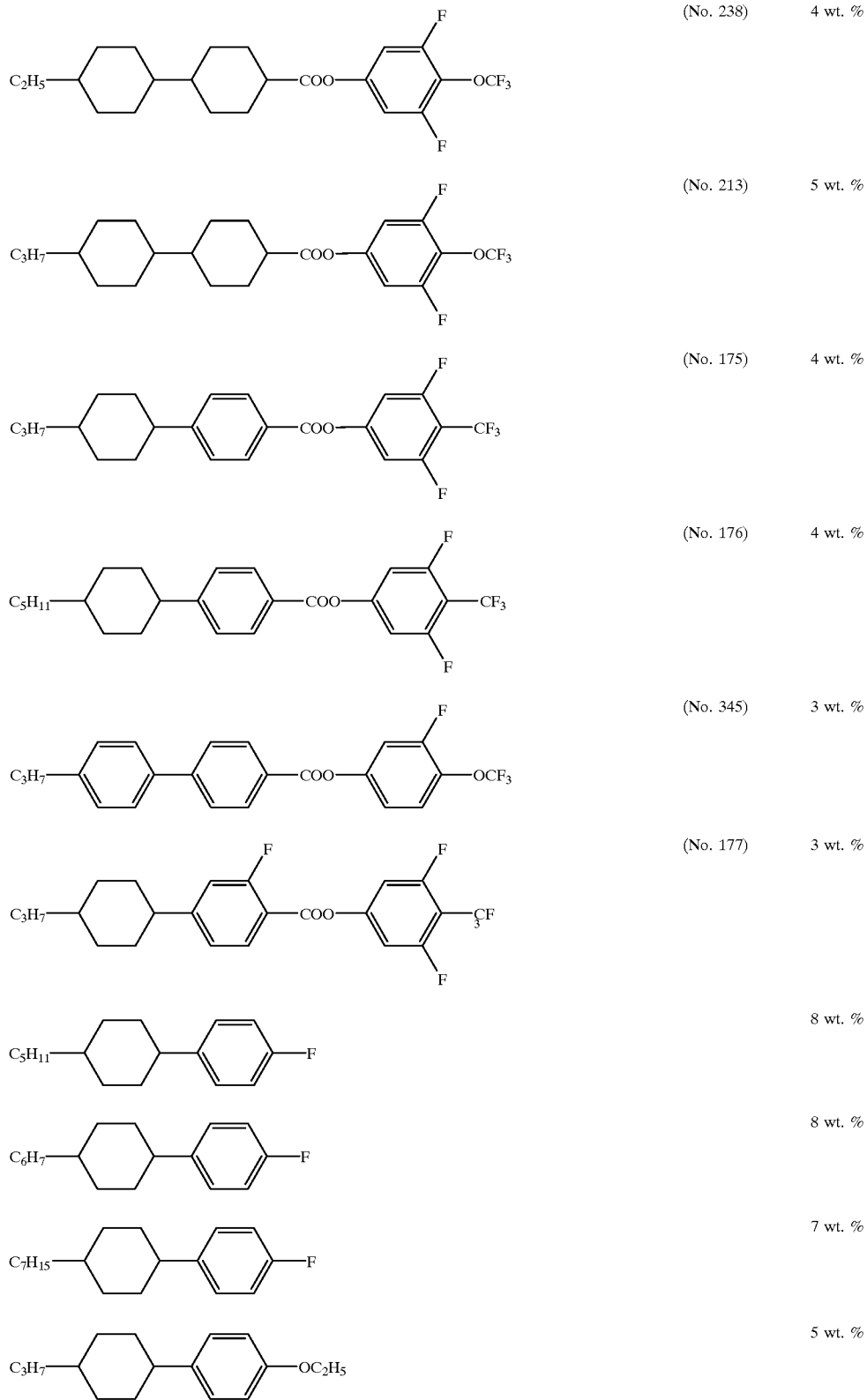
| | |
|---|---|
| (No. 238) | 4 wt. % |
| (No. 213) | 5 wt. % |
| (No. 175) | 4 wt. % |
| (No. 176) | 4 wt. % |
| (No. 345) | 3 wt. % |
| (No. 177) | 3 wt. % |
| | 8 wt. % |
| | 8 wt. % |
| | 7 wt. % |
| | 5 wt. % |

-continued

| Structure | Amount |
|---|---|
| C₃H₇–(Cy)–(Ph)–OC₄H₉ | 4 wt. % |
| C₂H₅–(Cy)–(Cy)–(Ph)–OCF₃ | 7 wt. % |
| C₃H₇–(Cy)–(Cy)–(Ph)–OCF₃ | 7 wt. % |
| C₅H₁₁–(Cy)–(Cy)–(Ph)–OCF₃ | 7 wt. % |
| C₃H₇–(Cy)–(Cy)–CH₂CH₂–(Ph)–OCF₃ | 2 wt. % |
| C₅H₁₁–(Cy)–(Cy)–CH₂CH₂–(Ph)–OCF₃ | 2 wt. % |
| C₃H₇–(Cy)–(Ph)–(Ph-3,4-F₂) | 8 wt. % |
| C₅H₁₁–(Cy)–(Ph)–(Ph-3,4-F₂) | 8 wt. % |
| C₅H₁₁–(Cy)–(Ph)–(Ph)–(Cy)–C₃H₇ | 4 wt. % |

Composition Example 29

| Structure | | Amount |
|---|---|---|
| C₂H₅–(Cy)–COO–(Ph-3,5-F₂-4-CF₃) | (No. 3) | 5 wt. % |
| C₃H₇–(Cy)–COO–(Ph-3,5-F₂-4-CF₃) | (No. 5) | 4 wt. % |

-continued
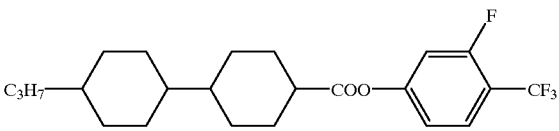 (No. 215) 3 wt. %
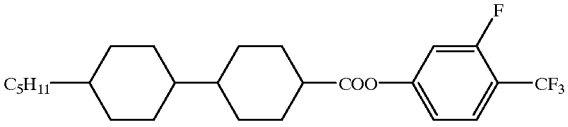 (No. 216) 3 wt. %
 5 wt. %
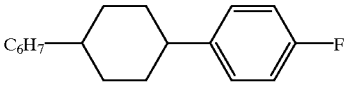 5 wt. %
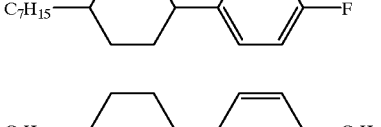 4 wt. %
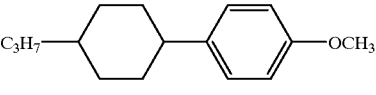 5 wt. %
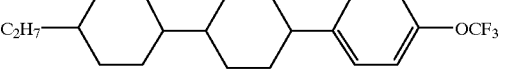 4 wt. %
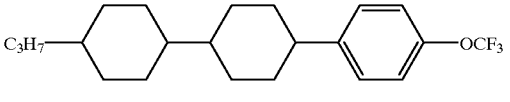 6 wt. %
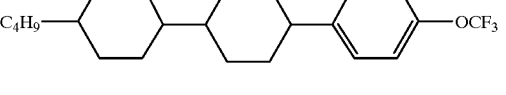 6 wt. %
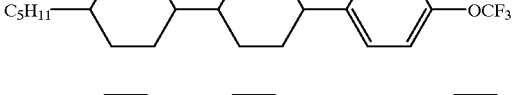 6 wt. %
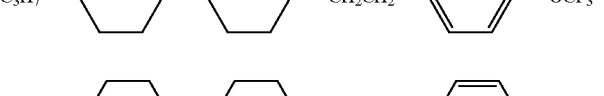 4 wt. %
 2 wt. %
 2 wt. %

-continued
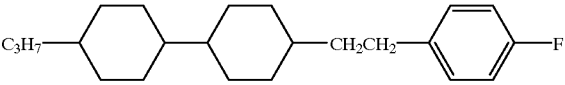 4 wt. %
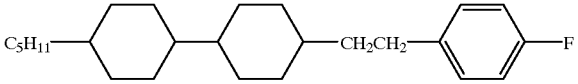 3 wt. %
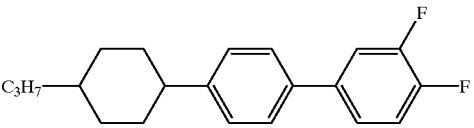 5 wt. %
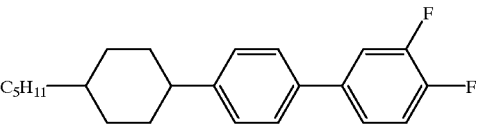 6 wt. %
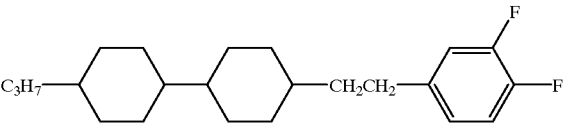 6 wt. %
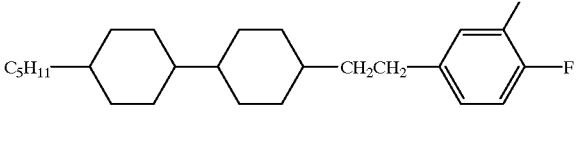 6 wt. %
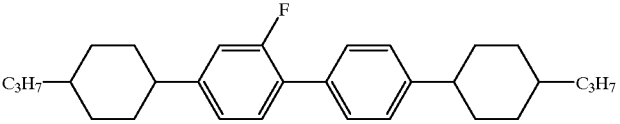 2 wt. %
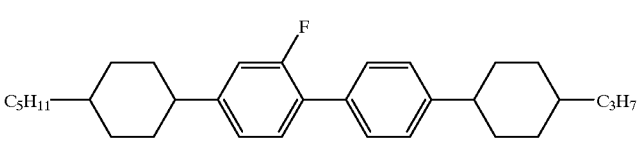 2 wt. %
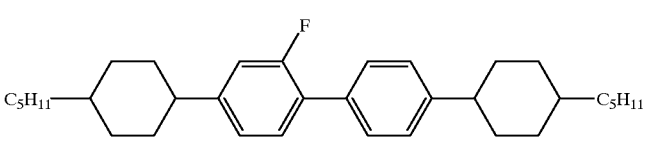 2 wt. %
Composition Example 30
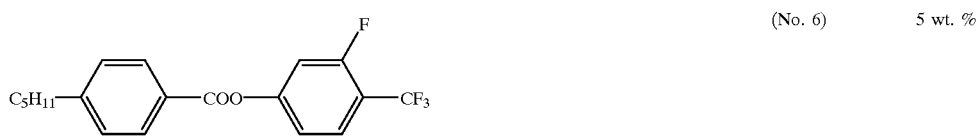 (No. 6) 5 wt. %

-continued

| Structure | No. | wt% |
|---|---|---|
| C₂H₅–⟨phenyl⟩–⟨phenyl⟩–COO–⟨phenyl(F,F)⟩–CF₃ | (No. 334) | 3 wt. % |
| C₂H₅–⟨cyclohexyl⟩–⟨phenyl(F,F)⟩–COO–⟨phenyl(F,F)⟩–CF₃ | (No. 179) | 3 wt. % |
| C₂H₅–⟨cyclohexyl⟩–⟨phenyl(F,F)⟩–COO–⟨phenyl(F,F)⟩–CF₃ | (No. 180) | 3 wt. % |
| C₃H₇–⟨cyclohexyl⟩–⟨cyclohexyl⟩–⟨phenyl(F)⟩–COO–⟨phenyl(F)⟩–CF₃ | (No. 354) | 3 wt. % |
| C₃H₇–⟨cyclohexyl⟩–⟨cyclohexyl⟩–CH₂O–⟨phenyl(F,F)⟩–CF₃ | (No. 424) | 3 wt. % |
| C₅H₁₁–⟨cyclohexyl⟩–⟨phenyl⟩–F | | 5 wt. % |
| C₃H₇–⟨cyclohexyl⟩–⟨cyclohexyl⟩–OCH₃ | | 4 wt. % |
| C₃H₇–⟨cyclohexyl⟩–⟨cyclohexyl⟩–OC₃H₇ | | 4 wt. % |
| C₅H₁₁–⟨cyclohexyl⟩–⟨cyclohexyl⟩–OCH₃ | | 4 wt. % |
| C₃H₇–⟨cyclohexyl⟩–⟨cyclohexyl⟩–⟨phenyl⟩–OCF₂H | | 6 wt. % |
| C₅H₁₁–⟨cyclohexyl⟩–⟨cyclohexyl⟩–⟨phenyl⟩–OCF₂H | | 6 wt. % |

-continued
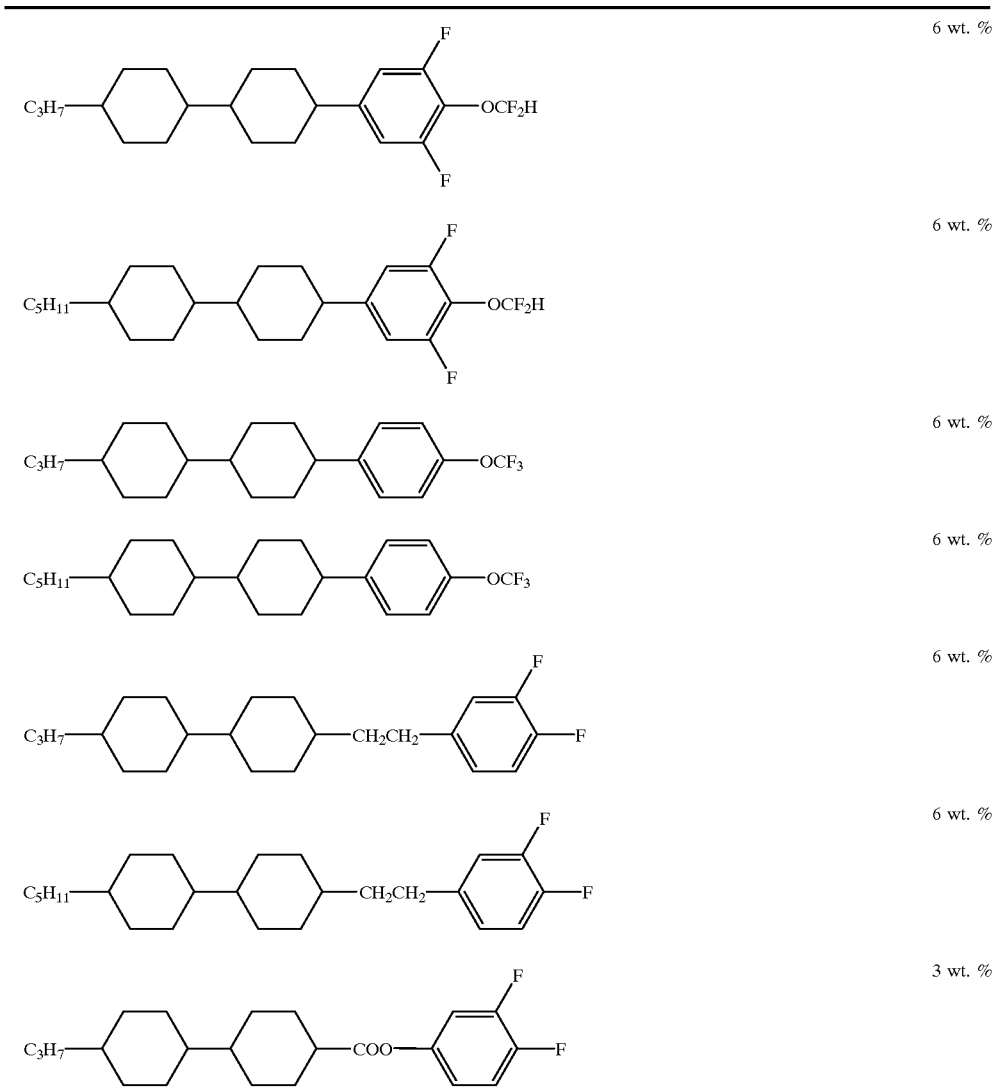
6 wt. %
6 wt. %
6 wt. %
6 wt. %
6 wt. %
6 wt. %
3 wt. %
Composition Example 31
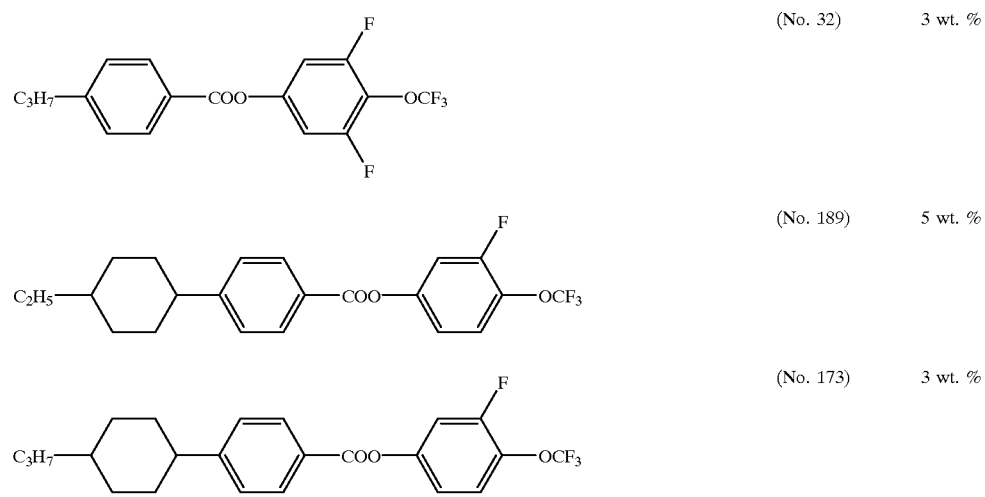
(No. 32)  3 wt. %
(No. 189)  5 wt. %
(No. 173)  3 wt. %

-continued
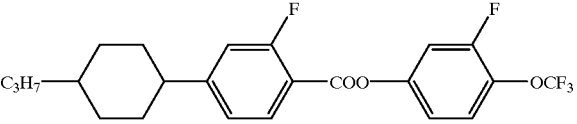 (No. 195) 4 wt. %
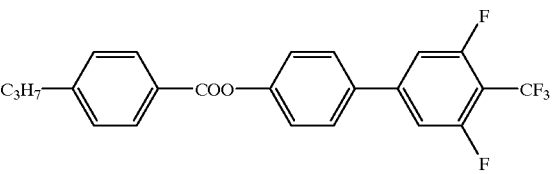 (No. 310) 4 wt. %
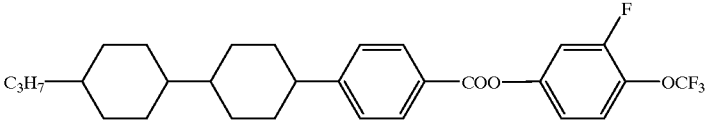 (No. 350) 2 wt. %
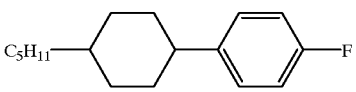 8 wt. %
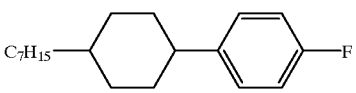 5 wt. %
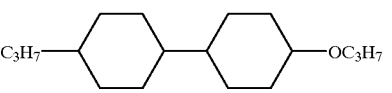 4 wt. %
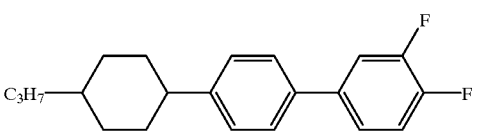 10 wt. %
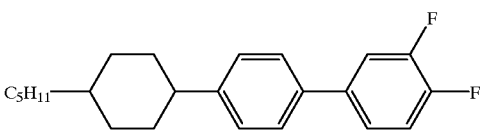 10 wt. %
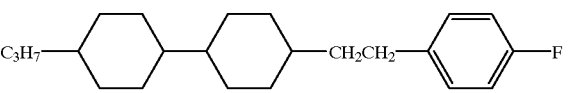 7 wt. %
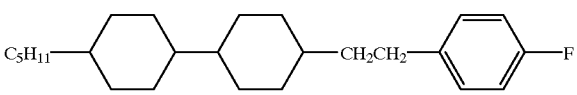 8 wt. %
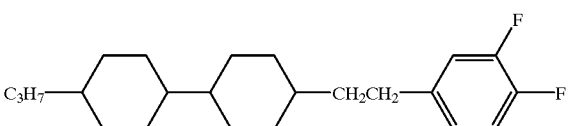 8 wt. %

-continued
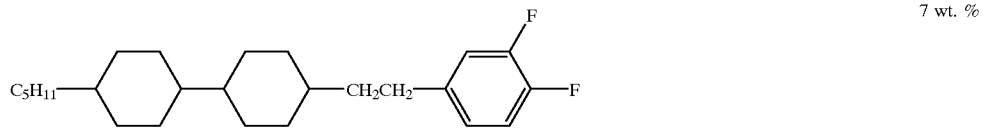 7 wt. %
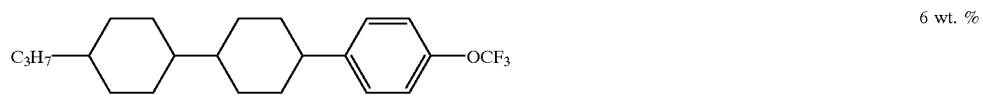 6 wt. %
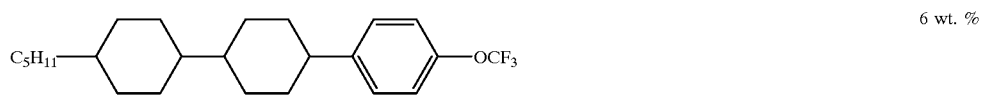 6 wt. %
Composition Example 32
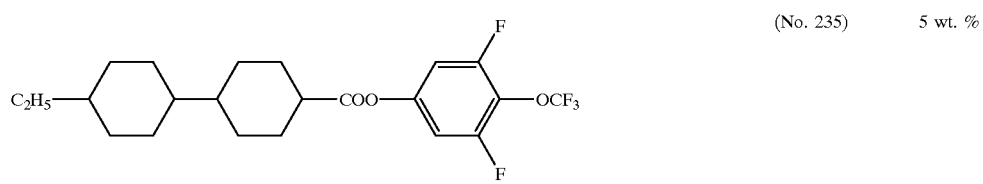 (No. 235) 5 wt. %
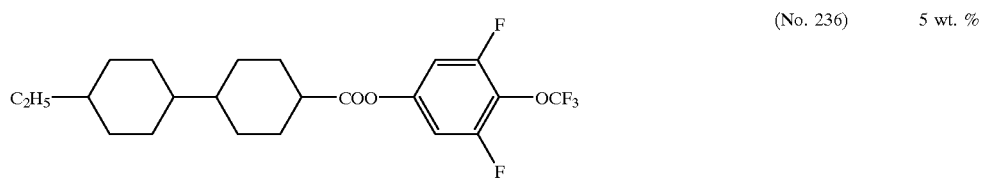 (No. 236) 5 wt. %
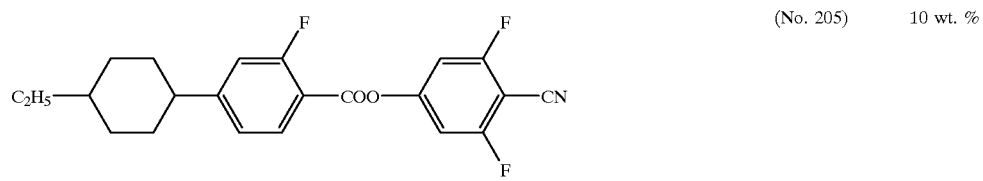 (No. 205) 10 wt. %
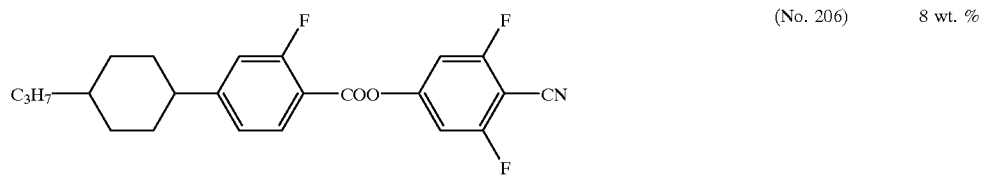 (No. 206) 8 wt. %
 7 wt. %
 5 wt. %
 5 wt. %

-continued
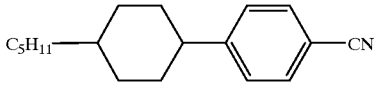 5 wt. %
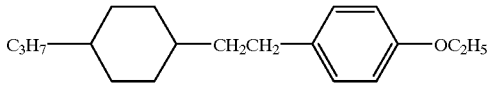 4 wt. %
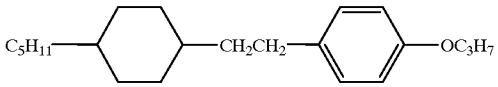 6 wt. %
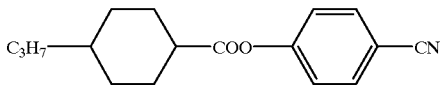 3 wt. %
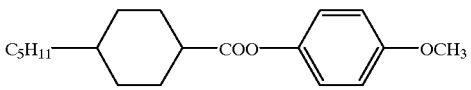 7 wt. %
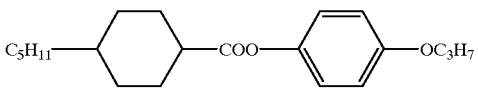 5 wt. %
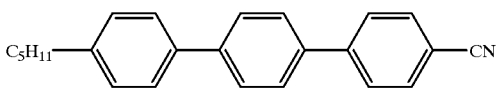 2 wt. %
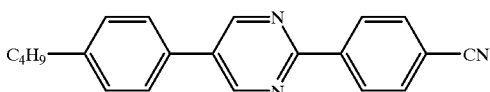 4 wt. %
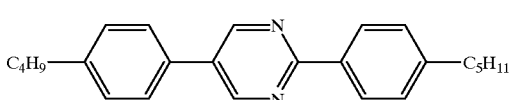 4 wt. %
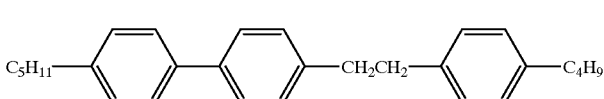 2 wt. %
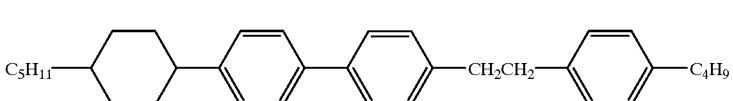 2 wt. %
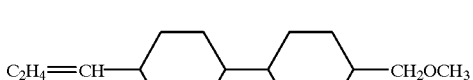 6 wt. %
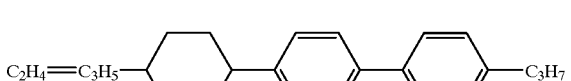 5 wt. %

-continued

Composition Example 33

| Structure | No. | Amount |
|---|---|---|
| C₂H₅–(Cy)–(Ph-2F)–COO–(Ph-3,5F)–CN | (No. 205) | 5 wt. % |
| C₃H₇–(Cy)–(Ph-2F)–COO–(Ph-3,5F)–CN | (No. 206) | 3 wt. % |
| C₂H₅–(Cy)–CH₂CH₂–(Ph-2F)–COO–(Ph-3,5F)–CN | (No. 276) | 5 wt. % |
| C₃H₇–(Cy)–CH₂CH₂–(Ph-2F)–COO–(Ph-3,5F)–CN | (No. 277) | 5 wt. % |
| C₄H₉–(Ph)–COO–(Ph-3,4F) | | 6 wt. % |
| C₅H₁₁–(Ph)–COO–(Ph-3,4F) | | 6 wt. % |
| C₂H₅–(Ph)–COO–(Ph-3F)–CN | | 4 wt. % |
| C₅H₁₁–(Ph)–COO–(Ph-3F)–F | | 3 wt. % |
| C₄H₉–(Ph)–COO–(Ph-3F)–CN | | 5 wt. % |

-continued
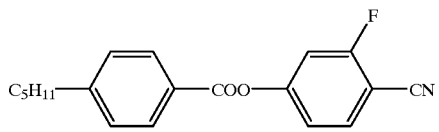 5 wt. %
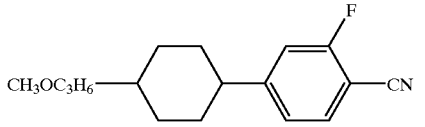 5 wt. %
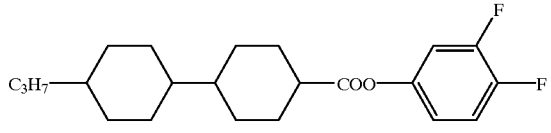 4 wt. %
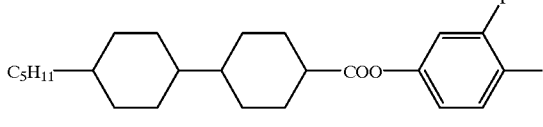 4 wt. %
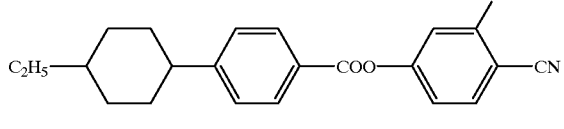 6 wt. %
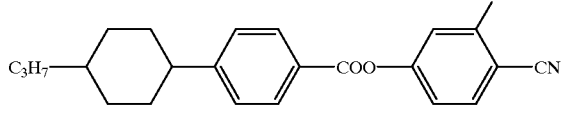 5 wt. %
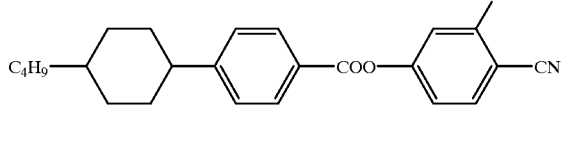 5 wt. %
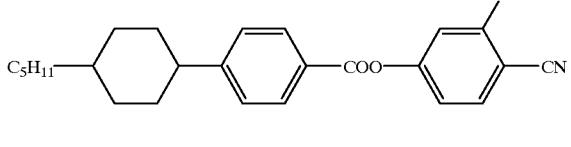 4 wt. %
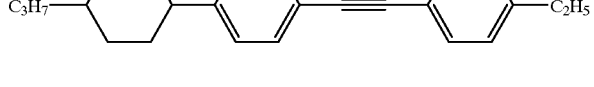 12 wt. %
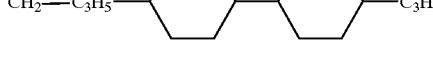 4 wt. %
 4 wt. %

-continued

Composition Example 34

| Structure | No. | wt% |
|---|---|---|
| C₂H₅–[Cy]–[Ph(F)]–COO–[Ph(F,F)]–CN | (No. 205) | 5 wt. % |
| C₃H₇–[Cy]–CH₂CH₂–[Ph(F)]–COO–[Ph(F,F)]–CN | (No. 277) | 5 wt. % |
| C₅H₁₁–[Cy]–CH₂CH₂–[Ph(F)]–COO–[Ph(F,F)]–CN | (No. 249) | 3 wt. % |
| C₂H₅–[Cy]–[Cy]–CH₂O–[Ph(F,F)]–CF₃ | (No. 425) | 8 wt. % |
| C₃H₇–[Cy]–[Cy]–CH₂O–[Ph(F,F)]–CF₃ | (No. 424) | 7 wt. % |
| C₂H₅–[Ph]–[Ph]–CN | | 10 wt. % |
| C₄H₉–[Ph]–[Ph]–CN | | 6 wt. % |
| C₂H₅–[Ph]–COO–[Ph]–CN | | 4 wt. % |
| C₄H₉–[Ph]–COO–[Ph]–CN | | 4 wt. % |
| C₅H₁₁–[Ph]–COO–[Ph]–CN | | 3 wt. % |

-continued
| | |
|---|---|
| C₂H₅—⟨⟩—COO—⟨F⟩—CN | 2 wt. % |
| C₃H₇—⟨⟩—COO—⟨F⟩—CN | 2 wt. % |
| C₄H₉—⟨⟩—COO—⟨F⟩—CN | 2 wt. % |
| C₃H₇—⟨H⟩—COO—⟨⟩—OC₂H₅ | 8 wt. % |
| C₄H₉—⟨H⟩—COO—⟨⟩—OC₂H₅ | 8 wt. % |
| C₅H₁₁—⟨H⟩—COO—⟨⟩—OCH₃ | 8 wt. % |
| C₃H₇—⟨H⟩—⟨H⟩—COO—⟨⟩—F,F | 4 wt. % |
| C₂H₅—⟨H⟩—⟨⟩—COO—⟨F⟩—CN | 4 wt. % |
| C₃H₇—⟨H⟩—⟨⟩—COO—⟨F⟩—CN | 5 wt. % |
| C₃H₇—⟨H⟩—⟨H⟩—COO—⟨⟩—⟨H⟩—C₃H₇ | 2 wt. % |
Composition Example 35
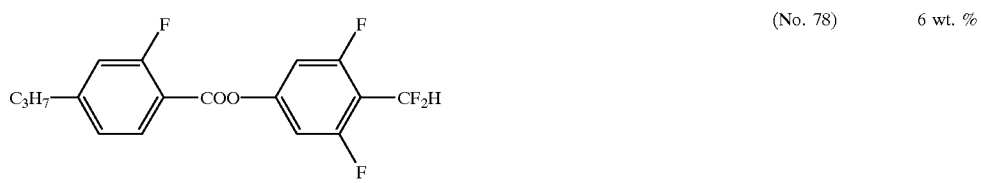 (No. 78) 6 wt. %

-continued
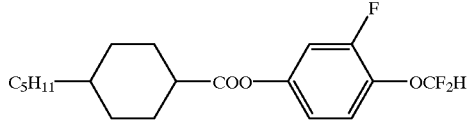 (No. 164) 4 wt. %
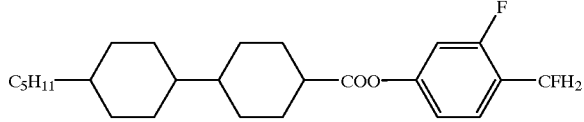 (No. 229) 6 wt. %
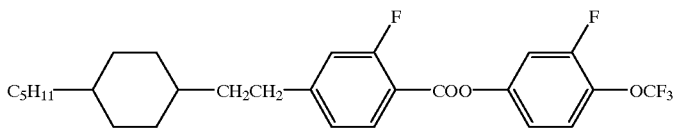 (No. 267) 6 wt. %
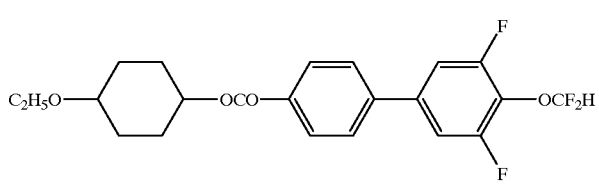 (No. 331) 2 wt. %
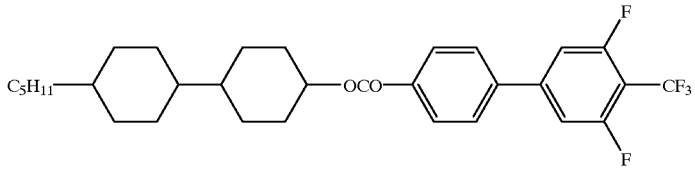 (No. 352) 2 wt. %
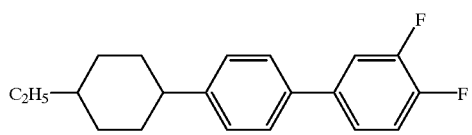 3 wt. %
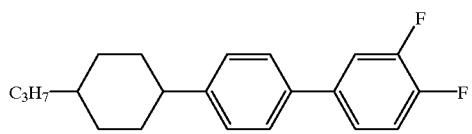 3 wt. %
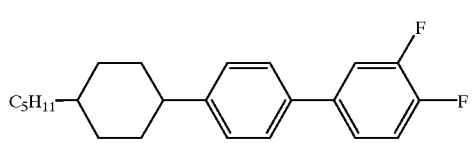 6 wt. %
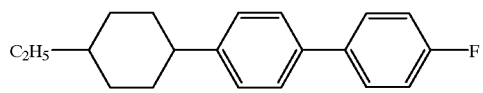 2 wt. %
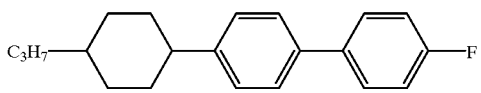 2 wt. %

-continued
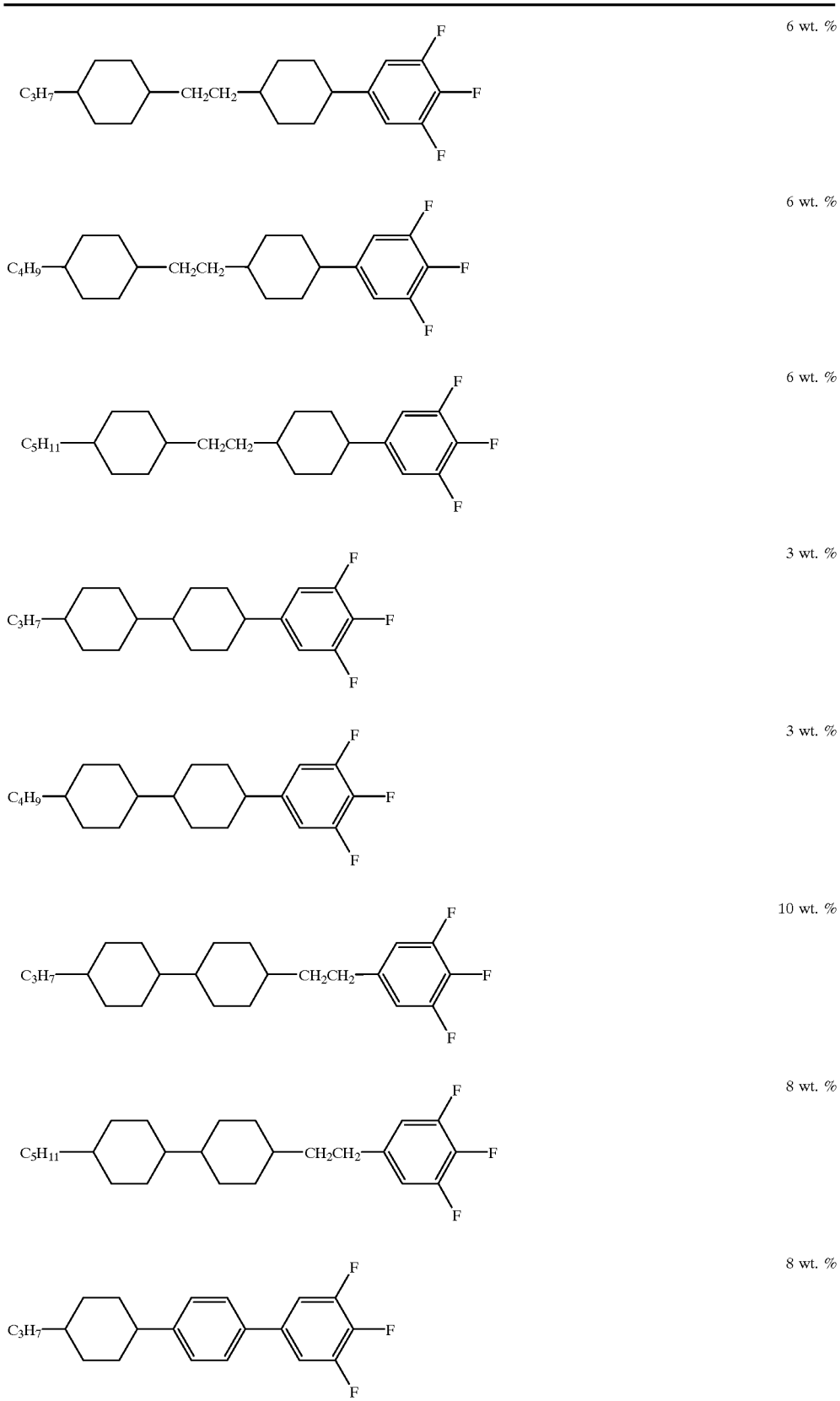
6 wt. %
6 wt. %
6 wt. %
3 wt. %
3 wt. %
10 wt. %
8 wt. %
8 wt. %

-continued
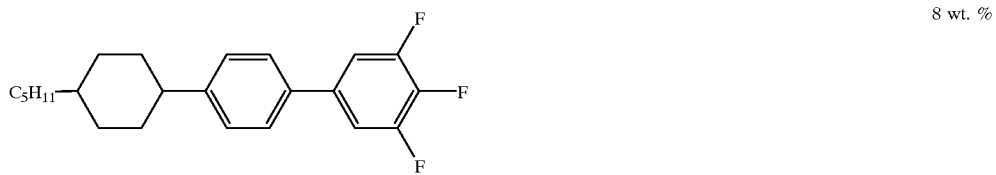 8 wt. %
Composition Example 36
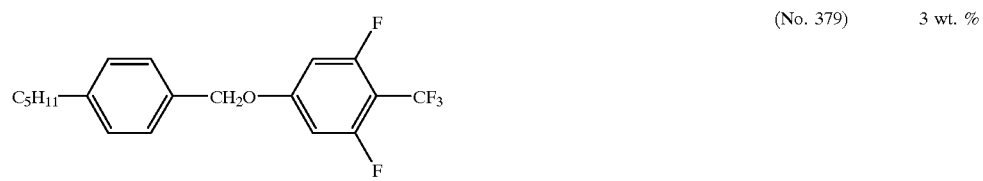 (No. 379) 3 wt. %
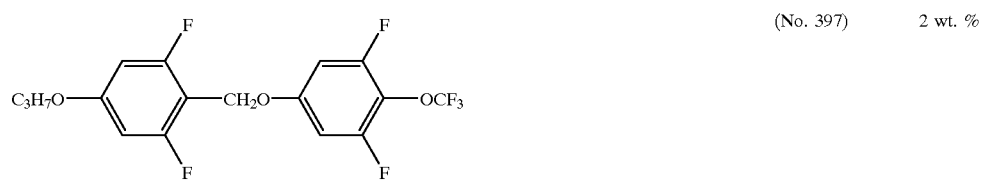 (No. 397) 2 wt. %
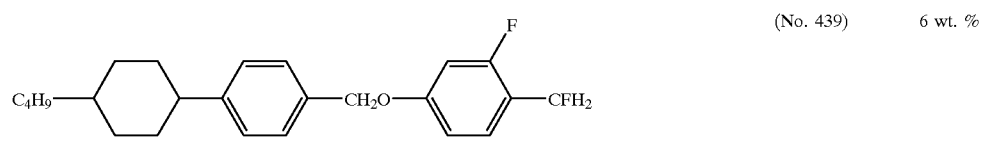 (No. 439) 6 wt. %
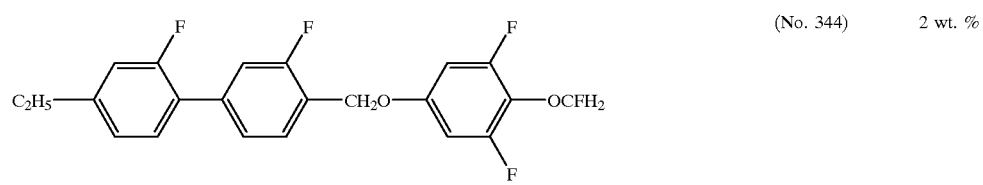 (No. 344) 2 wt. %
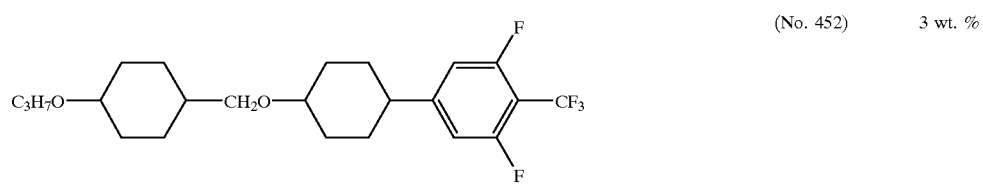 (No. 452) 3 wt. %
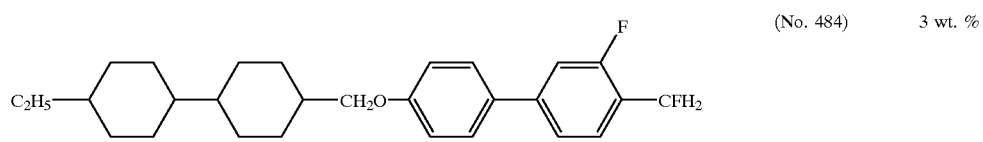 (No. 484) 3 wt. %
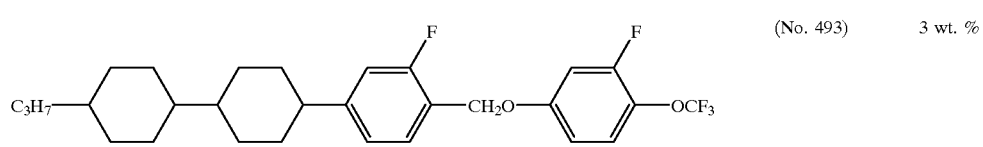 (No. 493) 3 wt. %

-continued

| Structure | Amount |
|---|---|
| C₇H₁₅-cyclohexyl-C₆H₂(F)(F)(F) (3,4,5-trifluorophenyl) | 6 wt. % |
| C₅H₁₁-cyclohexyl-CH₂CH₂-C₆H₃(F)(F) (3,4-difluorophenyl) | 5 wt. % |
| C₂H₅-cyclohexyl-cyclohexyl-C₆H₃(F)(F) (3,4-difluorophenyl) | 4 wt. % |
| C₃H₇-cyclohexyl-cyclohexyl-C₆H₃(F)(F) (3,4-difluorophenyl) | 4 wt. % |
| C₅H₁₁-cyclohexyl-cyclohexyl-C₆H₃(F)(F) (3,4-difluorophenyl) | 4 wt. % |
| C₂H₅-cyclohexyl-phenyl-C₆H₃(F)(F) (3,4-difluoro) | 7 wt. % |
| C₃H₇-cyclohexyl-phenyl-C₆H₃(F)(F) (3,4-difluoro) | 7 wt. % |
| C₅H₁₁-cyclohexyl-phenyl-C₆H₃(F)(F) (3,4-difluoro) | 14 wt. % |
| C₃H₇-cyclohexyl-cyclohexyl-C₆H₃(F)(Cl) (3-fluoro-4-chloro) | 2 wt. % |
| C₃H₇-cyclohexyl-C₆H₃(F)-C≡C-C₆H₄-C₂H₅ | 5 wt. % |

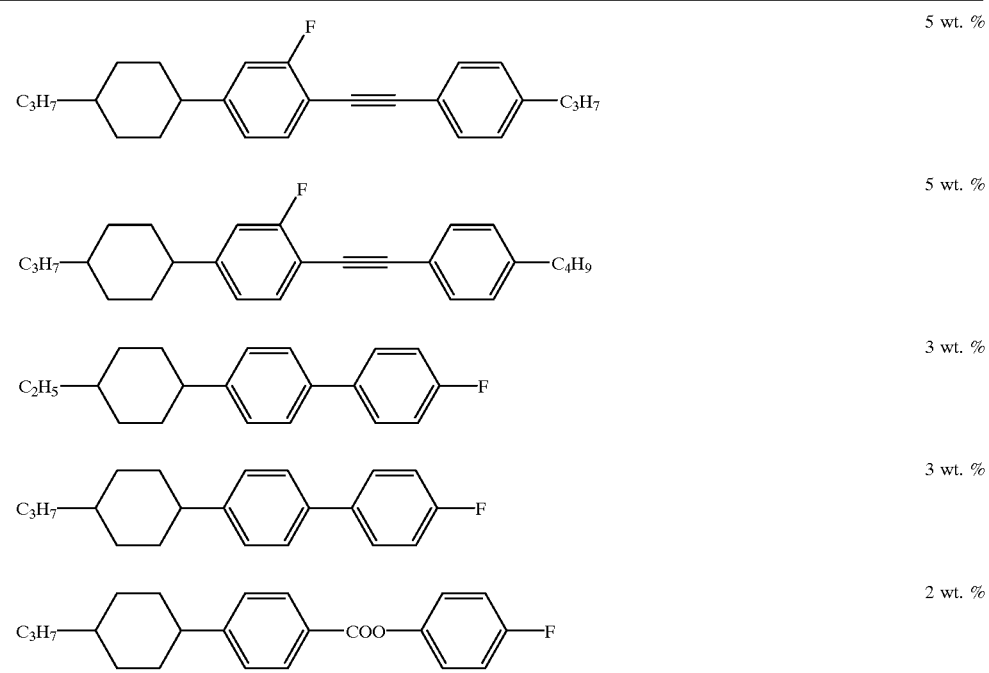
| | |
|---|---|
| | 5 wt. % |
| | 5 wt. % |
| | 3 wt. % |
| | 3 wt. % |
| | 2 wt. % |
Composition Example 37
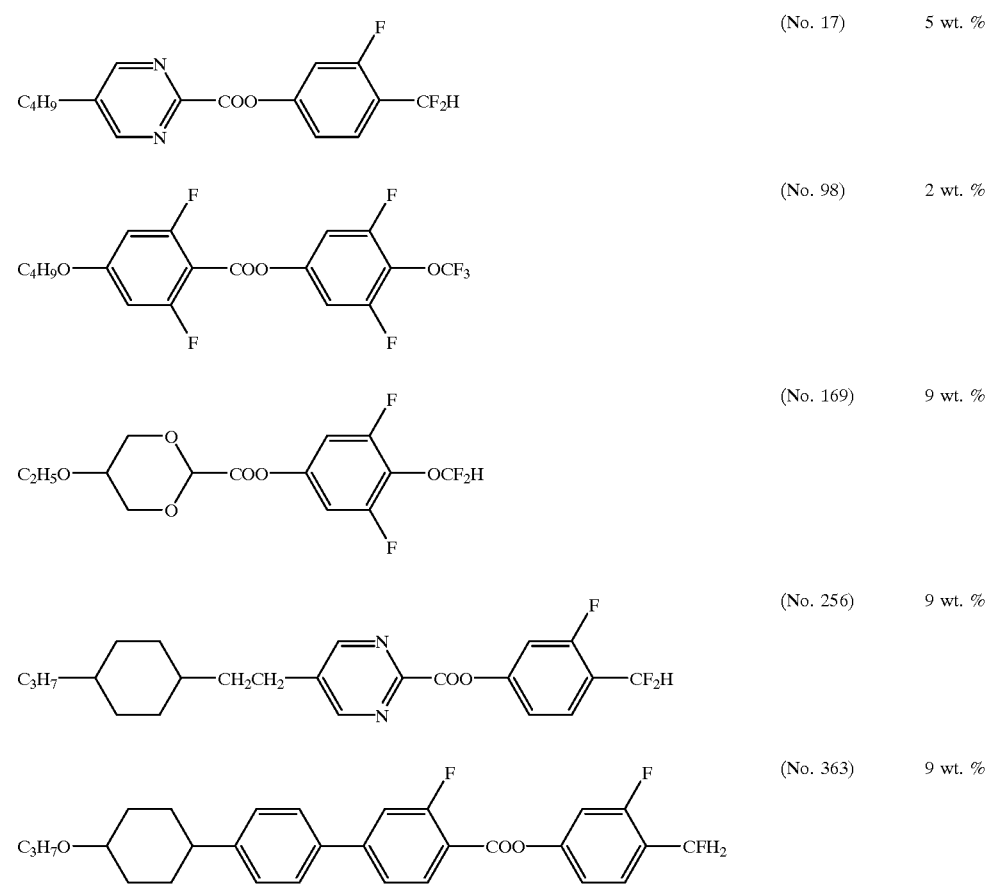
| | | |
|---|---|---|
| | (No. 17) | 5 wt. % |
| | (No. 98) | 2 wt. % |
| | (No. 169) | 9 wt. % |
| | (No. 256) | 9 wt. % |
| | (No. 363) | 9 wt. % |

-continued
| | | |
|---|---|---|
| 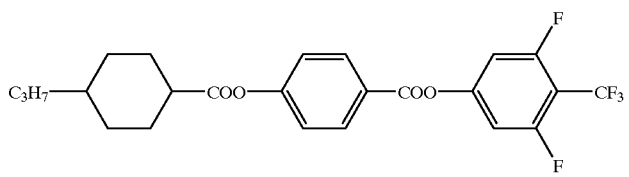 | (No. 286) | 3 wt. % |
| 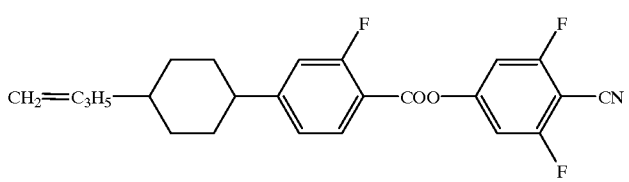 | (No. 209) | 9 wt. % |
| 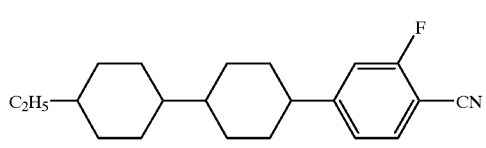 | | 10 wt. % |
| 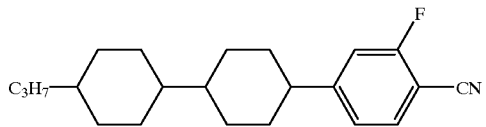 | | 10 wt. % |
| 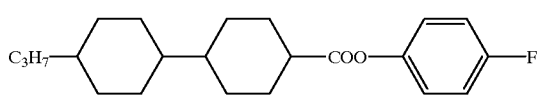 | | 3 wt. % |
| 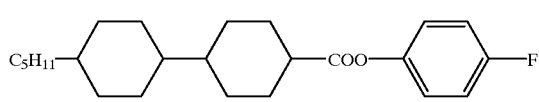 | | 3 wt. % |
| 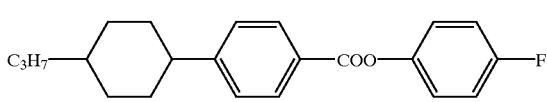 | | 3 wt. % |
| 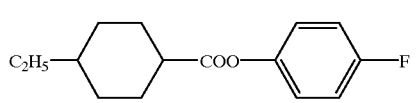 | | 2 wt. % |
| 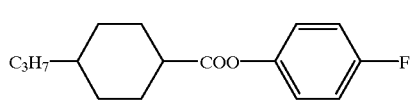 | | 2 wt. % |
| 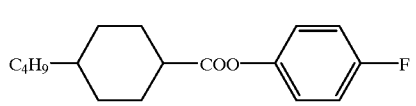 | | 2 wt. % |
| 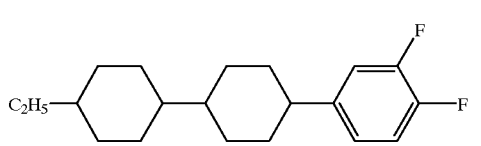 | | 6 wt. % |

-continued
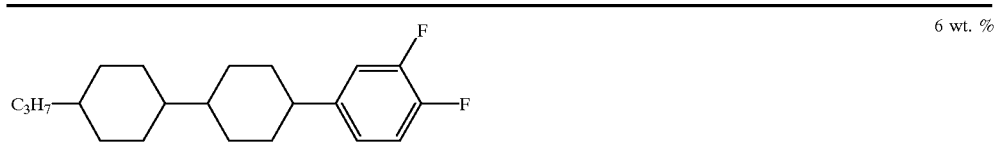 6 wt. %
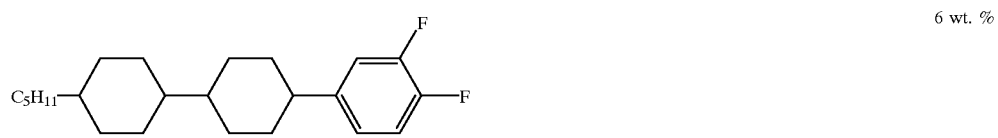 6 wt. %
Composition Example 38
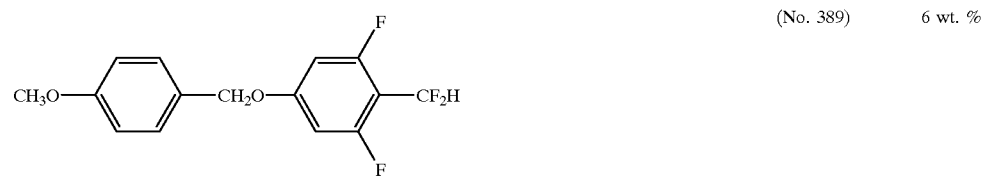 (No. 389) 6 wt. %
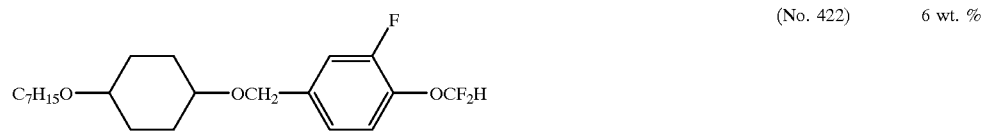 (No. 422) 6 wt. %
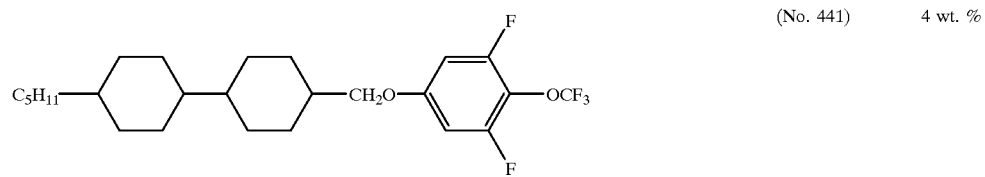 (No. 441) 4 wt. %
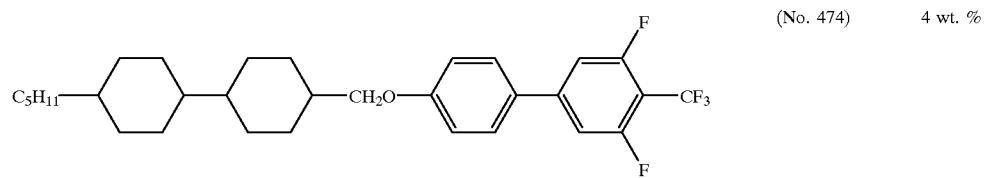 (No. 474) 4 wt. %
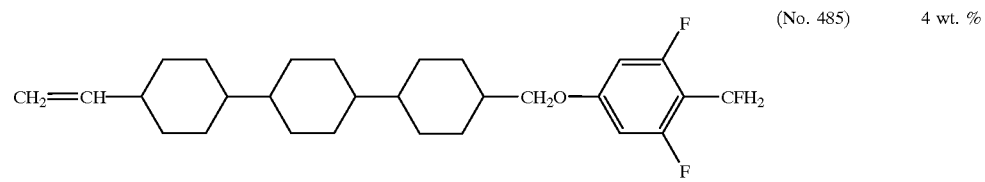 (No. 485) 4 wt. %
 6 wt. %
 6 wt. %
 10 wt. %

-continued

C₃H₇—⟨benzene⟩—COO—⟨benzene⟩—CN     4 wt. %

C₃H₇—⟨pyrimidine⟩—⟨benzene(3,4-diF)⟩     5 wt. %

C₃H₇—⟨cyclohexane⟩—COO—⟨benzene⟩—OC₄H₉     8 wt. %

C₄H₉—⟨cyclohexane⟩—COO—⟨benzene⟩—OC₂H₅     6 wt. %

C₅H₁₁—⟨cyclohexane⟩—COO—⟨benzene⟩—OCH₃     6 wt. %

C₃H₇—⟨cyclohexane⟩—COO—⟨benzene⟩—OC₂H₅     5 wt. %

C₅H₁₁—⟨cyclohexane⟩—COO—⟨benzene⟩—OC₂H₅     4 wt. %

C₃H₇—⟨cyclohexane⟩—⟨cyclohexane⟩—COO—⟨benzene⟩—⟨benzene⟩—CN     2 wt. %

C₃H₇—⟨cyclohexane⟩—⟨benzene⟩—COO—⟨benzene⟩—⟨benzene⟩—CN     2 wt. %

C₃H₇—⟨cyclohexane⟩—⟨cyclohexane⟩—COO—⟨benzene⟩—⟨benzene⟩—F     2 wt. %

C₃H₇—⟨cyclohexane⟩—⟨cyclohexane⟩—⟨benzene⟩—CH₃     5 wt. %

Composition Example 39

C₂H₅—⟨cyclohexane⟩—⟨benzene(2F)⟩—COO—⟨benzene(2,6-diF)⟩—CN     (No. 205)    5 wt. %

-continued
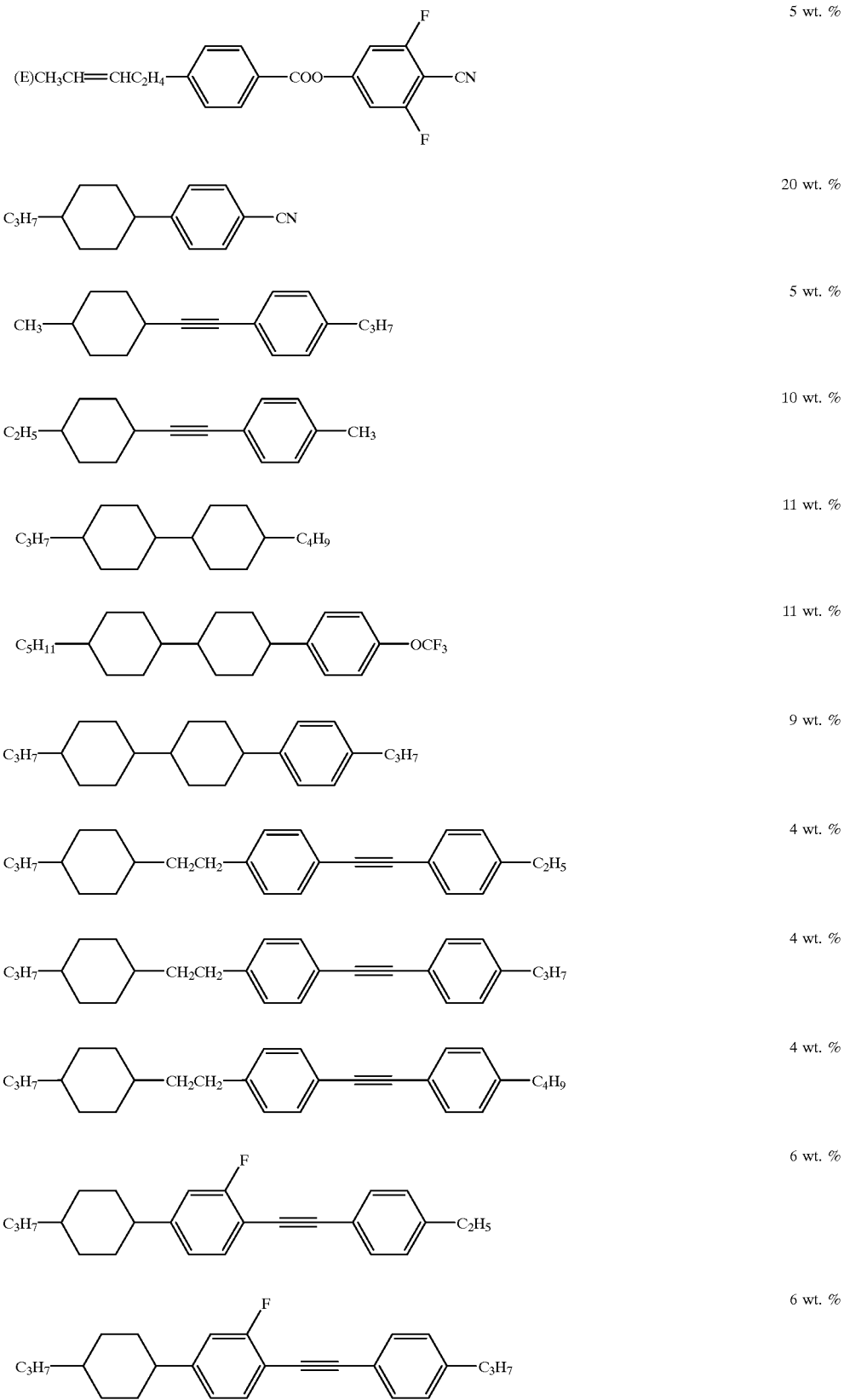
| | |
|---|---|
| | 5 wt. % |
| | 20 wt. % |
| | 5 wt. % |
| | 10 wt. % |
| | 11 wt. % |
| | 11 wt. % |
| | 9 wt. % |
| | 4 wt. % |
| | 4 wt. % |
| | 4 wt. % |
| | 6 wt. % |
| | 6 wt. % |

-continued
Composition Example 40
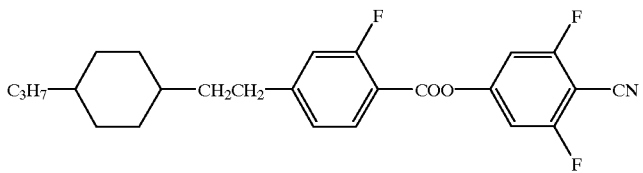 (No. 277)  10 wt. %
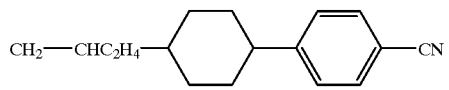  11 wt. %
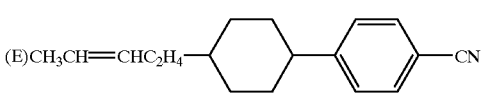  10 wt. %
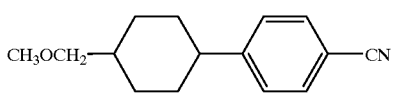  10 wt. %
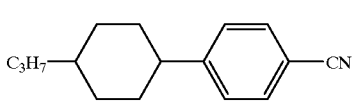  5 wt. %
  6 wt. %
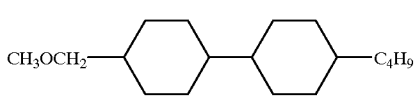  8 wt. %
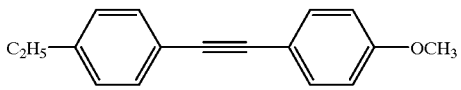  4.2 wt. %
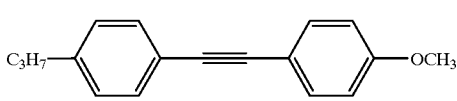  4.2 wt. %
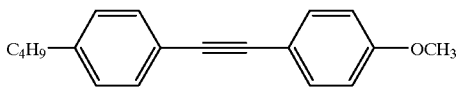  4.2 wt. %
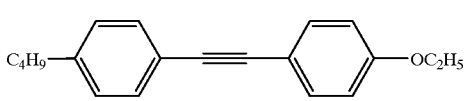  4.2 wt. %
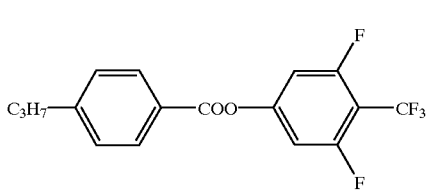  4.2 wt. %

-continued
 5 wt. %
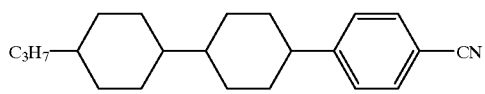 5 wt. %
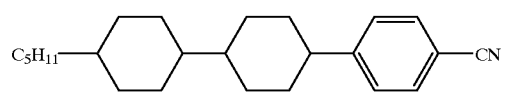 5 wt. %
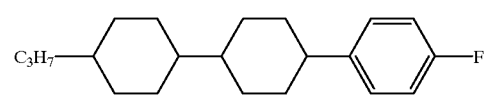 4 wt. %
Composition Example 41
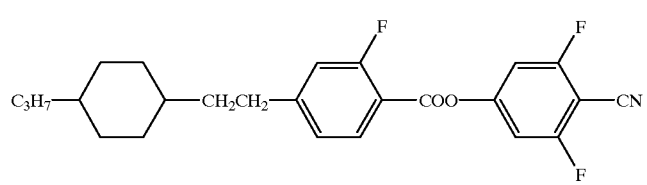 (No. 277) 10 wt. %
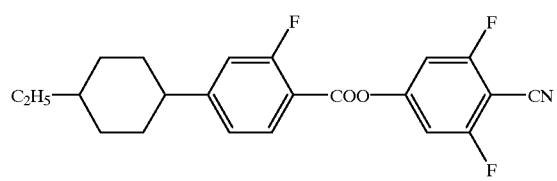 (No. 205) 5 wt. %
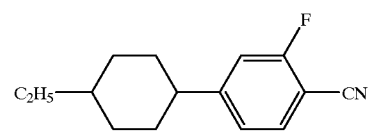 10 wt. %
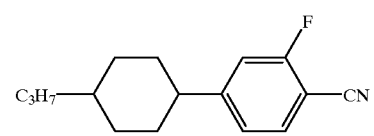 10 wt. %
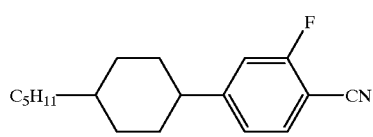 7 wt. %
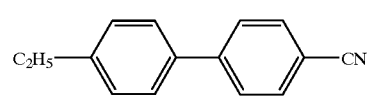 13 wt. %
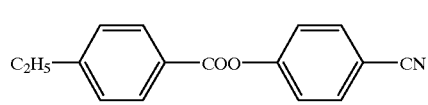 12 wt. %

| | |
|---|---|
| C₃H₇—⟨Cy⟩—COO—⟨Ph⟩—CN | 4 wt. % |
| C₂H₅—⟨Cy⟩—⟨Cy⟩—⟨Ph(F)⟩—CN | 6 wt. % |
| C₃H₇—⟨Cy⟩—⟨Cy⟩—⟨Ph(F)⟩—CN | 9 wt. % |
| C₂H₅—⟨Cy⟩—⟨Cy⟩—⟨Ph⟩—CN | 3 wt. % |
| C₃H₇—⟨Cy⟩—⟨Cy⟩—⟨Ph⟩—CN | 3 wt. % |
| C₃H₇—⟨Pyrimidine⟩—⟨Ph⟩—⟨Ph⟩—F | 8 wt. % |

Composition Example 42

| | | |
|---|---|---|
| C₃H₇—⟨Cy⟩—⟨Cy⟩—CH₂O—⟨Ph(F)⟩—OCF₃ | (No. 440) | 10 wt. % |
| C₃H₇OCH₂—⟨Ph⟩—COO—⟨Ph(F)⟩—CN | | 8 wt. % |
| CH₂=CHCH₂—⟨Cy⟩—⟨Ph⟩—CN | | 4 wt. % |
| C₃H₇—⟨Cy⟩—⟨Ph⟩—OC₂H₅ | | 4 wt. % |
| C₃H₇—⟨Pyrimidine⟩—⟨Ph⟩—OCH₃ | | 3 wt. % |
| C₂H₅—⟨Ph⟩—C≡C—⟨Ph⟩—OCH₃ | | 6 wt. % |

-continued

| Structure | Amount |
|---|---|
| C₃H₇–⟨phenyl⟩–C≡C–⟨phenyl⟩–OCH₃ | 6 wt. % |
| C₄H₉–⟨phenyl⟩–C≡C–⟨phenyl⟩–OCH₃ | 6 wt. % |
| C₄H₉–⟨cyclohexyl⟩–C≡C–⟨phenyl⟩–OC₂H₅ | 6 wt. % |
| C₅H₁₁–⟨phenyl⟩–C≡C–⟨phenyl⟩–OCH₃ | 6 wt. % |
| C₃H₇–⟨cyclohexyl⟩–⟨cyclohexyl⟩–⟨phenyl⟩–OCH₃ | 3 wt. % |
| C₃H₇–⟨cyclohexyl⟩–CH₂CH₂–⟨phenyl⟩–C≡C–⟨phenyl⟩–C₃H₇ | 4 wt. % |
| C₃H₇–⟨cyclohexyl⟩–CH₂CH₂–⟨phenyl⟩–C≡C–⟨phenyl⟩–C₄H₉ | 4 wt. % |
| C₃H₇–⟨cyclohexyl⟩–⟨phenyl(F)⟩–C≡C–⟨phenyl⟩–C₂H₅ | 6 wt. % |
| C₃H₇–⟨cyclohexyl⟩–⟨phenyl(F)⟩–C≡C–⟨phenyl⟩–C₃H₇ | 6 wt. % |
| C₃H₇–⟨cyclohexyl⟩–⟨phenyl(F)⟩–C≡C–⟨phenyl⟩–C₄H₉ | 6 wt. % |
| C₂H₅–⟨pyrimidine⟩–⟨phenyl⟩–⟨cyclohexyl⟩–C₃H₇ | 4 wt. % |
| C₂H₅–⟨pyrimidine⟩–⟨phenyl⟩–⟨cyclohexyl⟩–C₃H₇ | 4 wt. % |
| C₃H₇–⟨pyrimidine⟩–⟨phenyl⟩–⟨phenyl⟩–C₂H₅ | 4 wt. % |

-continued
Composition Example 43
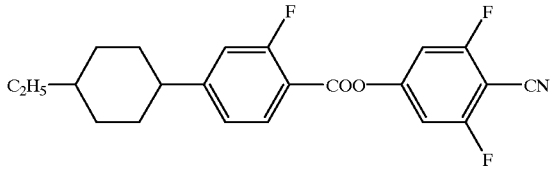 (No. 205) 6 wt. %
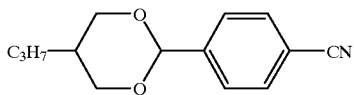 10 wt. %
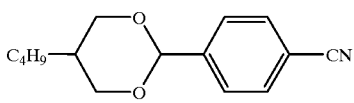 10 wt. %
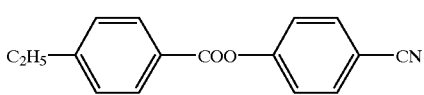 10 wt. %
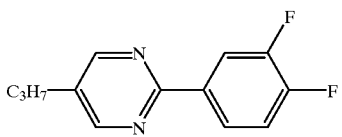 3 wt. %
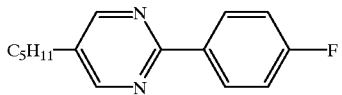 3 wt. %
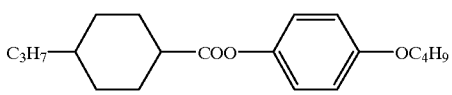 10.2 wt. %
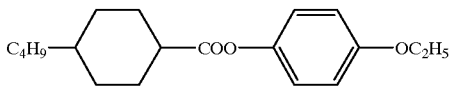 7.7 wt. %
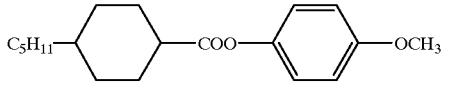 7.7 wt. %
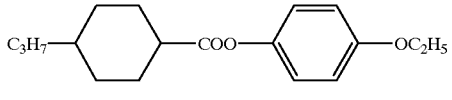 6.3 wt. %
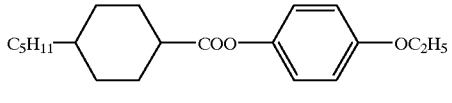 5.1 wt. %
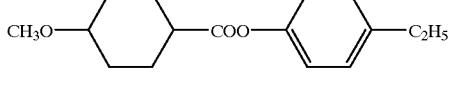 2 wt. %

-continued
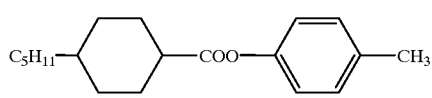 2 wt. %
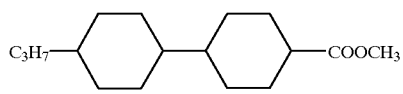 2 wt. %
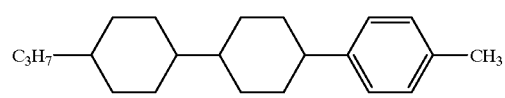 6 wt. %
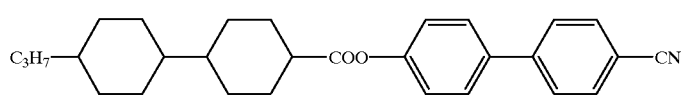 3 wt. %
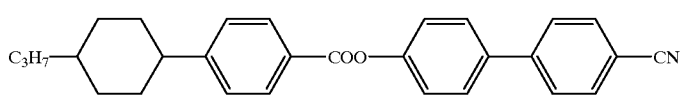 3 wt. %
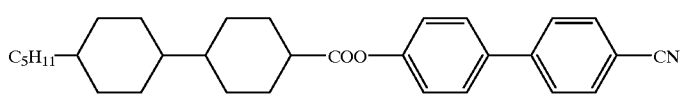 3 wt. %
Composition Example 44
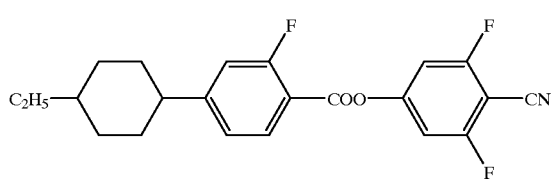 (No. 205)  12 wt. %
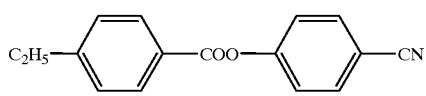 12 wt. %
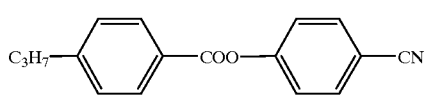 3 wt. %
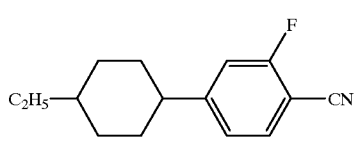 12 wt. %
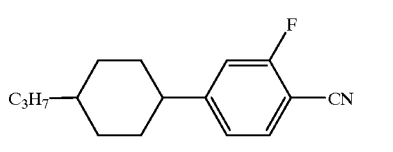 15 wt. %
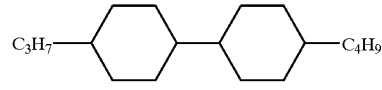 6 wt. %

-continued

C3H7—⌬—⌬—COO—⌬—F  5 wt. %

C5H11—⌬—⌬—COO—⌬—F  3 wt. %

C3H7—⌬—⌬—COO—⌬—F  2 wt. %

C3H7—⌬—⌬—⌬—CH3  8 wt. %

C3H7—⌬—⌬—⌬—OCH3  4 wt. %

C3H7—⌬—CH2CH2—⌬—C≡C—⌬—C2H5  5 wt. %

C3H7—⌬—CH2CH2—⌬—C≡C—⌬—C3H7  5 wt. %

C3H7—⌬—⌬(F)—C≡C—⌬—C2H5  3 wt. %

C3H7—⌬—COO—⌬—COO—⌬—F  3 wt. %

C3H7—⌬—COO—⌬—COO—⌬—CH3  2 wt. %

Composition Example 45

C3H7—⌬—CH2CH2—⌬(F)—COO—⌬(F,F)—CN  (No. 277)  7 wt. %

C2H5—⌬—⌬(F)—COO—⌬(F,F)—CN  (No. 205)  3 wt. %

-continued

| | |
|---|---|
| C₃H₇—〔Cy〕—〔Ph(2-F)〕—CN | 5 wt. % |
| C₃H₇OCH₂—〔Ph〕—COO—〔Ph(2,6-F)〕—CN | 5 wt. % |
| CH₂=CH—〔Cy〕—〔Ph〕—CN | 10 wt. % |
| (E) CH₃CH=CH—〔Cy〕—〔Ph〕—CN | 10 wt. % |
| C₂H₅—〔Ph〕—C≡C—〔Ph〕—OCH₃ | 10 wt. % |
| C₃H₇—〔Cy〕—〔Ph〕—OC₂H₅ | 10 wt. % |
| CH₂=CHC₂H₄—〔Cy〕—〔Cy〕—C₃H₇ | 5 wt. % |
| CH₂=CH—〔Cy〕—〔Cy〕—C₄H₉ | 5 wt. % |
| CH₂=CH—〔Cy〕—〔Cy〕—〔Ph〕—CH₃ | 10 wt. % |
| (E) CH₃CH=CHC₂H₄—〔Cy〕—〔Ph〕—〔Ph〕—CH₃ | 10 wt. % |
| C₃H₇—〔Cy〕—〔Cy〕—〔Ph〕—CH₃ | 10 wt. % |

Composition Example 46

| | | |
|---|---|---|
| C₂H₅—〔Cy〕—〔Ph〕—COO—〔Ph(3-F)〕—OCF₃ | (No. 189) | 5 wt. % |

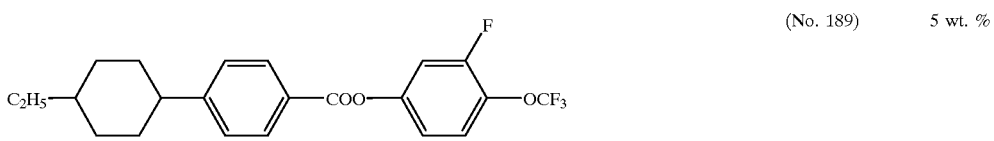

-continued
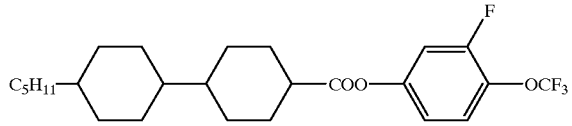 (No. 237) 5 wt. %
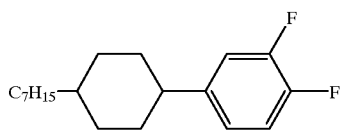 9 wt. %
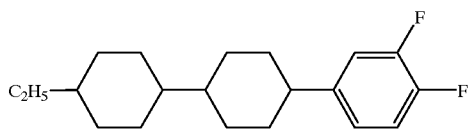 10 wt. %
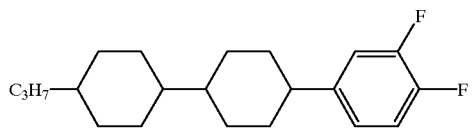 10 wt. %
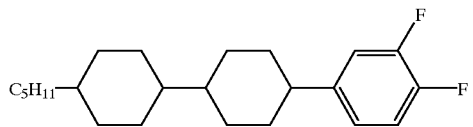 10 wt. %
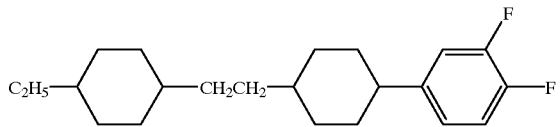 8.4 wt. %
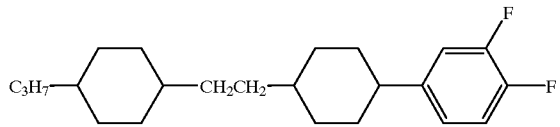 4.2 wt. %
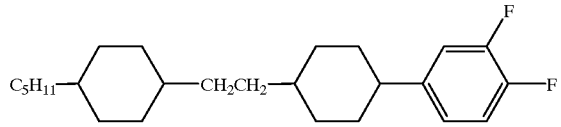 8.4 wt. %
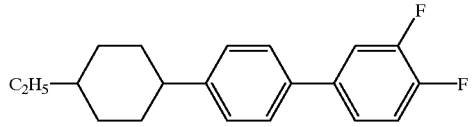 7.5 wt. %
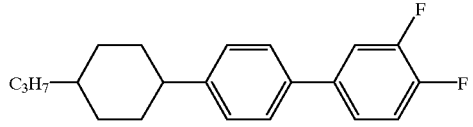 7.5 wt. %

-continued
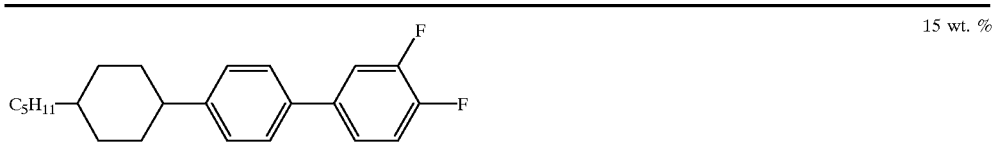
15 wt. %
Composition Example 47
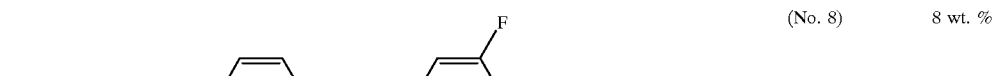
(No. 8)  8 wt. %
10 wt. %
3 wt. %
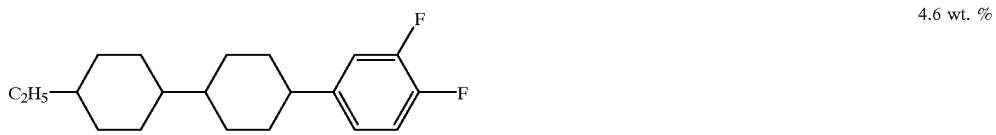
4.6 wt. %
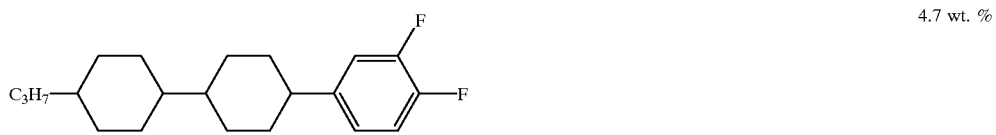
4.7 wt. %
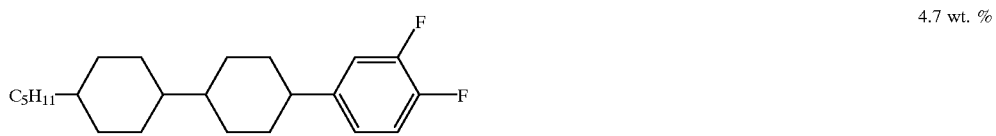
4.7 wt. %
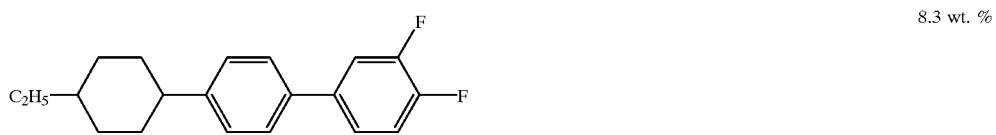
8.3 wt. %
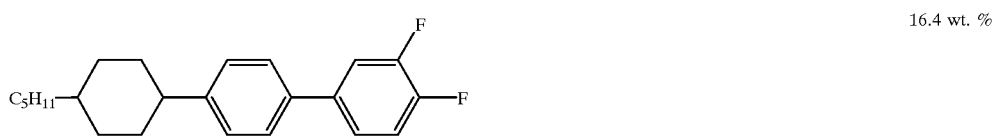
16.4 wt. %
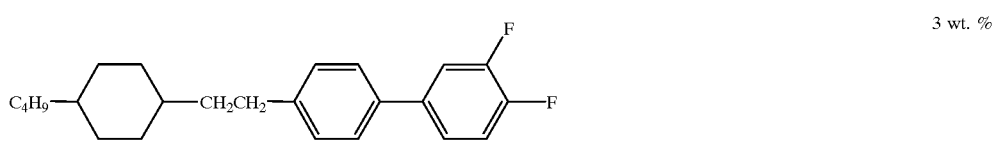
3 wt. %

-continued
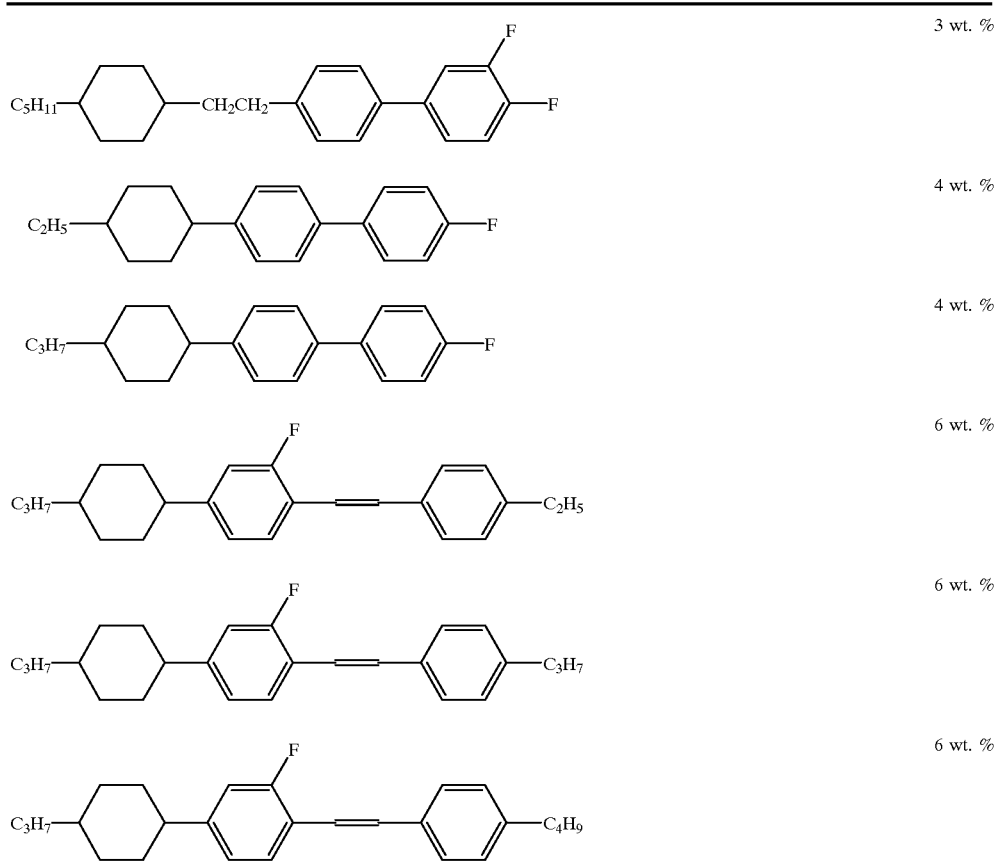
| | |
|---|---|
| | 3 wt. % |
| | 4 wt. % |
| | 4 wt. % |
| | 6 wt. % |
| | 6 wt. % |
| | 6 wt. % |
Composition Example 48
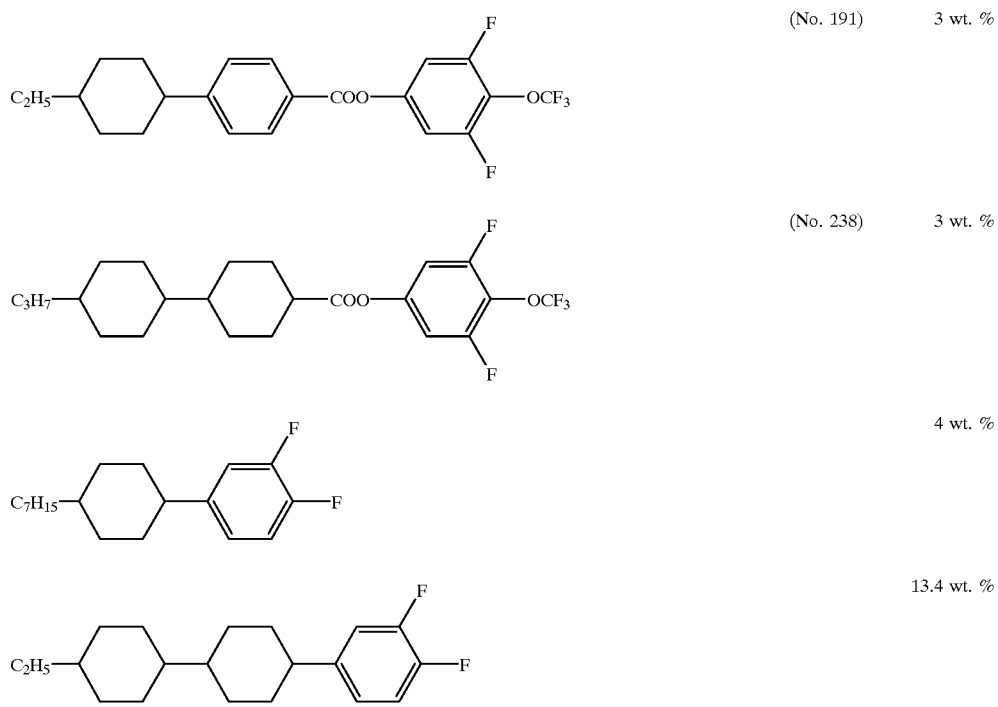
| | | |
|---|---|---|
| (No. 191) | 3 wt. % |
| (No. 238) | 3 wt. % |
| | 4 wt. % |
| | 13.4 wt. % |

-continued
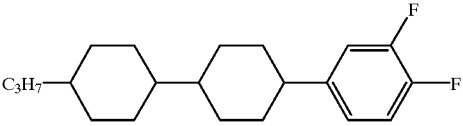 13.3 wt. %
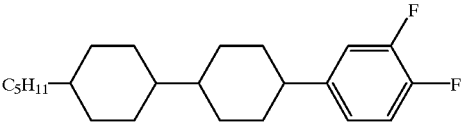 13.3 wt. %
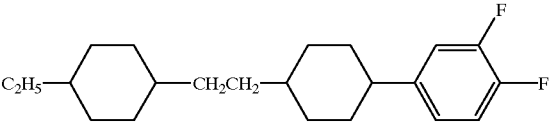 7.2 wt. %
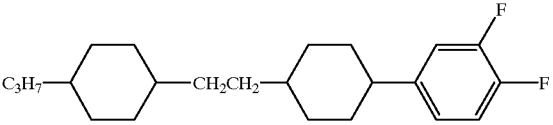 3.6 wt. %
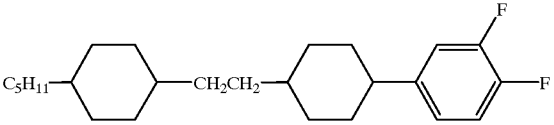 7.2 wt. %
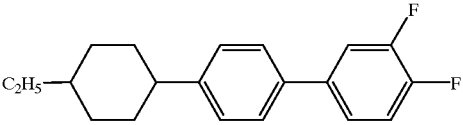 3.3 wt. %
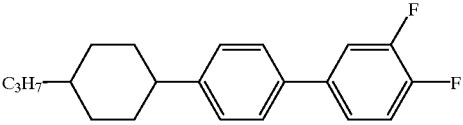 3.3 wt. %
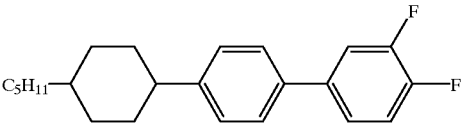 6.4 wt. %
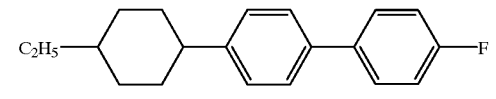 2 wt. %
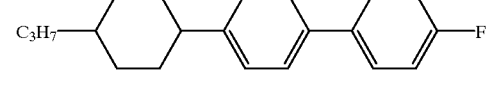 4 wt. %
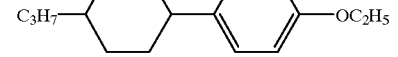 6 wt. %

-continued
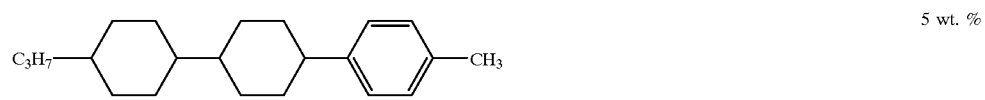 5 wt. %
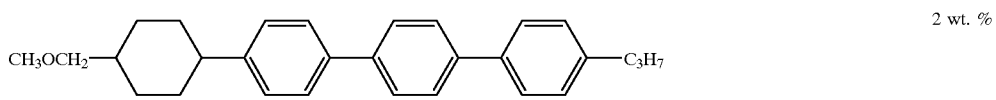 2 wt. %
Composition Example 49
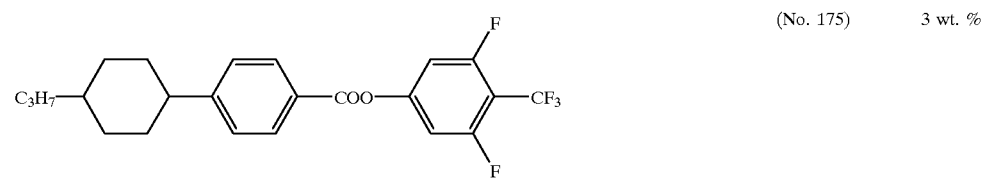 (No. 175) 3 wt. %
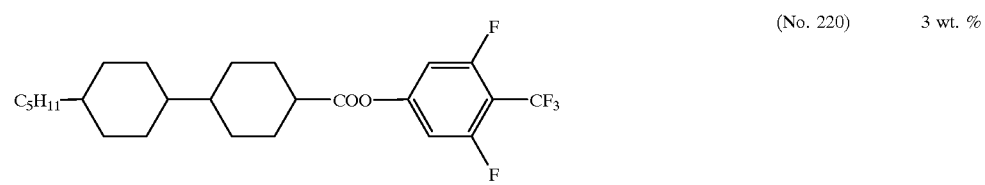 (No. 220) 3 wt. %
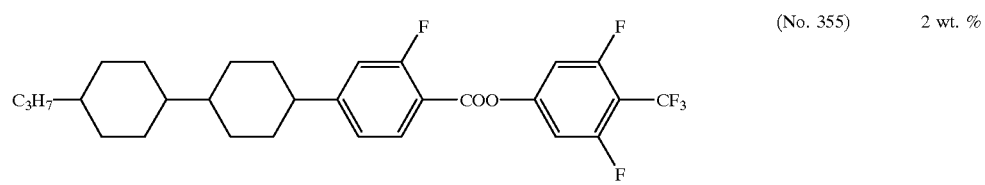 (No. 355) 2 wt. %
 9 wt. %
 4 wt. %
 9 wt. %
 4 wt. %
 4 wt. %
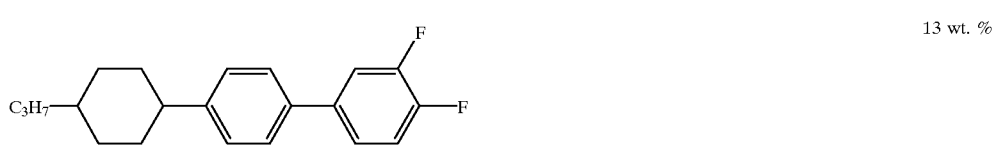 13 wt. %

-continued
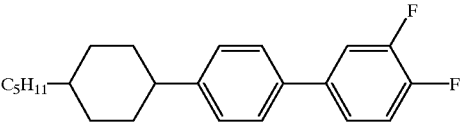 13 wt. %
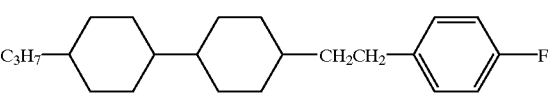 9 wt. %
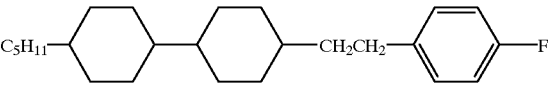 11 wt. %
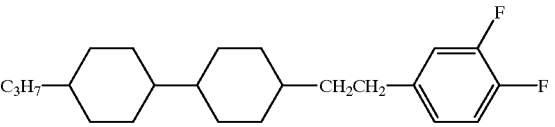 6 wt. %
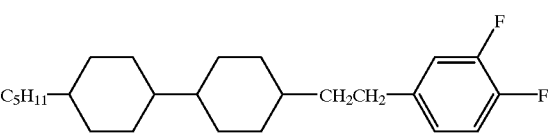 10 wt. %
Composition Example 50
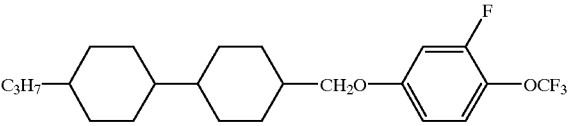  (No. 440)  10 wt. %
 4 wt. %
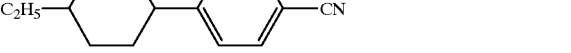 10.2 wt. %
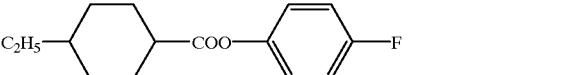 10.2 wt. %
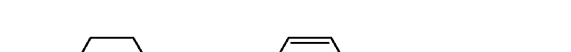 10.2 wt. %
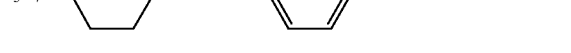 3 wt. %
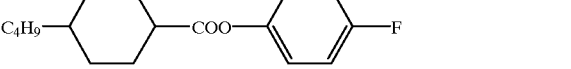 3 wt. %

-continued

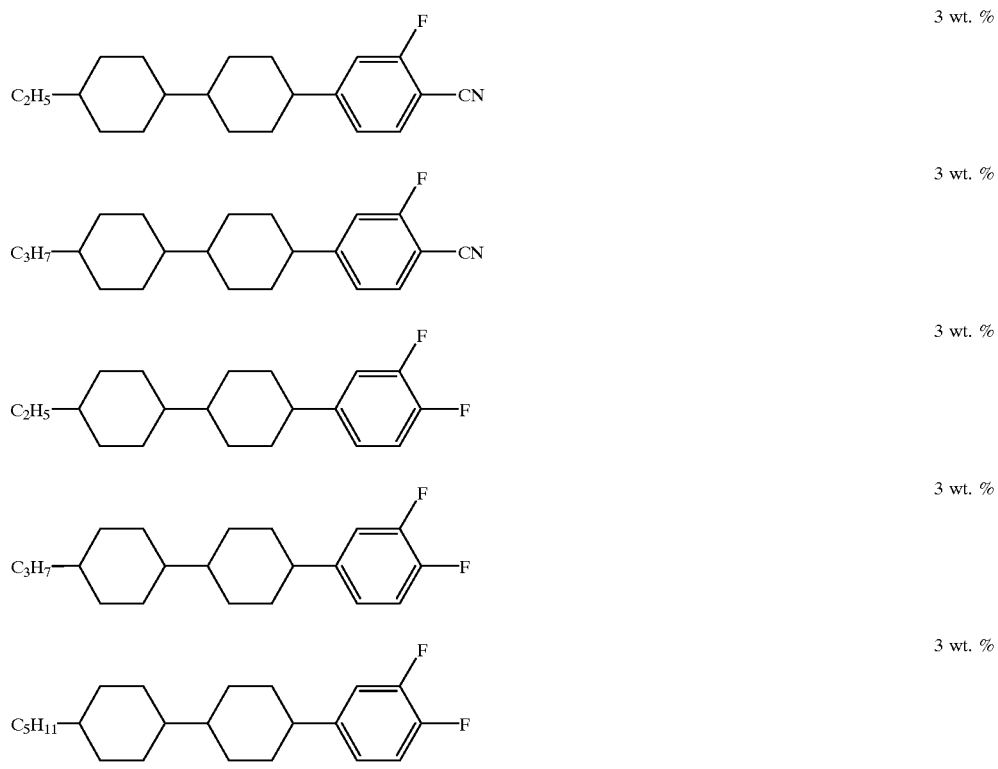

Now, the present invention will be described in more detail below with reference to Examples.

In each of the Examples, Cr represents crystal, $S_A$ does smectic A phase, $S_B$ does smectic B phase, $S_C$ does smectic C phase, $S_X$ does smectic phase structure of which has not yet been analyzed, N does nematic phase, and Iso represents isotropic liquid, and all of the unit of phase transition temperature is ° C.

EXAMPLE 1

Preparation of 3,5-difluoro-4-trifluoromethylphenyl 4-pentylbenzoate (Compound No. 1 expressed by general formula (1) in which R represents $C_5H_{11}$, both m and n are 0, $A_1$ is 1,4-phenylene group, $Z_1$ is —COO—, X is $CF_3$, and Y is F.)

First, 1.2 g (6.1 mmol) of 4-pentyl benzoic acid was mixed with 1.1 g (9.1 mmol) of thionyl chloride, 0.1 ml of pyridine, and 3 ml of toluene, and reacted at 80° C. for 2 hours. Excess amount of thionyl chloride and toluene were distilled off at a reduced pressure to obtain a crude 4-pentylbenzoyl chloride.

Then, 1.2 g (6.1 mmol) of 3,5-difluoro-4-trifluoromethylphenol, 0.7 ml of pyridine, and 2 ml of toluene were mixed. To this mixture was added dropwise 3 ml of toluene solution containing 6.1 mmol of 4-pentylbenzoyl chloride at room temperature in 10 minutes. After the dropping was finished, they were reacted at 50° C. for 2 hours. After finishing of the reaction, 10 ml of water was added to the reaction product, and then extracted with 30 ml of toluene. The organic layer thus obtained was washed with 6N-hydrochloric acid thrice, 2N-sodium hydroxide thrice, and water thrice, and then dried over anhydrous magnesium sulfate. Solvent was distilled off at a reduced pressure, and the residue was subjected to a silica gel column chromatography (eluent: toluene) to obtain 2.1 g of a crude 3,5-difluoro-4-trifluoromethylphenyl 4-pentylbenzoate. This crude product was recrystallized from a mixed solvent of heptane/ether (1/1) to obtain 1.5 g (yield: 65.2%) of the subject compound.

Data of mass spectrum well supported its structure.

Mass analysis: 373 (M+1)

Following compounds (No. 2 to No. 65) are prepared according to the method of Example 1.

In the followings, each compound is indicated by extracting parameters R; A which represents —$(A_3$—$Z_3)_n$—$(A_2$—$Z_2)_m$—$A_1$—$Z_1$—; X; and Y in the compounds expressed by general formula (1), and the same rule is applied even in Example 2 and so on.

| No. | R | Y | A | X |
|---|---|---|---|---|
| 2 | C₂H₅ | H | 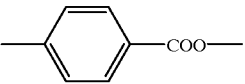 | CF₃ |
| 3 | C₂H₅ | F | 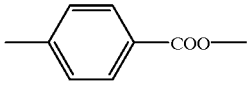 | CF₃ |
| 4 | C₃H₇ | H | 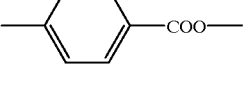 | CF₃ |
| 5 | C₃H₇ | F | 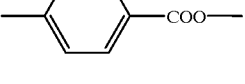 | CF₃ |
| 6 | C₅H₁₁ | H | 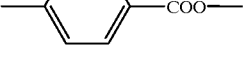 | CF₃ |
| 7 | C₉H₁₉ | F | 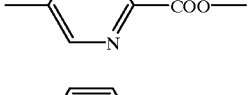 | CF₃ |
| 8 | 3E-C₅H₉ | F | 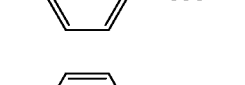 | CF₃ Cr 63.7–64.3 Iso |
| 9 | C₂H₅O | F | 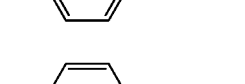 | CF₃ |
| 10 | C₃H₇O | H | 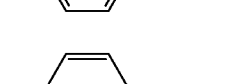 | CF₃ |
| 11 | C₄H₉O | F |  | CF₃ |
| 12 | C₅H₁₁O | F | 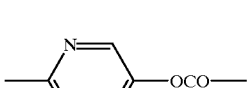 | CF₃ |
| 13 | Z-C₂H₄=C₅H₉O | F | 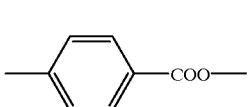 | CF₃ |
| 14 | CH₃ | F | 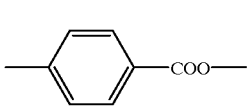 | CF₂H |
| 15 | C₂H₅ | F |  | CF₂H |

-continued
| No. | R | Y | A | X |
|---|---|---|---|---|
| 16 | CH$_2$=C$_2$H$_3$ | F | 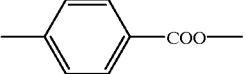 | CF$_2$H |
| 17 | C$_4$H$_9$ | H | 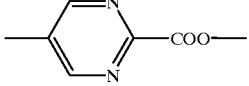 | CF$_2$H |
| 18 | 3E-C$_5$H$_9$ | H | 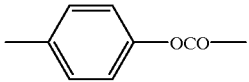 | CF$_2$H |
| 19 | C$_6$H$_{13}$ | F | 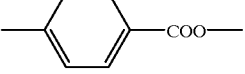 | CF$_2$H |
| 20 | C$_{10}$H$_{21}$ | F | 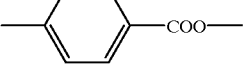 | CF$_2$H |
| 21 | CH$_3$O | F | 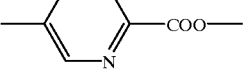 | CF$_2$H |
| 22 | C$_2$H$_5$O | H | 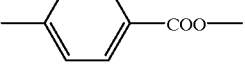 | CF$_2$H |
| 23 | C$_3$H$_7$O | F | 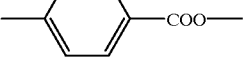 | CF$_2$H |
| 24 | E-C$_2$H$_4$=C$_2$H$_3$O | F | 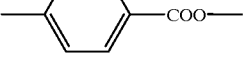 | CF$_2$H |
| 25 | C$_5$H$_{11}$O | H | 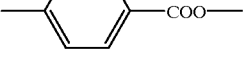 | CF$_2$H |
| 26 | C$_7$H$_{15}$O | F | 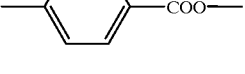 | CF$_2$H |
| 27 | CH$_3$ | F | 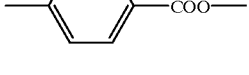 | CFH$_2$ |
| 28 | C$_2$H$_5$ | F | 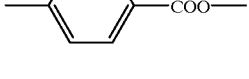 | CFH$_2$ |

-continued

| No. | R | Y | A | X |
|---|---|---|---|---|
| 29 | C$_3$H$_7$ | F | ⟨phenyl-COO⟩ | CFH$_2$ |
| 30 | C$_4$H$_9$ | F | ⟨phenyl-COO⟩ | CFH$_2$ |
| 31 | 2Z-C$_5$H$_9$ | F | ⟨phenyl-COO⟩ | CFH$_2$ |
| 32 | C$_6$H$_{13}$ | H | ⟨phenyl-COO⟩ | CFH$_2$ |
| 33 | C$_{10}$H$_{21}$ | H | ⟨phenyl-COO⟩ | CFH$_2$ |
| 34 | CH$_3$O | F | ⟨phenyl-COO⟩ | CFH$_2$ |
| 35 | C$_2$H$_5$O | F | ⟨phenyl-COO⟩ | CFH$_2$ |
| 36 | C$_3$H$_7$O | H | ⟨pyridyl-COO⟩ | CFH$_2$ |
| 37 | C$_4$H$_9$O | F | ⟨phenyl-COO⟩ | CFH$_2$ |
| 38 | C$_8$H$_{17}$O | F | ⟨phenyl-COO⟩ | CFH$_2$ |
| 39 | CH$_3$ | F | ⟨phenyl-COO⟩ | CFH$_2$ |
| 40 | C$_2$H$_5$ | H | ⟨phenyl-COO⟩ | OCF$_3$ |
| 41 | C$_2$H$_5$ | F | ⟨phenyl-COO⟩ | OCF$_3$ |
| 42 | C$_3$H$_7$ | H | ⟨phenyl-COO⟩ | OCF$_3$ |

-continued
| No. | R | Y | A | X |
|---|---|---|---|---|
| 43 | C$_3$H$_7$ | F | 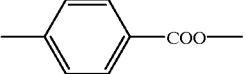 -COO- | OCF$_3$ |
| 44 | CH$_2$=C$_3$H$_5$ | F | 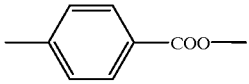 -COO- | OCF$_3$ |
| 45 | C$_5$H$_{11}$ | H | 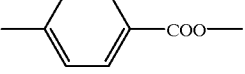 -COO- | OCF$_3$ |
| 46 | C$_5$H$_{11}$ | F | 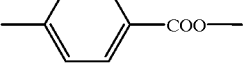 -COO- | OCF$_3$ |
| 47 | CH$_3$O | H | 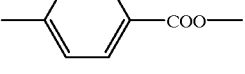 -COO- | OCF$_3$ |
| 48 | C$_2$H$_5$O | F | 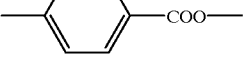 -COO- | OCF$_3$ |
| 49 | C$_3$H$_7$O | F | 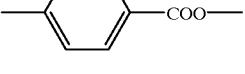 -COO- | OCF$_3$ |
| 50 | C$_4$H$_9$O | F | 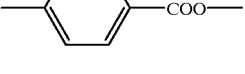 -COO- | OCF$_3$ |
| 51 | C$_5$H$_{11}$O | F | 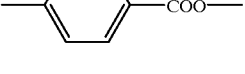 -COO- | OCF$_3$ |
| 52 | C$_7$H$_{15}$O | H | 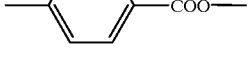 -COO- | OCF$_3$ |
| 53 | CH$_3$ | F | 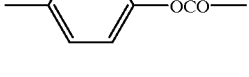 -OCO- | OCF$_2$H |
| 54 | C$_2$H$_5$ | H | 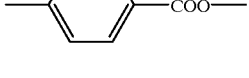 -COO- | OCF$_2$H |
| 55 | C$_3$H$_7$ | H | 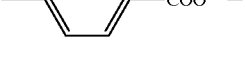 -COO- | OCF$_2$H |

-continued

| No. | R | Y | A | X |
|---|---|---|---|---|
| 56 | $C_4H_9$ | F | —⟨phenyl⟩—COO— | $OCF_2H$ |
| 57 | $CH_2=C_4H_7$ | H | —⟨phenyl⟩—COO— | $OCF_2H$ |
| 58 | $C_6H_{12}$ | F | —⟨pyrimidine⟩—OCO— | $OCF_2H$ |
| 59 | $C_9H_{19}$ | F | —⟨phenyl⟩—COO— | $OCF_2H$ |
| 60 | $CH_3O$ | H | —⟨phenyl⟩—OCO— | $OCF_2H$ |
| 61 | $C_2H_5O$ | F | —⟨pyridine⟩—COO— | $OCF_2H$ |
| 62 | $C_3H_7O$ | F | —⟨phenyl⟩—COO— | $OCF_2H$ |
| 63 | $C_4H_9O$ | H | —⟨phenyl⟩—COO— | $OCF_2H$ |
| 64 | $C_5H_{11}O$ | F | —⟨phenyl⟩—COO— | $OCF_2H$ |
| 65 | $C_{10}H_{21}O$ | H | —⟨pyrimidine⟩—COO— | $OCF_2H$ |

EXAMPLE 2

Preparation of 3,5-difluoro-4-trifluoromethylphenyl 2-fluoro-4-propylbenzoate (Compound No. 66 expressed by general formula (1) in which R is $C_3H_7$, both m and n are 0, $A_1$ is 2-fluoro-1,4-phenylene group, $Z_1$ is —COO—, X is $CF_3$, and Y is F.)

First, 1.1 g (6.1 mmol) of 2-fluoro-4-propylbenzoic acid was mixed with 1.1 g (9.1 mmol) of thionyl chloride, 0.1 ml of pyridine, and 3 ml of toluene, and reacted at 80° C. for 2 hours. Excess amount of thionyl chloride and toluene were distilled off at a reduced pressure to obtain a crude 2-fluoro-4-propylbenzoyl chloride.

Then, 1.2 g (6.1 mmol) of 3,5-difluoro-4-trifluoromethyl-phenol, 0.7 ml of pyridine, and 2 ml of toluene were mixed. To this mixture was added dropwise 3 ml of toluene solution containing 6.1 mmol 2-fluoro-4-propylbenzoyl chloride at room temperature in 10 minutes. After the dropping was finished, they were reacted at 50° C. for 2 hours. After finishing of the reaction, 10 ml of water was added to the reaction product and then extracted with 30 ml of toluene. The organic layer thus obtained was washed with 6N-hydrochloric acid thrice, 2N-sodium hydroxide thrice, and water thrice, and then dried over anhydrous magnesium sulfate. Solvent was distilled off at a reduced pressure and the residue was subjected to a silica gel column chromatography (eluent: toluene) to obtain 2.0 g of a crude 3,5-difluoro-4-trifluormethylphenyl 2-fluoro-4-propylbenzoate. This product was recrystallized from a mixed solvent of heptane/ether (1/1) to obtain 1.1 g (yield: 50.2%) of the subject compound.

Data of mass spectrum well supported its structure.

Mass analysis: 363 (M+1)

Following compounds (No. 67 to No. 107) are prepared according to the method of Example 2:

| No. | R | Y | A | X |
|---|---|---|---|---|
| 67 | $C_2H_5$ | H | 2-F-phenyl-COO- | $CF_3$ |
| 68 | $CH_2=C_3H_5$ | F | 2-F-phenyl-COO- | $CF_3$ |
| 69 | $C_9H_{19}$ | F | 2-F-phenyl-COO- | $CF_3$ |
| 70 | $CH_3$ | F | 2,6-diF-phenyl-COO- | $CF_3$ |
| 71 | $C_3H_7$ | H | 2,6-diF-phenyl-COO- | $CF_3$ |
| 72 | $CH_3O$ | H | 2-F-phenyl-COO- | $CF_3$ |
| 73 | $C_3H_7O$ | H | 2-F-phenyl-COO- | $CF_3$ |
| 74 | $C_4H_9O$ | F | 2,6-diF-phenyl-COO- | $CF_3$ |
| 75 | $C_8H_{17}O$ | H | 2,6-diF-phenyl-COO- | $CF_3$ |
| 76 | $CH_3$ | H | 2,6-diF-phenyl-COO- | $CF_2H$ |
| 77 | $C_2H_5$ | F | 2,6-diF-phenyl-OCO- | $CF_2H$ |
| 78 | $C_3H_7$ | F | 2-F-phenyl-COO- | $CF_2H$ |
| 79 | $C_5H_{11}$ | H | 2-F-phenyl-COO- | $CF_2H$ |
| 80 | $C_4H_9O$ | F | 2-F-phenyl-COO- | $CF_2H$ |
| 81 | $C_{10}H_{21}O$ | H | 2-F-phenyl-COO- | $CF_2H$ |
| 82 | $C_2H_5O$ | F | 2,6-diF-phenyl-COO- | $CF_2H$ |
| 83 | $CH_3$ | F | 2-F-phenyl-COO- | $CFH_2$ |
| 84 | $C_3H_7$ | F | 2-F-phenyl-COO- | $CFH_2$ |

-continued

| No. | R | Y | A | X |
|---|---|---|---|---|
| 85 | C₆H₁₃ | H | (2-F phenyl, COO) | CFH₂ |
| 86 | C₂H₅ | H | (2,6-diF phenyl, COO) | CFH₂ |
| 87 | C₇H₁₅ | F | (2,6-diF phenyl, COO) | CFH₂ |
| 88 | C₂H₅O | H | (2-F phenyl, COO) | CFH₂ |
| 89 | C₃H₇O | F | (2-F phenyl, COO) | CFH₂ |
| 90 | C₃H₇O | F | (2,6-diF phenyl, COO) | CFH₂ |
| 91 | C₅H₁₁O | H | (2,6-diF phenyl, COO) | CFH₂ |
| 92 | C₃H₇ | H | (2,6-diF phenyl, COO) | OCF₃ |
| 93 | 2Z-C₆H₁₁ | F | (2,6-diF phenyl, OCO) | OCF₃ |

-continued

| No. | R | Y | A | X |
|---|---|---|---|---|
| 94 | C₄H₉ | F | (2-F phenyl, COO) | OCF₃ |
| 95 | C₅H₁₁ | H | (2-F phenyl, COO) | OCF₃ |
| 96 | CH₃O | F | (2-F phenyl, OCO) | OCF₃ |
| 97 | C₄H₉O | H | (2-F phenyl, COO) | OCF₃ |
| 98 | C₄H₉O | F | (2,6-diF phenyl, COO) | OCF₃ |
| 99 | C₂H₅ | H | (2-F phenyl, COO) | OCF₂H |
| 100 | C₄H₉ | F | (2-F phenyl, COO) | OCF₂H |
| 101 | C₅H₁₁ | F | (2-F phenyl, COO) | OCF₂H |
| 102 | C₃H₇ | F | (2,6-diF phenyl, OCO) | OCF₂H |

-continued

| No. | R | Y | A | X |
|---|---|---|---|---|
| 103 | CH₂=C₈H₁₅ | H | 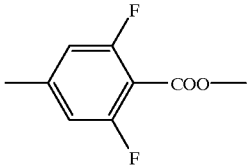 | OCF₂H |
| 104 | CH₃O | F | 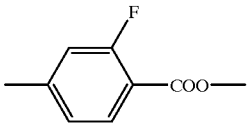 | OCF₂H |
| 105 | C₄H₉O | H | 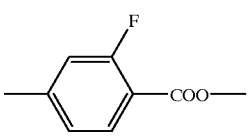 | OCF₂H |
| 106 | C₂H₅O | F | 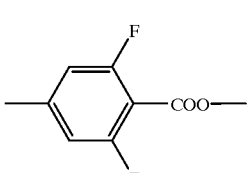 | OCF₂H |
| 107 | C₇H₁₅O | H | 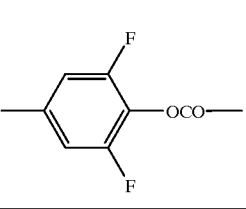 | OCF₂H |

EXAMPLE 3

Preparation of 3-fluoro-4-trifluoromethoxyphenyl trans-4-ethycyclohexylcarboxylate (Compound No. 108 expressed by general formula (1) in which R is $C_2H_5$, both m and n are 0, $A_1$ is trans-1,4-cyclohexylene group, $Z_1$ is —COO—, X is $OCF_3$, and Y is H.)

First, 1.0g (6.1 nmmol) of trans-4-ethylcyclohexane carboxylic acid was mixed with 1.1 g (9.2 mmol) of thionyl chloride, 0.1 ml of pyridine, and 3 ml of toluene, and reacted at 60° C. for hours. Excess amount of thionyl chloride and toluene were distilled off at a reduced pressure to obtain a crude trans-4-ethylcyclohexylcarbonylchloride.

Then, 1.2 g (6.1 mmol) of 3-fluoro-4-trifluoromethoxyphenol, 0.7 ml of pyridine, and 2 ml of toluene were mixed. To this mixture was added dropwise 3 ml of toluene solution containing 6.1 mmol of trans-4-ethylcyclohexylcarbonylchloride at room temperature in 5 minutes. After the dropping was finished, they were reacted at 50° C. for 2 hours. After finishing the reaction, 10 ml of water was added and then extracted with 30 ml of toluene. The organic layer thus obtained was washed with 6N-hydrochloric acid thrice, 2N-sodium hydroxide thrice, and water thrice, and then dried over magnesium sulfate. Solvent was distilled off at a reduced pressure and the residue was subjected to a silica gel column chromatography (eluent: toluene) to obtain 2.0 g of a crude 3-fluoro-4-trifluoromethoxyphenyl=trans-4-ethylcyclohexyl-carboxylate. This product was recrystallized from a mixed solvent of heptane/ether (1/1) to obtain 1.6 g (yield: 78.0%) of the subject compound.

Data of mass spectrum well supported its structure.

Mass analysis: 335 (M+1)

Following compounds (No. 109 to No. 172) are prepared according to the method of Example 3:

| No. | R | Y | A | X |
|---|---|---|---|---|
| 109 | CH₂=CH | F | 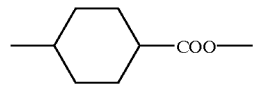 | CF₃ |
| 110 | C₂H₅ | H | 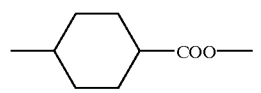 | CF₃ |
| 111 | C₃H₇ | F | 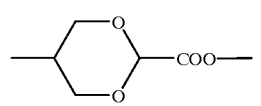 | CF₃ |
| 112 | C₄H₉ | F | 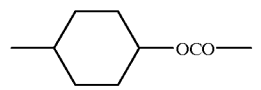 | CF₃ |
| 113 | C₅H₁₁ | F | 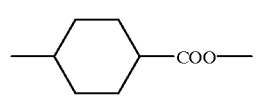 | CF₃ |

-continued
| No. | R | Y | A | X |
|-----|---|---|---|---|
| 114 | C₆H₁₃ | F | 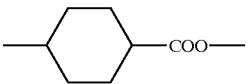 | CF₃ |
| 115 | CH₃O | H | 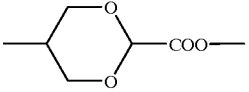 | CF₃ |
| 116 | C₂H₅O | F | 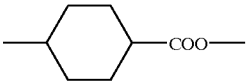 | CF₃ |
| 117 | C₃H₇O | H | 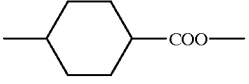 | CF₃ |
| 118 | C₄H₉O | F | 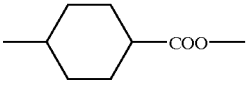 | CF₃ |
| 119 | C₅H₁₁O | F | 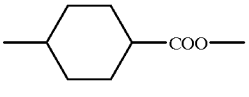 | CF₃ |
| 120 | C₆H₁₃O | F | 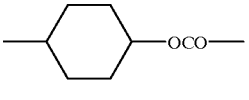 | CF₃ |
| 121 | CH₃ | F | 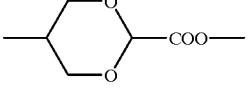 | CF₂H |
| 122 | C₂H₅ | F | 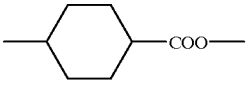 | CF₂H |
| 123 | C₃H₇ | F | 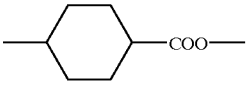 | CF₂H |
| 124 | C₄H₉ | H | 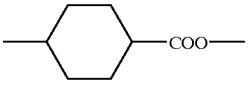 | CF₂H |
| 125 | 3E-C₅H₉ | H | 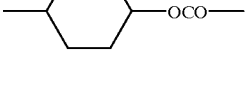 | CF₂H |
| 126 | C₆H₁₃ | F | 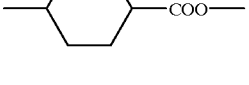 | CF₂H |

-continued
| No. | R | Y | A | X |
|---|---|---|---|---|
| 127 | C₁₀H₂₁ | F | 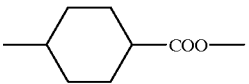 | CF₂H |
| 128 | CH₃O | F | 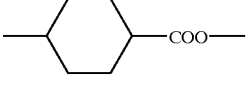 | CF₂H |
| 129 | C₂H₅O | H | 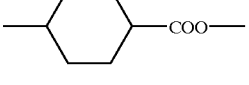 | CF₂H |
| 130 | C₃H₇O | F | 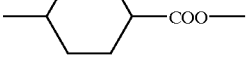 | CF₂H |
| 131 | C₄H₉O | F | 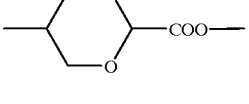 | CF₂H |
| 132 | C₅H₁₁O | H | 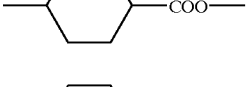 | CF₂H |
| 133 | C₇H₁₅O | F | 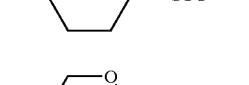 | CF₂H |
| 134 | CH₃ | F | 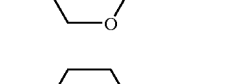 | CFH₂ |
| 135 | C₂H₅ | F | 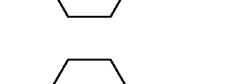 | CFH₂ |
| 136 | C₃H₇ | F |  | CFH₂ |
| 137 | C₄H₉ | F | 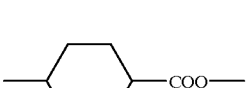 | CFH₂ |
| 138 | C₅H₁₁ | F | 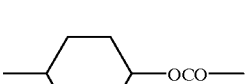 | CFH₂ |
| 139 | C₆H₁₃ | H | 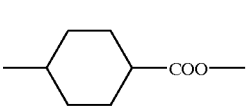 | CFH₂ |
| 140 | C₁₀H₂₁ | H |  | CFH₂ |

-continued
| No. | R | Y | A | X |
|---|---|---|---|---|
| 141 | CH₃O | F | 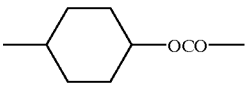 | CFH₂ |
| 142 | C₂H₅O | F | 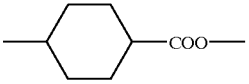 | CFH₂ |
| 143 | C₃H₇O | H | 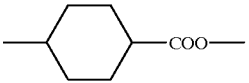 | CFH₂ |
| 144 | C₄H₉O | F | 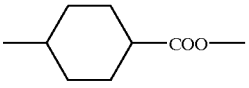 | CFH₂ |
| 145 | C₅H₁₁O | F | 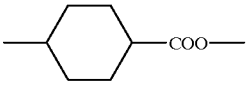 | CFH₂ |
| 146 | C₈H₁₇O | F | 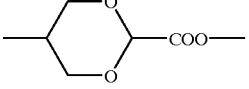 | CFH₂ |
| 147 | CH₃ | F | 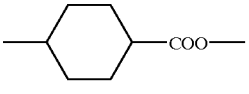 | OCF₃ |
| 148 | C₃H₇ | H | 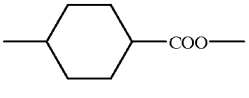 | OCF₃ |
| 149 | C₄H₉ | F | 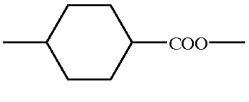 | OCF₃ |
| 150 | C₅H₁₁ | H | 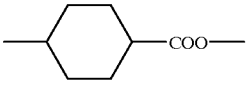 | OCF₃ |
| 151 | CH₂=C₂H₃OCH₂ | F | 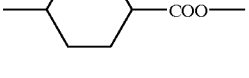 | OCF₃ |
| 152 | C₅H₁₁ | F | 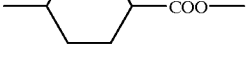 | OCF₃ |
| 153 | C₇H₁₅ | F | 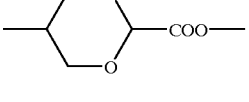 | OCF₃ |

-continued
| No. | R | Y | A | X |
|---|---|---|---|---|
| 154 | CH$_3$O | H | 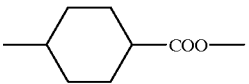 | OCF$_3$ |
| 155 | C$_2$H$_5$O | F | 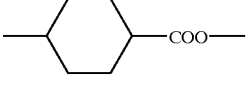 | OCF$_3$ |
| 156 | C$_3$H$_7$O | F | 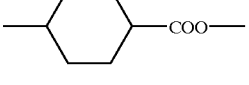 | OCF$_3$ |
| 157 | C$_4$H$_9$O | F | 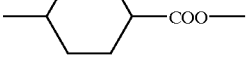 | OCF$_3$ |
| 158 | C$_5$H$_{11}$O | F | 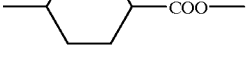 | OCF$_3$ |
| 159 | C$_7$H$_{15}$O | H | 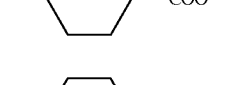 | OCF$_3$ |
| 160 | CH$_3$ | F | 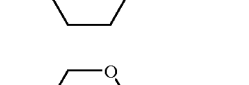 | OCF$_2$H |
| 161 | C$_2$H$_5$ | H | 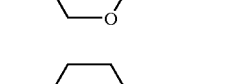 | OCF$_2$H |
| 162 | C$_3$H$_7$ | H | 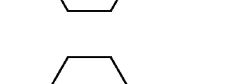 | OCF$_2$H |
| 163 | C$_4$H$_9$ | F |  | OCF$_2$H |
| 164 | C$_5$H$_{11}$ | H | 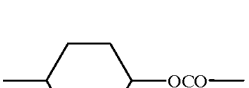 | OCF$_2$H |
| 165 | C$_6$H$_{12}$ | F | 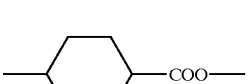 | OCF$_2$H |
| 166 | C$_9$H$_{19}$ | F | 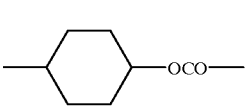 | OCF$_2$H |
| 167 | CH$_3$O | H |  | OCF$_2$H |

-continued

| No. | R | Y | A | X |
|-----|---|---|---|---|
| 168 | $C_2H_5O$ | F | (dioxane)-COO— | $OCF_2H$ |
| 169 | $C_3H_7O$ | F | (cyclohexylene)-COO— | $OCF_2H$ |
| 170 | Z-$CH_3OCH=C_2H_3$ | H | (cyclohexylene)-COO— | $OCF_2H$ |
| 171 | $C_5H_{11}O$ | F | (cyclohexylene)-COO— | $OCF_2H$ |
| 172 | $C_{10}H_{21}O$ | H | (cyclohexylene)-COO— | $OCF_2H$ |

EXAMPLE 4

Preparation of 3-fluoro-4-trifluoromethoxyphenyl 4-(trans-4-propycyclohexyl)benzoate (Compound No. 173 expressed by general formula (1) in which R is $C_3H_7$, m is 1, n is 0, $A_1$ is 1,4-phenylene group, $A_2$ is trans-1,4-cyclohexylene group, $Z_1$ is —COO—, $Z_2$ is a covalent bond, X is $OCF_3$, and Y is H.)

First, 1.6 g (6.5 mmol) of 4-(trans-4-propylcyclohexyl)benzoic acid was mixed with 1.2 g (9.7 mmol) of thionyl chloride, 0.1 ml of pyridine, and 4 ml of toluene, and reacted at 60° C. for 4 hours. Excess amount of thionyl chloride and toluene were distilled off at a reduced pressure to obtain a crude 4-(trans-4-propylcycohexyl)benzoyl chloride.

Then, 1.3 g (6.5 mmol) of 3-fluoro-4-trifluoromethoxyphenol, 0.8 ml of pyridine, and 3 ml of toluene were mixed. To this mixture was added dropwise 3 ml of toluene solution containing 6.5 mmol of 4-(trans-4-propylcyclohexyl)benzoyl chloride at room temperature in 5 minutes. After the dropping was finished, they were reacted at 50° C. for 3 hours. After finishing of the reaction, 15 ml of water was added to the reaction product, and then extracted with 40 ml of toluene. The organic layer thus obtained was washed with 6N-hydrochloric acid thrice, 2N-sodium hydroxide thrice, and water thrice, and then dried over anhydrous magnesium sulfate. Solvent was distilled off at a reduced pressure and the residue was subjected to a silica gel column chromatography (eluent: toluene) to obtain 2.6 g of a crude 3-fluoro-4-trifluoromethoxyphenyl 4-(trans-4-propyl-cyclohexyl)benzoate. This product was recrystallized from a mixed solvent of heptane/ether (1/1) to obtain 2.4 g (yield: 85.6%) of the subject compound.

Data of mass spectrum well supported its structure.

Mass analysis: 425 (M+1)

Following compounds (No. 174 to No. 212) are prepared according to the method of Example 4:

| No. | R | Y | A | X |
|-----|---|---|---|---|
| 174 | $C_2H_5$ | F | (cyclohexyl-phenylene)-COO— | $CF_3$ |
| 175 | $C_3H_7$ | F | (cyclohexyl-phenylene)-COO— | $CF_3$ Cr 114.6–115.0 Iso |
| 176 | $C_5H_{11}$ | F | (cyclohexyl-phenylene)-COO— | $CF_3$ |

-continued
| No. | R | Y | A | X |
|---|---|---|---|---|
| 177 | $C_3H_7$ | F | 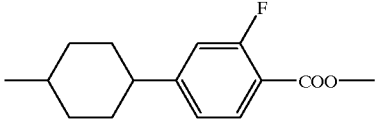 | $CF_3$ |
| 178 | $C_5H_{11}$ | F | 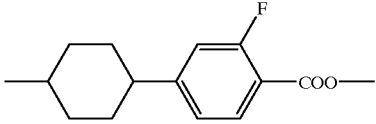 | $CF_3$ |
| 179 | $C_2H_5$ | F | 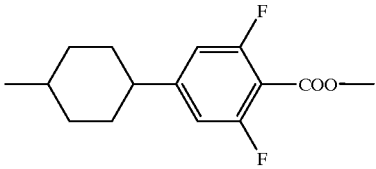 | $CF_3$ |
| 180 | $C_3H_7$ | H | 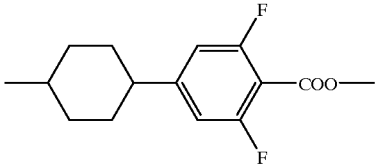 | $CF_3$ |
| 181 | $C_3H_7$ | F | 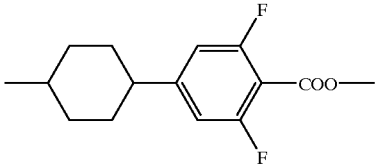 | $CF_3$ |
| 182 | $C_5H_{11}$ | F | 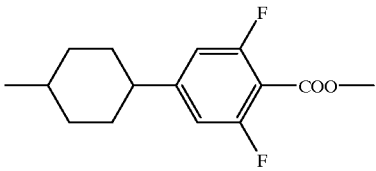 | $CF_3$ |
| 183 | $C_3H_7$ | F | 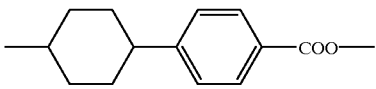 | $CF_2H$ |
| 184 | $C_2H_5O$ | H | 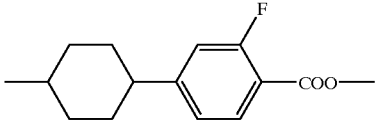 | $CF_2H$ |
| 185 | $C_4H_9$ | F | 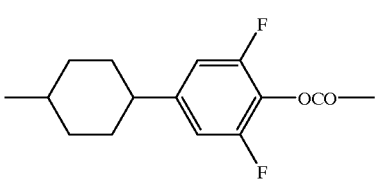 | $CF_2H$ |

-continued

| No. | R | Y | A | X |
|---|---|---|---|---|
| 186 | $C_{10}H_{21}O$ | F | cyclohexyl-phenyl-COO— | $CFH_2$ |
| 187 | $C_5H_{11}$ | F | dioxane-phenyl(F)-COO— | $CFH_2$ |
| 188 | $C_3H_7$ | H | cyclohexyl-phenyl(F)-COO— | $CFH_2$ |
| 189 | $C_2H_5$ | H | cyclohexyl-phenyl-COO— | $OCF_3$ Cr 85.7–87.2 N 116.5 Iso |
| 190 | $C_5H_{11}$ | H | cyclohexyl-phenyl-COO— | $OCF_3$ |
| 191 | $C_2H_5$ | F | cyclohexyl-phenyl-COO— | $OCF_3$ |
| 192 | $C_5H_{11}$ | F | cyclohexyl-phenyl-COO— | $OCF_3$ |
| 193 | $C_3H_7$ | F | cyclohexyl-phenyl(F)-COO— | $OCF_3$ |
| 194 | $C_2H_5$ | F | cyclohexyl-phenyl(F)-COO— | $OCF_3$ |
| 195 | $C_3H_7$ | H | cyclohexyl-phenyl(F)-COO— | $OCF_3$ |
| 196 | $C_5H_{11}$ | H | cyclohexyl-phenyl(F)-COO— | $OCF_3$ |

-continued
| No. | R | Y | A | X |
|---|---|---|---|---|
| 197 | $C_5H_{11}$ | F | 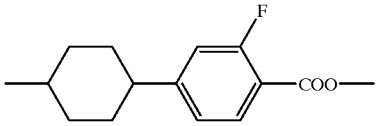 | $OCF_3$ |
| 198 | $C_2H_5$ | H | 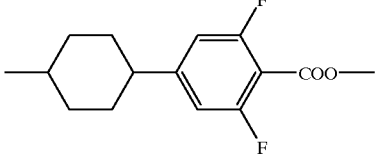 | $OCF_3$ |
| 199 | $C_2H_5$ | F | 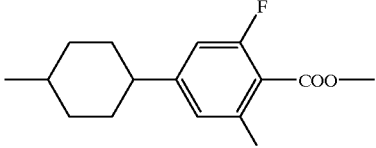 | $OCF_3$ |
| 200 | $C_3H_7$ | F | 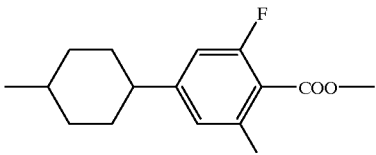 | $OCF_3$ |
| 201 | $C_3H_7$ | H | 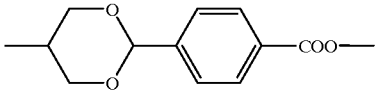 | $OCF_2H$ |
| 202 | $C_4H_9O$ | F | 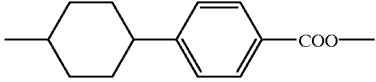 | $OCF_2H$ |
| 203 | $CH_3O$ | F | 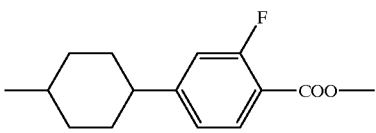 | $OCF_2H$ |
| 204 | $C_6H_{13}O$ | H | 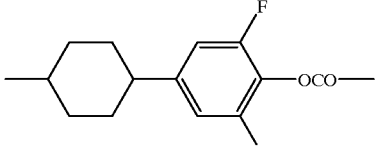 | $OCF_2H$ |
| 205 | $C_2H_5$ | F | 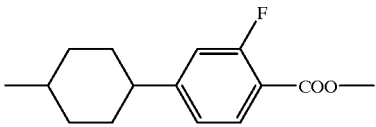 | CN Cr 56.9–57.4 N 121.3 Iso |
| 206 | $C_3H_7$ | F | 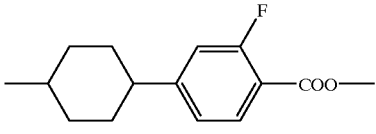 | CN |

-continued

| No. | R | Y | A | X |
|---|---|---|---|---|
| 207 | $C_5H_{11}$ | F | cyclohexyl–(2-F-phenyl)–COO– | CN |
| 208 | $C_8H_{17}$ | F | cyclohexyl–(2,6-diF-phenyl)–COO– | CN |
| 209 | $CH_2=C_3H_5$ | F | cyclohexyl–(2-F-phenyl)–COO– | CN |
| 210 | $C_2H_5O$ | F | cyclohexyl–(2-F-phenyl)–COO– | CN |
| 211 | $C_4H_9O$ | F | cyclohexyl–(2-F-phenyl)–COO– | CN |
| 212 | $C_{10}H_{21}O$ | F | cyclohexyl–(2-F-phenyl)–COO– | CN |

EXAMPLE 5

Preparation of 3,5-difluoro-4-trifluoromethoxyphenyl trans-4-(trans-4-propylcyclohexyl)cyclohexylcarboxylate (Compound No. 213 expressed by general formula (1) in which R is $C_3H_7$, m is 1, n is 0, both $A_1$ and $A_2$ are trans-1,4-cyclohexylene group, $Z_1$ is —COO—, $Z_2$ is a covalent bond, X is $OCF_3$, and Y is F.)

First, 1.5 g (6.1 mmol) of trans-4-(trans-4-propyl-cyclohexyl)cyclohexanecarboxylic acid, 1.3 g (6.1 mmol) of 3,5-difluoro-4-trifluoromethoxyphenol, 0.2 g (1.8 mmol) of DMAP, and 15 ml of dichloromethane were mixed. To this mixture was added dropwise 5 ml of dichloromethane solution containing 1.5 g (7.3 mmol) of DCC at room temperature in 5 minutes, and reacted as they were while stirring for 12 hours. The crystals thus precipitated were filtered off. Toluene in an amount of 20 ml was added to the filtrate, washed with 2N-sodium hydroxide 5 times and water thrice, and then dried over anhydrous magnesium sulfate. Solvent was distilled off at a reduced pressure and the residue was subjected to a silica gel column chromatography (eluent: toluene) to obtain 2.7 g of a crude 3,5-difluoro-4-trifluoromethoxyphenyl trans-4-(trans-4-propylcyclohexyl) cyclohexylcarboxylate. This product was recrystallized from a mixed solvent of heptane/ether to obtain 1.6 g (yield: 58.8%) of the subject compound.

Data of mass spectrum well supported its structure.

Mass analysis: 449 (M+1)

Following compounds (No. 214 to No. 248) are prepared according to the method of Example 5:

| No. | R | Y | A | X |
|---|---|---|---|---|
| 214 | C$_2$H$_5$ | H | -Cy-Cy-COO- | CF$_3$ |
| 215 | C$_3$H$_7$ | H | -Cy-Cy-COO- | CF$_3$ |
| 216 | C$_5$H$_{11}$ | H | -Cy-Cy-COO- | CF$_3$ |
| 217 | CH$_3$O | F | -Cy-Cy-COO- | CF$_3$ |
| 218 | C$_2$H$_5$ | F | -Cy-Cy-COO- | CF$_3$ |
| 219 | C$_4$H$_9$ | F | -Cy-Cy-COO- | CF$_3$ |
| 220 | C$_5$H$_{11}$ | F | -Cy-Cy-COO- | CF$_3$ Cr 88.4–88.9 N 121.0 Iso |
| 221 | C$_8$H$_{17}$ | F | -Cy-Cy-COO- | CF$_3$ |
| 222 | 1E-C$_4$H$_7$ | H | -Cy-Cy-COO- | CF$_2$H |
| 223 | C$_3$H$_7$ | F | -Cy-Cy-OCO- | CF$_2$H |
| 224 | C$_6$H$_{13}$ | F | -Cy-Cy-COO- | CF$_2$H |
| 225 | C$_2$H$_5$ | H | -Cy-Cy-COO- | CF$_2$H |
| 226 | C$_6$H$_{13}$O | F | -Cy-Cy-COO- | CF$_2$H |
| 227 | C$_3$H$_7$O | H | -Cy-Dio-COO- | CF$_2$H |

-continued

| No. | R | Y | A | X |
|-----|---|---|---|---|
| 228 | CH₃ | F | -Cy-Cy-COO- | CFH₂ |
| 229 | C₅H₁₁ | H | -Cy-Cy-COO- | CFH₂ |
| 230 | C₇H₁₅ | F | -Cy-Cy-OCO- | CFH₂ |
| 231 | CH₃O | F | -Cy-Cy-COO- | CFH₂ |
| 232 | C₅H₁₁O | H | -Cy-Cy-COO- | CFH₂ |
| 233 | C₉H₁₉O | F | -Cy-Cy-COO- | CFH₂ |
| 234 | C₅H₁₁O | H | -Dio-Cy-COO- | CFH₂ |
| 235 | C₂H₅ | H | -Cy-Cy-COO- | OCF₃ |
| 236 | C₃H₇ | H | -Cy-Cy-COO- | OCF₃ |
| 237 | C₅H₁₁ | H | -Cy-Cy-COO- | OCF₃ Cr 54.7–55.2 N 160.1 Iso |
| 238 | C₃H₇ | F | -Cy-Cy-COO- | OCF₃ |
| 239 | C₅H₁₁ | F | -Cy-Cy-COO- | OCF₃ |
| 240 | CH₂=C₃H₅O | H | -Cy-Cy-COO- | OCF₃ |

-continued

| No. | R | Y | A | X |
|---|---|---|---|---|
| 241 | $C_7H_{15}O$ | F | dioxane-cyclohexyl-OCO— | $OCF_3$ |
| 242 | $CH_3$ | F | cyclohexyl-cyclohexyl-COO— | $OCF_2H$ |
| 243 | $C_2H_5$ | H | cyclohexyl-cyclohexyl-COO— | $OCF_2H$ |
| 244 | $C_8H_{17}$ | F | cyclohexyl-cyclohexyl-COO— | $OCF_2H$ |
| 245 | $C_2H_5O$ | H | cyclohexyl-cyclohexyl-OCO— | $OCF_2H$ |
| 246 | $C_3H_7O$ | F | cyclohexyl-cyclohexyl-COO— | $OCF_2H$ |
| 247 | $C_5H_{11}O$ | H | cyclohexyl-cyclohexyl-COO— | $OCF_2H$ |
| 248 | $C_8H_{17}$ | F | cyclohexyl-dioxane-OCO— | $OCF_2H$ |

EXAMPLE 6

Preparation of 3,5-difluoro-4-cyanophenyl 2-fluoro-4-(2-(trans-4-pentylcyclohexyl)ethyl)benzoate (Compound No. 249 expressed by general formula (1) in which R is $C_5H_{11}$, m is 1, n is 0, $A_1$ is 2-fluoro-1,4-phenylene group, $A_2$ is trans-1,4-cyclohexylene group, $Z_1$ is —COO—, $Z_2$ is —$(CH_2)_2$—, X is CN, and Y is F.)

First, 2.1 g (6.4 mmol) of 2-fluoro-4-(2-(trans-4-pentylcyclohexyl)ethyl)benzoic acid was mixed with 1.1 g (9.6 mmol) of thionyl chloride, 0.1 ml of pyridine, and 3 ml of toluene, and reacted at 80° C. for 3 hours. Excess amount of thionyl chloride and toluene were distilled off at a reduced pressure to obtain a crude 2-fluoro-4-(2-(trans-4-pentyl-cyclohexyl)ethyl)benzoyl chloride.

Then, 1.1 g (6.4 mmol) of 2,6-difluoro- 4-hydroxybenzonitrile, 0.8 ml of pyridine, and 2 ml of toluene were mixed. To this mixture, was added dropwise 3 ml of toluene solution containing 6.4 mmol of 2-fluoro-4-(2-(trans-4-pentylcyclohexyl)ethyl)benzoyl chloride at room temperature in 5 minutes. After the dropping was finished, they were reacted at 50° C. for 2 hours. After finishing of the reaction, 10 ml of water was added to the reaction product, and then extracted with 30 ml of toluene. The organic layer thus obtained was washed with 6N-hydrochloric acid thrice, 2N-sodium hydroxide thrice, and water thrice, and then dried over anhydrous magnesium sulfate. Solvent was distilled off at a reduced pressure, and the residue was subjected to a silica gel column chromatography (eluent: toluene) to obtain 2.8 g of a crude 3,5-difluoro-4-cyanophenyl 2-fluoro-4-(2-(trans-4-pentylcyclohexyl)ethyl)benzoate. This product was recrystallized from a mixed solvent of heptane/ether to obtain 2.4 g of (yield: 81.6%) the subject compound.

Data of mass spectrum well supported its structure.

Mass analysis: 458 (M+1)

Following compounds (No. 250 to No. 307) are prepared according to the method of Example 6:

| No. | R | Y | A | X |
|---|---|---|---|---|
| 250 | $C_2H_5$ | F | —[Cy]—CH₂CH₂—[Ph]—COO— | $CF_3$ |
| 251 | $C_3H_7$ | F | —[Cy]—CH₂CH₂—[Ph(2-F)]—COO— | $CF_3$ |
| 252 | $C_2H_5O$ | F | —[Dioxane]—CH₂O—[Ph]—COO— | $CF_3$ |
| 253 | $C_5H_{11}O$ | F | —[Cy]—CH₂CH₂—[Ph]—COO— | $CF_3$ |
| 254 | $C_8H_{17}$ | H | —[Cy]—CH₂CH₂—[Ph(2,6-F₂)]—OCO— | $CF_3$ |
| 255 | $C_3H_7$ | F | —[Cy]—CH₂CH₂—[Ph]—COO— | $CF_2H$ |
| 256 | $C_4H_9$ | F | —[Ph]—CH₂CH₂—[Pyrimidine]—COO— | $CF_2H$ |
| 257 | $C_{10}H_{21}O$ | F | —[Cy]—CH₂CH₂—[Ph]—COO— | $CF_2H$ |
| 258 | $C_5H_{11}$ | F | —[Cy]—CH₂CH₂—[Ph(2-F)]—COO— | $CF_2H$ |
| 259 | $C_3H_7$ | F | —[Cy]—CH₂CH₂—[Cy]—COO— | $CF_2H$ |
| 260 | $CH_3$ | F | —[Cy]—CH₂CH₂—[Ph(2-F)]—COO— | $CFH_2$ |
| 261 | $C_6H_{13}$ | F | —[Cy]—CH₂CH₂—[Ph]—COO— | $CFH_2$ |

-continued
| No. | R | Y | A | X |
|---|---|---|---|---|
| 262 | $C_3H_7O$ | F | 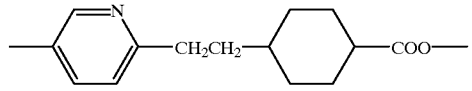 | $CFH_2$ |
| 263 | $C_4H_9O$ | F | 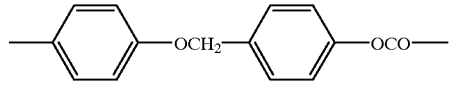 | $CFH_2$ |
| 264 | $CH_2=CH$ | F | 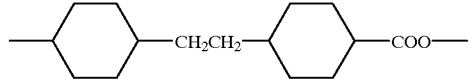 | $CFH_2$ |
| 265 | $C_3H_7$ | F | 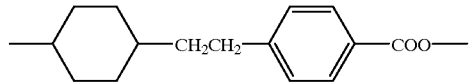 | $OCF_3$ |
| 266 | $C_5H_{11}$ | F |  | $OCF_3$ |
| 267 | $C_4H_9$ | H |  | $OCF_3$ |
| 268 | $C_2H_5$ | H | 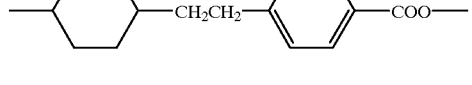 | $OCF_3$ |
| 269 | $C_3H_7O$ | F | 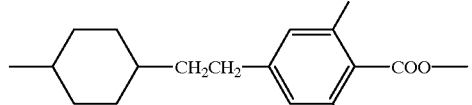 | $OCF_3$ |
| 270 | $C_7H_{15}O$ | F |  | OCF3 |
| 271 | $C_2H_5$ | F |  | $OCF_2H$ |
| 272 | $C_3H_7$ | H |  | $OCF_2H$ |
| 273 | $CH_3$ | F |  | $OCF_2H$ |

-continued
| No. | R | Y | A | X |
|---|---|---|---|---|
| 274 | C₂H₅O | F | 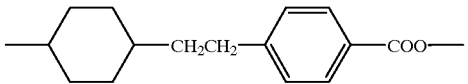 | OCF₂H |
| 275 | C₅H₁₁O | F | 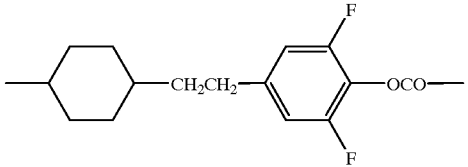 | OCF₂H |
| 276 | C₂H₅ | F | 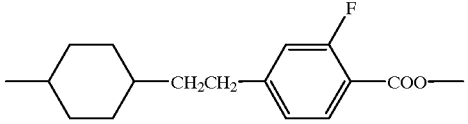 | CN |
| 277 | C₃H₇ | F | 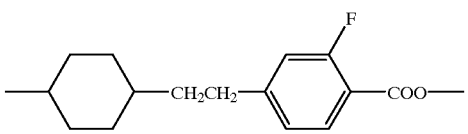 | CN Cr 41.0–41.7 N 125.8 Iso |
| 278 | C₄H₉ | F | 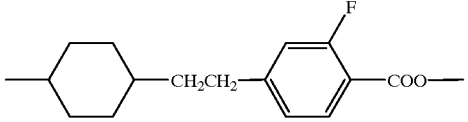 | CN |
| 279 | 3E-C₄H₇ | F | 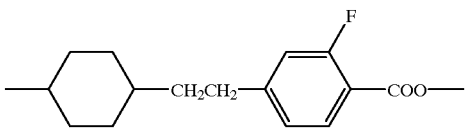 | CN |
| 280 | C₃H₇O | F | 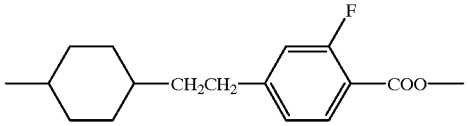 | CN |
| 281 | C₅H₁₁O | F | 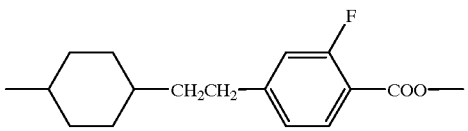 | CN |
| 282 | CH₃ | F | 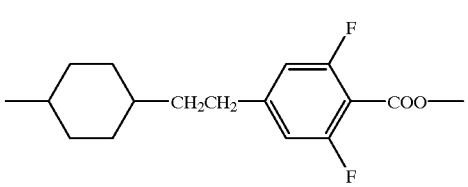 | CN |
| 283 | C₄H₇ | F | 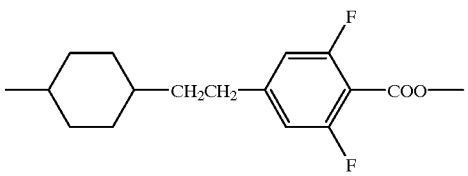 | CN |

-continued
| No. | R | Y | A | X |
|---|---|---|---|---|
| 284 | CH₃O | F | 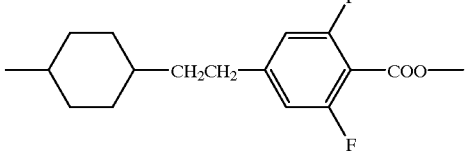 | CN |
| 285 | C₄H₉ | F | 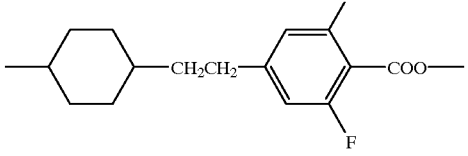 | CN |
| 286 | C₃H₇ | F | 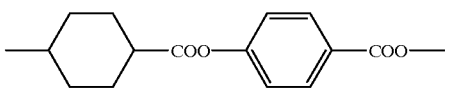 | CF₃ |
| 287 | C₅H₁₁O | F | 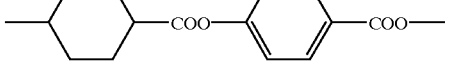 | CF₃ |
| 288 | C₄H₉ | H | 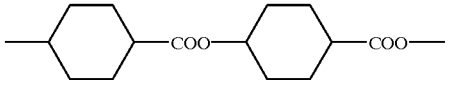 | CF₃ |
| 289 | C₇H₁₅O | F | 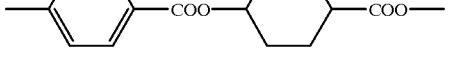 | CF₃ |
| 290 | C₃H₇ | F | 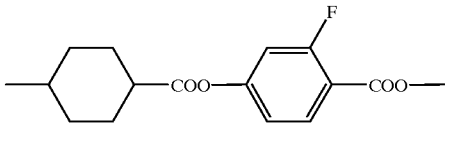 | CF₃ |
| 291 | C₈H₁₇O | H | 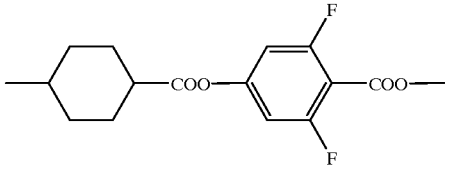 | CF₃ |
| 292 | C₅H₁₁ | F | 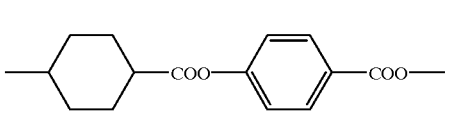 | CF₂H |
| 293 | C₃H₇O | F | 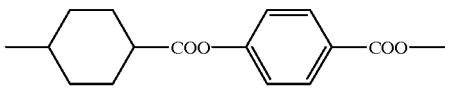 | CF₂H |
| 294 | C₇H₁₅O | H | 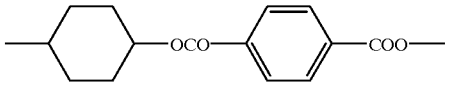 | CF₂H |

-continued

| No. | R | Y | A | X |
|---|---|---|---|---|
| 295 | $C_7H_{15}O$ | H | (2-F-phenyl)-COO-(cyclohexyl)-COO- | $CF_2H$ |
| 296 | $C_4H_9$ | F | (cyclohexyl)-COO-(phenyl)-COO- | $CFH_2$ |
| 297 | $CH_3O$ | F | (cyclohexyl)-COO-(phenyl)-COO- | $CFH_2$ |
| 298 | $CH_3$ | H | (cyclohexyl)-OCO-(cyclohexyl)-OCO- | $CFH_2$ |
| 299 | $C_7H_{15}O$ | F | (2,6-diF-phenyl)-COO-(2,6-diF-phenyl)-COO- | $CFH_2$ |
| 300 | $C_2H_5$ | F | (cyclohexyl)-COO-(phenyl)-COO- | $OCF_3$ |
| 301 | $C_2H_5O$ | F | (cyclohexyl)-COO-(phenyl)-COO- | $OCF_3$ |
| 302 | $C_5H_{11}$ | H | (cyclohexyl)-COO-(cyclohexyl)-OCO- | $OCF_3$ |
| 303 | $C_3H_7$ | H | (cyclohexyl)-COO-(2-F-phenyl)-COO- | $OCF_3$ |
| 304 | $C_3H_7$ | F | (cyclohexyl)-COO-(phenyl)-COO- | $OCF_2H$ |
| 305 | $C_8H_{17}O$ | F | (cyclohexyl)-COO-(phenyl)-COO- | $OCF_2H$ |
| 306 | $C_{10}H_{21}$ | H | (phenyl)-COO-(cyclohexyl)-OCO- | $OCF_2H$ |

-continued

| No. | R | Y | A | X |
|---|---|---|---|---|
| 307 | $C_3H_7$ | H | —[cyclohexyl]—COO—[2,6-difluorophenyl]—COO— | $OCF_2H$ |

EXAMPLE 7

Preparation of 3'-fluoro-4'-difluoromethoxybiphenyl-4-yl trans-4-methylcyclohexylcarboxylate (Compound No. 308 expressed by general formula (1) in which R is $CH_3$, m is 1, n is 0, $A_1$ is 1,4-phenylene group, $A_2$ is trans-1,4-cyclohexylene group, $Z_1$ is a covalent bond, $Z_2$ is —COO—, X is $OCF_2H$, and Y is H.)

First, 0.9 g (6.7 mmol) of trans-4-methylcyclohexane carboxylic acid, 1.7 g (6.7 mmol) of 3'-fluoro-4'-difluoromethoxy-4-hydroxybiphenyl, 0.2 g (2.0 mmol) of DMAP, and 15 ml of dichloromethane were mixed. To this mixture was added dropwise 5 ml of dichloromethane solution containing 1.7 g (8.0 mmol) of DCC at room temperature in 5 minutes, and reacted as they were while stirring for 12 hours. The crystals thus precipitated were filtered off. Toluene in an amount of 15 ml was added to the filtrate, washed with 2N-sodium hydroxide 5 times, and water thrice, and then dried over anhydrous magnesium sulfate. Solvent was distilled off at a reduced pressure and the residue was subjected to a silica gel column chromatography (eluent: toluene) to obtain 2.5 g of a crude 3'-fluoro-4'-di-fluoro-methoxybiphenyl-4-yl trans-4-methylcyclohexylcarboxylate. This product was recrystallized from a mixed solvent of heptane/ether (1/1) to obtain 2.1 g (yield: 83.0%) of the subject compound.

Data of mass spectrum well supported its structure.

Mass analysis: 379 (M+1)

Following compounds (No. 309 to No. 348) are prepared according to the method of Example 7:

| No. | R | Y | A | X |
|---|---|---|---|---|
| 309 | $C_2H_5$ | F | —[cyclohexyl]—COO—[phenyl]— | $CF_3$ |
| 310 | $C_3H_7$ | F | —[cyclohexyl]—COO—[phenyl]— | $CF_3$ |
| 311 | $C_5H_{11}$ | F | —[cyclohexyl]—COO—[phenyl]— | $CF_3$ |
| 312 | $C_3H_7O$ | H | —[cyclohexyl]—COO—[2-fluorophenyl]— | $CF_3$ |
| 313 | $C_5H_{11}$ | F | —[phenyl]—COO—[2,6-difluorophenyl]— | $CF_3$ |
| 314 | $CH_3$ | F | —[cyclohexyl]—COO—[phenyl]— | $CF_2H$ |

-continued
| No. | R | Y | A | X |
|---|---|---|---|---|
| 315 | $C_7H_{15}O$ | H | 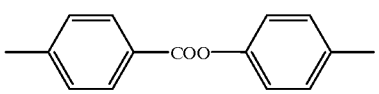 | $CF_2H$ |
| 316 | $C_3H_7$ | F | 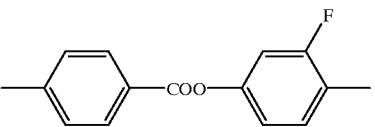 | $CF_2H$ |
| 317 | $C_8H_{17}$ | H | 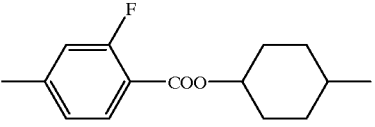 | $CF_2H$ |
| 318 | $C_4H_9O$ | F | 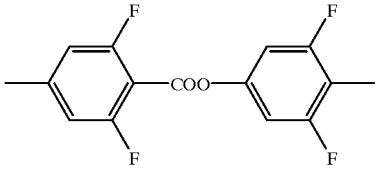 | $CF_2H$ |
| 319 | $C_2H_5$ | F | 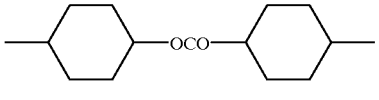 | $CFH_2$ |
| 320 | $C_3H_7O$ | H | 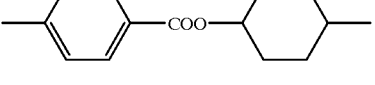 | $CFH_2$ |
| 321 | $C_5H_{11}$ | F | 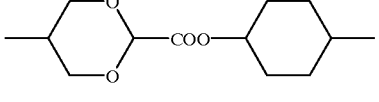 | $CFH_2$ |
| 322 | $C_3H_7$ | H | 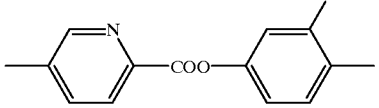 | $CFH_2$ |
| 323 | $CH_3O$ | F | 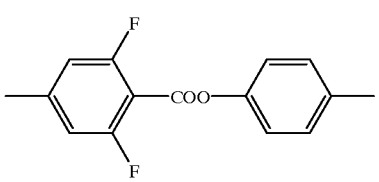 | $CFH_2$ |
| 324 | $C_4H_9O$ | H | 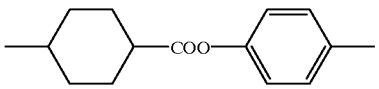 | $OCF_3$ |
| 325 | $C_4H_9$ | F | 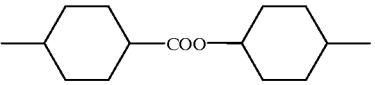 | $OCF_3$ |

-continued

| No. | R | Y | A | X |
|---|---|---|---|---|
| 326 | C₂H₅ | H | [2-F-phenyl-COO-phenyl] | OCF₃ |
| 327 | C₁₀H₂₁ | H | [pyrimidine-COO-3,5-difluorophenyl] | OCF₃ |
| 328 | C₄H₉ | H | [phenyl-COO-3,5-difluorophenyl] | OCF₃ |
| 329 | C₃H₇ | F | [cyclohexyl-COO-cyclohexyl] | OCF₂H |
| 330 | CH₃O | H | [phenyl-COO-phenyl] | OCF₂H |
| 331 | C₂H₅O | F | [cyclohexyl-CCO-phenyl] | OCF₂H |
| 332 | C₄H₉ | H | [cyclohexyl-COO-3-fluorophenyl] | OCF₂H |
| 333 | C₅H₁₁ | F | [2-F-phenyl-COO-3,5-difluorophenyl] | OCF₂H |
| 334 | C₂H₅ | F | [biphenyl-COO-] | CF₃ |
| 335 | C₃H₇ | H | [biphenyl-COO-] | CF₃ |
| 336 | C₅H₁₁ | F | [biphenyl(3-F)-COO-] | CF₃ |

-continued

| No. | R | Y | A | X |
|---|---|---|---|---|
| 337 | CH₃O | H | (pyrimidine-phenyl-COO—) | CF₂H |
| 338 | E-C₂H₄=C₂H₃O | F | (phenyl-cyclohexyl-COO—) | CF₂H |
| 339 | C₃H₇ | F | (difluorophenyl-difluorophenyl-COO—) | CF₂H |
| 340 | C₈H₁₇ | H | (fluorophenyl-phenyl-OCO—) | CFH₂ |
| 341 | CH₃ | F | (difluorophenyl-cyclohexyl-COO—) | CFH₂ |
| 342 | C₁₀H₂₁O | H | (pyridine-fluorophenyl-COO—) | CFH₂ |
| 343 | C₂H₅ | H | (phenyl-phenyl-COO—) | OCF₃ |
| 344 | C₂H₅ | F | (pyridine-phenyl-COO—) | OCF₃ |
| 345 | C₃H₇ | H | (phenyl-phenyl-COO—) | OCF₃ |
| 346 | CH₃O | H | (difluorophenyl-fluorophenyl-COO—) | OCF₂H |
| 347 | C₆H₁₃ | F | (phenyl-dioxane-OCO—) | OCF₂H |

-continued

| No. | R | Y | A | X |
|---|---|---|---|---|
| 348 | $C_2H_5$ | H | (2-F, 3-F, 5-F biphenyl with COO) | $OCF_2H$ |

EXAMPLE 8

Preparation of 3,5-difluoro-4-fluoromethylphenyl 4-(trans-4-(trans-4-ethylcyclohexyl)cyclohexyl)benzoate (Compound No. 349 expressed by general formula (1) in which R is $C_2H_5$, both m and n are 1, $A_1$ is 1,4-phenylene group, both $A_2$ and $A_3$ are trans-1,4-cyclohexylene group, $Z_1$ is —COO—, both $Z_2$ and $Z_3$ are a covalent bond, X is $CFH_2$, and Y is F.)

First, 1.5 g (4.8 mmol) of 4-(trans-4-(trans-4-ethylcyclohexyl)cyclohexyl)benzoic acid, 0.8 g (4.8 mmol) of 3,5-difluoro-4-fluoromethylphenol, 0.2 g (1.4 mmol) of DMAP, and 25 ml of dichloromethane were mixed. To this mixture was added dropwise 5 ml of dichoromethane solution containing 1.2 g (5.7 mmol) of DCC at room temperature in 5 minutes, and reacted as they were while stirring for 12 hours. The crystal thus precipitated were filtered off. Toluene in an amount of 30 ml was added to the filtrate, and washed with 2N-sodium hydroxide 5 times and water thrice, and then dried over anhydrous magnesium sulfate. Solvent was distilled off at a reduced pressure and the residue was subjected to a silica gel column chromatography (eluent: toluene) to obtain 2.1 g of a crude 3,5-difluoro-4-fluoromethylphenyl 4-(trans-4-(trans-4-ethylcyclohexyl) cyclohexyl)benzoate. This product was recrystallized from a mixed solvent of heptane/ethyl (1/1) acetate to obtain 1.9 g (yield: 86.3%) of the subject compound.

Data of mass spectrum well supported its structure.

Mass analysis: 459 (M+1)

Following compounds (No. 350 to No. 376) are prepared according to the method of Example 8.

| No. | R | Y | A | X |
|---|---|---|---|---|
| 350 | $C_3H_7$ | H | (Cy-Cy-Ph-COO) | $CF_3$ |
| 351 | $C_3H_7$ | F | (Cy-Cy-Ph-COO) | $CF_3$ |
| 352 | $C_5H_{11}$ | F | (Cy-Cy-COO-Ph) | $CF_3$ |
| 353 | 3E-$C_4H_7$ | F | (Ph-Ph-COO-Ph) | $CF_3$ |
| 354 | $C_3H_7$ | H | (Cy-Cy-Ph(F)-COO) | $CF_3$ |
| 355 | $C_3H_7$ | F | (Cy-Cy-Ph(F)-COO) | $CF_3$ Cr 125.9–126.7 N 221.5–221.7 Iso |

-continued
| No. | R | Y | A | X |
|---|---|---|---|---|
| 356 | C_2H_5 | F | 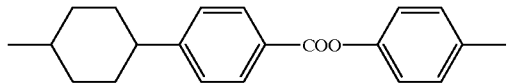 | CF_2H |
| 357 | C_3H_7 | F | 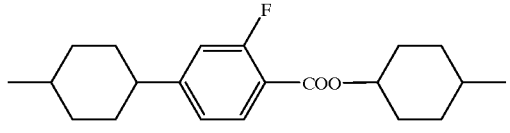 | CF_2H |
| 358 | C_6H_13O | H | 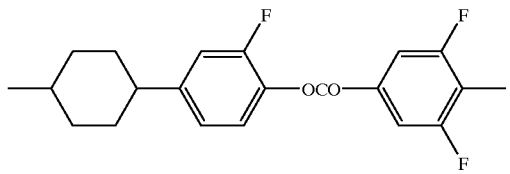 | CF_2H |
| 359 | CH_3 | F | 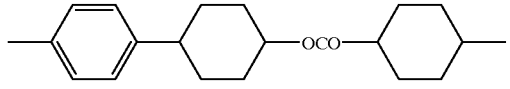 | CF_2H |
| 360 | C_2H_5 | F | 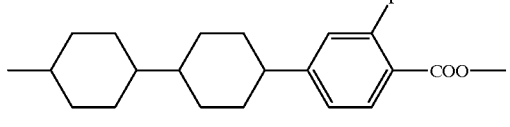 | CFH_2 |
| 361 | C_10H_21O | F | 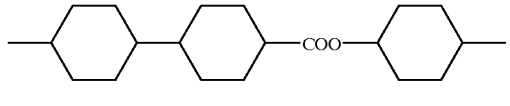 | CFH_2 |
| 362 | C_5H_11 | H | 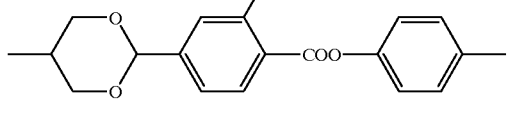 | CFH_2 |
| 363 | C_3H_7O | H | 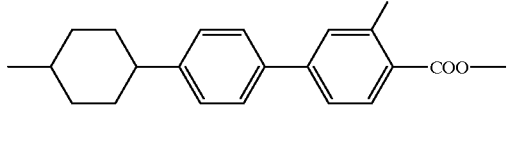 | CFH_2 |
| 364 | C_7H_15 | F | 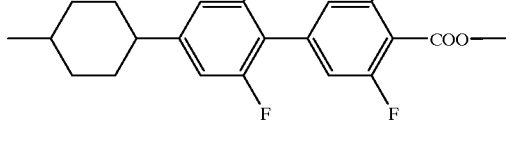 | CFH_2 |
| 365 | C_3H_7 | H | 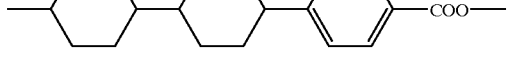 | OCF_3 |
| 366 | C_3H_7 | F | 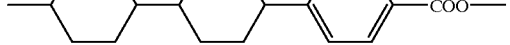 | OCF_3 |

-continued

| No. | R | Y | A | X |
|---|---|---|---|---|
| 367 | $C_3H_7$ | H | 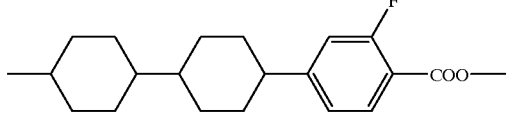 | $OCF_3$ |
| 368 | $C_3H_7$ | F | 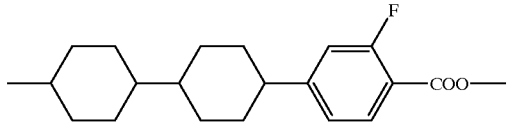 | $OCF_3$ |
| 369 | $C_5H_{11}$ | H | 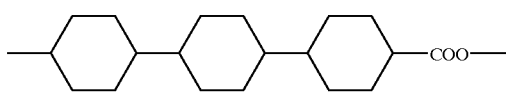 | $OCF_3$ |
| 370 | $C_4H_9O$ | F | 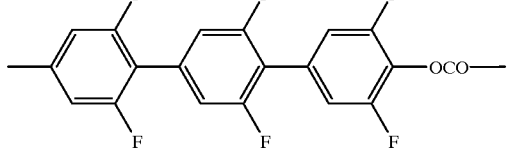 | $OCF_3$ |
| 371 | $C_5H_{11}$ | H | 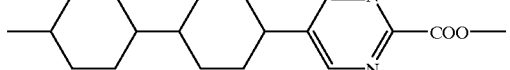 | $OCF_2H$ |
| 372 | $C_3H_7$ | F | 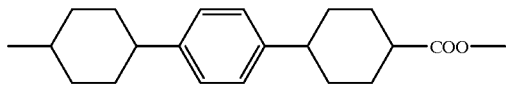 | $OCF_2H$ |
| 373 | $CH_3O$ | F | 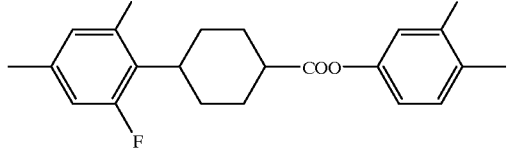 | $OCF_2H$ |
| 374 | $C_2H_5$ | F | 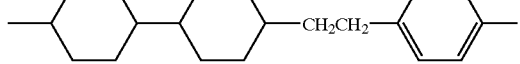 | $OCF_2H$ |
| 375 | $C_6H_{13}O$ | H | 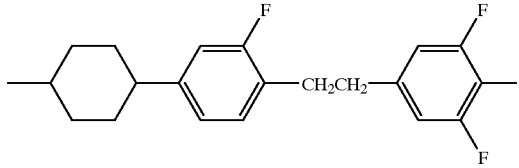 | $OCF_2H$ |
| 376 | $C_9H_{19}$ | H | 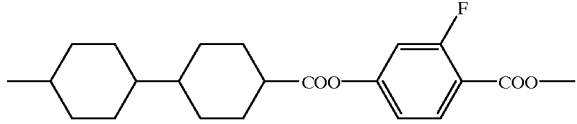 | $OCF_2H$ |

EXAMPLE 9

Preparation of (4-propylphenyl)methyl=3,5-difluoro-4-trifluoromethylphenyl=ether (Compound No. 377 expressed by general formula (1) in which R is $C_3H_7$, both m and n are 0, $A_1$ is 1,4-phenylene group, $Z_1$ is —$CH_2O$—, X is $CF_3$, and Y is F.)

First, 18 ml of tetrahydrofuran (THF) solution containing 1.8 g (9.1 mmol) of 3,5-difluoro-4-trifluoromethylphenol was added dropwise to the mixture of 0.22 g (9.1 mmol) of sodium hydride and 4 ml of THF at room temperature in 20 minutes, and then reacted at room temperature for 1 hour.

Subsequently, a catalytic amount of potassium iodide was added to the mixture, and then 5 ml of THF solution containing 2.1 g (10.0 mmol) of 4-propylbenzyl bromide was added dropwise at room temperature in 5 minutes. After the dropping was finished, they were reacted at 60° C. for 3 hours. After finishing of the reaction, 5 ml of water was added to the reaction product, and then extracted with 20 ml of ethyl acetate. The organic layer thus obtained was washed with 2N-hydrochloric acid thrice, 2N-sodium bicarbonate thrice, and water thrice, and then dried over anhydrous magnesium sulfate. Solvent was distilled off at a reduced pressure and the residue was subjected to a silica gel column chromatography (eluent: heptane/ethyl acetate) to obtain 2.7 g of a crude (4-propylphenyl)methyl=3,5-difluoro-4-trifluoromethylphenyl ether. This product was recrystallized from a mixed solvent of ethanol/ethyl (1/1) acetate to obtain 1.7 g (yield: 56.7%) of the subject compound.

Data of mass spectrum well supported its structure.

Mass analysis: 331 (M+1)

Following compounds (No. 378 to No. 399) are prepared according to the method of Example 9:

| No. | R | Y | A | X |
|---|---|---|---|---|
| 378 | $CH_3$ | F | —⌬—$CH_2O$— | $CF_3$ |
| 379 | $C_5H_{11}$ | F | —⌬—$CH_2O$— | $CF_3$ |
| 380 | $C_8H_{17}$ | H | —⌬—$CH_2O$— | $CF_3$ |
| 381 | $C_2H_5O$ | F | —⌬—$CH_2O$— | $CF_3$ |
| 382 | $C_5H_{11}O$ | H | —⌬—$CH_2O$— | $CF_3$ |
| 383 | 3E-$C_5H_9$ | F | —⌬—$CH_2O$— | $CF_3$ |
| 384 | $C_5H_{11}O$ | H | —⌬(F)—$CH_2O$— | $CF_3$ |
| 385 | $C_3H_7$ | H | —⌬(F,F)—$OCH_2$— | $CF_3$ |
| 386 | $C_2H_5$ | F | —⌬—$CH_2O$— | $CF_2H$ |
| 387 | $C_4H_9$ | F | —⌬—$OCH_2$— | $CF_2H$ |
| 388 | $C_{10}H_{21}O$ | F | —⌬—$CH_2O$— | $CF_2H$ |
| 389 | $CH_3O$ | F | —⌬(F)—$CH_2O$— | $CF_2H$ |
| 390 | $C_6H_{13}O$ | F | —pyrimidinyl—$CH_2O$— | $CFH_2$ |
| 391 | $CH_3$ | F | —⌬—$OCH_2$— | $CFH_2$ |
| 392 | $C_3H_7O$ | H | —pyridinyl—$CH_2O$— | $CFH_2$ |
| 393 | $C_3H_7$ | H | —⌬(F)—$OCH_2$— | $CFH_2$ |
| 394 | $C_3H_7$ | H | —⌬—$CH_2O$— | $OCF_3$ |
| 395 | $C_4H_9O$ | F | —⌬—$CH_2O$— | $OCF_3$ |
| 396 | $C_2H_5O$ | H | —⌬—$OCH_2$— | $OCF_3$ |

-continued

| No. | R | Y | A | X |
|---|---|---|---|---|
| 397 | C₃H₇O | F | 2,6-difluorophenyl-CH₂O— | OCF₃ |
| 398 | C₉H₁₉ | F | pyrimidin-2,5-diyl-OCH₂— | OCF₂H |
| 399 | CH₃O | F | 3-fluorophenyl-CH₂O— | OCF₂H |

EXAMPLE 10

Preparation of (trans-4-pentylcyclohexyl)methyl 3-fluoro-4-trifluoromethoxyphenyl ether (Compound No. 400 expressed by general formula (1) in which R is $C_5H_{11}$, both m and n are 0, $A_1$ is trans-1,4-cyclohexylene group, $Z_1$ is —CH₂O—, X is OCF₃, and Y is H.)

First, 14 ml of dimethyl formamide (DMF) solution containing 1.4 g (7.1 mmol) of 3-fluoro-4-trifluoromethoxyphenol was added dropwise to the mixture of 0.17 g (7.1 mmol) of sodium hydride and 3 ml of DMF at room temperature in 25 minutes, and then reacted at room temperature for 1 hour.

Subsequently, a catalytic amount of potassium iodide was added to the mixture, and then 5 ml of DMF solution containing 1.9 g (7.9 mmol) of trans-4-pentyl-bromomethylcyclohexane was added dropwise to the mixture at room temperature in 5 minutes. After the dropping was finished, they were reacted at 80° C. for 5 hours. After finishing of the reaction, 10 ml of water was added to the reaction product, and then extracted with 30 ml of ethyl acetate. The organic layer thus obtained was washed with 2N-hydrochloric acid thrice, 2N-sodium bicarbonate thrice, and water thrice, and then dried over anhydrous magnesium sulfate. Solvent was distilled off at a reduced pressure and the residue was subjected to a silica gel column chromatography (eluent: heptane/ethyl acetate) to obtain 2.4 g of a crude (trans-4-pentylcyclohexyl)methyl 3-fluoro-4-trifluoromethoxyphenyl=ether. This product was recrystallized from a mixed solvent of ethanol/ethyl (1/1) acetate to obtain 1.8 g (yield 69.2%) of the subject compound.

Data of mass spectrum well supported its structure.

Mass analysis: 363 (M+1)

Following compounds (No. 401 to No. 423) are prepared according to the method of Example 10:

| No. | R | Y | A | X |
|---|---|---|---|---|
| 401 | C₂H₅ | F | cyclohexylene-CH₂O— | CF₃ |
| 402 | C₅H₁₁ | H | cyclohexylene-OCH₂— | CF₃ |
| 403 | C₃H₇O | F | cyclohexylene-CH₂O— | CF₃ |
| 404 | C₄H₉O | H | cyclohexylene-OCH₂— | CF₃ |
| 405 | 3E-C₅H₉ | H | cyclohexylene-CH₂O— | CF₃ |
| 406 | CH₂=CH | F | cyclohexylene-OCH₂— | CF₃ |
| 407 | C₃H₇ | H | cyclohexylene-CH₂O— | CF₂H |

-continued
| No. | R | Y | A | X |
|-----|---|---|---|---|
| 408 | $C_5H_{11}O$ | F | 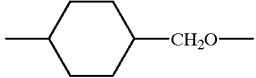 | $CF_2H$ |
| 409 | $C_8H_{17}O$ | H | 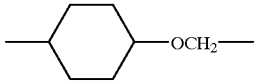 | $CF_2H$ |
| 410 | $CH_2=C_3H_5O$ | H | 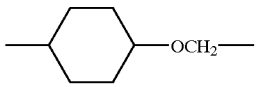 | $CF_2H$ |
| 411 | $CH_3$ | F | 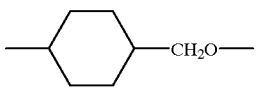 | $CFH_2$ |
| 412 | $C_8H_{17}$ | H | 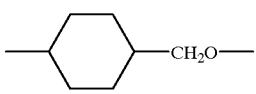 | $CFH_2$ |
| 413 | $C_2H_5O$ | F | 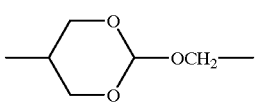 | $CFH_2$ |
| 414 | $2Z-C_4H_7$ | F | 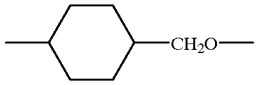 | $CFH_2$ |
| 415 | $C_3H_7$ | F | 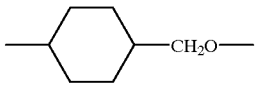 | $OCF_3$ |
| 416 | $C_4H_9$ | H | 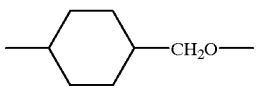 | $OCF_3$ |
| 417 | $CH_3O$ | H | 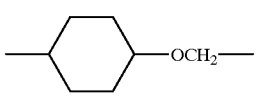 | $OCF_3$ |
| 418 | $1E-C_4H_7$ | H | 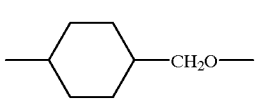 | $OCF_3$ |
| 419 | $CH_2=CH$ | F | 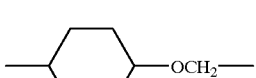 | $OCF_3$ |
| 420 | $C_5H_{11}$ | H | 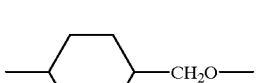 | $OCF_2H$ |
| 421 | $C_2H_5O$ | F | 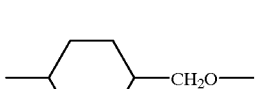 | $OCF_2H$ |

-continued

| No. | R | Y | A | X |
|---|---|---|---|---|
| 422 | $C_7H_{15}O$ | H | —⟨cyclohexyl⟩—OCH$_2$— | $OCF_2H$ |
| 423 | $CH_2$=$C_2H_3OCH_2$ | H | —⟨cyclohexyl⟩—OCH$_2$— | $OCF_2H$ |

EXAMPLE 11

Preparation of (trans-4-(trans-4-propylcyclohexyl)cyclohexyl)methyl 3,5-difluoro-4-trifluoromethylphenyl=ether (Compound No. 424 expressed by general formula (1) in which R is $C_3H_7$, m is 1, n is 0, both $A_1$ and $A_2$ are trans-1,4-cyclohexylene group, $Z_1$ is —$CH_2O$—, $Z_2$ is a covalent bond, X is $CF_3$, and Y is F.)

First, 14 ml of DMF solution containing 1.4 g (7.1 mmol) of 3,5-difluoro-4-trifluoromethylphenol was added dropwise to the mixture of 0.17 g (7.1 mmol) of sodium hydride and 3 ml of DMF at room temperature in 20 minutes, and then reacted at room temperature for 1 hour.

Subsequently, a catalytic amount of potassium iodide was added to the mixture, and then 5 ml of DMF solution containing 2.3 g (7.8 mmol) of trans,trans-4'-propyl-4-bromomethylbicyclo-hexane was added dropwise to the mixture at room temperature in 5 minutes. After the dropping was finished, they were reacted at 80° C. for 5 hours. After finishing of the reaction, 10 ml of water was added to the reaction product, and then extracted with 30 ml of ethyl acetate. The organic layer thus obtained was washed with 2N-hydrochloric acid thrice, 2N-sodium bicarbonate thrice, and water thrice, and then dried over anhydrous magnesium sulfate. Solvent was distilled off at a reduced pressure and the residue was subjected to a silica gel column chromatography (eluent: heptane/ethyl acetate) to obtain 2.6 g of a crude (trans-4-(trans-4-pentylcyclohexyl)cyclohexyl)methyl=3,5-difluoro-4-trifluoromethylphenyl ether. This product was recrystallized from a mixed solvent of ethanol/ethyl (1/1) acetate to obtain 2.3 g (yield 77.8%) of the subject compound.

Data of mass spectrum well supported its structure.

Mass analysis: 419 (M+1)

Following compounds (No. 425 to No. 448) are prepared according to the method of Example 11:

| No. | R | Y | A | X |
|---|---|---|---|---|
| 425 | $C_2H_5$ | F | —⟨Cy⟩—⟨Cy⟩—CH$_2$O— | $CF_3$ |
| 426 | $C_7H_{15}$ | H | —⟨Cy⟩—⟨Cy⟩—CH$_2$O— | $CF_3$ |
| 427 | $C_2H_5$ | F | —⟨Cy⟩—⟨Ph⟩—CH$_2$O— | $CF_3$ |
| 428 | 3E-$C_5H_{11}$ | F | —⟨Cy⟩—⟨Ph⟩—CH$_2$O— | $CF_3$ |
| 429 | $C_3H_7$ | F | —⟨Cy⟩—⟨Ph(F)⟩—CH$_2$O— | $CF_3$ |

-continued
| No. | R | Y | A | X |
|---|---|---|---|---|
| 430 | CH$_3$ | F | 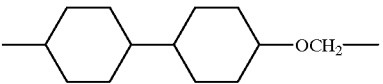 | CF$_2$H |
| 431 | C$_3$H$_7$O | H | 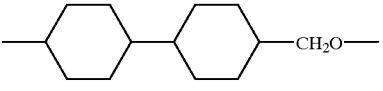 | CF$_2$H |
| 432 | C$_3$H$_7$ | F | 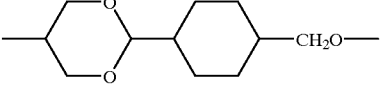 | CF$_2$H |
| 433 | C$_4$H$_9$ | F | 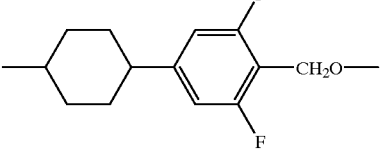 | CF$_2$H |
| 434 | C$_5$H$_{11}$ | F | 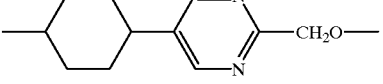 | CF$_2$H |
| 435 | C$_2$H$_5$ | H | 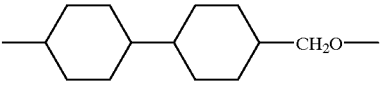 | CFH$_2$ |
| 436 | CH$_2$=CH | F | 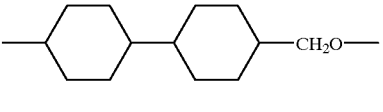 | CFH$_2$ |
| 437 | C$_8$H$_{17}$ | F | 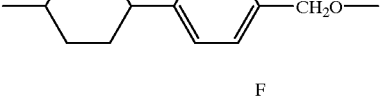 | CFH$_2$ |
| 438 | C$_5$H$_{11}$ | F | 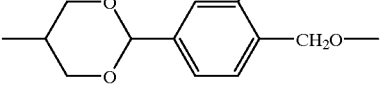 | CFH$_2$ |
| 439 | C$_4$H$_9$ | H | 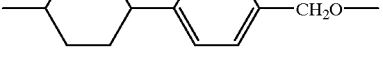 | CFH$_2$ |
| 440 | C$_3$H$_7$ | H | 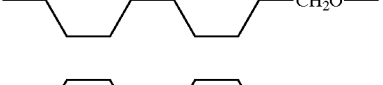 | OCF$_3$ Cr 57.6–58.3 N 106.1 Iso |
| 441 | C$_5$H$_{11}$ | F | 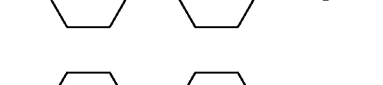 | OCF$_3$ |
| 442 | C$_8$H$_{17}$O | H | 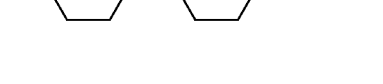 | OCF$_3$ |

-continued

| No. | R | Y | A | X |
|---|---|---|---|---|
| 443 | $C_5H_{11}$ | F | 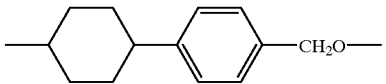 | $OCF_3$ |
| 444 | $C_3H_7$ | H | 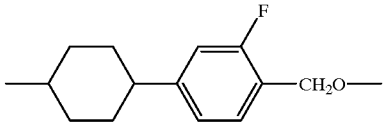 | $OCF_3$ |
| 445 | $C_3H_7O$ | H | 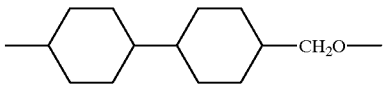 | $CF_2H$ |
| 446 | $C_5H_{11}$ | F | 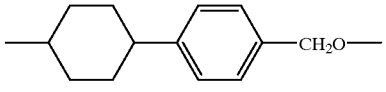 | $CF_2H$ |
| 447 | $C_5H_{11}$ | F | 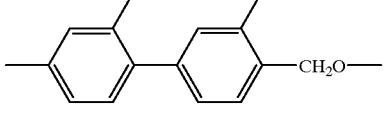 | $CF_2H$ |
| 448 | $C_5H_{11}$ | F | 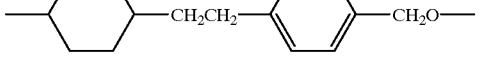 | $OCF_3$ |

EXAMPLE 12

Preparation of (trans-4-butylcyclohexyl)methyl=3',5'-difluoro-4'-trifluoromethylbiphenyl-4-yl ether (Compound No. 449 expressed by general formula (1) in which R is $C_4H_9$, m is 1, n is 0, $A_1$ is 1,4-phenylene group, $A_2$ is trans-1,4-cyclohexylene group, $Z_1$ is a covalent bond, $Z_2$ is —$CH_2O$—, X is $CF_3$, and Y is F.)

First, 17 ml of DMF solution containing 1.7 g (6.2 mmol) of 3',5'-difluoro-4'-trifluoromethyl-4-hydroxybiphenyl was added dropwise to the mixture of 0.15 g (6.2 mmol) of sodium hydride and 3 ml of DMF at room temperature in 20 minutes, and then reacted at room temperature for 1 hour.

Subsequently, a catalytic amount of potassium iodide was added to the mixture, and then 5 ml of DMF solution containing 1.6 g (6.8 mmol) of trans-4-butyl-bromomethylcyclohexane was added dropwise to the mixture at room temperature in 5 minutes. After the dropping was finished, they were reacted at 80° C. for 5 hours. After finishing of the reaction, 10 ml of water was added to the reaction product, and then extracted with 30 ml of ethyl acetate. The organic layer thus obtained was washed with 2N-hydrochloric acid thrice, 2N-sodium bicarbonate thrice, and water thrice, and then dried over anhydrous magnesium sulfate. Solvent was distilled off at a reduced pressure and the residue was subjected to a silica gel column chromatography (eluent: heptane/ethyl acetate) to obtain 2.4 g of a crude (trans-4-butylcyclohhexyl)methyl 3',5'-difluoro-4'-trifluoromethyl-biphenyl-4-yl=ether. This product was recrystallized from a mixed solvent of ethanol/ethyl (1/1) acetate to obtain 1.9 g (yield 73.1%) of the subject compound.

Data of mass spectrum well supported its structure.

Mass analysis: 427 (M+1)

Following compounds (No. 450 to No. 472) are prepared according to the method of Example 12:

| No. | R | Y | A | X |
|---|---|---|---|---|
| 450 | $C_2H_5$ | F | 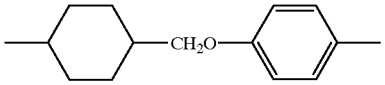 | $CF_3$ |

-continued
| No. | R | Y | A | X |
|---|---|---|---|---|
| 451 | $C_5H_{11}$ | H | 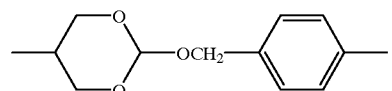 | $CF_3$ |
| 452 | $C_3H_7O$ | F | 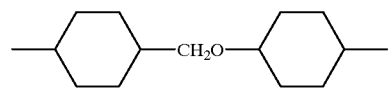 | $CF_3$ |
| 453 | $C_4H_9O$ | H |  | $CF_3$ |
| 454 | $3E-C_5H_9$ | H | 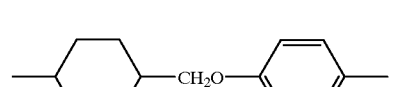 | $CF_3$ |
| 455 | $CH_2=CH$ | F | 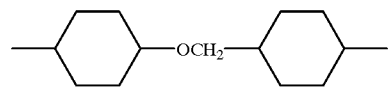 | $CF_3$ |
| 456 | $C_3H_7$ | H | 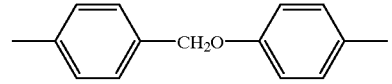 | $CF_2H$ |
| 457 | $C_5H_{11}O$ | F | 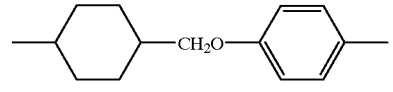 | $CF_2H$ |
| 458 | $C_8H_{17}O$ | H | 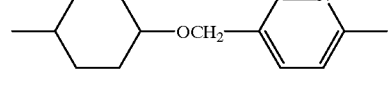 | $CF_2H$ |
| 459 | $CH_2=C_3H_5O$ | H | 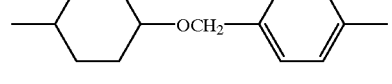 | $CF_2H$ |
| 460 | $CH_3$ | F | 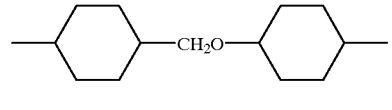 | $CFH_2$ |
| 461 | $C_8H_{17}$ | H | 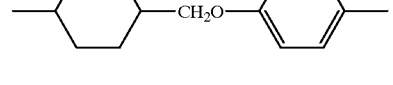 | $CFH_2$ |
| 462 | $C_2H_5O$ | F | 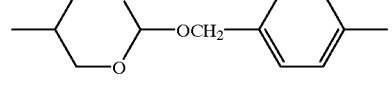 | $CFH_2$ |
| 463 | $2Z-C_4H_7$ | F | 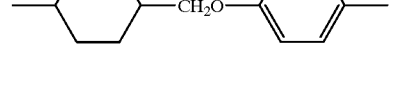 | $CFH_2$ |

-continued

| No. | R | Y | A | X |
|---|---|---|---|---|
| 464 | $C_3H_7$ | F | 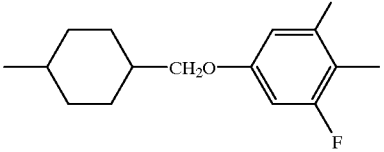 | $OCF_3$ |
| 465 | $C_4H_9$ | H | 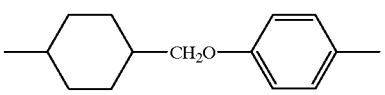 | $OCF_3$ |
| 466 | $CH_3O$ | H | 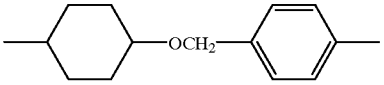 | $OCF_3$ |
| 467 | $1E-C_4H_7$ | H | 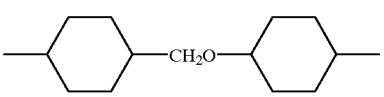 | $OCF_3$ |
| 468 | $CH_2=CH$ | F | 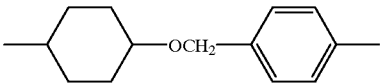 | $OCF_3$ |
| 469 | $C_5H_{11}$ | H | 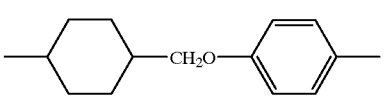 | $OCF_2H$ |
| 470 | $C_2H_5O$ | F | 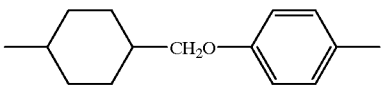 | $OCF_2H$ |
| 471 | $C_7H_{15}O$ | H | 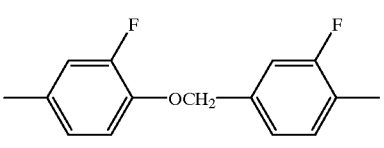 | $OCF_2H$ |
| 472 | $CH_2=C_2H_3OCH_2$ | H | 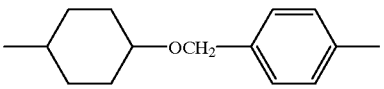 | $OCF_2H$ |

EXAMPLE 13

Preparation of (trans-4-(trans-4-propylcyclohexyl)cyclohexyl)methyl 3',5'-difluoro-4'-trifluoromethylbiphenyl-4-yl=ether (Compound No. 473 expressed by general formula (1) in which R is $C_3H_7$, both m and n are 1, $A_1$ is 1,4-phenylene group, both $A_2$ and $A_3$ are trans-1,4-cyclohexylene group, both $Z_1$ and $Z_3$ are a covalent bond, $Z_2$ is —$CH_2O$—, X is $CF_3$, and Y is F.)

First, 15 ml of DMF solution containing 1.5 g (5.5 mmol) of 3',5'-difluoro-4'-trifluoromethyl-4-hydroxybiphenyl was added dropwise to the mixture of 0.13 g (5.5 mmol) of sodium hydride and 3 ml of DMF at room temperature in 20 minutes, and then reacted at room temperature for 1 hour.

Subsequently, a catalytic amount of potassium iodide was added to the mixture, and then 5 ml of DMF solution containing 1.8 g (6.0 mmol) of trans,trans-4'-propyl-4-bromomethylbicyclo-hexane was added dropwise to the mixture at room temperature in 5 minutes. After the dropping was finished, they were reacted at 80° C. for 5 hours. After finishing of the reaction, 10 ml of water was added to the reaction product, and then extracted with 50 ml of ethyl acetate. The organic layer thus obtained was washed with 2N-hydrochloric acid thrice, 2N-sodium bicarbonate thrice, and water thrice, and then dried over anhydrous magnesium sulfate. Solvent was distilled off at a reduced pressure and the residue was subjected to a silica gel column chromatography (eluent: heptane/ethyl acetate) to obtain 2.5 g of a crude (trans-4-(trans-4-propylcyclohexyl)cyclohexyl) methyl 3',5'-difluoro-4'-trifluoromethylbiphenyl-4-yl ether. This product was recrystallized from a mixed solvent of ethanol/ethyl (1/1) acetate to obtain 1.8 g (yield 66.7%) of the subject compound.

Data of mass spectrum well supported its structure.
Mass analysis: 495 (M+1)
Following compounds (No. 474 to No. 497) are prepared according to the method of Example 13:
| No. | R | Y | A | X |
|---|---|---|---|---|
| 474 | $C_5H_{11}$ | F | 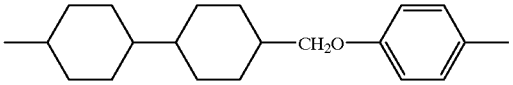 | $CF_3$ |
| 475 | $C_7H_{15}$ | H | 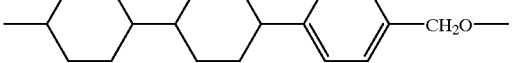 | $CF_3$ |
| 476 | $C_2H_5$ | F | 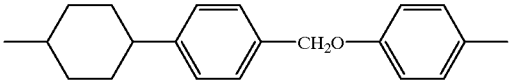 | $CF_3$ |
| 477 | $3E-C_5H_{11}$ | F | 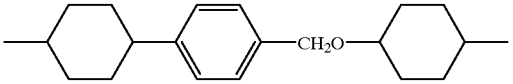 | $CF_3$ |
| 478 | $C_3H_7$ | F | 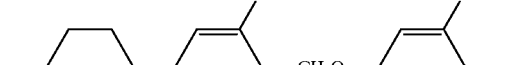 | $CF_3$ |
| 479 | $CH_3$ | F | 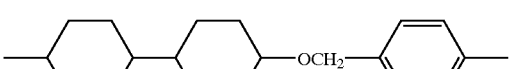 | $CF_2H$ |
| 480 | $C_3H_7O$ | H | 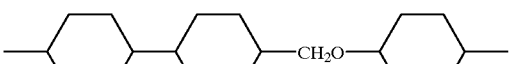 | $CF_2H$ |
| 481 | $C_3H_7$ | F | 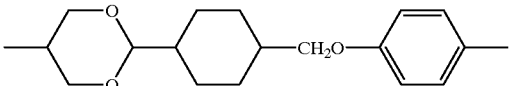 | $CF_2H$ |
| 482 | $C_4H_9$ | F | 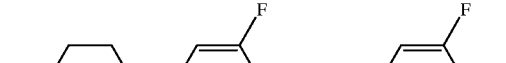 | $CF_2H$ |
| 483 | $C_5H_{11}$ | F | 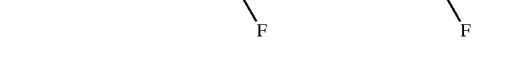 | $CF_2H$ |
| 484 | $C_2H_5$ | H | 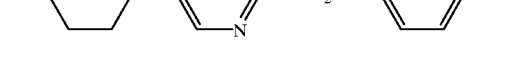 | $CFH_2$ |
| 485 | $CH_2=CH$ | F | 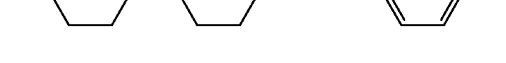 | $CFH_2$ |

-continued

| No. | R | Y | A | X |
|---|---|---|---|---|
| 486 | $C_8H_{17}$ | F | 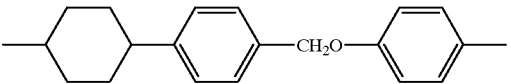 | $CFH_2$ |
| 487 | $C_5H_{11}$ | F | 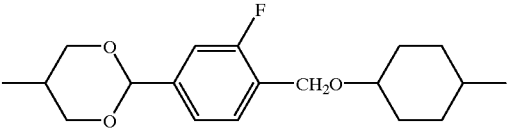 | $CFH_2$ |
| 488 | $C_4H_9$ | H | 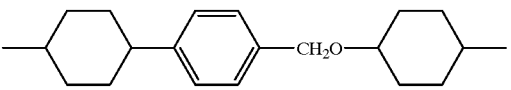 | $CFH_2$ |
| 489 | $CH_3$ | F | 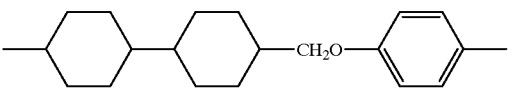 | $OCF_3$ |
| 490 | $C_5H_{11}$ | F | 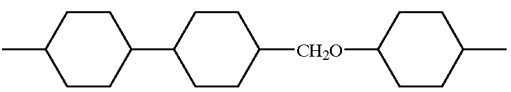 | $OCF_3$ |
| 491 | $C_8H_{17}O$ | H | 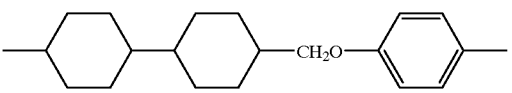 | $OCF_3$ |
| 492 | $C_5H_{11}$ | F | 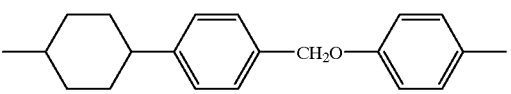 | $OCF_3$ |
| 493 | $C_3H_7$ | H | 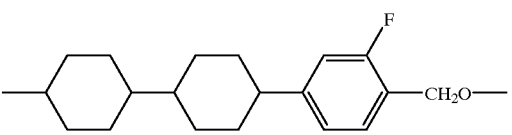 | $OCF_3$ |
| 494 | $C_3H_7O$ | H | 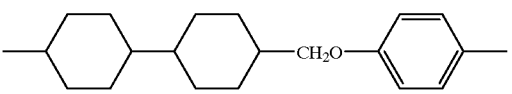 | $OCF_2H$ |
| 495 | $C_5H_{11}$ | F | 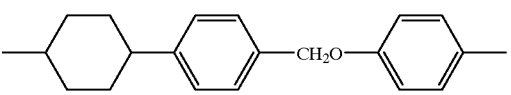 | $OCF_2H$ |
| 496 | $C_5H_{11}$ | F | 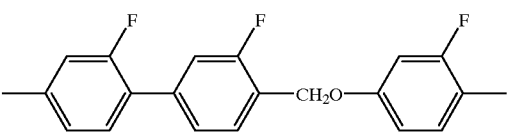 | $OCF_2H$ |
| 497 | $C_5H_{11}$ | F | 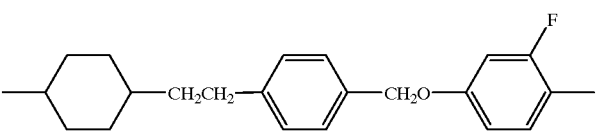 | $OCF_2H$ |

Examples in which the liquid crystalline compounds of the present invention were used as component of liquid crystal compositions are demonstrated below. In each of the Use Examples, NI represents clearing point (° C.), Δε does the value of dielectric anisotropy, Δn does optical anisotropy, η does viscosity (mPa.s) at 20° C., and $V_{10}$ represents threshold voltage (V).

EXAMPLE 14 (Use Example 1)

Liquid crystal composition comprising cyanophenylcyclohexane type liquid crystalline compounds and has the following specific composition

| | |
|---|---|
| 4-(trans-4-propylcyclohexyl)benzonitrile | 24% by weight |
| 4-(trans-4-pentylcyclohexyl)benzonitrile | 36% by weight |
| 4-(trans-4-heptylcyclohexyl)benzonitrile | 25% by weight |
| 4-(trans-4-pentylcyclohexyl)-4'-cyanobiphenyl | 15% by weight | had the following parameters:

NI: 72.4, Δε: 11.0, Δn: 0.137, η: 26.9, and $V_{10}$ at a cell thickness of 9μ: 1.78

This composition in an amount of 85% by weight was mixed with 15% by weight of Compound No. 205 to obtain a nematic liquid crystal composition. Parameters of the liquid crystal composition thus obtained were as follows:

NI: 75.1, Δε: 17.7, Δn: 0.138, η: 38.7, and $V_{10}$ at a cell thickness of 8.8μ: 1.29

While this composition was left in a freezer at −20° C., precipitation of crystals was not observed even after the lapse of 60 days.

EXAMPLE 15 (Use Example 2)

Example 14 was repeated to obtain a nematic liquid crystal composition except that Compound No. 277 was used in place of Compound No. 205. Parameters of the liquid crystal composition thus obtained were as follows:

NI: 75.4, Δε: 16.8, Δn: 0.139, η: 37.4, and $V_{10}$ at a cell thickness of 8.8μ: 1.40

While this composition was left in a freezer at −20° C., precipitation of crystals was not observed even after the lapse of 60 days.

EXAMPLE 16 (Use Example 3)

Parameters of the nematic liquid crystal composition shown in Composition Example 39 were as follows:

NI: 94.3, Δε: 8.2, Δn: 0.164, η: 16.0, and $V_{10}$ at a cell thickness of 8.8μ: 1.91

EXAMPLE 17 (Use Example 4)

Parameters of the nematic liquid crystal composition shown in Composition Example 40 were as follows:

NI: 82.3, Δε:12.1, Δn: 0.151, η: 23.5, and $V_{10}$ at a cell thickness of 8.9μ: 1.49

EXAMPLE 18 (Use Example 5)

Parameters of the nematic liquid crystal composition shown in Composition Example 41 were as follows:

NI: 71.3, Δε: 25.1, Δn: 0.160, η: 25.1, and $V_{10}$ at a cell thickness of 8.8μ: 0.85

EXAMPLE 19 (Use Example 6)

Parameters of the nematic liquid crystal composition shown in Composition Example 42 were as follows:

NI: 100.7, Δε: 4.4, Δn: 0.216, η: 34.0, and $V_{10}$ at a cell thickness of 9.0μ: 2.39

EXAMPLE 20 (Use Example 7)

Parameters of the nematic liquid crystal composition shown in Composition Example 43 were as follows:

NI: 76.2, Δε: 13.6, Δn: 0.125, η: 42.6, and $V_{10}$ at a cell thickness of 8.9μ: 1.33

EXAMPLE 21 (Use Example 8)

Parameters of the nematic liquid crystal composition shown in Composition Example 44 were as follows:

NI: 84.1, Δε: 18.1, Δn: 0.137, η: 36.8, and $V_{10}$ at a cell thickness of 8.9μ: 1.20

EXAMPLE 22 (Use Example 9)

Parameters of the nematic liquid crystal composition shown in Composition Example 45 were as follows:

NI: 74.5, Δε: 10.9, Δn: 0.132, η: 22.7, and $V_{10}$ at a cell thickness of 8.8μ: 1.36

EXAMPLE 23 (Use Example 10)

Parameters of the nematic liquid crystal composition shown in Composition Example 46 were as follows:

NI: 82.0, Δε: 6.4, Δn: 0.094, η: 25.2, and $V_{10}$ at a cell thickness of 8.8μ: 1.90

EXAMPLE 24 (Use Example 11)

Parameters of the nematic liquid crystal composition shown in Composition Example 47 were as follows:

NI: 84.9, Δε: 7.1, Δn: 0.135, η: 27.7, and $V_{10}$ at a cell thickness of 8.9μ: 1.69

EXAMPLE 25 (Use Example 12)

Parameters of the nematic liquid crystal composition shown in Composition Example 48 were as follows:

NI: 100.3, Δε: 4.1, Δn: 0.091, η: 28.0, and $V_{10}$ at a cell thickness of 8.8μ: 2.31

EXAMPLE 26 (Use Example 13)

Parameters of the nematic liquid crystal composition shown in Composition Example 49 were as follows:

NI: 92.0, Δε: 5.4, Δn: 0.093, η: 21.8, and $V_{10}$ at a cell thickness of 9.0μ: 2.32

EXAMPLE 27 (Use Example 14)

Parameters of the nematic liquid crystal composition shown in Composition Example 50 were as follows:

NI: 101.6, Δε: 10.5, Δn: 0.098, η39.2, and $V_{10}$ at a cell thickness of 8.9μ: 1.53

APPLICATION IN INDUSTRY

As described above, any of the liquid crystalline compounds of the present invention has a large dielectric anisotropy. Besides, it can be seen that the compound is small particularly in the change of threshold voltage depending of temperature and can be improved in solubility in other liquid crystal materials at low temperatures.

Accordingly, when the compound of the present invention was used as component of liquid crystal compositions, novel liquid crystal compositions having desired physical characteristics can be provided by properly selecting molecule constituting elements, that is, six-membered rings, substituents and/or bonding groups, in addition to the characteristic that the solubility to other liquid crystal compositions is excellent.

We claim:

1. A liquid crystalline compound expressed by general formula (1)

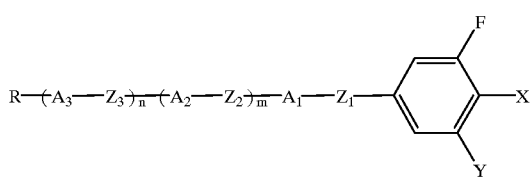

(1)

wherein R represents an alkyl group or alkoxy group having 1 to 10 carbon atoms, or an alkenyl group having 2 to 10 carbon atoms (any methylene group (—$CH_2$—) in the alkenyl group may be replaced by oxygen atom (—O—) provided that in no case two or more methylene groups are continually replaced by oxygen atom), m and n are independently 0 or 1, $A_1$, $A_2$, and $A_3$ are independently trans-1,4-cyclohexylene group, 1,4-phenylene group one or more hydrogen atoms on the ring of which may be replaced by F, pyrimidine-2,5-diyl group, pyridine-2,5-diyl group, or 1,3-dioxane-2,5-diyl group, $Z_1$, $Z_2$, and $Z_3$ independently represent —COO—, —OCO—, —$(CH_2)_2$—, —$CH_2O$—, —$OCH_2$—, or a covalent bond provided that at least one of $Z_1$, $Z_2$, and $Z_3$ represents ester bond, —$CH_2O$—, or —$OCH_2$—; X represents $CF_3$, $CF_2H$, $CFH_2$, $OCF_3$, $OCF_2H$, or CN, and Y represents H or F, provided that when X is CN, then n is 0, m is 1, $A_2$ is trans-1,4-cyclohexylene group, $A_1$ is 1,4-phenylene group one or more hydrogen atoms on the ring of which are replaced by F, $Z_2$ represents a covalent bond, $Z_1$ is ester bond, and Y represents F.

2. The liquid crystalline compound according to claim 1 wherein m and n are 0.

3. The liquid crystalline compound according to claim 1 wherein m is 1, and n is 0.

4. The liquid crystalline compound according to claim 1 wherein both m and n are 1.

5. The liquid crystalline compound according to claim 2 wherein $A_1$ is 1,4-phenylene group one or more hydrogen atoms on the ring of which may be replaced by F.

6. The liquid crystalline compound according to claim 2 wherein $A_1$ is trans-1,4-cyclohexylene group.

7. The liquid crystalline compound according to claim 3 wherein $A_2$ is trans-1,4-cyclohexylene group.

8. The liquid crystalline compound according to claim 4 wherein both $A_2$ and $A_3$ are trans-1,4-cyclohexylene group, and $Z_3$ is a covalent bond.

9. The liquid crystalline compound according to claim 7 wherein $A_1$ is 1,4-phenylene group one or more hydrogen atoms on the ring of which may be replaced by F, and $Z_2$ is a covalent bond.

10. The liquid crystalline compound according to claim 7 wherein $A_1$ is trans-1,4-cyclohexylene group, and $Z_2$ is a covalent bond.

11. The liquid crystalline compound according to claim 7 wherein $A_1$ is 1,4-phenylene group one or more hydrogen atoms on the ring of which are replaced by F, $Z_1$ is ester bond, $Z_2$ is a covalent bond, X is CN, and Y is F.

12. The liquid crystalline compound according to claim 8 wherein $A_1$ is 1,4-phenylene group one or more hydrogen atoms on the ring of which may be replaced by F, and $Z_2$ is a covalent bond.

13. The liquid crystalline compound according to claim 8 wherein $A_1$ is trans-1,4-cyclohexylene group or 1,4-phenylene group one or more hydrogen atoms on the ring of which may be replaced by F, and $Z_1$ is a covalent bond.

14. A liquid crystal composition containing at least one liquid crystalline compound defined in any one of claims 1 to 13.

15. A liquid crystal composition containing, as a first component, at least one liquid crystalline compound defined in any one of claims 1 to 13, and, as a second component, at least one compound selected from the group consisting of the compounds expressed by any one of general formulas (2), (3), and (4)

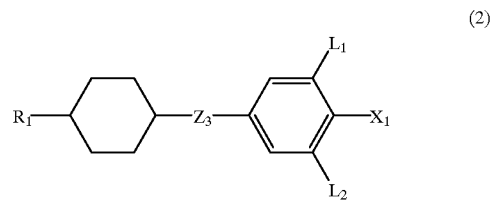

(2)

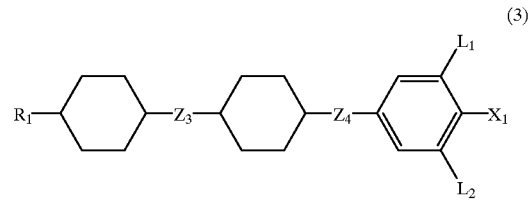

(3)

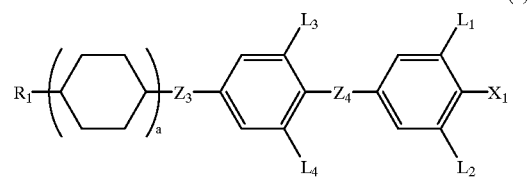

(4)

wherein $R_1$ represents an alkyl group having 1 to 10 carbon atoms, $X_1$ represents F, Cl, $OCF_3$, $OCF_2H$, $CF_3$, $CF_2H$, or $CFH_2$, $L_1$, $L_2$, $L_3$, and $L_4$ independently represent H or F, $Z_4$ and $Z_5$ independently represent —$(CH_2)_2$—, —CH=CH—, or a covalent bond, and a is 1 or 2.

16. A liquid crystal composition containing, as a first component, at least one liquid crystalline compound defined in any one of claims 1 to 13, and, as a second component, at least one compound selected from the group consisting of the compounds expressed by any one of general formulas (5), (6), (7), (8), and (9)

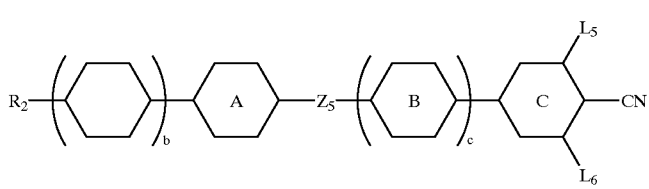

(5)

wherein $R_2$ represents F, an alkyl group having 1 to 10 carbon atoms or an alkenyl group having 2 to 10 carbon atoms, any methylene group (—$CH_2$—) in the alkyl group or alkenyl group may be replaced by oxygen atom (—O—) provided that in no case two or more methylene groups are continually replaced by oxygen atom, ring A represents trans-1,4-cyclohexylene group, 1,4-phenylene group, or 1,3-dioxane-2,5-diyl group, ring B represents trans-1,4-cyclohexylene group, 1,4-phenylene group, or pyrimidine-2,5-diyl group, ring C represents trans-1,4-cyclohexylene group or 1,4-phenylene group, $Z_6$ represents —$(CH_2)_2$—, —COO—, or a covalent bond, $L_5$ and $L_6$ independently represent H or F, and b and c are independently 0 or 1,

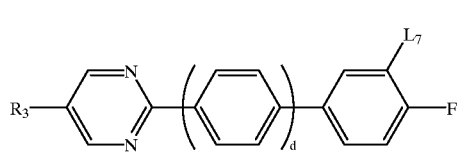

(6)

wherein $R_3$ represents an alkyl group having 1 to 10 carbon atoms, $L_7$ represents H or F, and d is 0 or 1,

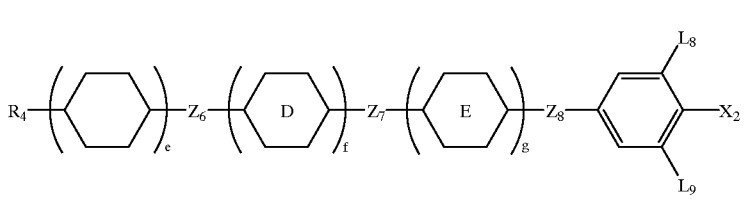

(7)

wherein $R_4$ represents an alkyl group having 1 to 10 carbon atoms, rings D and E independently represent trans-1,4-cyclohexylene group or 1,4-phenylene group, $Z_7$ and $Z_8$ independently represent —COO— or a covalent bond, $Z_9$ represents —COO— or —C≡C—, $L_8$ and $L_9$ independently represent H or F, $X_2$ represents F, $OCF_3$, $OCF_2H$, $CF_3$, $CF_2H$, or $CFH_2$, provided that when $X_2$ represents $OCF_3$, $OCF_2H$, $CF_3$, $CF_2H$, or $CFH_2$, both $L_8$ and $L_9$ represent H; and e, f, and g are independently 0 or 1,

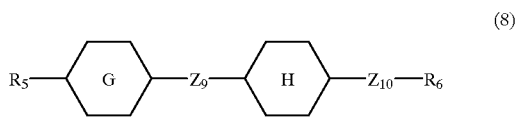

(8)

wherein $R_5$ and $R_6$ independently represent an alkyl group having 1 to 10 carbon atoms or an alkenyl group having 2 to 10 carbon atoms, in either case any methylene group (—$CH_2$—) in the alkyl group or alkylene group may be replaced by oxygen atom (—O—) provided that in no case two or more methylene groups are continually replaced by oxygen atom, ring G represents trans-1,4-cyclohexylene group, 1,4-phenylene group, or pyrimidine-2,5-diyl group, ring H represents trans-1,4-cyclohexylene group or 1,4-phenylene group, $Z_{10}$ represents —C≡C—, —COO—, —$(CH_2)_2$—, —CH=CH—C≡C—, or a covalent bond, and $Z_1$, represents —COO— or a covalent bond,

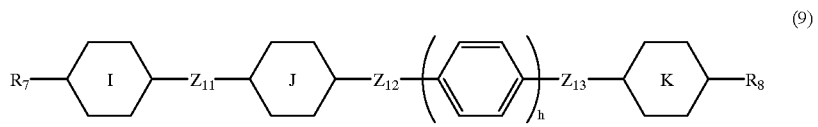

(9)

wherein $R_7$ and $R_8$ independently represent an alkyl group having 1 to 10 carbon atoms or an alkenyl group having 2 to 10 carbon atoms, in either case any methylene group (—$CH_2$—) in the alkyl group or alkylene group may be replaced by oxygen atom (—O—) provided that in no case two or more methylene groups are continually replaced by oxygen atom, ring I represents trans-1,4-cyclohexylene group, 1,4-phenylene group, or pyrimidine-2,5-diyl group, ring J represents trans-1,4-cyclohexylene group, 1,4-phenylene group one or more hydrogen atoms on the ring of which may be replaced by F, or pyrimidine-2,5-diyl group, ring K represents trans-1,4-cyclohexylene group or 1,4-phenylene group, $Z_{12}$ and $Z_{14}$ independently represent —COO—, —(CH$_2$)$_2$—, or covalent bond, $Z_{13}$ represents —CH=CH—, —C≡C—, —COO—, or a covalent bond, and h is 0 or 1.

17. A liquid crystal display device comprising a liquid crystal composition defined in claim 1.

18. A liquid crystal composition containing, as a first component, at least one liquid crystalline compound defined in any one of claims 1 to 13, as a part of a second component, at least one liquid crystalline compound selected from the group consisting of the compounds expressed by any one of general formulas (2), (3), and (4)

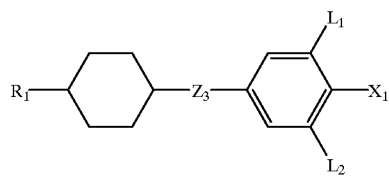
(2)

-continued

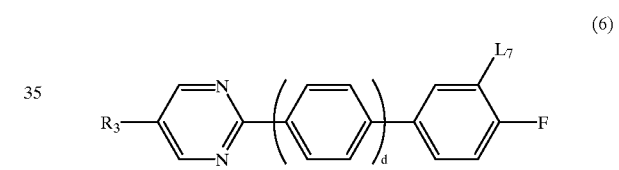
(4)

(5)

wherein $R_1$ represents an alkyl group having 1 to 10 carbon atoms, $X_1$ represents F, Cl, OCF$_3$, OCF$_2$H, CF$_3$, CF$_2$H, or CFH$_2$, $L_1$, $L_2$, $L_3$, and $L_4$ independently represent H or F, $Z_4$ and $Z_5$ independently represent —(CH$_2$)$_2$—, —CH=CH—, or a covalent bond, and a is 1 or 2, and as the other part of the second component, at least one liquid crystalline compound selected from the group consisting of the compounds expressed by any one of general formulas (5), (6), (7), (8), wherein $R_2$ represents F, an alkyl group having 1 to 10 carbon atoms or an alkenyl group having 2 to 10 carbon atoms, any methylene group (—CH$_2$—) in the alkyl group or alkenyl group may be replaced by oxygen atom (—O—) provided that in no case two or more methylene groups are continually replaced by oxygen atom, ring A represents trans-1,4-cyclohexylene group, 1,4-phenylene group, or 1,3-dioxane-2,5-diyl group, ring B represents trans-1,4-cyclohexylene group, 1,4-phenylene group, or pyrimidine-2,5-diyl group, ring C represents trans-1,4-cyclohexylene group or 1,4-phenylene group, $Z_6$ represents —(CH$_2$)$_2$—, —COO—, or a covalent bond, $L_5$ and $L_6$ independently represent H or F, and b and c are independently 0 or 1,

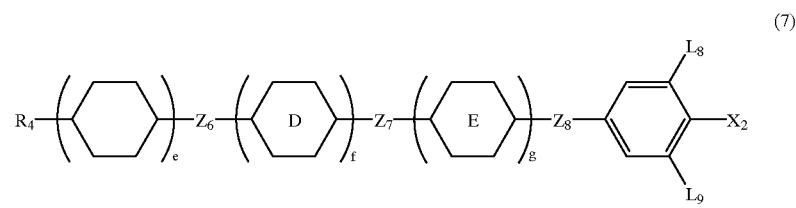
(6)

wherein $R_3$ represents an alkyl group having 1 to 10 carbon atoms, $L_7$ represents H or F, and d is 0 or 1, (7)

-continued
(3)

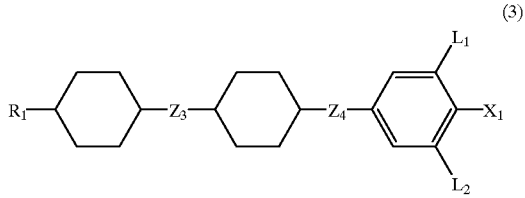

wherein $R_4$ represents an alkyl group having 1 to 10 carbon atoms, rings D and E independently represent trans-1,4-cyclohexylene group or 1,4-phenylene group, $Z_7$ and $Z_8$ independently represent —COO— or a covalent bond, $Z_9$ represents —COO— or —C≡C—, $L_8$ and $L_9$ independently represent H or F, $X_2$ represents F, OCF$_3$, OCF$_2$H, CF$_3$, CF$_2$H, or CFH$_2$, provided that when $X_2$ represents OCF$_3$, OCF$_2$H, CF$_3$, CF$_2$H, or CFH$_2$, both $L_8$ and L9 represent H; and e, f, and g are independently 0 or 1,

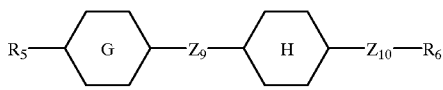

(8)

wherein $R_5$ and $R_6$ independently represent an alkyl group having 1 to 10 carbon atoms or an alkenyl group having 2 to 10 carbon atoms, in either case any methylene group (—$CH_2$—) in the alkyl group or alkylene group may be replaced by oxygen atom (—O—) provided that in no case two or more methylene groups are continually replaced by oxygen atom, ring G represents trans-1,4-cyclohexylene group, 1,4-phenylene group, or pyrimidine-2,5-diyl group, ring H represents trans-1,4-cyclohexylene group or 1,4-phenylene group, $Z_{10}$ represents —C≡C—, —COO—, —($CH_2$)$_2$—, —CH=CH—C≡C—, or a covalent bond, and $Z_{11}$ represents —COO— or a covalent bond,

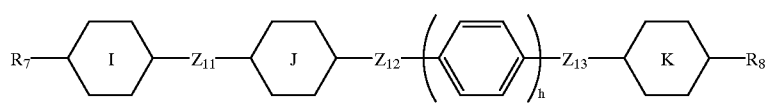

(9)

wherein $R_7$ and $R_8$ independently represent an alkyl group having 1 to 10 carbon atoms or an alkenyl group having 2 to 10 carbon atoms, in either case any methylene group(—$CH_2$—) in the alkyl group or alkylene group may be replaced by oxygen atom (—O—) provided that in no case two or more methylene groups are continually replaced by oxygen atom, ring I represents trans-1,4-cyclohexylene group, 1,4-phenylene group, or pyrimidine-2,5-diyl group, ring J represents trans-1,4-cyclohexylene group, 1,4-phenylene group one or more hydrogen atoms on the ring of which may be replaced by F, or pyrimidine-2,5-diyl group, ring K represents trans-1,4-cyclohexylene group or 1,4-phenylene group, $Z_{12}$ and $Z_{14}$ independently represent —COO—, —($CH_2$)$_2$—, or covalent bond, $Z_{13}$ represents —CH=CH—, —C≡C—, —COO—, or a covalent bond, and h is 0 or 1.

19. A liquid crystal display device comprising a liquid crystal composition defined in claim 15.

20. A liquid crystal display device comprising a liquid crystal composition defined in claim 16.

21. A liquid crystal display,device comprising a liquid crystal composition defined in claim 18.

* * * * *